US012788410B2

(12) United States Patent
Scanlan et al.

(10) Patent No.: US 12,788,410 B2
(45) Date of Patent: Nov. 10, 2026

(54) PATIENT-SPECIFIC OSTEOTOMY SYSTEMS, METHODS, AND INSTRUMENTATION

(71) Applicant: Treace Medical Concepts, Inc., Ponte Vedra Beach, FL (US)

(72) Inventors: Sean Scanlan, Jacksonville, FL (US); Jason May, St. John's, FL (US); Tyler Gleason, Ponte Vedra Beach, FL (US); Steve Norton, Jacksonville, FL (US); James Q. Spitler, Winter Garden, FL (US)

(73) Assignee: Treace Medical Concepts, Inc., Ponte Vedra, FL (US)

( * ) Notice: Subject to any disclaimer, the term of this patent is extended or adjusted under 35 U.S.C. 154(b) by 0 days.

(21) Appl. No.: 18/982,986

(22) Filed: Dec. 16, 2024

(65) Prior Publication Data

US 2025/0195081 A1 Jun. 19, 2025

Related U.S. Application Data

(60) Provisional application No. 63/610,303, filed on Dec. 14, 2023.

(51) Int. Cl.
*A61B 17/15* (2006.01)

(52) U.S. Cl.
CPC .................................. *A61B 17/154* (2013.01)

(58) Field of Classification Search
CPC ............... A61B 17/1775; A61B 17/15–17/158
See application file for complete search history.

(56) References Cited

U.S. PATENT DOCUMENTS 3,664,022 A 5/1972 Small
4,069,824 A 1/1978 Weinstock
(Continued)

FOREIGN PATENT DOCUMENTS

AU 2009227957 B2 7/2014
AU 2009222469 B2 2/2015
(Continued)

OTHER PUBLICATIONS

Tricot et al., "3D-corrective osteotomy using surgical guides for posttraumatic distal humeral deformity," Acta Orthopaedica Belgica, vol. 78, No. 4, 2012, pp. 538-542.
(Continued)

*Primary Examiner* — Zade Coley
(74) *Attorney, Agent, or Firm* — Fredrikson & Byron, P.A.

(57) ABSTRACT

An apparatus, system, and method are disclosed for remediating a condition present in a patient's foot. In some implementations, a resection guide includes a bone engagement feature configured to engage at least a portion of at least one foot bone to position the resection guide. The bone engagement feature may be least partially determined based on a model of the patient's foot, which is defined based on medical imaging of the patient's foot. The resection guide further includes a resection feature that extends through the resection guide from a superior side of the resection guide to an inferior side. The resection feature is configured to guide a cutting tool to form a first osteotomy in a first bone along a first trajectory. Additionally, the resection guide includes a first bone attachment feature configured to engage the first bone and a second bone attachment feature configured to engage a second bone.

15 Claims, 19 Drawing Sheets

(56) References Cited

U.S. PATENT DOCUMENTS

| | | | |
|---|---|---|---|
| 4,159,716 | A | 7/1979 | Borchers |
| 4,187,840 | A | 2/1980 | Watanabe |
| 4,335,715 | A | 6/1982 | Kirkley |
| 4,338,927 | A | 7/1982 | Volkov et al. |
| 4,349,018 | A | 9/1982 | Chambers |
| 4,409,973 | A | 10/1983 | Neufeld |
| 4,436,684 | A | 3/1984 | White |
| 4,440,168 | A | 4/1984 | Warren |
| 4,509,511 | A | 4/1985 | Neufeld |
| 4,565,191 | A | 1/1986 | Slocum |
| 4,570,624 | A | 2/1986 | Wu |
| 4,628,919 | A | 12/1986 | Clyburn |
| 4,736,737 | A | 4/1988 | Fargie et al. |
| 4,750,481 | A | 6/1988 | Reese |
| 4,754,746 | A | 7/1988 | Cox |
| 4,757,810 | A | 7/1988 | Reese |
| 4,839,822 | A | 6/1989 | Dormond et al. |
| 4,895,141 | A | 1/1990 | Koeneman et al. |
| 4,959,066 | A | 9/1990 | Dunn et al. |
| 4,978,347 | A | 12/1990 | Ilizarov |
| 4,988,349 | A | 1/1991 | Pennig |
| 4,995,875 | A | 2/1991 | Coes |
| 5,049,149 | A | 9/1991 | Schmidt |
| 5,053,039 | A | 10/1991 | Hofmann et al. |
| 5,112,334 | A | 5/1992 | Alchermes et al. |
| 5,147,364 | A | 9/1992 | Comparetto |
| 5,171,244 | A | 12/1992 | Caspari et al. |
| 5,176,685 | A | 1/1993 | Rayhack |
| 5,207,676 | A | 5/1993 | Canadell et al. |
| 5,254,119 | A | 10/1993 | Schreiber |
| 5,312,412 | A | 5/1994 | Whipple |
| 5,358,504 | A | 10/1994 | Paley et al. |
| 5,364,402 | A | 11/1994 | Mumme et al. |
| 5,374,271 | A | 12/1994 | Hwang |
| 5,417,694 | A | 5/1995 | Marik et al. |
| 5,449,360 | A | 9/1995 | Schreiber |
| 5,470,335 | A | 11/1995 | Du Toit |
| 5,490,854 | A | 2/1996 | Fisher et al. |
| 5,529,075 | A | 6/1996 | Clark |
| 5,540,695 | A | 7/1996 | Levy |
| 5,578,038 | A | 11/1996 | Slocum |
| 5,586,564 | A | 12/1996 | Barrett et al. |
| 5,601,565 | A | 2/1997 | Huebner |
| 5,613,969 | A | 3/1997 | Jenkins, Jr. |
| 5,620,442 | A | 4/1997 | Bailey et al. |
| 5,643,270 | A | 7/1997 | Combs |
| 5,662,656 | A | 9/1997 | White |
| 5,667,510 | A | 9/1997 | Combs |
| H1706 | H | 1/1998 | Mason |
| 5,722,978 | A | 3/1998 | Jenkins, Jr. |
| 5,749,875 | A | 5/1998 | Puddu |
| 5,779,709 | A | 7/1998 | Harris, Jr. et al. |
| 5,788,695 | A | 8/1998 | Richardson |
| 5,803,924 | A | 9/1998 | Oni et al. |
| 5,810,822 | A | 9/1998 | Mortier |
| 5,836,950 | A | 11/1998 | Hansson |
| 5,839,438 | A | 11/1998 | Graettinger et al. |
| 5,843,085 | A * | 12/1998 | Graser ................. A61B 17/151 606/87 |
| 5,893,553 | A | 4/1999 | Pinkous |
| 5,911,724 | A | 6/1999 | Wehrli |
| 5,935,128 | A | 8/1999 | Carter et al. |
| 5,941,877 | A | 8/1999 | Viegas et al. |
| 5,951,556 | A | 9/1999 | Faccioli et al. |
| 5,957,927 | A | 9/1999 | Magee et al. |
| 5,980,526 | A | 11/1999 | Johnson et al. |
| 5,984,931 | A | 11/1999 | Greenfield |
| 6,007,535 | A | 12/1999 | Rayhack et al. |
| 6,030,391 | A | 2/2000 | Brainard et al. |
| 6,162,223 | A | 12/2000 | Orsak et al. |
| 6,171,309 | B1 | 1/2001 | Huebner |
| 6,203,545 | B1 | 3/2001 | Stoffella |
| 6,248,109 | B1 | 6/2001 | Stoffella |
| 6,391,031 | B1 | 5/2002 | Toomey |
| 6,416,465 | B2 | 7/2002 | Brau |
| 6,478,799 | B1 | 11/2002 | Williamson |
| 6,511,481 | B2 | 1/2003 | Von Hoffmann et al. |
| 6,676,662 | B1 | 1/2004 | Bagga et al. |
| 6,712,824 | B2 | 3/2004 | Millard et al. |
| 6,719,773 | B1 | 4/2004 | Boucher et al. |
| 6,743,233 | B1 | 6/2004 | Baldwin et al. |
| 6,755,838 | B2 | 6/2004 | Trnka |
| 6,780,190 | B2 | 8/2004 | Maroney |
| 6,796,986 | B2 | 9/2004 | Duffner |
| 6,859,661 | B2 | 2/2005 | Tuke |
| 6,944,518 | B2 | 9/2005 | Roose |
| 6,964,645 | B1 | 11/2005 | Smits |
| 7,033,361 | B2 | 4/2006 | Collazo |
| 7,097,647 | B2 | 8/2006 | Segler |
| 7,153,310 | B2 | 12/2006 | Ralph et al. |
| 7,182,766 | B1 | 2/2007 | Mogul |
| 7,241,298 | B2 | 7/2007 | Nemec et al. |
| 7,282,054 | B2 | 10/2007 | Steffensmeier et al. |
| 7,351,203 | B2 | 4/2008 | Jelliffe et al. |
| 7,377,924 | B2 | 5/2008 | Raistrick et al. |
| 7,465,303 | B2 | 12/2008 | Riccione et al. |
| 7,473,255 | B2 | 1/2009 | Mcgarity et al. |
| 7,540,874 | B2 | 6/2009 | Trumble et al. |
| 7,572,258 | B2 | 8/2009 | Stiernborg |
| 7,641,660 | B2 | 1/2010 | Lakin et al. |
| D610,257 | S | 2/2010 | Horton |
| 7,670,345 | B2 | 3/2010 | Plassky et al. |
| 7,686,811 | B2 | 3/2010 | Byrd et al. |
| 7,691,108 | B2 | 4/2010 | Lavallee |
| 7,763,026 | B2 | 7/2010 | Egger et al. |
| 7,789,885 | B2 | 9/2010 | Metzger |
| D629,900 | S | 12/2010 | Fisher |
| 7,875,058 | B2 | 1/2011 | Holmes, Jr. |
| 7,972,338 | B2 | 7/2011 | O'Brien |
| 7,983,777 | B2 | 7/2011 | Melton et al. |
| D646,389 | S | 10/2011 | Claypool et al. |
| 8,057,473 | B2 | 11/2011 | Orsak et al. |
| 8,057,478 | B2 | 11/2011 | Kuczynski et al. |
| D651,315 | S | 12/2011 | Bertoni et al. |
| D651,316 | S | 12/2011 | May et al. |
| 8,080,010 | B2 | 12/2011 | Schulz et al. |
| 8,080,045 | B2 | 12/2011 | Wotton |
| 8,114,087 | B2 | 2/2012 | Long et al. |
| 8,123,753 | B2 | 2/2012 | Poncet |
| 8,147,530 | B2 | 4/2012 | Strnad et al. |
| 8,167,918 | B2 | 5/2012 | Strnad et al. |
| 8,172,848 | B2 | 5/2012 | Tomko et al. |
| 8,187,280 | B2 | 5/2012 | May et al. |
| 8,192,441 | B2 | 6/2012 | Collazo |
| 8,197,487 | B2 | 6/2012 | Poncet et al. |
| 8,206,153 | B2 | 6/2012 | Suttin et al. |
| 8,231,623 | B1 | 7/2012 | Jordan |
| 8,231,663 | B2 | 7/2012 | Kay et al. |
| 8,246,561 | B1 | 8/2012 | Agee et al. |
| 8,246,680 | B2 | 8/2012 | Betz et al. |
| D666,721 | S | 9/2012 | Wright et al. |
| 8,262,664 | B2 | 9/2012 | Justin et al. |
| 8,262,665 | B2 | 9/2012 | Massoud |
| 8,277,455 | B2 | 10/2012 | Couture et al. |
| 8,282,644 | B2 | 10/2012 | Edwards |
| 8,282,645 | B2 | 10/2012 | Lawrence et al. |
| 8,287,541 | B2 | 10/2012 | Nelson et al. |
| 8,292,966 | B2 | 10/2012 | Morton |
| 8,303,596 | B2 | 11/2012 | Plaky et al. |
| 8,323,281 | B2 | 12/2012 | Hotchkiss et al. |
| 8,323,289 | B2 | 12/2012 | Re |
| 8,357,111 | B2 | 1/2013 | Caillouette et al. |
| 8,377,105 | B2 | 2/2013 | Bscher |
| 8,388,690 | B2 | 3/2013 | Singhatat et al. |
| D679,395 | S | 4/2013 | Wright et al. |
| 8,435,246 | B2 | 5/2013 | Fisher et al. |
| 8,475,462 | B2 | 7/2013 | Thomas et al. |
| 8,484,001 | B2 | 7/2013 | Glozman et al. |
| 8,518,045 | B2 | 8/2013 | Szanto |
| 8,523,870 | B2 | 9/2013 | Green et al. |
| 8,529,568 | B2 | 9/2013 | Bouadi |
| 8,532,807 | B2 | 9/2013 | Metzger |
| 8,551,106 | B2 | 10/2013 | Harrold |
| D694,884 | S | 12/2013 | Mooradian et al. |

(56) References Cited

U.S. PATENT DOCUMENTS

D695,402 S 12/2013 Dacosta et al.
8,641,721 B2 2/2014 Aram et al.
8,652,142 B2 2/2014 Geissler
8,657,820 B2 2/2014 Kubiak et al.
D701,303 S 3/2014 Cook
8,663,234 B2 3/2014 Grimm et al.
8,668,700 B2 3/2014 Catanzarite et al.
8,685,030 B2 4/2014 Gtte et al.
8,696,719 B2 4/2014 Lofthouse et al.
8,702,686 B2 4/2014 Geebelen et al.
8,702,712 B2 4/2014 Jordan et al.
8,715,289 B2 5/2014 Smith
8,715,363 B2 5/2014 Ratron et al.
8,728,084 B2 5/2014 Berelsman et al.
8,758,354 B2 6/2014 Habegger et al.
8,777,948 B2 7/2014 Bernsteiner
8,784,457 B2 7/2014 Graham
8,795,286 B2 8/2014 Sand et al.
8,808,298 B2 8/2014 Raub et al.
8,808,301 B1 8/2014 Nofsinger
8,808,302 B2 8/2014 Roose et al.
8,828,012 B2 9/2014 May et al.
8,838,263 B2 9/2014 Sivak et al.
8,858,602 B2 10/2014 Weiner et al.
8,864,773 B2 10/2014 Paul et al.
8,882,778 B2 11/2014 Ranft
8,882,816 B2 11/2014 Kartalian et al.
8,892,235 B2 11/2014 Choi et al.
8,898,043 B2 11/2014 Ashby et al.
D720,456 S 12/2014 Dacosta et al.
8,900,247 B2 12/2014 Tseng et al.
8,911,444 B2 12/2014 Bailey
8,920,428 B2 12/2014 Zakaria et al.
8,926,612 B2 1/2015 Graham
8,932,299 B2 1/2015 Bono et al.
8,939,982 B2 1/2015 Chellaoui
8,939,984 B2 1/2015 Budoff
8,945,132 B2 2/2015 Play et al.
8,965,075 B2 2/2015 Arnaud et al.
8,974,460 B2 3/2015 De La Fuente et al.
8,979,856 B2 3/2015 Catanzarite et al.
8,992,531 B2 3/2015 Chow et al.
8,992,532 B2 3/2015 Wong
8,998,903 B2 4/2015 Price et al.
8,998,904 B2 4/2015 Zeetser et al.
8,998,907 B2 4/2015 Myers
8,998,909 B2 4/2015 Gillman et al.
9,005,207 B2 4/2015 Dodds et al.
9,011,451 B2 4/2015 Long et al.
9,011,452 B2 4/2015 Iannotti et al.
9,011,456 B2 4/2015 Ranawat et al.
9,014,835 B2 4/2015 Azernikov et al.
9,017,329 B2 4/2015 Tyber et al.
9,017,336 B2 4/2015 Park et al.
9,023,052 B2 5/2015 Lietz et al.
9,044,250 B2 6/2015 Olsen et al.
9,060,788 B2 6/2015 Bollinger
9,060,822 B2 6/2015 Wright et al.
9,089,376 B2 7/2015 Medoff et al.
9,101,421 B2 8/2015 Blacklidge
9,107,715 B2 8/2015 Blitz et al.
9,113,915 B2 8/2015 Thomas et al.
9,113,957 B2 8/2015 Axelson, Jr. et al.
9,138,237 B2 9/2015 Meade et al.
9,138,332 B2 9/2015 Harris et al.
D740,424 S 10/2015 Dacosta et al.
9,173,665 B2 11/2015 Couture
9,173,691 B2 11/2015 Orbay et al.
9,186,154 B2 11/2015 Li
9,186,160 B1 11/2015 Song
9,198,678 B2 12/2015 Frey et al.
9,204,897 B2 12/2015 Jones et al.
9,211,128 B2 12/2015 Gillman et al.
9,220,509 B2 12/2015 Boyer et al.
9,220,518 B2 12/2015 Neal et al.
9,220,519 B2 12/2015 Kaneyama et al.
9,220,551 B2 12/2015 Waizenegger
9,232,951 B2 1/2016 Johannaber
9,232,955 B2 1/2016 Bonin, Jr. et al.
9,254,155 B2 2/2016 Iannotti et al.
9,295,497 B2 3/2016 Schoenefeld et al.
9,301,768 B2 4/2016 Buza et al.
9,301,783 B2 4/2016 Gerold et al.
9,308,006 B2 4/2016 Martin et al.
9,308,037 B2 4/2016 Richter et al.
9,320,609 B2 4/2016 Schon et al.
9,345,497 B2 5/2016 Gonzalvez et al.
9,351,738 B2 5/2016 Aram et al.
9,351,743 B2 5/2016 Kehres et al.
9,370,380 B2 6/2016 Riccione
9,375,220 B2 6/2016 Horan et al.
9,402,636 B2 8/2016 Collazo
9,402,640 B2 8/2016 Reynolds et al.
9,408,641 B2 8/2016 Zhang et al.
9,414,846 B2 8/2016 Gillman et al.
9,414,847 B2 8/2016 Kurtz
9,414,877 B2 8/2016 Helenbolt et al.
9,421,021 B2 8/2016 Keppler
9,427,240 B2 8/2016 Von Zabern et al.
D765,844 S 9/2016 Dacosta
D766,434 S 9/2016 Dacosta
D766,437 S 9/2016 Dacosta
D766,438 S 9/2016 Dacosta
D766,439 S 9/2016 Dacosta
9,433,452 B2 9/2016 Weiner et al.
9,445,823 B2 9/2016 Harris et al.
9,452,050 B2 9/2016 Miles et al.
9,456,902 B2 10/2016 Hacking et al.
9,463,034 B2 10/2016 Wong et al.
9,492,182 B2 11/2016 Keefer
9,517,145 B2 12/2016 Meridew et al.
9,522,023 B2 12/2016 Haddad et al.
9,526,514 B2 12/2016 Kelley et al.
9,545,276 B2 1/2017 Buchanan et al.
9,561,041 B2 2/2017 Snider et al.
9,566,103 B2 2/2017 Mayer
9,579,106 B2 2/2017 Lo et al.
9,579,107 B2 2/2017 Schoenefeld
9,579,112 B2 2/2017 Catanzarite et al.
9,592,084 B2 3/2017 Grant
9,603,605 B2 3/2017 Collazo
9,603,640 B2 3/2017 Palmer et al.
9,622,820 B2 4/2017 Baloch et al.
9,629,726 B2 4/2017 Reiley et al.
9,652,889 B2 5/2017 Young et al.
9,662,220 B2 5/2017 Warburton
9,668,746 B2 6/2017 Lee et al.
9,675,471 B2 6/2017 Bojarski et al.
9,687,261 B2 6/2017 Serbousek et al.
9,693,787 B2 7/2017 Ammann et al.
9,693,878 B2 7/2017 Kunz et al.
9,700,433 B2 7/2017 Myers
9,713,484 B2 7/2017 Sammarco
9,737,311 B2 8/2017 Lavallee et al.
9,737,367 B2 8/2017 Steines et al.
9,750,538 B2 9/2017 Soffiatti et al.
9,785,747 B2 10/2017 Geebelen
9,788,958 B2 10/2017 Melamed et al.
9,788,975 B2 10/2017 Li
9,795,392 B2 10/2017 Zajac
9,795,394 B2 10/2017 Bonutti
9,814,474 B2 11/2017 Montoya et al.
9,820,868 B2 11/2017 Witt et al.
9,826,981 B2 11/2017 Schoenefeld et al.
9,839,438 B2 12/2017 Eash
9,848,929 B2 12/2017 Dacosta et al.
9,849,019 B2 12/2017 Miller et al.
9,877,754 B2 1/2018 Patel et al.
9,883,954 B1 2/2018 Murphy
9,888,931 B2 2/2018 Bake
9,888,950 B2 2/2018 Perez et al.
9,918,658 B2 3/2018 Mccaulley et al.
9,918,769 B2 3/2018 Provencher et al.
9,925,049 B2 3/2018 Goldstein et al.

(56) References Cited

U.S. PATENT DOCUMENTS 9,925,068 B2 3/2018 Bays et al.
9,956,089 B2 5/2018 Kelman et al.
9,968,456 B2 5/2018 Song
9,980,760 B2 5/2018 Dacosta et al.
9,987,092 B2 6/2018 Hladio et al.
9,990,765 B2 6/2018 Ju et al.
9,993,256 B2 6/2018 Lipman et al.
10,002,227 B2 6/2018 Netravali et al.
10,004,516 B2 6/2018 Johannaber
10,010,431 B2 7/2018 Eraly et al.
10,016,177 B2 7/2018 Aram et al.
10,022,170 B2 7/2018 Leemrijse et al.
10,028,756 B2 7/2018 Liu
10,034,753 B2 7/2018 Dressler et al.
10,052,114 B2 8/2018 Keppler et al.
10,055,536 B2 8/2018 Maes et al.
10,058,335 B2 8/2018 Lee et al.
10,089,413 B2 10/2018 Wirx-Speetjens et al.
10,098,761 B2 10/2018 Sherman et al.
10,105,145 B2 10/2018 Lavallee
10,123,807 B2 11/2018 Geebelen
10,130,378 B2 11/2018 Bryan
10,149,722 B2 12/2018 Aram et al.
10,159,480 B2 12/2018 Tuten
10,159,499 B2 12/2018 Dacosta et al.
10,159,512 B2 12/2018 Robinson
10,201,357 B2 2/2019 Aram et al.
10,206,692 B2 2/2019 Sanders
10,217,530 B2 2/2019 Couture et al.
10,219,812 B2 3/2019 Torrie et al.
10,226,292 B2 3/2019 Lundquist et al.
10,231,745 B2 3/2019 Geebelen et al.
10,238,382 B2 3/2019 Terrill et al.
10,251,654 B2 4/2019 Fritzinger
10,251,690 B2 4/2019 Katrana et al.
10,262,084 B2 4/2019 Lavallee et al.
10,265,080 B2 4/2019 Hughes et al.
10,271,886 B2 4/2019 Abiven
10,278,713 B2 5/2019 Richter et al.
10,282,488 B2 5/2019 Eash
10,286,197 B2 5/2019 Pouliot et al.
10,292,713 B2 * 5/2019 Fallin .................. A61B 17/151
10,325,065 B2 6/2019 Li et al.
10,327,829 B2 6/2019 Dacosta et al.
10,342,529 B2 7/2019 Fallin et al.
10,350,022 B2 7/2019 Jansen et al.
10,357,261 B2 7/2019 Kugler et al.
10,357,299 B2 7/2019 Weiner et al.
10,363,052 B2 7/2019 Park et al.
10,398,510 B2 9/2019 Goto
10,420,613 B2 9/2019 Azevedo Da Silva et al.
10,456,205 B2 10/2019 Meridew et al.
10,512,470 B1 12/2019 Bays et al.
10,524,808 B1 * 1/2020 Hissong .............. A61B 17/151
10,524,845 B2 1/2020 Orsak et al.
10,537,392 B2 1/2020 Millahn et al.
10,543,100 B2 1/2020 Couture et al.
10,548,667 B2 2/2020 Flett et al.
10,548,668 B2 2/2020 Furrer et al.
10,582,969 B2 3/2020 Couture et al.
10,610,241 B2 * 4/2020 Wagner ............... A61B 17/151
10,631,878 B2 4/2020 Fritzinger
10,631,902 B2 4/2020 Weiner et al.
10,653,432 B2 5/2020 Luttrell et al.
10,653,464 B2 5/2020 Hill et al.
10,653,467 B2 5/2020 Brumfield et al.
10,675,096 B2 6/2020 Utz et al.
10,682,147 B2 6/2020 Grant et al.
10,709,567 B2 7/2020 Welker et al.
10,716,581 B2 7/2020 Fritzinger et al.
10,722,309 B2 7/2020 Gillman
10,722,310 B2 7/2020 Luby
10,779,867 B2 9/2020 Penzimer et al.
10,779,890 B2 9/2020 Weir
10,786,291 B2 9/2020 Weiner et al.
10,792,081 B2 10/2020 Weiner et al.
10,806,469 B2 10/2020 Fiechter et al.
10,849,665 B2 12/2020 Singh et al.
10,849,670 B2 12/2020 Santrock et al.
10,856,891 B2 12/2020 Rhodes et al.
10,856,925 B1 12/2020 Pontell
10,869,722 B2 12/2020 Caldwell et al.
10,874,408 B2 12/2020 Couture
10,881,416 B2 1/2021 Couture et al.
10,881,417 B2 1/2021 Mahfouz
10,888,340 B2 1/2021 Awtrey et al.
10,898,211 B2 * 1/2021 Fallin .................. A61B 17/152
10,905,444 B2 2/2021 Siccardi et al.
10,912,574 B2 2/2021 Kim et al.
10,925,622 B2 2/2021 Kehres et al.
10,939,926 B2 3/2021 Kam et al.
10,939,939 B1 3/2021 Gil et al.
10,973,529 B2 4/2021 Lavallee et al.
11,000,327 B2 5/2021 Schlotterback et al.
11,020,128 B2 6/2021 Guilloux et al.
11,033,333 B2 * 6/2021 Singh .................. A61B 17/151
11,033,336 B2 6/2021 Bohl
11,065,011 B2 7/2021 Bake et al.
11,074,688 B2 7/2021 Chabin et al.
11,090,069 B2 8/2021 Park
11,090,161 B2 8/2021 Hodorek
11,112,770 B2 9/2021 Roh et al.
11,116,518 B2 9/2021 Hafez
11,129,625 B2 9/2021 Song et al.
11,129,678 B2 9/2021 Park
11,154,362 B2 10/2021 Kim et al.
11,158,047 B2 10/2021 Shah
11,160,567 B2 11/2021 Fallin et al.
11,160,568 B1 11/2021 Park
11,166,732 B2 11/2021 Maxson et al.
11,172,945 B1 11/2021 Lian
11,179,165 B2 11/2021 Schoenefeld
11,179,168 B2 11/2021 Dacosta et al.
11,207,134 B2 12/2021 Hafez
11,213,305 B2 1/2022 Tannotti et al.
11,213,406 B2 1/2022 Rodriguez et al.
11,219,526 B2 1/2022 Mahfouz
11,224,448 B2 1/2022 Bailey
11,259,817 B2 3/2022 Fallin et al.
11,284,909 B2 3/2022 Castricini et al.
11,304,705 B2 4/2022 Fallin et al.
11,304,735 B2 4/2022 Sayger et al.
11,324,522 B2 5/2022 Metzger et al.
11,324,607 B2 5/2022 Mauldin et al.
11,331,148 B2 5/2022 Fritzinger
11,331,205 B2 5/2022 Parr
11,344,347 B2 5/2022 Treace et al.
11,389,221 B2 7/2022 Tyber et al.
11,399,849 B2 8/2022 Larche et al.
11,419,726 B2 8/2022 Miller et al.
11,426,184 B2 8/2022 Rivet-Sabourin et al.
11,432,931 B2 9/2022 Lang
11,436,801 B2 9/2022 Haslam et al.
11,439,412 B2 9/2022 Woodard et al.
11,457,980 B2 10/2022 Bonny et al.
11,484,354 B2 11/2022 Singh et al.
11,497,557 B2 11/2022 Haslam et al.
11,508,102 B2 11/2022 Su et al.
11,510,738 B2 11/2022 Stifter et al.
11,532,402 B2 12/2022 Farley et al.
11,557,036 B2 1/2023 Mansi et al.
11,583,298 B2 2/2023 Robichaud et al.
11,596,421 B2 3/2023 Saltzman et al.
11,596,443 B2 3/2023 Treace et al.
11,602,386 B2 3/2023 Smith et al.
11,607,250 B2 3/2023 Treace et al.
11,627,954 B2 4/2023 May et al.
11,628,003 B2 4/2023 Nachtrab et al.
11,633,195 B2 4/2023 Dhillon
11,648,019 B2 5/2023 Bays et al.
11,653,938 B2 5/2023 Siegler
11,684,423 B2 6/2023 Jaramaz et al.
11,690,725 B2 7/2023 Gemon et al.
11,717,359 B2 8/2023 Chi

(56) References Cited

U.S. PATENT DOCUMENTS

| | | | |
|---|---|---|---|
| 11,741,277 | B2 | 8/2023 | Dayal et al. |
| 11,751,892 | B2 | 9/2023 | Woodard et al. |
| 11,756,051 | B2 | 9/2023 | Indani et al. |
| 11,766,268 | B2 | 9/2023 | Iannotti et al. |
| 11,779,467 | B2 | 10/2023 | Mimnaugh et al. |
| 11,786,257 | B2 | 10/2023 | Dayton et al. |
| 11,793,549 | B2 | 10/2023 | Rhodes et al. |
| 11,812,978 | B2 | 11/2023 | Trabish et al. |
| 11,819,223 | B2 | 11/2023 | Lee |
| 11,819,224 | B2 | 11/2023 | Allard et al. |
| 11,849,933 | B2 | 12/2023 | Denham et al. |
| 11,849,957 | B2 | 12/2023 | Couture et al. |
| 11,849,961 | B2 | 12/2023 | Khatibi et al. |
| 11,849,962 | B2 | 12/2023 | Singh et al. |
| 11,854,683 | B2 | 12/2023 | Casey et al. |
| D1,011,524 | S | 1/2024 | Santrock et al. |
| 11,857,206 | B2 | 1/2024 | Robichaud et al. |
| 11,864,778 | B2 | 1/2024 | Mcginley et al. |
| 11,864,959 | B2 | 1/2024 | Basta |
| 11,911,046 | B2 | 2/2024 | Carroll et al. |
| 11,925,417 | B2 | 3/2024 | Mosnier et al. |
| 11,931,106 | B2 | 3/2024 | Perler et al. |
| 11,944,546 | B2 | 4/2024 | Puncreobutr et al. |
| 11,950,786 | B2 | 4/2024 | Courtis et al. |
| 11,963,687 | B2 | 4/2024 | Langhorn et al. |
| 11,963,703 | B2 | 4/2024 | Dayton et al. |
| 11,963,729 | B2 | 4/2024 | Aljuri et al. |
| 11,980,377 | B2 | 5/2024 | Mauldin et al. |
| 12,004,789 | B2 | 6/2024 | Mcaleer et al. |
| 12,004,814 | B2 | 6/2024 | Ryan et al. |
| D1,034,985 | S | 7/2024 | Hartson et al. |
| 12,035,929 | B2 | 7/2024 | Athwal et al. |
| 12,045,943 | B2 | 7/2024 | Chaoui et al. |
| 12,048,600 | B2 | 7/2024 | Azernikov et al. |
| 12,050,999 | B2 | 7/2024 | Poltaretskyi et al. |
| 12,053,242 | B2 | 8/2024 | Landon et al. |
| 12,062,183 | B2 | 8/2024 | Chaoui et al. |
| 12,097,129 | B2 | 9/2024 | Deransart et al. |
| 12,115,083 | B2 | 10/2024 | Mullen et al. |
| 12,121,272 | B2 | 10/2024 | Marien et al. |
| D1,051,382 | S * | 11/2024 | Kuyler ........................ D24/140 |
| D1,057,155 | S * | 1/2025 | Kuyler ........................ D24/140 |
| 12,396,770 | B2 * | 8/2025 | McAleer .............. A61B 17/151 |
| 12,490,992 | B2 * | 12/2025 | Perler .................. A61B 17/151 |
| 2002/0107519 | A1 | 8/2002 | Dixon et al. |
| 2003/0236522 | A1 | 12/2003 | Long et al. |
| 2004/0010259 | A1 | 1/2004 | Keller et al. |
| 2004/0039394 | A1 | 2/2004 | Conti et al. |
| 2004/0039396 | A1 | 2/2004 | Couture et al. |
| 2004/0097946 | A1 | 5/2004 | Dietzel et al. |
| 2004/0138669 | A1 | 7/2004 | Horn |
| 2005/0059978 | A1 | 3/2005 | Sherry et al. |
| 2005/0080424 | A1 | 4/2005 | Cuckler et al. |
| 2005/0267482 | A1 | 12/2005 | Hyde |
| 2005/0273112 | A1 | 12/2005 | Mcnamara |
| 2006/0129163 | A1 | 6/2006 | Mcguire |
| 2006/0206044 | A1 | 9/2006 | Simon |
| 2006/0229621 | A1 | 10/2006 | Cadmus |
| 2006/0241607 | A1 | 10/2006 | Myerson et al. |
| 2006/0241608 | A1 | 10/2006 | Myerson et al. |
| 2006/0264961 | A1 | 11/2006 | Murray-Brown |
| 2007/0010818 | A1 | 1/2007 | Stone et al. |
| 2007/0123857 | A1 | 5/2007 | Deffenbaugh et al. |
| 2007/0233138 | A1 | 10/2007 | Figueroa et al. |
| 2007/0265634 | A1 | 11/2007 | Weinstein |
| 2007/0276383 | A1 | 11/2007 | Rayhack |
| 2008/0009863 | A1 | 1/2008 | Bond et al. |
| 2008/0039850 | A1 | 2/2008 | Rowley et al. |
| 2008/0091197 | A1 | 4/2008 | Coughlin |
| 2008/0140081 | A1 | 6/2008 | Heavener et al. |
| 2008/0161815 | A1 | 7/2008 | Schoenefeld et al. |
| 2008/0172054 | A1 | 7/2008 | Claypool et al. |
| 2008/0288004 | A1 | 11/2008 | Schendel |
| 2009/0036931 | A1 | 2/2009 | Pech et al. |
| 2009/0089081 | A1 | 4/2009 | Haddad |

| | | | |
|---|---|---|---|
| 2009/0093849 | A1 | 4/2009 | Grabowski |
| 2009/0105767 | A1 | 4/2009 | Reiley |
| 2009/0198244 | A1 | 8/2009 | Leibel |
| 2009/0216089 | A1 | 8/2009 | Davidson |
| 2009/0222047 | A1 | 9/2009 | Graham |
| 2009/0254092 | A1 | 10/2009 | Albiol Llorach |
| 2009/0254126 | A1 | 10/2009 | Orbay et al. |
| 2009/0265012 | A1 | 10/2009 | Engh et al. |
| 2009/0287309 | A1 | 11/2009 | Walch et al. |
| 2010/0069910 | A1 | 3/2010 | Hasselman |
| 2010/0130981 | A1 | 5/2010 | Richards |
| 2010/0168799 | A1 | 7/2010 | Schumer |
| 2010/0185202 | A1 | 7/2010 | Lester et al. |
| 2010/0217270 | A1 | 8/2010 | Polinski et al. |
| 2010/0256687 | A1 | 10/2010 | Neufeld et al. |
| 2010/0274253 | A1 | 10/2010 | Ure |
| 2010/0318088 | A1 | 12/2010 | Warne et al. |
| 2011/0009865 | A1 | 1/2011 | Orfaly |
| 2012/0065689 | A1 | 3/2012 | Prasad et al. |
| 2012/0116203 | A1 | 5/2012 | Vancraen et al. |
| 2012/0123420 | A1 | 5/2012 | Honiball |
| 2012/0130434 | A1 | 5/2012 | Stemniski |
| 2012/0150242 | A1 | 6/2012 | Mannion |
| 2012/0191199 | A1 | 7/2012 | Raemisch |
| 2012/0234329 | A1 | 9/2012 | Vancraen et al. |
| 2012/0253350 | A1 | 10/2012 | Anthony et al. |
| 2012/0265301 | A1 | 10/2012 | Demers et al. |
| 2012/0277745 | A1 | 11/2012 | Lizee |
| 2013/0211410 | A1 | 8/2013 | Landes et al. |
| 2013/0236874 | A1 | 9/2013 | Iannotti et al. |
| 2013/0237989 | A1 | 9/2013 | Bonutti |
| 2013/0274778 | A1 | 10/2013 | Mercier et al. |
| 2013/0289570 | A1 | 10/2013 | Chao |
| 2013/0292870 | A1 | 11/2013 | Roger |
| 2014/0005672 | A1 | 1/2014 | Edwards et al. |
| 2014/0039501 | A1 | 2/2014 | Schickendantz et al. |
| 2014/0074099 | A1 | 3/2014 | Vigneron et al. |
| 2014/0094861 | A1 | 4/2014 | Fallin |
| 2014/0163568 | A1 | 6/2014 | Wong et al. |
| 2014/0257402 | A1 | 9/2014 | Barsoum |
| 2014/0259629 | A1 | 9/2014 | Dion et al. |
| 2014/0263674 | A1 | 9/2014 | Cerveny |
| 2014/0343555 | A1 | 11/2014 | Russi et al. |
| 2014/0371866 | A1 | 12/2014 | Chao et al. |
| 2014/0371897 | A1 | 12/2014 | Lin et al. |
| 2015/0032215 | A1 | 1/2015 | Slamin et al. |
| 2015/0045903 | A1 | 2/2015 | Neal |
| 2015/0066094 | A1 | 3/2015 | Anderson et al. |
| 2015/0081029 | A1 | 3/2015 | Bojarski et al. |
| 2015/0088142 | A1 | 3/2015 | Gibson |
| 2015/0093283 | A1 | 4/2015 | Miller et al. |
| 2015/0112348 | A1 | 4/2015 | Schoenefeld et al. |
| 2015/0142000 | A1 | 5/2015 | Seedhom et al. |
| 2015/0182342 | A1 | 7/2015 | Hafez |
| 2015/0227679 | A1 | 8/2015 | Kamer et al. |
| 2015/0230843 | A1 | 8/2015 | Palmer et al. |
| 2015/0305752 | A1 | 10/2015 | Eash |
| 2015/0342616 | A1 | 12/2015 | Fryman |
| 2015/0351780 | A1 | 12/2015 | Anderson et al. |
| 2015/0351916 | A1 | 12/2015 | Kosarek et al. |
| 2016/0015426 | A1 | 1/2016 | Dayton |
| 2016/0038161 | A1 | 2/2016 | Gibson |
| 2016/0100773 | A1 | 4/2016 | Ching et al. |
| 2016/0100847 | A1 | 4/2016 | Maxson |
| 2016/0128701 | A1 * | 5/2016 | Neal ..................... A61F 2/4202<br>606/87 |
| 2016/0151165 | A1 | 6/2016 | Fallin et al. |
| 2016/0175089 | A1 | 6/2016 | Fallin et al. |
| 2016/0192951 | A1 | 7/2016 | Gelaude et al. |
| 2016/0199076 | A1 * | 7/2016 | Fallin ................ A61B 17/1739<br>606/301 |
| 2016/0199198 | A1 | 7/2016 | Dietz et al. |
| 2016/0213384 | A1 * | 7/2016 | Fallin ................... A61B 17/151 |
| 2016/0256176 | A9 | 9/2016 | Lowery et al. |
| 2016/0270829 | A1 | 9/2016 | Duggal et al. |
| 2016/0270855 | A1 | 9/2016 | Kunz et al. |
| 2016/0287395 | A1 | 10/2016 | Khalili et al. |
| 2016/0338715 | A1 | 11/2016 | Bojarski et al. |
| 2016/0354128 | A1 | 12/2016 | Jeng et al. |

(56) References Cited

U.S. PATENT DOCUMENTS

| | | | | |
|---|---|---|---|---|
| 2016/0367270 | A1 | 12/2016 | Garlock et al. | |
| 2017/0014143 | A1* | 1/2017 | Dayton | A61B 17/8061 |
| 2017/0014169 | A1 | 1/2017 | Dean et al. | |
| 2017/0020537 | A1 | 1/2017 | Tuten | |
| 2017/0027593 | A1 | 2/2017 | Bojarski et al. | |
| 2017/0079803 | A1 | 3/2017 | Lang | |
| 2017/0143511 | A1 | 5/2017 | Cachia | |
| 2017/0209189 | A9 | 7/2017 | Hatch et al. | |
| 2017/0231645 | A1 | 8/2017 | Metzger et al. | |
| 2017/0245906 | A1 | 8/2017 | Kugler et al. | |
| 2017/0245935 | A1 | 8/2017 | Kugler et al. | |
| 2017/0249440 | A1 | 8/2017 | Lang et al. | |
| 2017/0281353 | A1 | 10/2017 | Al Hares et al. | |
| 2017/0360578 | A1 | 12/2017 | Shin et al. | |
| 2018/0021145 | A1 | 1/2018 | Seavey et al. | |
| 2018/0028325 | A1 | 2/2018 | Bojarski et al. | |
| 2018/0049758 | A1 | 2/2018 | Amis et al. | |
| 2018/0116804 | A1 | 5/2018 | Hafez et al. | |
| 2018/0221071 | A1 | 8/2018 | Isch | |
| 2018/0235706 | A1 | 8/2018 | Asseln et al. | |
| 2018/0242987 | A1 | 8/2018 | Lintula et al. | |
| 2018/0289423 | A1 | 10/2018 | Singh et al. | |
| 2018/0317986 | A1* | 11/2018 | Jackman | A61B 17/151 |
| 2018/0344326 | A1 | 12/2018 | Chan et al. | |
| 2019/0000629 | A1 | 1/2019 | Winslow | |
| 2019/0008532 | A1 | 1/2019 | Fitz et al. | |
| 2019/0099189 | A1* | 4/2019 | Fallin | A61B 17/151 |
| 2019/0117239 | A1 | 4/2019 | Verma | |
| 2019/0175277 | A1 | 6/2019 | Chav et al. | |
| 2019/0175351 | A1 | 6/2019 | Bojarski et al. | |
| 2019/0274745 | A1* | 9/2019 | Smith | A61B 17/8866 |
| 2019/0307495 | A1 | 10/2019 | Geldwert | |
| 2019/0336140 | A1 | 11/2019 | Dacosta et al. | |
| 2019/0365543 | A1 | 12/2019 | Slamin et al. | |
| 2020/0008813 | A1 | 1/2020 | Bonny et al. | |
| 2020/0046425 | A1 | 2/2020 | Lopes et al. | |
| 2020/0100909 | A1 | 4/2020 | Lang et al. | |
| 2020/0155323 | A1 | 5/2020 | Lang et al. | |
| 2020/0163721 | A1 | 5/2020 | Aghazadeh | |
| 2020/0205844 | A1* | 7/2020 | Hissong | A61B 17/151 |
| 2020/0214719 | A1 | 7/2020 | Fraone et al. | |
| 2020/0337714 | A1 | 10/2020 | Hafez et al. | |
| 2020/0356073 | A1 | 11/2020 | Tokushima | |
| 2020/0405322 | A1 | 12/2020 | Brailovski et al. | |
| 2021/0007760 | A1 | 1/2021 | Reisin | |
| 2021/0022781 | A1 | 1/2021 | Dacosta et al. | |
| 2021/0030429 | A1 | 2/2021 | Rose et al. | |
| 2021/0038212 | A1* | 2/2021 | May | A61B 17/025 |
| 2021/0045756 | A1 | 2/2021 | Zakhary et al. | |
| 2021/0059691 | A1 | 3/2021 | Zille | |
| 2021/0059837 | A1 | 3/2021 | Rhodes | |
| 2021/0077120 | A1 | 3/2021 | Hatch et al. | |
| 2021/0077192 | A1* | 3/2021 | Perler | A61B 17/151 |
| 2021/0085338 | A1 | 3/2021 | Dacosta et al. | |
| 2021/0090248 | A1 | 3/2021 | Choi et al. | |
| 2021/0106427 | A1 | 4/2021 | Mahfouz | |
| 2021/0113223 | A1 | 4/2021 | Schaumann et al. | |
| 2021/0121297 | A1 | 4/2021 | Cavanagh et al. | |
| 2021/0137537 | A1 | 5/2021 | Zille | |
| 2021/0137538 | A1* | 5/2021 | Fallin | A61B 17/152 |
| 2021/0161543 | A1 | 6/2021 | Mcauliffe et al. | |
| 2021/0186704 | A1 | 6/2021 | Fitz et al. | |
| 2021/0192759 | A1 | 6/2021 | Lang | |
| 2021/0196290 | A1 | 7/2021 | Iannotti et al. | |
| 2021/0212705 | A1 | 7/2021 | Reynolds et al. | |
| 2021/0219989 | A1 | 7/2021 | Chao | |
| 2021/0244477 | A1 | 8/2021 | Singh et al. | |
| 2021/0256171 | A1 | 8/2021 | Hosseini | |
| 2021/0275196 | A1 | 9/2021 | Wodajo | |
| 2021/0282790 | A1 | 9/2021 | Sellman et al. | |
| 2021/0282823 | A1 | 9/2021 | Day et al. | |
| 2021/0290250 | A1 | 9/2021 | Denham et al. | |
| 2021/0298766 | A1 | 9/2021 | Loring et al. | |
| 2021/0307763 | A1 | 10/2021 | Fallin et al. | |
| 2021/0307833 | A1 | 10/2021 | Farley et al. | |
| 2021/0307834 | A1 | 10/2021 | Gillman et al. | |
| 2021/0346038 | A1 | 11/2021 | Fiechter et al. | |
| 2021/0378752 | A1 | 12/2021 | Paul et al. | |
| 2021/0386437 | A1 | 12/2021 | Dacosta et al. | |
| 2021/0391058 | A1 | 12/2021 | Kostrzewski et al. | |
| 2021/0393304 | A1 | 12/2021 | Geldwert | |
| 2022/0039965 | A1 | 2/2022 | Casey et al. | |
| 2022/0079602 | A1* | 3/2022 | Branthover, III | A61B 17/151 |
| 2022/0087822 | A1 | 3/2022 | Radermacher et al. | |
| 2022/0096157 | A1 | 3/2022 | Pollock et al. | |
| 2022/0133484 | A1 | 5/2022 | Lang | |
| 2022/0151642 | A1 | 5/2022 | Cundiff et al. | |
| 2022/0160405 | A1 | 5/2022 | Casey et al. | |
| 2022/0167998 | A1 | 6/2022 | Siccardi et al. | |
| 2022/0192685 | A1 | 6/2022 | Gazonnet et al. | |
| 2022/0202495 | A1 | 6/2022 | Pack | |
| 2022/0211387 | A1* | 7/2022 | Perler | A61B 17/151 |
| 2022/0233203 | A1 | 7/2022 | Rhodes et al. | |
| 2022/0249106 | A1 | 8/2022 | Akallal et al. | |
| 2022/0249143 | A1 | 8/2022 | Hollis et al. | |
| 2022/0270762 | A1 | 8/2022 | Crawford et al. | |
| 2022/0273450 | A1 | 9/2022 | Steines et al. | |
| 2022/0296285 | A1 | 9/2022 | Besque et al. | |
| 2022/0313284 | A1 | 10/2022 | Korman | |
| 2022/0323086 | A1 | 10/2022 | Stemniski et al. | |
| 2022/0338934 | A1 | 10/2022 | Perler et al. | |
| 2022/0346806 | A1 | 11/2022 | Leemrijse et al. | |
| 2023/0013727 | A1 | 1/2023 | Korman et al. | |
| 2023/0014384 | A1 | 1/2023 | Cordonnier et al. | |
| 2023/0077222 | A1 | 3/2023 | Awtrey | |
| 2023/0157705 | A1 | 5/2023 | Reynolds | |
| 2023/0190306 | A1 | 6/2023 | Kowalczyk et al. | |
| 2023/0263536 | A1* | 8/2023 | Kuyler | A61B 17/15 606/57 |
| 2023/0281842 | A1 | 9/2023 | Ribeiro et al. | |
| 2023/0310013 | A1 | 10/2023 | Perler et al. | |
| 2023/0310051 | A1 | 10/2023 | Hafez et al. | |
| 2023/0363773 | A1 | 11/2023 | Perler et al. | |
| 2023/0371966 | A1 | 11/2023 | Spitler | |
| 2023/0389937 | A1 | 12/2023 | Penner et al. | |
| 2023/0404673 | A1* | 12/2023 | Spitler | A61B 34/10 |
| 2024/0005504 | A1 | 1/2024 | Ribeiro et al. | |
| 2024/0008880 | A1 | 1/2024 | Spitler et al. | |
| 2024/0099778 | A1 | 3/2024 | Hlad et al. | |
| 2024/0108414 | A1 | 4/2024 | Dreyer et al. | |

FOREIGN PATENT DOCUMENTS

| | | | |
|---|---|---|---|
| AU | 2015203808 | B2 | 9/2017 |
| AU | 2020220169 | A1 | 9/2020 |
| AU | 2021286392 | A1 | 1/2022 |
| CA | 2491824 | A1 | 9/2005 |
| CA | 2608464 | C | 7/2012 |
| CA | 2854997 | A1 | 5/2013 |
| CA | 2713309 | C | 7/2013 |
| CH | 695846 | A5 | 9/2006 |
| CN | 2930668 | Y | 8/2007 |
| CN | 201558162 | U | 8/2010 |
| CN | 201572172 | U | 9/2010 |
| CN | 201586060 | U | 9/2010 |
| CN | 201912210 | U | 8/2011 |
| CN | 101237835 | B | 11/2012 |
| CN | 202801773 | U | 3/2013 |
| CN | 103462675 | A | 12/2013 |
| CN | 103505276 | A | 1/2014 |
| CN | 203458450 | U | 3/2014 |
| CN | 102860860 | B | 5/2014 |
| CN | 203576647 | U | 5/2014 |
| CN | 104490460 | A | 4/2015 |
| CN | 104510523 | A | 4/2015 |
| CN | 104523327 | A | 4/2015 |
| CN | 104546102 | A | 4/2015 |
| CN | 204379413 | U | 6/2015 |
| CN | 204410951 | U | 6/2015 |
| CN | 204428143 | U | 7/2015 |
| CN | 204428144 | U | 7/2015 |
| CN | 204428145 | U | 7/2015 |
| CN | 204446081 | U | 7/2015 |
| CN | 106236185 | A | 12/2016 |

(56) References Cited

FOREIGN PATENT DOCUMENTS

| | | | | |
|---|---|---|---|---|
| CN | 205924106 | U | 2/2017 | |
| CN | 206151532 | U | 5/2017 | |
| CN | 105105853 | B | 7/2017 | |
| CN | 108030532 | A | 5/2018 | |
| CN | 207721902 | U | 8/2018 | |
| CN | 112914724 | B | 2/2022 | |
| CN | 117297772 | B | 2/2024 | |
| CN | 117322951 | B | 2/2024 | |
| CN | 109223098 | B | 5/2024 | |
| DE | 2910627 | A1 | 9/1980 | |
| DE | 202006010241 | U1 | 3/2007 | |
| DE | 102007053058 | B3 | 4/2009 | |
| EP | 685206 | B1 | 9/2000 | |
| EP | 1508316 | B1 | 5/2007 | |
| EP | 1897509 | B1 | 7/2009 | |
| EP | 2124832 | B1 | 8/2012 | |
| EP | 2750617 | A1 | 7/2014 | |
| EP | 2856951 | A1 | 4/2015 | |
| EP | 2624764 | B1 | 12/2015 | |
| EP | 3000443 | A3 | 7/2016 | |
| EP | 2083758 | B1 | 11/2017 | |
| EP | 2632349 | B1 | 3/2018 | |
| EP | 3013256 | B1 | 11/2018 | |
| EP | 3171795 | B1 | 11/2018 | |
| EP | 3672535 | A1 | 7/2020 | |
| EP | 2558010 | B1 | 5/2021 | |
| EP | 3948895 | A1 | 2/2022 | |
| EP | 3740141 | B1 | 4/2022 | |
| EP | 2844162 | B1 | 7/2022 | |
| FR | 2362616 | A1 | 3/1978 | |
| FR | 2764183 | A1 | 12/1998 | |
| FR | 2953120 | B1 | 1/2012 | |
| FR | 3030221 | A1 | 6/2016 | |
| FR | 3117328 | B1 | 3/2023 | |
| GB | 2154143 | A | 9/1985 | |
| GB | 2154144 | A | 9/1985 | |
| GB | 2334214 | B | 1/2003 | |
| GB | 2589960 | A | 6/2021 | |
| JP | S635739 | A | 1/1988 | |
| JP | 2004174265 | A | 6/2004 | |
| JP | 2006158972 | A | 6/2006 | |
| JP | 4134243 | B2 | 8/2008 | |
| JP | 2011092405 | A | 5/2011 | |
| JP | 4796943 | B2 | 10/2011 | |
| JP | 2014511207 | A | 5/2014 | |
| JP | 2014521384 | A | 8/2014 | |
| KR | 100904142 | B1 | 6/2009 | |
| KR | 1020160090006 | A | 7/2016 | |
| KR | 1020180118476 | A | 10/2018 | |
| KR | 101952368 | B1 | 2/2019 | |
| MD | 756Z | B1 | 7/1997 | |
| RU | 2098036 | C1 | 12/1997 | |
| RU | 2195892 | C2 | 1/2003 | |
| RU | 2320287 | C1 | 3/2008 | |
| RU | 2321366 | C2 | 4/2008 | |
| RU | 2321369 | C1 | 4/2008 | |
| RU | 2346663 | C2 | 2/2009 | |
| RU | 2412662 | C1 | 2/2011 | |
| RU | 182499 | U1 | 8/2018 | |
| RU | 2789960 | C2 | 2/2023 | |
| SU | 1333328 | A2 | 8/1987 | |
| WO | 0166022 | A1 | 9/2001 | |
| WO | 03075775 | A1 | 9/2003 | |
| WO | 2004089227 | A2 | 10/2004 | |
| WO | 2008051064 | A1 | 5/2008 | |
| WO | 2009001083 | A1 | 12/2008 | |
| WO | 2009029798 | A1 | 3/2009 | |
| WO | 2009032101 | A2 | 3/2009 | |
| WO | 2010099231 | A3 | 11/2010 | |
| WO | 2011005327 | A1 | 1/2011 | |
| WO | 2011037885 | A1 | 3/2011 | |
| WO | 2012024317 | A2 | 2/2012 | |
| WO | 2012029008 | A1 | 3/2012 | |
| WO | 2012176077 | A1 | 12/2012 | |
| WO | 2013026786 | A1 | 2/2013 | |
| WO | 2013041618 | A1 | 3/2013 | |
| WO | 2013134387 | A1 | 9/2013 | |
| WO | 2013156816 | A2 | 10/2013 | |
| WO | 2014020561 | A1 | 2/2014 | |
| WO | 2014020562 | A1 | 2/2014 | |
| WO | 2014022055 | A1 | 2/2014 | |
| WO | 2014085882 | A1 | 6/2014 | |
| WO | 2014147099 | A1 | 9/2014 | |
| WO | 2014152219 | A2 | 9/2014 | |
| WO | 2014200017 | A1 | 12/2014 | |
| WO | 2015003284 | A2 | 1/2015 | |
| WO | 2015094409 | A1 | 6/2015 | |
| WO | 2015127515 | A2 | 9/2015 | |
| WO | 2016012731 | A1 | 1/2016 | |
| WO | 2016102025 | A1 | 6/2016 | |
| WO | 2017031000 | A1 | 2/2017 | |
| WO | 2017122076 | A2 | 7/2017 | |
| WO | 2017151833 | A1 | 9/2017 | |
| WO | 2018167369 | A1 | 9/2018 | |
| WO | 2019060780 | A2 | 3/2019 | |
| WO | 2019052622 | A4 | 5/2019 | |
| WO | 2019180747 | A1 | 9/2019 | |
| WO | 2020060349 | A1 | 3/2020 | |
| WO | WO-2020231490 | A1 * | 11/2020 | ........... A61B 17/151 |
| WO | 2021054518 | A1 | 3/2021 | |
| WO | 2021091071 | A1 | 5/2021 | |
| WO | 2021118733 | A1 | 6/2021 | |
| WO | 2021127625 | A1 | 6/2021 | |
| WO | 2021240290 | A1 | 12/2021 | |
| WO | 2022155208 | A1 | 7/2022 | |
| WO | 2022182312 | A1 | 9/2022 | |
| WO | 2023096516 | A1 | 6/2023 | |
| WO | 2024025840 | A1 | 2/2024 | |

OTHER PUBLICATIONS

Vaida et al., "Effect on Foot Width With Triplanar Tarsometatarsal Arthrodesis for Hallux Valgus," Foot & Ankle Orthopaedics, vol. 5, No. 3, 2020, pp. 1-5.

Nyska, Synergy 3D Med, "Anatomical Model: Calcaneus" , 2022, p. 3.

Okuda et al., "Postoperative Incomplete Reduction of the Sesamoids as a Risk Factor for Recurrence of Hallux Valgus," The Journal of Bone and Joint Surgery, vol. 91-A, No. 1, Jul. 2009, pp. 1637-1645.

Okuda et al., "The Shape of the Lateral Edge of the First Metatarsal Head as a Risk Factor for Recurrence of Hallux Valgus," The Journal of Bone and Joint Surgery, vol. 89, 2007, pp. 2163-2172.

Osher et al., "Accurate Determination of Relative Metatarsal Protrusion with a Small Intermetatarsal Angle: A Novel Simplified Method," The Journal of Foot & Ankle Surgery, vol. 53, No. 5, Sep./Oct. 2014, published online: Jun. 3, 2014, pp. 548-556.

Otsuki et al., "Developing a novel custom cutting guide for curved per-acetabular osteotomy," International Orthopaedics (SICOT), vol. 37, 2013, pp. 1033-1038.

Park et al., "Comparative analysis of clinical outcomes of fixed-angle versus variable-angle locking compression plate for the treatment of Lisfranc injuries," Foot and Ankle Surgery, vol. 26, 2020, pp. 338-342.

Patel et al., "Modified Lapidus Arthrodesis: Rate of Nonunion in 227 Cases," The Journal of Foot & Ankle Surgery, vol. 43, No. 1, Jan./Feb. 2004, pp. 37-42.

Pentikainen et al., "Preoperative Radiological Factors Correlated to Long-Term Recurrence of Hallux Valgus Following Distal Chevron Osteotomy," Foot & Ankle International, vol. 35, No. 12, 2014, pp. 1262-1267.

Perler, " Cuboid Suspension in Charcot Reconstruction. Using 3D Imaging for Planning, Printing and Execution for Complex Deformity Correction" Downloaded Apr. 2021, p. 4.

Peters et al., "Flexor Hallucis Longus Tendon Laceration as a Complication of Total Ankle Arthroplasty," Foot & Ankle International, vol. 34, No. 1, 2013, pp. 148-149.

Ray et al., "Hallux Valgus," Foot & Ankle Orthopaedics, vol. 4, No. 2, 2019, pp. 1-12.

Ray et al., "Multicenter Early Radiographic Outcomes of Triplanar Tarsometatarsal Arthrodesis With Early Weightbearing," Foot & Ankle International, vol. 40, No. 8, Aug. 1, 2019, published online: May 5, 2019, 7 pages.

(56) References Cited

OTHER PUBLICATIONS

Rodriguez et al., "Ilizarov method of fixation for the management of pilon and distal tibial fractures in the compromised diabetic patient: A technique guide," The Foot and Ankle Journal Online, vol. 7, No. 2, 2014, 9 pages.
Rx-Fix Mini Rail External Fixator, Wright Medical Technology, Brochure, Aug. 15, 2014, 2 pages.
Saltzman et al., "Prospective Controlled Trial of STAR Total Ankle Replacement Versus Ankle Fusion: Initial Results," Foot & Ankle International, vol. 30, No. 7, Jul. 2009, pp. 579-596.
Sammarco, "Surgical Strategies: Mau Osteotomy for Correction of Moderate and Severe Hallux Valgus Deformity," Foot & Ankle International, vol. 28, No. 7, Jul. 2007, pp. 857-864.
Sandhu et al., "Digital Arthrodesis With a One-Piece Memory Nitinol Intramedullary Fixation Device: A Retrospective Review," Foot and Ankle Specialist, vol. 6, No. 5, Oct. 2013, pp. 364-366.
Santrock et al., "Hallux Valgus Deformity and Treatment: A Three-Dimensional Approach: Lapiplasty," Foot & Ankle Clinics, vol. 23, No. 2, 2018, pp. 281-295.
Scanlan et al. "Technique Tip: Subtalar Joint Fusion Using a Parallel Guide and Double Screw Fixation," The Journal of Foot and Ankle Surgery, vol. 49, Issue 3, May-Jun. 2010, pp. 305-309, (Abstract Only).
Schon et al., "Cuneiform-Metatarsal Arthrodesis for Hallux Valgus," The Foot and Ankle, Second Edition, Chapter 8, 2002, pp. 99-117.
Scranton Jr et al., "Anatomic Variations in the First Ray: Part I. Anatomic Aspects Related to Bunion Surgery," Clinical Orthopaedics and Related Research, vol. 151, Sep. 1980, pp. 244-255.
Shima et al., "Operative Treatment for Hallux Valgus With Moderate to Severe Metatarsus Adductus," Foot & Ankle International, vol. 40, No. 6, 2019, pp. 641-647.
Shurnas et al., "Proximal Metatarsal Opening Wedge Osteotomy," Operative Techniques in Foot and Ankle Surgery, Section I, Chapter 13, 2011, pp. 73-78.
Siddiqui et al. "Fixation Of Metatarsal Fracture With Bone Plate In A Dromedary Heifer," Open Veterinary Journal, vol. 3, No. 1, 2013, pp. 17-20.
Sidekick Stealth Rearfoot Fixator, Wright Medical Technology, Surgical Technique, Dec. 2, 2013, 20 pages.
Simons et al., "Short-Term Clinical Outcome of Hemiarthroplasty Versus Arthrodesis for End-Stage Hallux Rigidus," The Journal of Foot & Ankle Surgery, vol. 54, 2015, pp. 848-851.
Simpson et al., "Computer-Assisted Distraction Ostegogenesis By Ilizarov's Method," International Journal of Medical Robots and Computer Assisted Surgery, vol. 4, No. 4, Dec. 2008, pp. 310-320, (Abstract Only).
Small Bone External Fixation System, Acumed, Surgical Technique, Effective date Sep. 2014, 8 pages.
Smith et al., "Intraoperative Multiplanar Alignment System to Guide Triplanar Correction of Hallux Valgus Deformity," Techniques in Foot & Ankle Surgery, 2017, 8 pages.
Smith et al., "Opening Wedge Osteotomies for Correction of Hallux Valgus: A Review of Wedge Plate Fixation," Foot and Ankle Specialist, vol. 2, No. 6, Dec. 2009, pp. 277-282.
Smith et al., "Understanding Frontal Plane Correction in Hallux Valgus Repair," Clinics in Podiatric Medicine and Surgery, vol. 35, 2018, pp. 27-36.
Sokoloff, "Lapidus Procedure," Textbook of Bunion Surgery, Chapter 15, 1981, pp. 277-287.
Stableloc External Fixation System, Acumed, Product Overview, Effective date Sep. 2015, 4 pages.
Stahl et al., "Derotation Of Post-Traumatic Femoral Deformities By Closed Intramedullary Sawing," Injury, vol. 37, No. 2, Feb. 2006, pp. 145-151, (Abstract Only).
Stamatis et al., "Mini Locking Plate as Medial Buttress for Oblique Osteotomy for Hallux Valgus," Foot & Ankle International, vol. 31, No. 10, Oct. 2010, pp. 920-922.
Stryker, "PROstep Minimally Invasive Surgery" https://www.stryker.com/us/en/foot-and-ankle/products/prostep. html, Downloaded Jun. 23, 2023, p. 10.
Synergy 3D Med, "Anatomical Model: Calcaneus" Downloaded Mar. 2, 2023, p. 2.
Synopsys, "Medical Image Segmentation with Machine Learning - Simpleware Automated Solution Modules" , https://www.synopsys.com/simpleware/software/auto-segmenter-modules.html#simpleware-as-ortho, 2022, p. 12.
Talbot et al., " Assessing Sesamoid Subluxation: How Good is the AP Radiograph?," Foot and Ankle International, vol. 19, No. 8, Aug. 1998, pp. 547-554.
TempFix Spanning the Ankle Joint Half Pin and Transfixing Pin Techniques, Biomet Orthopedics, Surgical Technique, 2012, 16 pages.
Tornier Technology, "Tornier Blueprint 3D Planning + PSI" , https://www.wrightemedia.com/ProductFiles/Files/PDFs/CAW-8609_EN_HR_LE.pdf, Feb. 2017, p. 12.
Total Ankle Institute, "Prophecy: Preoperative Navigation Guides" , https://www.totalankleinstitute.com/infinity-products/prophecy-preoperative-navigation-guides/, 2019, p. 6.
Toth et al., "The Effect of First Ray Shortening in the Development of Metatarsalgia in the Second Through Fourth Rays After Metatarsal Osteotomy," Foot & Ankle International, vol. 28, No. 1, Jan. 2007, pp. 61-63.
TREACE "FastGrafter Autograft Harvesting System"' Downloaded from https://www.lapiplasty.com/surgeons/other-products/fastgrafter/, Dec. 4, 2024, p. 8.
Treace Medical Concepts, "Adductoplasty Midfoot Correction System", https://www.lapiplasty.com/surgeons/other-products/adductoplasty-system/, Downloaded May 2, 2022, p. 9.
Use for BME Speed Nitinol Staple Fixation for the Lapidus Procedure, "date unknown, 1 page.".
Mrzi et al. "Comprehensive Review of 3D Segmentation Software Tools for MRI Usable for Pelvic Surgery Planning", Journal of Digital Imaging (2020) 33, pp. 99-110.
Prior Art Publications, Exhibit A of Defendant Fusion Orthopedics LLC's Invalidity Contentions, No. CV-22-00490-PHX-Srb, US District Court for the District of Arizona, Aug. 27, 2022, 3 pages.
Decarbo et al., "The Weil Osteotomy: A Refresher," Techniques in Foot and Ankle Surgery, vol. 13, No. 4, Dec. 2014, pp. 191-198.
Defendant Fusion Orthopedics LLC's Invalidity Contentions, No. CV-22-00490-PHX-SRB, US District Court for the District of Arizona, Aug. 27, 2022, 41 pages.
Didomenico et al., "Correction of Frontal Plane Rotation of Sesamoid Apparatus during the Lapidus Procedure: A Novel Approach," The Journal of Foot and Ankle Surgery, vol. 53, 2014, pp. 248-251.
Didomenico et al., "Lapidus Bunionectomy: First Metatarsal-Cuneiform Arthrodesis," McGlamrys Comprehensive Textbook of Foot and Ankle Surgery, Fourth Edition, vol. 1, Chapter 31, 2013, 24 pages.
Dinapoli et al., "Metatarsal Osteotomy for the Correction of Metatarsus Adductus," Reconstructive Surgery of the Foot and Leg, 1989, pp. 242-250.
Disior, "Bonelogic Foot & Ankle Module" , https://www.disior.com/foot--ankle.html, Downloaded Jun. 1, 2022, p. 6.
Dobbe et al. "Patient-Tailored Plate For Bone Fixation And Accurate 3D Positioning In Corrective Osteotomy," Medical and Biological Engineering and Computing, vol. 51, No. 1-2, Feb. 2013, pp. 19-27, (Abstract Only).
Doty et al., "Hallux valgus and hypermobility of the first ray: facts and fiction," International Orthopaedics, vol. 37, 2013, pp. 1655-1660.
Dubovik et al., "Talonavicular Joint Arthrodesis and Medial Displacement Calcaneal Osteotomy for Treatment of Patients With Planovalgus Deformity" Traumatology and Orthopedics of Russia, vol. 18, No. 3, Sep. 30, 2012, pp. 83-88.
Easley et al., "Current Concepts Review: Hallux Valgus Part I: Pathomechanics, Clinical Assessment, and Nonoperative Management," Foot and Ankle International, vol. 28, No. 5, May 2007, pp. 654-659.
Easley et al., "Current Concepts Review: Hallux Valgus Part II: Operative Treatment," Foot and Ankle International, vol. 28, No. 6, Jun. 2007, pp. 748-758.

(56) References Cited

OTHER PUBLICATIONS

Easley et al., "What is the Best Treatment for Hallux Valgus?," Evidence-Based Orthopaedics - The Best Answers to Clinical Questions, Chapter 73, 2009, pp. 479-491.
EBI Extra Small Rail Fixator, Biomet Trauma, retrieved Dec. 19, 2014, from the Internet: <http://footandanklefixation.com/product/biomet-trauma-ebi-extra-small-rail-fixator>, 7 pages.
Holmes, Jr., "Correction of the Intermetatarsal Angle Component of Hallux Valgus Using Fiberwire-Attached Endo- buttons," Revista Internacional de Ciencias Podologicas, vol. 6, No. 2, 2012, pp. 73-79.
Eustace et al., "Hallux valgus, first metatarsal pronation and collapse of the medial longitudinal arch—a radiological correlation," Skeletal Radiology, vol. 23, 1994, pp. 191-194.
Fallin et al., US Provisional Application Entitled Indexed Tri-Planar Osteotomy Guide and Method, US Pat. U.S. Appl. No. 62/118,378, filed Feb. 19, 2015, 62 pages.
Fazal et al., "First metatarsophalangeal joint arthrodesis with two orthogonal two hole plates," Acta Orthopaedica et Traumatologica Turcica, vol. 52, 2018, pp. 363-366.
Feilmeier et al., "Incidence of Surgical Site Infection in the Foot and Ankle with Early Exposure and Showering of Surgical Sites: A Prospective Observation," The Journal of Foot and Ankle Surgery, vol. 53, 2014, pp. 173-175.
Feilmeier et al., "Reduction of Intermetatarsal Angle after First Metatarsophalangeal Joint Arthrodesis in Patients with Hallux Valgus," The Journal of Foot and Ankle Surgery, vol. 53, 2014, pp. 29-31.
Ferrari et al., "A Radiographic Study of the Relationship Between Metatarsus Adductus and Hallux Valgus," The Journal of Foot and Ankle Surgery, vol. 42, No. 1, 2003, pp. 9-14.
Ferreyra et al., "Can we correct first metatarsal rotation and sesamoid position with the 3D Lapidus procedure?," Foot and Ankle Surgery, vol. 28, No. 3, Apr. 2022, pp. 313-318.
Fibretuff, "3D Printing, CNC Machining, Molding and Extruding Biocompatible material's with "bone like" Qualities for 3D Printing" https://fibretuff.us, Downloaded Feb. 24, 2023, p. 22.
Fishco, "A Straightforward Guide To The Lapidus Bunionectomy," Podiatry Today, Retrieved online from <https://www.hmpglobal-learningnetwork.com/site/podiatry/blogged/straightforward-guide-lapidus-bunionectomy>, dated Sep. 6, 2013, 5 pages.
Fishco, "Making the Lapidus Easy," The Podiatry Institute, Update 2014, Chapter 14, 2014, pp. 91-93.
Flavin et al., "Arthrodesis of the First Metatarsophalangeal Joint Using a Dorsal Titanium Contoured Plate," Foot & Ankle International, vol. 25, No. 11, Nov. 2004, pp. 783-787.
Fleming et al., "Results of Modified Lapidus Arthrodesis Procedure Using Medial Eminence as an Interpositional Autograft," The Journal of Foot & Ankle Surgery, vol. 50, 2011, pp. 272-275.
Fraissler et al., "Treatment of hallux valgus deformity," Efort Open Reviews, vol. 1, Aug. 2016, pp. 295-302.
Fuhrmann, "Arthrodesis of the First Tarsometatarsal Joint for Correction of the Advanced Splayfoot Accompanied by a Hallux Valgus," Operative Orthopadie und Traumatologie, No. 2, 2005, pp. 195-210.
Galli et al., "Enhanced Lapidus Arthrodesis: Crossed Screw Technique With Middle Cuneiform Fixation Further Reduces Sagittal Mobility," The Journal of Foot & Ankle Surgery, vol. 54, vol. 3, May/Jun. 2015, pp. 437-440.
Garthwait, "Accu-Cut System Facilitates Enhanced Precision," Podiatry Today, vol. 18, No. 6, Jun. 2005, 6 pages.
Gerard et al., "The Modified Lapidus Procedure," Orthopedics, vol. 31, No. 3, Mar. 2008, 7 pages.
Ghali et al., "The Management of Metatarsus Adductus et Supinatus," The Journal of Bone and Joint Surgery, vol. 66-B, No. 3, May 1984, pp. 376-380.
Giannoudis et al., "Hallux Valgus Correction," Practical Procedures in Elective Orthopaedic Surgery, Pelvis and Lower Extremity, Chapter 38, 2012, 22 pages.
Gonzalez Del Pino et al., "Variable Angle Locking Intercarpal Fusion System for Four-Corner Arthrodesis: Indications and Surgical Technique," Journal of Wrist Surgery, vol. 1, No. 1, Aug. 2012, pp. 73-78.
Gotte, "Entwicklung eines Assistenzrobotersystems fr die Knieendoprothetik," Forschungsberichte, Technische Universitat Munchen, 165, 2002, 11 pages, including partial English Translation.
Gould et al., "A Prospective Evaluation of First Metatarsophalangeal Fusion Using an Innovative Dorsal Compression Plating System," The Journal of Foot & Ankle Surgery, vol. 60, 2021, pp. 891-896.
Gregg et al., "Plantar plate repair and Weil osteotomy for metatarsophalangeal joint instability," Foot and Ankle Surgery, vol. 13, 2007, pp. 116-121.
Greiner, "The Jargon of Pedal Movements," Foot & Ankle International, vol. 28, No. 1, Jan. 2007, pp. 109-125.
Grondal et al., "A Guide Plate for Accurate Positioning of First Metatarsophalangeal Joint during Fusion," Operative Orthopdie Und Traumatologie, vol. 16, No. 2, 2004, pp. 167-178 (Abstract Only).
Groves, "Functional Position Joint Sectioning: Pre-Load Method for Lapidus Arthrodesis," The Podiatry Institute, Update 2015, Chapter 6, 2015, pp. 23-29.
Groves, "Operative Report," St. Tammany Parish Hospital, Date of Procedure, Mar. 26, 2014, 2 pages.
Gutteck et al., "Comparative study of Lapidus bunionectomy using different osteosynthesis methods," Foot and Ankle Surgery, vol. 19, 2013, pp. 218-221.
Gutteck et al., "Is it feasible to rely on intraoperative X ray in correcting hallux valgus?," Archives of Orthopaedic and Trauma Surgery, vol. 133, 2013, pp. 753-755.
Hardy et al., "Observations on Hallux Valgus," The Journal of Bone and Joint Surgery, vol. 33B, No. 3, Aug. 1951,pp. 376-391.
Hatch et al., "Analysis of Shortening and Elevation of the First Ray With Instrumented Triplane First Tarsometatarsal Arthrodesis," Foot & Ankle Orthopaedics, vol. 5, No. 4, 2020, pp. 1-8.
Hatch et al., "Triplane Hallux Abducto Valgus Classification," The Journal of Foot & Ankle Surgery, vol. 57, No. 5, September/Oct. 2018, published online: May 18, 2018, pp. 972-981.
Hetherington et al., "Evaluation of surgical experience and the use of an osteotomy guide on the apical angle of an Austin osteotomy," The Foot, vol. 18, 2008, pp. 159-164.
Hirao et al., "Computer assisted planning and custom-made surgical guide for malunited pronation deformity after first metatarsophalangeal joint arthrodesis in rheumatoid arthritis: A case report," Computer Aided Surgery, vol. 19, Nos. 1-3, 2014, pp. 13-19.
Ho et al., "Hallux rigidus," Efort Open Reviews, vol. 2, Jan. 2017, pp. 13-20.
D'Amico et al., "Motion of the First Ray: Clarification Through Investigation," Journal of the American Podiatry Association, vol. 69, No. 1, Jan. 1979, pp. 17-23.
Dayton et al., "Biwinged Excision for Round Pedal Lesions," The Journal of Foot and Ankle Surgery, vol. 35, No. 3, 1996, pp. 244-249.
Coughlin "Proximal Metatarsal Osteotomy and Distal Soft Tissue Reconstruction for Hallux Valgus in Juveniles" Orthopaedics and Traumatology, vol. 7, Published: Jun. 1999, pp. 133-143.
Dayton et al., "Medial Incision Approach to the First Metatarsophalangeal Joint," The Journal of Foot and Ankle Surgery, vol. 40, No. 6, November/Dec. 2001, pp. 414-417.
Dayton et al., "Reduction of the Intermetatarsal Angle after First Metatarsophalangeal Joint Arthrodesis in Patients with Moderate and Severe Metatarsus Primus Adductus," The Journal of Foot and Ankle Surgery, vol. 41, No. 5, Sep./Oct. 2002, pp. 316-319.
Dayton et al., "Use of the Z Osteotomy for Tailor Bunionectomy," The Journal of Foot and Ankle Surgery, vol. 42, No. 3, May/Jun. 2003, pp. 167-169.
Dayton et al., "Early Weightbearing After First Metatarsophalangeal Joint Arthrodesis: A Retrospective Observational Case Analysis," The Journal of Foot and Ankle Surgery, vol. 43, No. 3, May/Jun. 2004, pp. 156-159.

(56) References Cited

OTHER PUBLICATIONS

Dayton et al., "Dorsal Suspension Stitch: An Alternative Stabilization After Flexor Tenotomy for Flexible Hammer Digit Syndrome," The Journal of Foot and Ankle Surgery, vol. 48, No. 5, Sep./Oct. 2009, pp. 602-605.
Dayton et al., "The Extended Knee Hemilithotomy Position for Gastrocnemius Recession," The Journal of Foot and Ankle Surgery, vol. 49, 2010, pp. 214-216.
Dayton et al., "A User-Friendly Method of Pin Site Management for External Fixators," Foot and Ankle Specialist, Sep. 16, 2011, 4 pages.
Dayton et al., "Hallux Varus as Complication of Foot Compartment Syndrome," The Journal of Foot and Ankle Surgery, vol. 50, 2011, pp. 504-506.
Dayton et al., "Measurement of Mid-Calcaneal Length on Plain Radiographs: Reliability of a New Method," Foot and Ankle Specialist, vol. 4, No. 5, Oct. 2011, pp. 280-283.
Cottom, "Fixation of the Lapidus Arthrodesis with a Plantar Interfragmentary Screw and Medial Low Profile Locking Plate," The Journal of Foot & Ankle Surgery, vol. 51, 2012, pp. 517-522.
Dayton et al., "Does Postoperative Showering or Bathing of a Surgical Site Increase the Incidence of Infection? A Systematic Review of the Literature," The Journal of Foot and Ankle Surgery, vol. 52, 2013, pp. 612-614.
Dayton et al., "Effectiveness of a Locking Plate in Preserving Midcalcaneal Length and Positional Outcome after Evans Calcaneal Osteotomy: A Retrospective Pilot Study," The Journal of Foot and Ankle Surgery, vol. 52, 2013, pp. 710-713.
Dayton et al., "Principles of Management of Growth Plate Fractures in the Foot and Ankle," Clinics in Podiatric Medicine and Surgery, Pediatric Foot Deformities, Oct. 2013, 17 pages.
Crawford et al. "Metatarsus Adductus: Radiographic and Pathomechanical Analysis" Chapter 5, https:// www.podiatryinstitute.com/pdfs/ Update_2014/2014_05.pdf, Published 2014, pp. 25-30.
Dayton et al., "Clarification of the Anatomic Definition of the Bunion Deformity," The Journal of Foot and Ankle Surgery, vol. 53, 2014, pp. 160-163.
Dayton et al., "Observed Changes in First Metatarsal and Medial Cuneiform Positions after First Metatarsophalangeal Joint Arthrodesis," The Journal of Foot and Ankle Surgery, vol. 53, 2014, pp. 32-35.
Dayton et al., "Observed Changes in Radiographic Measurements of the First Ray after Frontal Plane Rotation of the First Metatarsal in a Cadaveric Foot Model," The Journal of Foot and Ankle Surgery, Article in Press, 2014, 5 pages.
Dayton et al., "Observed Changes in Radiographic Measurements of the First Ray after Frontal and Transverse Plane Rotation of the Hallux: Does the Hallux Drive the Metatarsal in a Bunion Deformity? ," The Journal of Foot and Ankle Surgery, Article in Press, 2014, 4 pages.
Dayton et al., "Observed Changes in Radiographic Measurements of the First Ray after Frontal and Transverse Plane Rotation of the Hallux: Does the Hallux Drive the Metatarsal in a Bunion Deformity? ," The Journal of Foot and Ankle Surgery, vol. 53, 2014, pp. 584-587.
Dayton et al., "Reduction of the Intermetatarsal Angle after First Metatarsal Phalangeal Joint Arthrodesis: A Systematic Review," The Journal of Foot and Ankle Surgery, Article in Press, 2014, 4 pages.
Dayton et al., "Technique for Minimally Invasive Reduction of Calcaneal Fractures Using Small Bilateral External Fixation," The Journal of Foot and Ankle Surgery, Article in Press, 2014, 7 pages.
Dayton, "Tarsal-Metatarsal Joint: Primary & Revision Arthrodesis" Disclosure: Speaker for Orthofix and Biomet, Apr. 2014, p. 38.
Dalat et al. "Does arthrodesis of the first metatarsophalangeal joint correct the intermetatarsal M1M2 angle? Analysis of a continuous series of 208 arthrodeses fixed with plates" Orthopaedics & Traumatology: Surgery & Research 101, 2015, pp. 709-714.
Dayton et al., "A new triplanar paradigm for bunion management," Lower Extremity Review, Apr. 2015, 9 pages.
Dayton et al., "Comparison of Complications for Internal and External Fixation for Charcot Reconstruction: A Systematic Review," The Journal of Foot and Ankle Surgery, Article in Press, 2015, 4 pages.
Dayton et al., "Complications of Metatarsal Suture Techniques for Bunion Correction: A Systematic Review of the Literature," The Journal of Foot and Ankle Surgery, Article in Press, 2015, 3 pages.
Dayton et al., "Is Our Current Paradigm for Evaluation and Management of the Bunion Deformity Flawed? A Discussion of Procedure Philosophy Relative to Anatomy," The Journal of Foot and Ankle Surgery, vol. 54, 2015, pp. 102-111.
Dayton et al., "Quantitative Analysis of the Degree of Frontal Rotation Required to Anatomically Align the First Metatarsal Phalangeal Joint During Modified Tarsal-Metatarsal Arthrodesis Without Capsular Balancing," The Journal of Foot and Ankle Surgery, 2015, pp. 1-6.
Dayton et al. "Comparison of Tibial Sesamoid Position on Anteroposterior and Axial Radiographs Before and After Triplane Tarsal Metatarsal Joint Arthrodesis" The Journal of Foot & Ankle Surgery 56, 2017, pp. 1041-1046.
Dayton "Evidence-Based Bunion Surgery: A Critical Examination of Current and Emerging Concepts and Techniques" Springer International Publishing, 2017, p. 254.
Dayton et al. "Biomechanical Characteristics of Biplane Multiplanar Tension-Side Fixation for Lapidus Fusion" The Journal of Foot & Ankle Surgery, 2018, pp. 1-5.
Dayton et al. "Progression of Healing on Serial Radiographs Following First Ray Arthrodesis in the Foot Using a Biplanar Plating Technique Without Compression" The Journal of Foot & Ankle Surgery, 2018, pp. 1-7.
Cruz et al., "Does Hallux Valgus Exhibit a Deformity Inherent to the First Metatarsal Bone?" The Journal of Foot & Ankle Surgery, vol. 58, No. 6, Nov. 2019, pp. 1210-1214.
Dahlgren et al., "First Tarsometatarsal Fusion Using Saw Preparation vs. Standard Preparation of the Joint: A Cadaver Study," Foot & Ankle Orthopaedics, vol. 4, No. 4, Oct. 2019, 2 pages.
Conti et al., "Effect of the Modified Lapidus Procedure for Hallux Valgus on Foot Width," Foot & Ankle International, Feb. 1, 2020, published online: Oct. 30, 2019, 6 pages.
Conti et al., "Effect of the Modified Lapidus Procedure on Pronation of the First Ray in Hallux Valgus," Foot & Ankle International, Feb. 1, 2020, published online: Oct. 16, 2019, 8 pages.
Dayton et al. "Comparison of Radiographic Measurements Before and After Triplane Tarsometatarsal Arthrodesis for Hallux Valgus" The Journal of Foot & Ankle Surgery 59, 2020, pp. 291-297.
Curran et al. "Functional Capabilities After First Metatarsal Phalangeal Joint Arthrodesis Using a Locking Plate and Compression Screw Construct" The Journal of Foot & Ankle Surgery, 2021, pp. 1-5.
De Carvalho, et al. "Automated Three-dimensional distance and coverage mapping of hallux valgus: a case- control study" Journal of Foot and Ankle, 2022; 16(1), p. 5.
Dayton et al., "Comparison of the Mechanical Characteristics of a Universal Small Biplane Plating Technique Without Compression Screw and Single Anatomic Plate With Compression Screw," The Journal of Foot & Ankle Surgery, vol. 55, No. 3, May/Jun. 2016, published online: Feb. 9, 2016, pp. 567-571.
Dayton et al., "Relationship of Frontal Plane Rotation of First Metatarsal to Proximal Articular Set Angle and Hallux Alignment in Patients Undergoing Tarsometatarsal Arthrodesis for Hallux Abducto Valgus: A Case Series and Critical Review of the Literature," The Journal of Foot & Ankle Surgery, 2013, Article in Press, Mar. 1, 2013, 7 pages.
Dayton et al., "Relationship Of Frontal Plane Rotation Of First Metatarsal To Proximal Articular Set Angle And Hallux Alignment In Patients Undergoing Tarsometatarsal Arthrodesis For Hallux Abducto Valgus: A Case Series And Critical Review Of The Literature," The Journal of Foot and Ankle Surgery, vol. 52, No. 3, May/Jun. 2013, pp. 348-354.
De Geer et al., "A New Measure of Tibial Sesamoid Position in Hallux Valgus in Relation to the Coronal Rotation of the First Metatarsal in CT Scans," Foot and Ankle International, Mar. 26, 2015, 9 pages.

(56) References Cited

OTHER PUBLICATIONS

De Heer et al., "Procedure-Specific Hardware Removal After Evans Osteotomy" Journal of the American Podiatric Medical Association, vol. 110, No. 2, Mar./Apr. 2020, pp. 1-7.
Decarbo et al., "Locking Plates: Do They Prevent Complications?," Podiatry Today, Apr. 2014, 7 pages.
Decarbo et al., "Resurfacing Interpositional Arthroplasty for Degenerative Joint Disease of the First Metatarsalphalangeal Joint," Podiatry Management, Jan. 2013, pp. 137-142.
Hunt et al., "Locked Versus Nonlocked Plate Fixation For Hallux MTP Arthrodesis," Foot and Ankle International, vol. 32, No. 7, Jul. 2011, pp. 704-709.
Integra, "Integra Large Qwix Positioning and Fixation Screw, Surgical Technique," 2012, 16 pages.
Jackson III et al., "The Surgical Learning Curve for Modified Lapidus Procedure for Hallux Valgus Deformity," Foot & Ankle Specialist, Jul. 2021, 5 pages.
Jeuken et al., "Long-term Follow-up of a Randomized Controlled Trial Comparing Scarf to Chevron Osteotomy in Hallux Valgus Correction," Foot & Ankle International, vol. 37, No. 7, 2016, pp. 687-695.
Kilmartin et al., "Combined rotation scarf and Akin osteotomies for hallux valgus: a patient focused 9 year follow up of 50 patients," Journal of Foot and Ankle Research, vol. 3, No. 2, 2010, 12 pages.
Kim et al., "A Multicenter Retrospective Review of Outcomes for Arthrodesis, Hemi-Metallic Joint Implant, and Resectional Arthroplasty in the Surgical Treatment of End-Stage Hallux Rigidus," The Journal of Foot and Ankle Surgery, vol. 51, 2012, pp. 50-56.
Kim et al., "A New Measure of Tibial Sesamoid Position in Hallux Valgus in Relation to the Coronal Rotation of the First Metatarsal in CT Scans," Foot and Ankle International, vol. 36, No. 8, 2015, pp. 944-952.
Klos et al., "Modified Lapidus arthrodesis with plantar plate and compression screw for treatment of hallux valgus with hypermobility of the first ray: A preliminary report," Foot and Ankle Surgery, vol. 19, 2013, pp. 239-244.
KLS Martin Group, "Individual Patient Solutions IPS Implants", https://www.klsmartin.com/en-na/products/individual-patient-solutions/ips-implants/, Downloaded: Jun. 1, 2022, p. 8.
Kurup et al., "Midfoot arthritis- current concepts review," Journal of Clinical Orthopaedics and Trauma, vol. 11, 2020, pp. 399-405.
La Reaux et al., "Metatarsus adductus and hallux abducto valgus: their correlation," The Journal of Foot Surgery, vol. 26, No. 4, Jul. 1987, pp. 304-308, Abstract Only.
Langan et al., "Maintenance of Correction of the Modified Lapidus Procedure With a First Metatarsal to Intermediate Cuneiform Cross-Screw Technique," Foot & Ankle International, vol. 41, No. 4, Apr. 1, 2020, published online: Dec. 26, 2019, pp. 426-436.
Lapidus, "The Author's Bunion Operation From 1931 to 1959," Clinical Orthopaedics, vol. 16, 1960, pp. 119-135.
Latif et al., "First metatarsophalangeal fusion using joint specific dorsal plate with interfragmentary screw augmentation: Clinical and radiological outcomes," Foot and Ankle Surgery, vol. 25, 2019, pp. 132-136.
Le et al., "Tarsometatarsal Arthrodesis," Operative Techniques in Foot and Ankle Surgery, Section II, Chapter 40, 2011, pp. 281-285.
Lee et al., "Technique Tip: Lateral Soft-Tissue Release for Correction of Hallux Valgus Through a Medial Incision Using A Dorsal Flap Over the First Metatarsal," Foot & Ankle International, vol. 28, No. 8, Aug. 2007, pp. 949-951.
Li et al., "Evolution of Thinking of the Lapidus Procedure and Fixation," Foot and Ankle Clinics, vol. 25, No. 1, Mar. 2020, published online: Dec. 16, 2019, p. 18 pages.
Lieske et al., "Implantation einer Sprunggelenktotalendo-prothese vom Typ Salto 2," Operative Orthopdie und Traumatologie, vol. 26, No. 4, 2014, pp. 401-413, including English Abstract on p. 403.
Little, "Joint Arthrodesis For Hallux Valgus," Clinics in Podiatric Medicine and Surgery, Hallux Abducto Valgus Surgery, updated Apr. 19, 2014, retrieved online from < https://www.footankleinstitute.com/first-metatarsophalangeal-joint-arthrodesis-in-the-treatment-of-hallux-valgus>, 7 pages.
Lopez et al., "Metatarsalgia: Assessment Algorithm and Decision Making," Foot and Ankle Clinics, vol. 24, No. 4, Dec. 2019, published online: Sep. 25, 2019, pp. 561-569.
MAC (Multi Axial Correction) Fixation System, Biomet Trauma, retrieved Dec. 19, 2014, from the Internet: < http:// footandanklefixation.com/product/biomet-trauma-mac-multi-axial-correction-fixation-system>, 7 pages.
Machacek Jr et al., "Salvage of a Failed Keller Resection Arthroplasty," The Journal of Bone and Joint Surgery, vol. 86A, No. 6, Jun. 2004, pp. 1131-1138.
Magin, "Computernavigierter Gelenkersatz am Knie mit dem Orthopilot," Operative Orthopdie und Traumatologie, vol. 22, No. 1, 2010, pp. 63-80, including English Abstract on p. 64.
Magin, "Die belastungsstabile Lapidus-Arthrodese bei Hallux-valgus-Deformitt mittels IVP-Plattenfixateur (V-TEK-System)," Operative Orthopdie und Traumatologie, vol. 26, No. 2, 2014, pp. 184-195, including English Abstract on p. 186.
Marshall et al., "The identification and appraisal of assessment tools used to evaluate metatarsus adductus: a systematic review of their measurement properties," Journal of Foot and Ankle Research, vol. 11, No. 25, 2018, 10 pages.
Mcaleer et al., "A systematic approach to the surgical correction of combined hallux valgus and metatarsus adductus deformities," The Journal of Foot & Ankle Surgery, May 21, 2021, 6 pages.
Mcaleer et al., "Radiographic Outcomes Following Triplanar Correction of Combined Hallux Valgus and Metatarsus Adductus Deformities," ACFAS Scientific Conference, Poster, Feb. 2022, 1 page.
Mccabe et al., "Anatomical reconstruction of first ray instability hallux valgus with a medial anatomical TMTJ1 plate," Foot and Ankle Surgery, vol. 27, No. 8, Dec. 2021, pp. 869-873.
Mehtar et al., "Outcomes of bilateral simultaneous hallux MTPJ fusion," Foot and Ankle Surgery, vol. 27, 2021, pp. 213-216.
Michelangelo Bunion System, Surgical Technique ", Instratek Incorporated, publication date unknown, 4 pages.".
Miller et al., "Variable Angle Locking Compression Plate as Alternative Fixation for Jones Fractures: A Case Series," Kansas Journal of Medicine, vol. 12, No. 2, May 2019, pp. 28-32.
Mini Joint Distractor, Arthrex, retrieved Dec. 19, 2014, from the Internet: <http://www.arthrex.com/foot-ankle/mini-joint-distractor/products>, 2 pages.
MiniRail System, Small Bone Innovations, Surgical Technique, 2010, 24 pages.
Miyake et al., "Three-Dimensional Corrective Osteotomy for Malunited Diaphyseal Forearm Fractures Using Custom-Made Surgical Guides Based on Computer Simulation," JBJS Essential Surgical Techniques, vol. 2, No. 4, 2012, 11 pages.
Mizuno et al., "Detorsion Osteotomy of the First Metatarsal Bone in Hallux Valgus," Japanese Orthopaedic Association, Tokyo, 1956; 30:813-819.
Modular Rail System: External Fixator, Smith & Nephew, Surgical Technique, 2013, 44 pages.
Monnich et al., "A Hand Guided Robotic Planning System for Laser Osteotomy in Surgery," World Congress on Medical Physics and Biomedical Engineering vol. 25/6: Surgery, Nimimal Invasive Interventions, Endoscopy and Image Guided Therapy, Sep. 7-12, 2009, pp. 59-62, (Abstract Only).
Moore et al., "Effect Of Ankle Flexion Angle On Axial Alignment Of Total Ankle Replacement," Foot and Ankle International, vol. 31, No. 12, Dec. 2010, pp. 1093-1098, (Abstract Only).
Mortier et al., "Axial Rotation of the First Metatarsal Head in a Normal Population and Hallux Valgus Patients," Orthopaedics and Traumatology: Surgery and Research, vol. 98, 2012, pp. 677-683.
Mote et al., "First Metatarsal-Cuneiform Arthrodesis for the Treatment of First Ray Pathology: A Technical Guide," JFAS Techniques Guide, vol. 48, No. 5, Sep./Oct. 2009, pp. 593-601.
Musculoskeletal Key "Arthrodesis of the Tarsmetatarsal Joint" https://musculoskeletalkey.com/arthrodesis-of- the-tarsometatarsal-joint/, Retrieved May 8, 2020, p. 11.

(56) References Cited

OTHER PUBLICATIONS

Myerson, "Cuneiform-Metatarsal Arthrodesis," The Foot and Ankle, Chapter 9, 1997, pp. 107-117.
Nagy et al., "The AO Ulnar Shortening Osteotomy System Indications and Surgical Technique," Journal of Wrist Surgery, vol. 3, No. 2, 2014, pp. 91-97.
NexFix from Nexa Orthopedics, MetaFix I from Merete Medical, Inc. and The BioPro Lower Extremities from BioPro, found in Foot & Ankle International Journal, vol. 28, No. 1, Jan. 2007, 4 pages.
Nix et al., "Prevalence of hallux valgus in the general population: a systematic review and meta-analysis," Journal of Foot and Ankle Research, vol. 3, No. 21, 2010, 9 pages.
Novastep, "Pecaplasty Percutaneous Bunion Correction" Downloaded Jun. 29, 2022, p. 24.
Novastep, "Pecaplasty Percutaneous Bunion Correction- Brochure Pecaplasty Targeting Guide" Downloaded Dec. 15, 2021, p. 4.
Odenbring et al., "A guide instrument for high tibial osteotomy," Acta Orthopaedica Scandinavica, vol. 60, No. 4, 1989, pp. 449-451.
Okuda et al., "Proximal Metatarsal Osteotomy for Hallux Valgus: Comparison of Outcome for Moderate and Severe Deformities," Foot and Ankle International, vol. 29, No. 7, Jul. 2008, pp. 664-670.
Instratek, "Michelangelo Bunion System, Surgical Technique", Instratek Incorporated, publication date unknown, 4 pages.
Wendl et al., "Navigation in der Knieendoprothetik," OP-Journal, vol. 17, 2002, pp. 22-27, including English Abstract.
Whipple et al., "Zimmer Herbert Whipple Bone Screw System: Surgical Techniques for Fixation of Scaphoid and Other Small Bone Fractures," Zimmer, 2003, 59 pages.
Weber et al., "A Simple System For Navigation Of Bone Alignment Osteotomies Of The Tibia," International Congress Series, vol. 1268, Jan. 2004, pp. 608-613, (Abstract Only).
Wukich et al., "Hypermobility of the First Tarsometatarsal Joint," Foot and Ankle Clinics, vol. 10, No. 1, Mar. 2005, pp. 157-166.
Weber et al., "Use of the First Ray Splay Test to Assess Transverse Plane Instability Before First Metatarsocuneiform Fusion," The Journal of Foot and Ankle Surgery, vol. 45, No. 4, Jul./Aug. 2006, pp. 278-282.
Mtek et al., "Die Behandlung des Hallux rigidus mit Cheilektomie und Akin-Moberg-Osteotomie unter Verwendung einer neuen Schnittlehre und eines neuen Schraubensystems," Orthopadische Praxis, vol. 44, Nov. 2008, pp. 563-566, including English Abstract on p. 564.
Mtek, "Neue Techniken in der Fuchirurgie Das V-tek-System," ABW Wissenschaftsverlag GmbH, 2009, 11 pages, including English Abstract.
Yakacki et al. "Compression Forces of Internal and External Ankle Fixation Devices with Simulated Bone Resorption," Foot and Ankle International, vol. 31, No. 1, Jan. 2010, pp. 76-85, (Abstract Only).
Weil et al., "Anatomic Plantar Plate Repair Using the Weil Metatarsal Osteotomy Approach," Foot & Ankle Specialist, vol. 4, No. 3, 2011, pp. 145-150.
Wienke et al., "Bone Stimulation For Nonunions: What the Evidence Reveals," Podiatry Today, vol. 24, No. 9, Sep. 2011, pp. 52-57.
Williams et al., "Metatarsus adductus: Development of a non-surgical treatment pathway," Journal of Paediatrics and Child Health, vol. 49, 2013, pp. E428-433.
Yasuda et al., "Proximal Supination Osteotomy of the First Metatarsal for Hallux Valgus," Foot and Ankle International, vol. 36, No. 6, Jun. 2015, pp. 696-704.
Walker et al., "The Role of First Ray Insufficiency in the Development of Metatarsalgia," Foot and Ankle Clinics, vol. 24, No. 4, Dec. 2019, published online: Sep. 5, 2019, pp. 641-648.
Weigelt et al., "Risk Factors for Nonunion After First Metatarsophalangeal Joint Arthrodesis With a Dorsal Locking Plate and Compression Screw Construct: Correction of Hallux Valgus Is Key," The Journal of Foot & Ankle Surgery, vol. 60, No. 6, Nov./Dec. 2021, pp. 1179-1183.
Wright Medical, "How BLUEPRINT Works - from CT to 3D [Caw -9389]", https://www.wrightmeded. com/videos/how-blueprint-works-from-ct-to-3d-caw-9389, video time mark 32 seconds to 48 seconds, Dated May 26, 2022.
International Searching Authority, "International Search Report and Written Opinion", From Application No. PCT/US2024/060401, Mailed Feb. 14, 2025, p. 14.
"Foot and Ankle Instrument Set," Smith & Nephew, 2013, 2 pages.
"Lapidus Pearls: Gaining Joint Exposure to Decrease Non-Union," Youtube, Retrieved online from <https://www.youtube.com/watch?v=-jqJyE7pj-Y>, dated Nov. 2, 2009, 3 pages.
"Reconstructive Surgery of the Foot & Ankle," The Podiatry Institute, Update 2015, Conference Program, May 2015, 28 pages.
"Speed Continuous Active Compression Implant," BioMedical Enterprises, Inc., A120-029 Rev. 3, 2013, 4 pages.
"Visionaire: Patient Matched Cutting Blocks Surgical Procedure," Smith & Nephew, Inc., 2009, 2 pages.
ACUMED "Acumed Osteotomy System" with partial English Translation, 2014, p. 19.
Additive Orthopaedics, "The First and Only FDA Approved Patient Specific Talus Spacer" , https://totaltalusreplacement.com, Downloaded: Mar. 4, 2022, p. 11.
Aiyer et al. "Prevalence of Metatarsus Adductus in Patients Undergoing Hallux Valgus Surgery" Foot & Ankle International 2014, vol. 35(12), pp. 1292-1297.
Albano et al. "Biomechanical Study of Transcortical or Transtrabecular Bone Fixation of Patellar Tendon Graft With Bioabsorbable Pins in Acl Reconstruction in Sheep" Rev Bras Ortop. 2012, 47(1), pp. 43-49.
Alvine et al. "Peg and Dowel Fusion of the Proximal Interphalangeal Joint" Foot & Ankle vol. 1, No. 2, 1980 American Orthopaedic Foot Society, p. 5.
ARTHREX "Chevron Osteotomy" https://www.arthrex.com/foot-ankle/chevron-osteotomy, Retrieved Nov. 30, 2022, p. 7.
ARTHREX "Comprehensive Foot System" https://www.arthrex.com/resources/animation/8U3iaPvY6kO8bwFAwZF50Q/comprehensive-foot-system?referringTeam=foot_and_ankle, Published Aug. 27, 2013, p. 3.
Arthrex, "Distal Tibia Allograft Workstation for Glenoid Bone Loss, Surgical Technique" Arthrex.com, 2018, p. 8.
Baravarian, "Why the Lapidus Procedure is Ideal for Bunions" Podiatry Today, https://www.hmpgloballearningnetwork.com/site/podiatry/article/5542, May 2006 p. 8.
Bauer et al. "Offset-V Osteotomy of the First Metatarsal Shaft in Hallux Abducto Valgus" Chapter 29, McGlamry's Comprehensive Textbook of Foot and Ankle Surgery, Fourth Edition, 2013, p. 26.
Bednarz et al. "Modified Lapidus Procedure for the Treatment of Hypermobile Hallux Valgus" Foot & Ankle, American Orthopaedic Foot & Ankle Society, 2000, p. 6.
Bennett et al. "Intraosseous Sliding Plate Fixation Used in Double Osteotomy Bunionectomy" Foot & Ankle International, 2019, vol. 40(1), pp. 85-88.
BIOPRO "Accu-Cut Osteotomy Guide System Accurate and consistent hallux valgus correction" Document Dates Sep. 16, 2019, p. 2.
Boffeli et al. "Can We Abandon Saw Wedge Resection in Lapidus Fusion? A Comparative Study of Joint Preparation Techniques Regarding Correction of Deformity, Union Rate, and Preservation of First Ray Length" The Journal of Foot & Ankle Surgery, 58, 2019, pp. 1118-1124.
Bouaicha et al. "Fixation of Maximal Shift Scarf Osteotomy with Inside-Out Plating: Technique Tip" Foot & Ankle International, vol. 32, No. 5, May 2011, pp. 567-569.
Buda et al. "Effect of Fixation Type and Bone Graft on Tarsometatarsal Fusion" Foot & Ankle International 2018, vol. 39(12), pp. 1394-1402.
Carr et al. "Correctional Osteotomy for Metatarsus Primus Varus and Hallux Valgus*" The Journal of Bone and Joint Surgery, vol. 50-A, No. 7, Oct. 1968, pp. 1353-1367.
Catanese et al. "Measuring Sesamoid Position in Hallux Valgus When Is the Sesamoid Axial View Necessary?" Foot & Ankle Specialist, Downloaded Aug. 15, 2016, pp. 1-3.

(56) References Cited

OTHER PUBLICATIONS

Chesser et al. "New Advances With The Tarsometatarsal" Podiatry Today, vol. 30, Issue 10, Oct. 2017, pp. 28-36.
Chomej et al. "Lateralising Dmmo (Mis) for simultaneous correction of a pes adductus during surgical treatment of a hallux valgus" Journal Pre-proof, The Foot, Accepted Jul. 16, 2020, p. 33.
Cichero et al. "Different fixation constructs and the risk of non-union following first metatarsophalangeal joint arthrodesis" Foot and Ankle Surgery, 27, 2021, Accepted Oct. 15, 2020, pp. 789-792.
Coetzee et al., "Revision Hallux Valgus Correction," Operative Techniques in Foot and Ankle Surgery, Section I, Chapter 15, 2011, pp. 84-96.
Collan et al., "The biomechanics of the first metatarsal bone in hallux valgus: A preliminary study utilizing a weight bearing extremity CT," Foot and Ankle Surgery, vol. 19, 2013, pp. 155-161.
"Futura Forefoot Implant Arthroplasty Products," Tornier, Inc., 2008, 14 pages.
"Hat-Trick Lesser Toe Repair System, Foot and Ankle Technique Guide, Metatarsal Shortening Osteotomy Surgical Technique," Smith & Nephew, 2014, 16 pages.
"Hat-Trick Lesser Toe Repair System," Smith & Nephew, Brochure, Aug. 2014, 12 pages.
"Hoffmann II Compact External Fixation System", Stryker, Brochure, Literature No. 5075-1-500, 2006, 12 pages.
"Hoffmann II Micro Lengthener", Stryker, Operative Technique, Literature No. 5075-2-002, 2008, 12 pages.
"Hoffmann Small System External Fixator Orthopedic Instruments," Stryker, retrieved Dec. 19, 2014, from the Internet: <http://www.alibaba.com/product-detail/Stryker-Hoffmann-Small-System-External-Fixator_1438850129.html>, 3 pages.
Patient to Patient Precision, Accu-Cut, Osteotomy Guide System, BioPro, Foot & Ankle International Journal, vol. 23, No. 8, Aug. 2002, 2 pages.
Blomer Problems and complications of knee endoprostheses from a manufacturer's point of view "Orthopade 200, 29, pp. 688-696, English Abstract."
"Prophecy Inbone Preoperative Navigation Guides", Wright Medical Technology, Inc., Nov. 2013, 6 pages.
"RAYHACK Ulnar Shortening Generation II Low-Profile Locking System Surgical Technique," Wright Medical Technology, Inc., Dec. 2013, 20 pages.
Smith & Nephew scores a Hat-Trick with its entry into the high-growth hammer toe repair market, Smith & Nephew, Jul. 31, 2014, 2 pages.
"Lag Screw Target Bow," Stryker Leibinger GmbH & Co. KG, Germany 2004, 8 pages.
Anderson et al., "Uncemented STAR Total Ankle Protheses" Journal of Bone Joint Surgery America, Sep. 2004, Abstract of Article, p. 6.
Coetzee et al., "The Lapidus Procedure: A Prospective Cohort Outcome Study," Foot & Ankle International, vol. 25, No. 8, Aug. 2004, pp. 526-531.
Claim Chart for Fishco, "A Straightforward Guide to the Lapidus Bunionectomy," HMP Global (Sep. 6, 2013), Exhibit B2 of Defendant Fusion Orthopedics LLC's Invalidity Contentions, No. CV-22-00490-PHX-SRB, US District Court for the District of Arizona, Aug. 27, 2022, 67 pages.
Claim Chart for Fishco, "Making the Lapidus Easy," The Podiatry Institute (Apr. 2014), Exhibit B1 of Defendant Fusion Orthopedics LLC's Invalidity Contentions, No. CV-22-00490-PHX-SRB, US District Court for the District of Arizona, Aug. 27, 2022, 97 pages.
Claim Chart for Groves Public Use (Mar. 26, 2014), Exhibit B4 of Defendant Fusion Orthopedics LLC's Invalidity Contentions, No. CV-22-00490-PHX-SRB, US District Court for the District of Arizona, Aug. 27, 2022, 161 pages.
Claim Chart for Groves, "Functional Position Joint Sectioning: Pre-Load Method for Lapidus Arthrodesis," Update 2015: Proceedings of the Annual Meeting of the Podiatry Institute, Chpt. 6, pp. 23-29 (Apr. 2015), Exhibit B3 of Defendant Fusion Orthopedics LLC's Invalidity Contentions, No. CV-22-00490-PHX-SRB, US District Court for the District of Arizona, Aug. 27, 2022, 151 pages.
Claim Chart for Mote, "First Metatarsal-Cuneiform Arthrodesis for the Treatment of First Ray Pathology: A Technical Guide," The Journal Foot & Ankle Surgery (Sep. 1, 2009), Exhibit B5 of Defendant Fusion Orthopedics LLC's Invalidity Contentions, No. CV-22-00490-PHX-SRB, US District Court for the District of Arizona, Aug. 27, 2022, 21 pages.
Claim Chart for U.S. Pat. No. 10,376,268 to Fallin et al., entitled "Indexed Tri-Planar Osteotomy Guide and Method," issued Aug. 13, 2019, Exhibit B6 of Defendant Fusion Orthopedics LLC's Invalidity Contentions, No. CV-22-00490- Phx-Srb, US District Court for the District of Arizona, Aug. 27, 2022, 155 pages.
Claim Chart for U.S. Pat. No. 8,282,645 to Lawrence et al., entitled "Metatarsal Bone Implant Cutting Guide," issued Jan. 18, 2010, Exhibit B7 of Defendant Fusion Orthopedics LLC's Invalidity Contentions, No. CV-22-00490-PHX-SRB, US District Court for the District of Arizona, Aug. 27, 2022, 76 pages.
Claim Chart for U.S. Pat. No. 9,452,057 to Dacosta et al., entitled "Bone Implants and Cutting Apparatuses and Methods," issued Apr. 8, 2011, Exhibit B8 of Defendant Fusion Orthopedics LLC's Invalidity Contentions, No. CV-22-00490-PHX-SRB, US District Court for the District of Arizona, Aug. 27, 2022, 110 pages.

* cited by examiner

PATIENT-SPECIFIC OSTEOTOMY SYSTEMS, METHODS, AND INSTRUMENTATION

CROSS-REFERENCE TO RELATED APPLICATIONS

This application claims the benefit of U.S. Provisional Application No. 63/610,303, filed Dec. 14, 2023, which is hereby incorporated by reference in its entirety.

TECHNICAL FIELD

The present disclosure relates to surgical devices, systems, instruments, and methods. More specifically, the present disclosure relates to patient-specific osteotomy instruments, implants, instruments, and/or methods of designing and using the same.

BACKGROUND

Various bone conditions may be corrected using surgical procedures, in which one or more tendons, ligaments, and/or bones may be cut, replaced, repositioned, reoriented, reattached, reduced, fixated and/or fused. These surgical procedures require the surgeon to accurately locate, position, deploy, and/or orient one or more osteotomy cuts, fixation guides, fixators, bone tunnels, implants, points of attachment for ends of grafts or soft tissue, and the like. Determining and locating an optimal location and trajectory for one or more steps of the surgical procedures and/or securing instruments that can guide or assist in steps of the surgical procedures such as performing osteotomies, deploying fixation and/or implants, and the like, can be challenging, given conventional techniques and instruments. For example, in a Lapidus surgical procedure or other procedure that is part of or intended to address a bunion deformity, performance of the osteotomies for the surgical procedures can be a challenge because of the small size of the bone(s), joints, and/or instruments involved in surgical procedure.

In a surgical procedure a surgeon desires clarity and assurance that the planned procedure will lead to the desired outcome. Thus, a surgeon may spend significant time planning and preparing for the surgical procedure before initiating the surgical procedure. One of the challenges with conventional techniques is how to translate, map, or convert from a model of a patient's anatomy and/or virtual instrumentation to the real, physical world for performing a surgical procedure. Often the ability for a surgeon to visualize intraoperatively where osteotomy cuts will be made using a given guide BEFORE the cuts are made can greatly increase the confidence of a surgeon that the desired outcome will be achieved.

Furthermore, surgical procedures can be extra challenging when working on anatomy such as bones of a patient's ankle, foot, or hand which are small in comparison to other bones, have unique surface configurations, landmarks, and/or deformities that called for extra accuracy and/or precision. In certain surgical procedures such as a joint fusion, arthroplasty, and/or arthrodesis one goal may be to minimize the amount of bone removed in order to successfully fuse the joint. Accomplishing this goal can require extra precision and accuracy in resecting the bone(s), reducing the bones, and/or deploying fixation to achieve a successful outcome.

What is needed is one or more instruments to facilitate locating, aligning, orienting, planning, mapping from virtual models to physical anatomy, preparing for, initiating, executing, and/or completing such surgical procedures. In addition, what is needed is methods, apparatus, systems, implants and/or instrumentation that is customized to a specific patient. In addition, what is needed is methods, apparatus, systems, implants and/or instrumentation that includes direct input from the surgeon to perform a surgical procedure customized to a particular patient. Existing solutions for guiding orthopedic surgical procedures are inadequate and/or error prone.

SUMMARY

The various apparatus, devices, systems, and/or methods of the present disclosure have been developed in response to the present state of the art and, in particular, in response to the problems and needs in the art that have not yet been fully solved by currently available technology.

In one general aspect, a resection guide may include a bone engagement feature configured to engage at least a portion of at least one foot bone to position the resection guide. The resection guide may also include a feature where the bone engagement feature is at least partially determined based on a model of a patient's foot, the model defined based on medical imaging of the patient's foot.

The guide may furthermore include a resection feature extending through the resection guide from a superior side of the resection guide to an inferior side. The resection feature is configured to guide a cutting tool to form a first osteotomy in a first bone along a first trajectory. The guide may also include a first bone attachment feature configured to engage the first bone and a second bone attachment feature configured to engage a second bone. Other embodiments of this aspect may include corresponding computer systems, apparatus, and computer programs recorded on one or more computer storage devices, each configured to perform the actions of the methods.

Implementations may include one or more of the following features: a resection guide where the resection feature is configured to provide visibility of an anatomical structure inferior to the resection guide when in use; a resection guide that includes a window extending from the superior side of the resection guide to the inferior side. The window provides visibility of an anatomical structure inferior to the resection guide when in use. The window may include an opening coupled to the resection feature. The window is configured to provide visibility of a distal end of the first bone and a proximal end of the second bone. The bone engagement feature is on an inferior side of the resection guide and is configured to extend from a medial surface of the at least one foot bone over a dorsal surface of the at least one foot bone and to a lateral surface of the at least one foot bone.

The resection feature is configured to guide the cutting tool to form a second osteotomy in the second bone along a second trajectory. The second bone attachment feature is positioned relative to the first bone attachment feature such that reduction of the first osteotomy and the second osteotomy aligns the second bone attachment feature and the first bone attachment feature and rotates the second bone within a frontal plane. The resection guide may include an alignment guide configured to identify a position of the second bone relative to a third bone of the patient. The resection guide may include a landmark registration feature configured to engage a landmark of the patient.

The landmark registration feature extends from a distal side of the resection guide, and the landmark registration feature is configured to engage a base of one of the first bone and the second bone. The landmark may include a feature of an implant deployed in the patient in a prior surgical procedure. Implementations of the described techniques may include hardware, a method or process, or a computer tangible medium.

In one general aspect, a resection guide may include a resection feature extending through the resection guide from a superior side of the resection guide to an inferior side. The resection feature is configured to guide a cutting tool to form a first osteotomy in a first bone along a first trajectory. The resection guide may also include a soft tissue engagement feature configured to engage at least a portion of soft tissue when the resection guide is used. The guide may include a first bone attachment feature configured to accept a first fastener that engages the first bone and a second bone attachment feature configured to accept a second fastener that engages a second bone. Other embodiments of this aspect include corresponding computer systems, apparatus, and computer programs recorded on one or more computer storage devices, each configured to perform the actions of the methods.

Implementations may include one or more of the following features: a resection guide where the resection feature may include an accommodation feature having a first surface and a second surface that connect at an edge. The second surface is angled relative to the first surface such that the second surface avoids contact with one or more anatomical structures of the patient when the resection guide is positioned for use. The resection guide may include a window extending from the superior side of the resection guide to the inferior side. The window provides visibility of an anatomical structure inferior to the resection guide when in use. The resection feature may include a radiolucent portion configured to provide medical imaging visibility of an anatomical structure inferior to the resection guide when in use. The resection guide may include an alignment guide configured to indicate a corrected position of the second bone relative to another bone of the patient. Implementations of the described techniques may include hardware, a method or process, or a computer tangible medium.

In one general aspect, a resection guide may include a bone engagement feature configured to engage at least a portion of at least one foot bone to position the resection guide. The resection guide may also include a soft tissue engagement feature configured to retain at least a portion of soft tissue within an operating field. The resection guide may furthermore include a proximal slot configured to guide a cutting tool to form a first osteotomy, a cuneiform. The proximal slot extends through the resection guide from a superior side to an inferior side along a first trajectory.

The resection guide may also include a distal slot configured to guide a cutting tool to form a second osteotomy in a metatarsal. The distal slot extends through the resection guide from the superior side to the inferior side along a second trajectory. The resection guide may moreover include a resection window between the proximal slot and the distal slot. The resection window extends from the superior side to the inferior side. The resection window is configured to enable observation of an articular surface of both the cuneiform and the metatarsal.

The resection guide may also include a first bone attachment feature configured to accept a first fastener that engages the cuneiform and a second bone attachment feature configured to accept a second fastener that engages the metatarsal. Other embodiments of this aspect may include corresponding computer systems, apparatus, and computer programs recorded on one or more computer storage devices, each configured to perform the actions of the methods.

Implementations may include one or more of the following features: a resection guide where one of the first trajectory and the second trajectory is at least partially determined based on a revised model of a patient's foot. The revised model may be defined based on changes made by a surgical procedure performed prior to using the resection guide for a second surgical procedure on a patient's foot. At least one of the first trajectory and the second trajectory is at least partially determined based on a tarsometatarsal (TMT) joint axis. The TMT joint axis is determined based on a model of a patient's foot. Implementations of the described techniques may include hardware, a method or process, or a computer tangible medium.

BRIEF DESCRIPTION OF THE DRAWINGS

The advantages, nature, and additional features of exemplary embodiments of the disclosure will become more fully apparent from the following description and appended claims, taken in conjunction with the accompanying drawings. Understanding that these drawings depict only exemplary embodiments and are, therefore, not to be considered limiting of the disclosure's scope, the exemplary embodiments of the disclosure will be described with additional specificity and detail through use of the accompanying drawings.

DETAILED DESCRIPTION

Figure 1A:
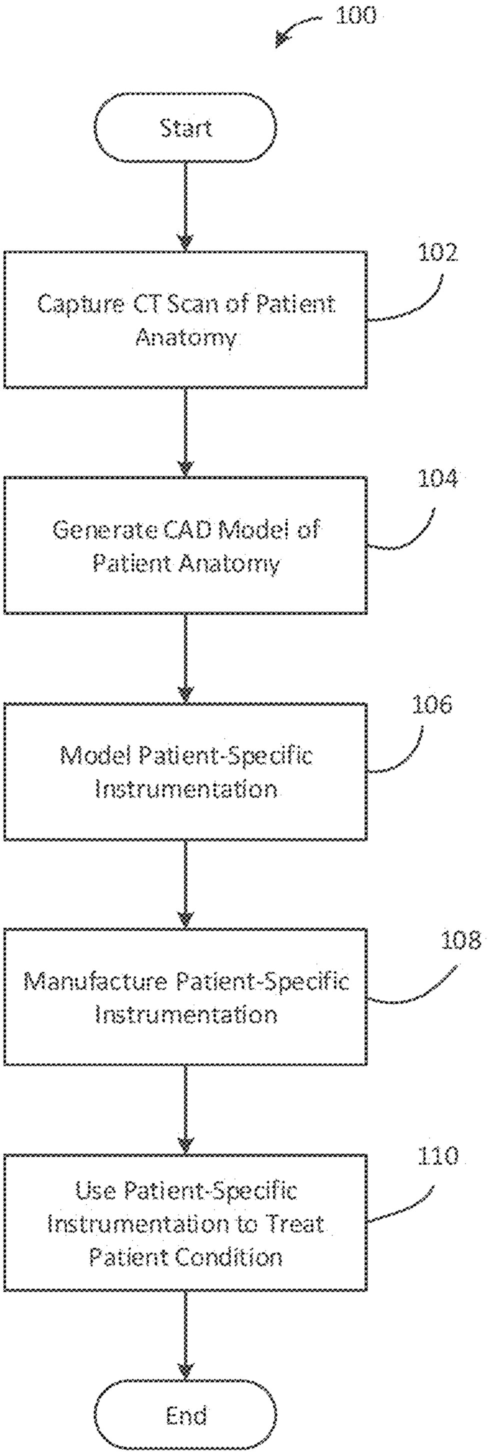
FIG. 1A is a flowchart diagram depicting a method for remediating a condition, according to one embodiment.

Exemplary embodiments of the disclosure will be best understood by reference to the drawings, wherein like parts are designated by like numerals throughout. It will be readily understood that the components, as generally described and illustrated in the Figures herein, could be arranged and designed in a wide variety of different configurations. Thus, the following more detailed description of the embodiments of the apparatus, system, and method is not intended to limit the scope of the disclosure but is merely representative of exemplary embodiments.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature can pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Standard medical planes of reference and descriptive terminology are employed in this disclosure. While these terms are commonly used to refer to the human body, certain terms are applicable to physical objects in general. A standard system of three mutually perpendicular reference planes is employed. A sagittal plane divides a body into right and left portions. A coronal plane divides a body into anterior and posterior portions. A transverse plane divides a body into superior and inferior portions. A mid-sagittal, mid-coronal, or mid-transverse plane divides a body into equal portions, which may be bilaterally symmetric. The intersection of the sagittal and coronal planes defines a superior-inferior or cephalad-caudal axis. The intersection of the sagittal and transverse planes defines an anterior-posterior axis. The intersection of the coronal and transverse planes defines a medial-lateral axis. The superior-inferior or cephalad-caudal axis, the anterior-posterior axis, and the medial-lateral axis are mutually perpendicular.

Anterior means toward the front of a body. Posterior means toward the back of a body. Superior or cephalad means toward the head. Inferior or caudal means toward the feet or tail. Medial means toward the midline of a body, particularly toward a plane of bilateral symmetry of the body. Lateral means away from the midline of a body or away from a plane of bilateral symmetry of the body. Axial means toward a central axis of a body. Abaxial means away from a central axis of a body. Ipsilateral means on the same side of the body. Contralateral means on the opposite side of the body from the side which has a particular condition or structure. Proximal means toward the trunk of the body. Proximal may also mean toward a user, viewer, or operator. Distal means away from the trunk. Distal may also mean away from a user, viewer, or operator. Dorsal means toward the top of the foot or other body structure. Plantar means toward the sole of the foot or toward the bottom of the body structure.

Antegrade means forward moving from a proximal location/position to a distal location/position or moving in a forward direction. Retrograde means backward moving from a distal location/position to a proximal location/position or moving in a backwards direction. Sagittal refers to a midline of a patient's anatomy, which divides the body into left or right halves. The sagittal plane may be in the center of the body, splitting it into two halves. Prone means a body of a person lying face down. Supine means a body of a person lying face up.

As used herein, "coupling", "coupling member", or "coupler" refers to a mechanical device, apparatus, member, component, system, assembly, or structure, that is organized, configured, designed, arranged, or engineered to connect, or facilitate the connection of, two or more parts, objects, or structures. In certain embodiments, a coupling can connect adjacent parts or objects at their ends. In certain embodiments, a coupling can be used to connect two shafts together at their ends for the purpose of transmitting power. In other embodiments, a coupling can be used to join two pieces of rotating equipment while permitting some degree of misalignment or end movement or both. In certain embodiments, couplings may not allow disconnection of the two parts, such as shafts during operation. (Search "coupling" on Wikipedia.com Jul. 26, 2021. CC-BY-SA 3.0 Modified. Accessed Jul. 27, 2021.) A coupler may be flexible, semi-flexible, pliable, elastic, or rigid. A coupler may join two structures either directly by connecting directly to one structure and/or directly to the other or indirectly by connecting indirectly (by way of one or more intermediary structures) to one structure, to the other structure, or to both structures.

"Patient specific" refers to a feature, an attribute, a characteristic, a structure, function, structure, device, guide, tool, instrument, apparatus, member, component, system, assembly, module, or subsystem or the like that is adjusted, tailored, modified, organized, configured, designed, arranged, engineered, and/or fabricated to specifically address the anatomy, physiology, condition, abnormalities, needs, or desires of a particular patient or surgeon serving the particular patient. In one aspect, a patient specific attribute or feature is unique to a single patient and may include features unique to the patient such as a number of cut channels, a number of bone attachment features, a number of bone engagement surfaces, a number of resection features, a depth of one or more cutting channels, an angle for one or more resection channels, a surface contour, component position, component orientation, a trajectory for an instrument, implant, or anatomical part of a patient, a lateral offset, and/or other features.

“Patient-specific positioning guide” or “Patient-specific positioner” refers to an instrument, implant, positioner, structure, or guide designed, engineered, and/or fabricated for use as a positioner with a specific patient. In one aspect, a patient-specific positioning guide is unique to a patient and may include features unique to the patient such as patient-specific offsets, translation distances, openings, angles, orientations, anchor a surface contour or other features.

“Patient-specific cutting guide” refers to a cutting guide designed, engineered, and/or fabricated for use with a specific patient. In one aspect, a patient-specific cutting guide is unique to a patient and may include features unique to the patient such as a surface contour or other features.

“Patient-specific resection guide” refers to a guide designed, engineered, and/or fabricated for use in resection for a specific patient. In one aspect, a patient-specific resection guide is unique to a patient and may include features unique to the patient such as a surface contour or other features.

“Patient-specific trajectory guide” refers to a trajectory guide designed, engineered, and/or fabricated for use with a specific patient. In one aspect, a patient-specific trajectory guide is unique to a single patient and may include features unique to the patient such as a surface contour or other features.

“Patient specific instrument” (PSI) refers to a structure, device, guide, tool, instrument, apparatus, member, component, system, assembly, module, or subsystem that is adjusted, tailored, modified, organized, configured, designed, arranged, engineered, and/or fabricated to specifically address the anatomy, physiology, condition, abnormalities, needs, or desires of a particular patient. In certain aspects, one patient. In one aspect, a patient specific instrument is unique to a single patient and may include features unique to the patient such as a surface contour, component position, component orientation, and/or other features. In other aspects, one patient specific instrument may be useable with a number of patients having a particular class of characteristics.

As used herein, a “handle” or “knob” refers to a structure used to hold, control, or manipulate a device, apparatus, component, tool, or the like. A “handle” may be designed to be grasped and/or held using one or two hands of a user. In certain embodiments, a handle or knob may be an elongated structure. In one embodiment, a knob may be a shorter stubby structure.

As used herein, “implant” refers to a medical device manufactured to replace a missing biological structure, support a damaged biological structure, or enhance an existing biological structure. Often medical implants are man-made devices, but implants can also be natural occurring structures. The surface of implants that contact the body may be made of, or include a biomedical material such as titanium, cobalt chrome, stainless steel, carbon fiber, another metallic alloy, silicone, polymer, Synthetic polyvinyl alcohol (PVA) hydrogels, biomaterials, biocompatible polymers such as PolyEther Ether Ketone (PEEK) or a polylactide polymer (e.g. PLLA) and/or others, or apatite, or any combination of these depending on what is functional and/or economical. Implants can have a variety of configurations and can be wholly, partially, and/or include a number of components that are flexible, semiflexible, pliable, elastic, supple, semi-rigid, or rigid. In some cases, implants contain electronics, e.g. artificial pacemaker and cochlear implants. Some implants are bioactive, such as subcutaneous drug delivery devices in the form of implantable pills or drug-eluting stents. Orthopedic implants may be used to alleviate issues with bones and/or joints of a patient’s body. Orthopedic implants can be used to treat bone fractures, osteoarthritis, scoliosis, spinal stenosis, discomfort, and pain. Examples of orthopedic implants include, but are not limited to, a wide variety of pins, rods, screws, anchors, spacers, sutures, all-suture implants, ball all-suture implants, self-locking suture implants, cross-threaded suture implants, plates used to anchor fractured bones while the bones heal or fuse together, and the like. (Search “implant (medicine)” on Wikipedia.com May 26, 2021. CC-BY-SA 3.0 Modified. Accessed Jun. 30, 2021.)

As used herein, a “body” refers to a main or central part of a structure. The body may serve as a structural component to connect, interconnect, surround, enclose, and/or protect one or more other structural components. A body may be made from a variety of materials including, but not limited to, metal, plastic, ceramic, wood, fiberglass, acrylic, carbon, biocompatible materials, biodegradable materials or the like. A body may be formed of any biocompatible materials, including but not limited to biocompatible metals such as Titanium, Titanium alloys, stainless steel alloys, cobalt-chromium steel alloys, nickel-titanium alloys, shape memory alloys such as Nitinol, biocompatible ceramics, and biocompatible polymers such as Polyether ether ketone (PEEK) or a polylactide polymer (e.g., PLLA) and/or others. In one embodiment, a body may include a housing or frame, or framework for a larger system, component, structure, or device. A body may include a modifier that identifies a particular function, location, orientation, operation, and/or a particular structure relating to the body. Examples of such modifiers applied to a body, include, but are not limited to, “inferior body,” “superior body,” “lateral body,” “medial body,” and the like.

As used herein, “bone engagement surface” refers to a surface of an object, instrument, or apparatus, such as an implant that is oriented toward or faces one or more bones of a patient. In one aspect, the bone engagement surface may abut, touch, or contact a surface of a bone. In another aspect, the bone engagement surface or parts of the bone engagement surface may be close to, but not abut, touch, or contact a surface of the bone. In certain aspects, the bone engagement surface can be configured to engage with a surface of one or more bones. Such a bone engagement surface may include projections and recesses that correspond to and match projections and recesses of the one or more bone surfaces. In certain embodiments, a bone engagement surface is an implementation and/or part of a structure that implements a bone engagement feature.

“Bone engagement feature” refers to a structure, feature, component, aspect configured to contact, touch, abut, and/or engage with a bone, a bone part, bony topography (e.g., bone spurs and calcifications), anatomical bone feature, and/or a bone fragment. A bone engagement feature may enable temporary engagement with a bone or bone fragment or permanent engagement with a bone or bone fragment. A bone engagement feature may include a bone engagement surface and/or a body section that supports the bone engagement surface. In certain embodiments, a bone engagement feature may include a bone probe or a joint seeker. In one embodiment, a bone engagement feature may include a landmark registration feature. Alternatively, or in addition, a bone engagement feature can include a bone attachment feature configured to engage with bone and/or to cooperate with a fastener to engage with bone.

A patient-specific bone engagement feature is a bone engagement feature that includes one or more aspects that are patient-specific. The patient-specific aspects can include, but are not limited to, a surface contour, a contour for a part of a surface, a position for a resection feature, a size, shape and/or configuration of a resection feature, a position, size, shape, and/or number of bone attachment features, or the like.

"Frangible" refers to a type of material designed, engineered, and/or configured to break easily under an expected force. Frangible objects may be designed to break easily under the expected force to provide a safety feature, a convenience feature, or the like. Frangible objects can be made from metal, plastic, ceramics, wood, paper, or the like. Frangible also includes something that is breakable or fragile; especially something that is intentionally made so. (Search "frangible" on wordhippo.com. WordHippo, 2023. Web. Accessed 11 May 2023. Modified.)

As used herein, "side" refers to a structure or part of a structure including, but not limited to one of a longer bounding surfaces or lines of an object especially contrasted with the ends, a line or surface forming a border or face of an object, either surface of a thin object, a bounding line or structure of a geometric figure or shape, and the like. (search "side" on Merriam-Webster.com. Merriam-Webster, 2021. Web. 3 Aug. 2021. Modified.) A side can also refer to a geometric edge of a polygon (two-dimensional shape) and/or a face or surface of a polyhedron (three-dimensional shape). (Search "side" on Wikipedia.com Jul. 21, 2021. CC-BY-SA 3.0 Modified. Accessed Aug. 3, 2021.) Side can also refer to a location on a structure. For example, a side can be a location on a structure at, or near, a furthest position away from a central axis of the structure. As used herein, the term "side" can include one or more modifiers that define and/or orient and/or distinguish the side of an object from others based on based on where and/or how the object is deployed within or in relation to a second object. For example, in the context of an implant for a patient, sides of the implant may be labeled based on where the sides are relative to the patient when the implant is deployed. As one example, an "anterior side" of an implant, instrument, anatomical structure, or other structure refers to a side that is anterior to other sides of the structure in relation to a patient when the structure is deployed in the patient. As another example, in the context of an instrument used with a patient, sides of the instrument may be labeled based on where the sides are when the instrument is being used for its purpose. As one example, a "front side" of an instrument refers to a side that is facing a user of the instrument when the instrument is in use.

As used herein, a "deploy" or "deployment" refers to an act, action, process, system, method, means, or apparatus for inserting an implant or prosthesis into a part, body part, and/or patient. "Deploy" or "deployment" can also refer to an act, action, process, system, method, means, or apparatus for placing something into therapeutic use. A device, system, component, medication, drug, compound, or nutrient may be deployed by a human operator, a mechanical device, an automated system, a computer system or program, a robotic system, or the like.

"Tissue" refers to a structure that makes up a one or more anatomical structures of a patient. Tissue can be soft tissue or hard tissue. "Soft tissue" refers to tissue of a patient. Examples of soft tissue include but are not limited to skin, ligament, tendon, fascia, fat muscle, fibrous tissue, blood vessels, lymph vessels, brain tissue, and/or nerves. "Hard tissue" refers to any human tissue that is not soft tissue. Examples of hard tissue include bone, teeth, tooth enamel, dentin, cementum, cartilage, or the like.

"Topographical" refers to the physical distribution of parts, structures, or features on the surface of, or within, an organ or other anatomical structure, or organism. (Search "define topographical" on google.com. Oxford Languages, Copyright 2022. Oxford University Press. Web., Modified. Accessed 15 Feb. 2022.)

As used herein, a "marking" or "marker" refers to a symbol, letter, lettering, word, phrase, icon, design, color, diagram, indicator, figure, structure, device, apparatus, surface, component, system, or combination of these designed, intended, structured, organized, configured, programmed, arranged, or engineered to communication information and/or a message to a user receiving, viewing, or encountering the marking. The marking or "marker" can include one or more of a tactile signal, a visual signal or indication, an audible signal, and the like. In one embodiment, a marking may comprise a number or set letters, symbols, or words positioned on a surface, structure, color, color scheme, or device to convey a desired message or set of information.

As used herein, an "indicator" refers to an apparatus, device, component, system, assembly, mechanism, hardware, software, firmware, circuit, module, set of data, text, number, code, symbol, a mark, or logic structured, organized, configured, programmed, designed, arranged, or engineered to convey information or indicate a state, condition, mode, context, location, or position to another apparatus, device, component, system, assembly, mechanism, hardware, software, firmware, circuit, module, and/or a user of an apparatus, device, component, system, assembly, mechanism, hardware, software, firmware, circuit, module that includes, or is associated with the indicator. The indicator can include one or more of an audible signal, a token, a presence of a signal, an absence of a signal, a tactile signal, a visual signal or indication, a visual marker, a visual icon, a visual symbol, a visual code, a visual mark, and/or the like. In certain embodiments, "indicator" can be used with an adjective describing the indicator. For example, a "mode indicator" is an indicator that identifies or indicates a mode.

"Boundary" refers to a structure, line, or area where an object, surface, line, area, or operation is or is expected to begin and/or end. A boundary can be similar to a border.

"Landmark registration feature" or "Landmark" refers to a structure configured to engage with a feature, aspect, attribute, or characteristic of a first object to orient and/or position a second object that includes the landmark registration feature with respect to the first object. A variety of structures can serve as a landmark registration feature. For example, a landmark registration feature may include a protrusion, a projection, a tuberosity, a cavity, a void, a divot, a tab, an extension, a hook, a curve, or the like. In the context of bones of a patient a landmark registration feature can include any protuberance, void, divot, concave section, sesamoid, bone spur or other feature on, or extending from, a bone of a patient. A landmark refers to any structure of an anatomical structure that is referenced, contacted, engaged with and/or associated with a landmark registration feature.

"Probe bone engagement surface" refers to a bone engagement surface on one surface of a probe or part of a probe.

"Bone attachment feature" refers to a structure, feature, component, aspect configured to securely connect, couple, attach, and/or engage a structure, component, object, or body with a bone and/or a bone fragment. Examples of a bone attachment feature, include, but are not limited to, a pin, a spike, a tine, a K-wire, a screw, or other fastener alone, or in combination with, a hole, passage, and/or opening.

As used herein, "patient-specific osteotomy procedure" refers to an osteotomy procedure that has been adjusted, tailored, modified, or configured to specifically address the needs or desires or a particular patient. In certain aspects, one patient-specific osteotomy procedure may be useable in connection with only one patient. In other aspects, one patient-specific osteotomy procedure may be useable with a number of patients having a particular class of characteristics.

"Ankle fusion procedure" refers to a surgical procedure that seeks to immobilize an ankle joint of a patient. The surgery fuses two or more bones of the ankle of the patient. The surgery involves the use of screws, plates, medical nails, and other hardware or fasteners to achieve bone union. Ankle fusion is considered to be the gold standard for treatment of end-stage ankle arthritis. Ankle fusion trades joint mobility for relief from pain. (Search "ankle fusion" on Wikipedia.com Dec. 21, 2022. CC-BY-SA 3.0 Modified. Accessed Jun. 28, 2023.) An ankle fusion procedure may also be referred to as ankle arthrodesis, talocrural joint fusion, tibiotalar arthrodesis, and tibiotalocalcaneal arthrodesis. An ankle fusion procedure can be performed using a variety of approaches to the ankle including an anterior approach, a posterior approach, a lateral approach and a medial approach. Each approach may use common or different instrumentation or implants for the procedure.

"Deformity" refers to any abnormality in or of an organism, a part of an organism, or an anatomical structure of a patient that appears or functions differently than is considered normal, or is common, in relation to the same organism, a part of an organism, or an anatomical structure of other subjects of the same species as the patient. (Search "deformity" on Wikipedia.com Jun. 13, 2023. CC-BY-SA 3.0 Modified. Accessed Jun. 28, 2023.)

A "deformed position" refers to an anatomical structure positioned to form, include, or is at least part of a deformity. A "corrected position" refers to an anatomical structure positioned to remediate, correct, eliminate, and/or overcome a deformity.

"User directions" refers to any request, instruction, direction, input, feedback, prescription, designation, order, directive, or the like from a user of an apparatus, system, device, component, subsystem, or other object. User directions can be created, sent, and/or received in a variety of forms and/or formats, including, but not limited to, a user action in a user interface, a prescription, a form, a conversation, an electronic mail message, a text message, a gesture by the user, or the like. In the context of an osteotomy procedure, user directions can include a set of default settings or choices or instructions for fabrication of a patient-specific instrument or set of instruments, an online form completed by a user (e.g., surgeon), a set of modifications to an original set of user directions, and the like.

"Position" refers to a place or location. (Search "position" on wordhippo.com. WordHippo, 2022. Web. Modified. Accessed 9 Aug. 2022.) Often, a position refers to a place or location of a first object in relation to a place or location of another object. One object can be positioned on, in, or relative to a second object. In addition, a position can refer to a place or location of a first object in relation to a place or location of another object in a virtual environment. For example, a model of one object can be positioned relative to a model of another object in a virtual environment such as a modeling software program.

"Predetermined Position" refers to a position that is decided, determined, finalized, and/or defined earlier in time. In certain embodiments, a predetermined position is a desired, designed, and/or engineered position of a first object in relation to a second object. Thus, a predetermined position is a planned position for the two objects in relation to each other. In certain embodiments, one or both of the two objects may be moved relative to each other to accomplish the predetermined position and the predetermined position may become the final position. In other embodiments, the two objects may be moved towards the predetermined position but may not reach the exact predetermined position due to some impediment and/or interference or a decision to change the predetermined position to a new position. In certain aspects, a predetermined position may be a position that is decided after a process of recommendation, review, and/or analysis, and final approval such that a position may not become a predetermined position until the process is completed. For example, in a medical patient-specific instrument or technique design process a position may not become the predetermined position until a surgeon or other doctor provides final approval for the position.

"Contour" refers to an outline representing or bounding a shape or form of an object. Contour can also refer to an outside limit of an object, area, or surface of the object. (Search "contour" on wordhippo.com. WordHippo, 2023. Web. Modified. Accessed 13 Jun. 2023.)

As used herein, a "stop" refers to an apparatus, instrument, structure, member, device, component, system, or assembly structured, organized, configured, designed, arranged, or engineered to prevent, limit, impede, stop, or restrict motion or movement and/or operation of the another object, member, structure, component, part, apparatus, system, or assembly. In one embodiment, a stop may be used to manage and/or control a cutting tool.

As used herein, a "fastener", "fixation device", or "fastener system" refers to any structure configured, designed, or engineered to join two structures. Fasteners may be made of a variety of materials including metal, plastic, composite materials, metal alloys, plastic composites, and the like. Examples of fasteners include, but are not limited to screws, rivets, bolts, nails, snaps, hook and loop, set screws, bone screws, nuts, posts, pins, thumb screws, and the like. Other examples of fasteners include, but are not limited to wires, Kirschner wires (K-wire), anchors, bone anchors, plates, bone plates, intramedullary nails or rods or pins, implants, sutures, soft sutures, soft anchors, tethers, interbody cages, fusion cages, and the like.

In certain embodiments, the term fastener may refer to a fastener system that includes two or more structures configured to combine to serve as a fastener. An example of a fastener system is a rod or shaft having external threads and an opening or bore within another structure having corresponding internal threads configured to engage the external threads of the rod or shaft.

In certain embodiments, the term fastener may be used with an adjective that identifies an object or structure that the fastener may be particularly configured, designed, or engineered to engage, connect to, join, contact, or couple together with one or more other structures of the same or different types. For example, a "bone fastener" may refer to an apparatus for joining or connecting one or more bones, one or more bone portions, soft tissue and a bone or bone portion, hard tissue and a bone or bone portion, an apparatus and a bone or portion of bone, or the like.

In certain embodiments, a fastener may be a temporary fastener. A temporary fastener is configured to engage and serve a fastening function for a relatively short period of time. Typically, a temporary fastener is configured to be used until another procedure or operation is completed and/or until a particular event. In certain embodiments, a user may remove or disengage a temporary fastener. Alternatively, or in addition, another structure, event, or machine may cause the temporary fastener to become disengaged.

As used herein, a "fixator" refers to an apparatus, instrument, structure, device, component, member, system, assembly, or module structured, organized, configured, designed, arranged, or engineered to connect two bones or bone fragments or a single bone or bone fragment and another fixator to position and retain the bone or bone fragments in a desired position and/or orientation. Examples of fixators include both those for external fixation as well as those for internal fixation and include, but are not limited to pins, wires, Kirschner wires, screws, anchors, bone anchors, plates, bone plates, intramedullary nails or rods or pins, implants, interbody cages, fusion cages, and the like. Fixation refers to the act of deploying or using a fixator to fix two structures together.

As used herein, an "anchor" refers to an apparatus, instrument, structure, member, part, device, component, system, or assembly structured, organized, configured, designed, arranged, or engineered to secure, retain, stop, and/or hold, an object to or at a fixed point, position, or location. Often, an anchor is coupled and/or connected to a flexible member such as a tether, chain, rope, wire, thread, suture, suture tape, or other like object. Alternatively, or in addition, an anchor may also be coupled, connected, and/or joined to a rigid object or structure. In certain embodiments, an anchor can be a fixation device. Said another way, a fixation device can function as an anchor. In certain embodiments, the term anchor may be used as an adjective that describes a function, feature, or purpose for the noun the adjective 'anchor' describes. For example, an anchor hole is a hole that serves as or can be used as an anchor. In another embodiment, an anchor may be a hole or opening or a plurality of holes or openings.

"Connector" refers to any structure configured, engineered, designed, adapted, and/or arranged to connect one structure, component, element, or apparatus to another structure, component, element, or apparatus. A connector can be rigid, pliable, elastic, flexible, and/or semiflexible. Examples of a connector include but are not limited to any fastener. A connector can be a slot, channel, tube, pipe, opening, or other structure the connects and/or joins two slots, channels, tubes, pipes, openings, or other structures.

"Clearance" refers to a space or opening that provides an unobstructed area to permit one object to move freely in relation to another object.

"Correction," in a medical context, refers to a process, procedure, device, instrument, apparatus, system, implant, or the like that is configured, designed, developed, fabricated, configured, and/or organized to adjust, translate, move, orient, rotate, or otherwise change an anatomical structure from an original position, location, and/or orientation to a new position, location, and/or orientation that provides a benefit to a patient. The benefit may be one of appearance, anatomical function, pain relief, increased mobility, increased strength, and the like.

"Uniplanar correction" refers to a medical correction, which can include an osteo correction, in one plane (e.g., one of a sagittal plane, a transverse plane, and a coronal/frontal plane) of an anatomical structure such as a foot, hand, or body of a patient.

"Biplanar correction" refers to a medical correction, which can include an osteo correction, in two planes (e.g., two of a sagittal plane, a transverse plane, and a coronal/frontal plane) of an anatomical structure such as a foot, hand, or body of a patient.

"Triplane correction" refers to a medical correction, which can include an osteo correction, in three planes (e.g., all three planes of a sagittal plane, a transverse plane, and a coronal/frontal plane) of an anatomical structure such as a foot, hand, or body of a patient.

"Wedge Angle" refers to an angle measured between two surfaces of a wedge shape. A wedge angle can also be an angle between two sides of a wedge shape.

"Bone Wedge" refers to a geometric shape of one or more bones characterized by having two flat, planar, and/or inclined sides or surfaces that converge to form an edge. A bone wedge resembles a triangular prism, with one end wider or thicker than the other. (© ChatGPT August 3 Version, Modified, accessed chat.openai.com/chat Sep. 28, 2023). In certain implementations, the edge formed by the two converging sides is within a bone or set of bones from which the bone wedge is formed. In other implementations, the edge formed by the two converging sides is outside of a bone or set of bones from which the bone wedge is formed.

"Window" refers to an opening and/or a plurality of openings in a body, side, wall, side door, roof, vehicle, system, component, or other structure that allows the passage of electromagnetic radiation including radio ways, x-rays, visible light, light, and the like. A window may also permit passage of sound, gases, fluids, liquids, or other elements. (Search "window" on Wikipedia.com Aug. 31, 2022. Modified. Accessed Sep. 21, 2022.). A window can be opaque, semi-opaque, translucent, radiolucent, or transparent. A window can include a single opening having a single geometric shape or a plurality of openings each of a single geometric shape or combination of a variety of geometric shapes. In certain embodiments, a window may be referred to as a radiolucent window. A radiolucent window may permit passage of some or all radio ways through the window.

"Radiolucent" refers to any structure, apparatus, surface, device, system, feature, or aspect that permits radio waves to pass from one side of the radiolucent structure to the opposite side. The radio waves can be any radio wave including light, x-rays, and the like. A radiolucent structure, apparatus, surface, device includes structures that define an opening or hole (e.g., a structural opening) in the structure, apparatus, surface, device such that radio waves from one side of the structure, apparatus, surface, device pass through one or more openings or holes to an opposite side of the structure, apparatus, surface, device. A radiolucent structure, apparatus, surface, device also includes structures that comprise a solid material (e.g., no holes or openings, not a structural opening) that is configured to permit passage of one type of radio wave but not another type of radio wave. For example, a radiolucent structure, apparatus, surface, device may be made of a material such as a plastic or polymer which may prevent passage of one radio wave, such as light, from one side of the structure, apparatus, surface, device to the other, but may permit passage of another radio wave, such as X-rays from one side of the structure, apparatus, surface, device to the other. In such an embodiment, the radiolucent structure may be solid and prevent passage of light but may appear transparent when viewed using an X-ray machine or fluoroscopy machine.

"Resection Window" refers to a window designed, engineered, configured, manufactured, developed, and/or fabricated to facilitate performing a resection step or procedure.

"Probe" refers to a medical instrument used to explore, identify, locate, or register to, wounds, organs, and/or anatomical structures including a joint or an articular surface. In certain embodiments, a probe can be thin and/or pointed. In one embodiment, a probe is connected, integrated with, and/or coupled to another structure or instrument. In such an embodiment, the probe may serve to facilitate proper positioning of the another structure or instrument. For example, the probe may be used to identify and/or locate a particular anatomical structure and the positioning of the probe may then cause the connected structure or instrument to also be positioned in a desired location relative to one or more anatomical structures.

As used herein, "manufacturing tool" or "fabrication tool" refers to a manufacturing or fabrication process, tool, system, or apparatus which creates an object, device, apparatus, feature, or component using one or more source materials. A manufacturing tool or fabrication tool can use a variety of manufacturing processes, including but not limited to additive manufacturing, subtractive manufacturing, forging, casting, and the like. The manufacturing tool can use a variety of materials including polymers, thermoplastics, metals, biocompatible materials, biodegradable materials, ceramics, biochemicals, and the like. A manufacturing tool may be operated manually by an operator, automatically using a computer numerical controller (CNC), or a combination of these techniques.

"Friction fit" refers to a type of joint or connection that is created between two components by means of friction. A joint or connection that is formed using a friction fit may or may not include the use of additional fasteners such as screws, bolts, or adhesives. In a friction fit, the components are designed or configured to fit tightly together, creating enough friction between the surfaces to hold them securely in place, at least temporarily. The friction force is generated by the compressive force that is experienced between the components and can be strong enough to prevent the components from separating under normal conditions. (© ChatGPT March 23 Version, Modified, accessed chat.openai.com/chat May 2, 2023).

As used herein, "osteotomy procedure" or "surgical osteotomy" or "osteotomy" refers to a surgical operation in which one or more bones are cut to shorten or lengthen them or to change their alignment. The procedure can include removing one or more portions of bone and/or adding one or more portions of bone or bone substitutes. (Search "osteotomy" on Wikipedia.com Feb. 3, 22, 2021. CC-BY-SA 3.0 Modified. Accessed Feb. 15, 2022.) As used herein, "patient-specific osteotomy procedure" refers to an osteotomy procedure that has been adjusted, tailored, modified, or configured to specifically address the anatomy, physiology, condition, abnormalities, needs, or desires of a particular patient. In certain aspects, one patient-specific osteotomy procedure may be useable in connection with only one patient. In other aspects, one patient-specific osteotomy procedure may be useable with a number of patients having a particular class of characteristics. In certain aspects, a patient-specific osteotomy procedure may refer to a non-patient-specific osteotomy procedure that includes one or more patient-specific implants and/or instrumentation. In another aspects, a patient-specific osteotomy procedure may refer to a patient-specific osteotomy procedure that includes one or more patient-specific implants, patient-specific surgical steps, and/or patient-specific instrumentation.

"Wedge osteotomy" refers to an osteotomy procedure in which one or more wedges are used as part of the procedure. Generally, wedge osteotomies can be of one of two types, open wedge and closing wedge. The type of osteotomy refers to how the procedure changes the relation between two parts of a bone involved in the osteotomy. In an open wedge osteotomy, a wedge of bone or graft or other material is inserted in between two parts of a bone. Consequently, a wedge shape is "opened" in the bone. In a close wedge osteotomy or closing wedge osteotomy a wedge of bone is removed from a bone. Consequently, a wedge shape formed in the bone is "closed."

"Midfoot Bone" refers to any bone of a foot of a human between the ankle and the toes. For example, in a human a midfoot bone can include any of the metatarsus including a first metatarsal bone, second metatarsal bone, third metatarsal bone, fourth metatarsal bone, and fifth metatarsal bone; a medial cuneiform bone, an intermediate cuneiform bone, a lateral cuneiform bone, a cuboid bone, a talus bone, and the like.

"Metatarsal" is a bone of a foot of a human. In a human, a foot typically includes five metatarsals which are identified by number starting from the most medial metatarsal, which is referred to as a first metatarsal and moving laterally the next metatarsal is the second metatarsal, and the naming continues in like manner for the third, fourth, and fifth metatarsal. The metatarsal bone includes three parts a base which is a part that is at a proximal end of the metatarsal, a head which is a part that is at a distal end of the metatarsal, and a shaft or neck connects the base to the head.

"Epiphyses" refers to the rounded end of a long bone, at long bone's joint with adjacent bone(s). Between the epiphysis and diaphysis (the long midsection of the long bone) lies the metaphysis, including the epiphyseal plate (growth plate). At the joint, the epiphysis is covered with articular cartilage; below that covering is a zone similar to the epiphyseal plate, known as subchondral bone. (Search 'epiphysis' on Wikipedia.com 17 Jun. 2022. Modified. Accessed Aug. 1, 2022.) "Metaphysis" refers to the neck portion of a long bone between the epiphysis and the diaphysis. The metaphysis contains the growth plate, the part of the bone that grows during childhood, and as the metaphysis grows the metaphysis ossifies near the diaphysis and the epiphyses. (Search 'metaphysis' on Wikipedia.com 17 Jun. 2022. Modified. Accessed Aug. 1, 2022.) "Diaphysis" refers to the main or midsection (shaft) of a long bone. The diaphysis is made up of cortical bone and usually contains bone marrow and adipose tissue (fat). The diaphysis is a middle tubular part composed of compact bone which surrounds a central marrow cavity which contains red or yellow marrow. In diaphysis, primary ossification occurs. (Search 'diaphysis' on Wikipedia.com 17 Jun. 2022. Modified. Accessed Aug. 1, 2022.)

"Metaphyseal Diaphyseal Junction" or "MDJ" refers to an area of a long bone between the Metaphysis and the Diaphysis. This area can also include or be referred to as the epiphyseal plate (growth) plate. For certain surgical procedures, performing an osteotomy at or near the metaphyseal diaphyseal junction may be advantageous and desirable to promote rapid fusion of two cut faces formed in the osteotomy and bone growth to close the osteotomy, and/or may mitigate the risk of a nonunion of the osteotomy.

"Vertex" refers to a point at which lines, structures, trajectories, or pathways intersect. (Search "vertex" on wordhippo.com. WordHippo, 2023. Web. Modified. Accessed 13 Jun. 2023.)

As used herein, a "base" refers to a main or central structure, component, or part of a structure. A base is often a structure, component, or part upon which, or from which other structures extend into, out of, away from, are coupled to, or connect to. A base may have a variety of geometric shapes and configurations. A base may be rigid or pliable. A base may be solid or hollow. A base can have any number of sides. In one embodiment, a base may include a housing, frame, or framework for a larger system, component, structure, or device. In certain embodiments, a base can be a part at the bottom or underneath a structure designed to extend vertically when the structure is in a desired configuration or position. Certain bones such as a metatarsal bone can include a base as one structural component of the bone.

As used herein, "anatomic data" refers to data identified, used, collected, gathered, and/or generated in connection with an anatomy of a human. Examples of anatomic data may include location data for structures, both independent, and those connected to other structures within a coordinate system. Anatomic data may also include data that labels or identifies one or more anatomical structures. Anatomic data can include volumetric data, material composition data, and/or the like. Anatomic data can be generated based on medical imaging data or measurements using a variety of instruments including monitors and/or sensors. Anatomic data can be gathered, measured, or collected from anatomical models and/or can be used to generate, manipulate, or modify anatomical models.

A bone model or anatomic model of a patient's body or body part(s) may be generated by computing devices that analyze medical imaging images. Structures of a patient's body can be determined using a process called segmentation.

"Positioner" or "positioning guide" refers to any structure, apparatus, surface, device, system, feature, or aspect configured to position, move, translate, manipulate, or arrange one object in relation to another. In certain embodiments, a positioner can be used for one step in surgical procedure to position, arrange, orient, and/or reduce one bone or bone fragment relative to another. In such embodiments, the positioner may be referred to as a bone positioner. In certain embodiments, the term positioner or positioning guide may be preceded by an adjective that identifies the structure, implement, component, or instrument that may be used with, positioned by, and/or guided by with the positioner. For example, a "pin positioner" may be configured to accept a pin or wire such as a K-wire and serve to position or place the pin relative to another structure such as a bone.

"Reduction guide" or "reducer" refers to any structure, apparatus, surface, device, system, feature, or aspect configured, designed, engineered, or fabricated to reduce or aide a user in the reduction of one bone or bone fragment or implant in relation to another bone or bone fragment or implant.

"Rotation guide" or "rotator" refers to any structure, apparatus, surface, device, system, feature, or aspect configured, designed, engineered, or fabricated to rotate or aid a user in the rotation of one structure relative to another structure. In certain embodiments, a rotation guide or rotator may be used to help a surgeon rotate one or more bones, parts of bones, bone fragment, an implant, or other anatomical structure, either alone or in relation to another one or more bones, parts of bones, bone fragments, implants, or other anatomical structures.

"Trajectory guide" or "trajectory indicator" or "targeting guide" refers to any structure, apparatus, surface, device, system, feature, or aspect configured to indicate, identify, guide, place, position, or otherwise assist in marking or deploying a fastener or other structure along a desired trajectory for one or more subsequent steps in a procedure.

"Trajectory" refers to a path a body travels or a path configured for a body to travel through space. (Search "trajectory" on wordhippo.com. WordHippo, 2023. Web. Modified. Accessed 13 Jun. 2023.)

"Metatarsal base resection guide" refers to a resection guide designed, engineered, fabricated, or intended for use with, one, in, or about a base part, section, surface, portion, or aspect of a metatarsal for one or more steps of a medical procedure. The metatarsal base resection guide may be used to form an osteotomy, to resect a wedge for a closing wedge procedure, resect a bone wedge that preserves a cortical layer of bone opposite the resected bone wedge, form an osteotomy that uniplanar wedge, a biplanar wedge, or a triplane wedge. Various embodiments of a metatarsal base resection guide may be used on a medial surface, a dorsal surface, a lateral surface, or a plantar surface of a single metatarsal. Alternatively, or in addition, various embodiments of a metatarsal base resection guide can be used on two or more metatarsals.

"Reduction guide" or "reducer" refers to any structure, apparatus, surface, device, system, feature, or aspect configured, designed, engineered, or fabricated to reduce or aide a user in the reduction of one bone or bone fragment or implant in relation to another bone or bone fragment or implant.

"Fastener guide" or "reducer" refers to any structure, apparatus, surface, device, system, feature, or aspect configured, designed, engineered, or fabricated to guide or direct a fastener into a bone as part of deploying the fastener. Examples of a fastener guide include an opening in a structure that is sized and/or oriented for deployment of a fastener such as a bone screw, a reference pin for aligning a fastener for deployment at a desired orientation and/or trajectory, and the like.

As used herein, a "guard" refers to an apparatus, instrument, structure, member, device, component, system, or assembly structured, organized, configured, designed, arranged, or engineered to prevent, limit, impede, stop, or restrict motion, action, or movement and/or operation of the another object, member, structure, component, part, apparatus, system, or assembly beyond a certain parameter such as a boundary. Said another way, a "guard" refers to an apparatus, instrument, structure, member, device, component, system, or assembly structured, organized, configured, designed, arranged, or engineered to retain, maintain, hold, keep, or restrict motion, action, or movement and/or operation of the another object, member, structure, component, part, apparatus, system, or assembly within or at one or more parameters such as a boundary.

As used herein, "artificial intelligence" refers to intelligence demonstrated by machines, unlike the natural intelligence displayed by humans, which involves consciousness and emotionality. The distinction between artificial intelligence and natural intelligence categories is often revealed by the acronym chosen. 'Strong' AI is usually labelled as artificial general intelligence (AGI) while attempts to emulate 'natural' intelligence have been called artificial biological intelligence (ABI). Leading AI textbooks define the field as the study of "intelligent agents": any device that perceives its environment and takes actions that maximize its chance of achieving its goals. The term "artificial intelligence" can also be used to describe machines that mimic "cognitive" functions that humans associate with the human mind, such as "learning" and "problem solving". (Search "artificial intelligence" on Wikipedia.com Jun. 25, 2021. CC-BY-SA 3.0 Modified. Accessed Jun. 25, 2021.)

As used herein, "segmentation" or "image segmentation" refers to the process of partitioning an image into different meaningful segments. These segments may correspond to different tissue classes, organs, pathologies, bones, or other biologically relevant structures. Medical image segmentation accommodates imaging ambiguities such as by low contrast, noise, and other imaging ambiguities.

Certain computer vision techniques can be used or adapted for image segmentation. For example, the techniques and or algorithms for segmentation may include, but are not limited to: Atlas-Based Segmentation: For many applications, a clinical expert can manually label several images; segmenting unseen images is a matter of extrapolating from these manually labeled training images. Methods of this style are typically referred to as atlas-based segmentation methods. Parametric atlas methods typically combine these training images into a single atlas image, while non-parametric atlas methods typically use all of the training images separately. Atlas-based methods usually require the use of image registration in order to align the atlas image or images to a new, unseen image.

Image registration is a process of correctly aligning images; Shape-Based Segmentation: Many methods parametrize a template shape for a given structure, often relying on control points along the boundary. The entire shape is then deformed to match a new image. Two of the most common shape-based techniques are Active Shape Models and Active Appearance Models; Image-Based Segmentation: Some methods initiate a template and refine its shape according to the image data while minimizing integral error measures, like the Active contour model and its variations; Interactive Segmentation: Interactive methods are useful when clinicians can provide some information, such as a seed region or rough outline of the region to segment. An algorithm can then iteratively refine such a segmentation, with or without guidance from the clinician. Manual segmentation, using tools such as a paint brush to explicitly define the tissue class of each pixel, remains the gold standard for many imaging applications. Recently, principles from feedback control theory have been incorporated into segmentation, which give the user much greater flexibility and allow for the automatic correction of errors; Subjective surface Segmentation: This method is based on the idea of evolution of segmentation function which is governed by an advection-diffusion model. To segment an object, a segmentation seed is needed (that is the starting point that determines the approximate position of the object in the image). Consequently, an initial segmentation function is constructed. With the subjective surface method, the position of the seed is the main factor determining the form of this segmentation function; and Hybrid segmentation which is based on combination of methods. (Search "medical image computing" on Wikipedia.com Jun. 24, 2021. CC-BY-SA 3.0 Modified. Accessed Jun. 24, 2021.)

As used herein, "medical imaging" refers to a technique and process of imaging the interior of a body for clinical analysis and medical intervention, as well as visual representation of the function of some organs or tissues (physiology). Medical imaging seeks to reveal internal structures hidden by the skin and bones, as well as to diagnose and treat disease. Medical imaging may be used to establish a database of normal anatomy and physiology to make possible identification of abnormalities. Medical imaging in its widest sense, is part of biological imaging and incorporates radiology, which uses the imaging technologies of X-ray radiography, magnetic resonance imaging, ultrasound, endoscopy, elastography, tactile imaging, thermography, medical photography, nuclear medicine functional imaging techniques as positron emission tomography (PET) and single-photon emission computed tomography (SPECT). Another form of X-ray radiography includes computerized tomography (CT) scans in which a computer controls the position of the X-ray sources and detectors. Magnetic Resonance Imaging (MRI) is another medical imaging technology. Measurement and recording techniques that are not primarily designed to produce images, such as electroencephalography (EEG), magnetoencephalography (MEG), electrocardiography (ECG), and others, represent other technologies that produce data susceptible to representation as a parameter graph vs. time or maps that contain data about the measurement locations. In certain embodiments bone imaging includes devices that scan and gather bone density anatomic data. These technologies may be considered forms of medical imaging in certain disciplines. (Search "medical imaging" on Wikipedia.com Jun. 16, 2021. CC-BY-SA 3.0 Modified. Accessed Jun. 23, 2021.) Data, including images, text, and other data associated with medical imaging is referred to as patient imaging data. As used herein, "patient imaging data" refers to data identified, used, collected, gathered, and/or generated in connection with medical imaging and/or medical imaging data. Patient imaging data can be shared between users, systems, patients, and professionals using a common data format referred to as Digital Imaging and Communications in Medicine (DICOM) data. DICOM data is a standard format for storing, viewing, retrieving, and sharing medical images.

As used herein, "medical image computing" or "medical image processing" refers to systems, software, hardware, components, and/or apparatus that involve and combine the fields of computer science, information engineering, electrical engineering, physics, mathematics and medicine. Medical image computing develops computational and mathematical methods for working with medical images and their use for biomedical research and clinical care. One goal for medical image computing is to extract clinically relevant information or knowledge from medical images. While closely related to the field of medical imaging, medical image computing focuses on the computational analysis of the images, not their acquisition. The methods can be grouped into several broad categories: image segmentation, image registration, image-based physiological modeling, and others. (Search "medical image computing" on Wikipedia.com Jun. 24, 2021. CC-BY-SA 3.0 Modified. Accessed Jun. 24, 2021.) Medical image computing may include one or more processors or controllers on one or more computing devices. Such processors or controllers may be referred to herein as medical image processors. Medical imaging and medical image computing together can provide systems and methods to image, quantify and fuse both structural and functional information about a patient in vivo. These two technologies include the transformation of computational models to represent specific subjects/patients, thus paving the way for personalized computational models. Individualization of generic computational models through imaging can be realized in three complementary directions: definition of the subject-specific computational domain (anatomy) and related subdomains (tissue types); definition of boundary and initial conditions from (dynamic and/or functional) imaging; and characterization of structural and functional tissue properties. Medical imaging and medical image computing enable the translation of models to the clinical setting with both diagnostic and therapeutic applications. (Id.) In certain embodiments, medical image computing can be used to generate a bone model, a patient-specific model, and/or a patent specific instrument from medical imaging and/or medical imaging data.

"Visibility" refers to a state of feature, aspect, structure, or thing being capable of being observed, seen, or perceived.

"Medical Imaging Visibility" refers to the ability to observe or visualize a feature, aspect, structure, or object with the aid of medical imaging systems, devices, instruments, or the like. Such visibility may include features that are inherently visible, enhanced, or made visible solely through the use of medical imaging technologies. (© ChatGPT 4o Version, Modified, accessed chat.openai.com/chat Dec. 9, 2024).

As used herein, "model" refers to an informative representation of an object, person or system. Representational models can be broadly divided into the concrete (e.g., physical form) and the abstract (e.g. behavioral patterns, especially as expressed in mathematical form). In abstract form, certain models may be based on data used in a computer system or software program to represent the model. Such models can be referred to as computer models. Computer models can be used to display the model, modify the model, print the model (either on a 2D medium or using a 3D printer or additive manufacturing technology). Computer models can also be used in environments with models of other objects, people, or systems. Computer models can also be used to generate simulations, display in virtual environment systems, display in augmented reality systems, or the like. Computer models can be used in Computer Aided Design (CAD) and/or Computer Aided Manufacturing (CAM) systems. Certain models may be identified with an adjective that identifies the object, person, or system the model represents. For example, a "bone" model is a model of a bone, and a "heart" model is a model of a heart. (Search "model" on Wikipedia.com Jun. 13, 2021. CC-BY-SA 3.0 Modified. Accessed Jun. 23, 2021.) As used herein, "additive manufacturing" refers to a manufacturing process in which materials are joined together in a process that repeatedly builds one layer on top of another to generate a three-dimensional structure or object. Additive manufacturing may also be referred to using different terms including: additive processes, additive fabrication, additive techniques, additive layer manufacturing, layer manufacturing, freeform fabrication, ASTM F2792 (American Society for Testing and Materials), and 3D printing. Additive manufacturing can build the three-dimensional structure or object using computer-controlled equipment that applies successive layers of the material(s) based on a three-dimensional model that may be defined using Computer Aided Design (CAD) software. Additive manufacturing can use a variety of materials including polymers, thermoplastics, metals, ceramics, biochemicals, and the like. Additive manufacturing may provide unique benefits, as an implant together with the pores and/or lattices can be directly manufactured (without the need to generate molds, tool paths, perform any milling, and/or other manufacturing steps).

"Repository" refers to any data source or dataset that includes data or content. In one embodiment, a repository resides on a computing device. In another embodiment, a repository resides on a remote computing or remote storage device. A repository may comprise a file, a folder, a directory, a set of files, a set of folders, a set of directories, a database, an application, a software application, content of a text, content of an email, content of a calendar entry, and the like. A repository, in one embodiment, comprises unstructured data. A repository, in one embodiment, comprises structured data such as a table, an array, a queue, a look up table, a hash table, a heap, a stack, or the like. A repository may store data in any format including binary, text, encrypted, unencrypted, a proprietary format, or the like.

"Reference" refers to any apparatus, structure, device, system, component, marking, and/or indicator organized, configured, designed, engineered, and/or arranged to serve as a source of information or a point of comparison used to support or establish knowledge, truth, or quality. (© ChatGPT January 9 Version, Modified, accessed chat.openai.com/chat Jan. 28, 2023). In certain embodiments, a reference can serve as a starting point or initial position for one or more steps in a surgical procedure. A reference may be a type of fiducial. In certain embodiments, "reference" can be combined with an adjective describing the reference. For example, a "model reference" is a reference within a model such as a computer model. A model reference refers to any feature, aspect, and/or component within a model. Examples of a model reference include, but are not limited to, a point, a plane, a line, a plurality of points, a surface, an anatomical structure, a shape, or the like. An "anatomical reference" is a reference within, on, near, or otherwise associated with an anatomical structure such as a bone. A reference (e.g., model, actual, virtual, and/or real) may also be referred to as a reference feature.

"Reference feature" refers to a feature configured for use as a point, plane, axis, or line of reference (aka a reference). A reference or reference feature can be used to position, measure, orient, fixation, couple, engage, and/or align one object or structure with another object or structure. In certain embodiments, a reference or reference feature can serve as a baseline, a ground truth, a waypoint, a control point, a landmark, and/or the like. A reference feature can facilitate moving from one coordinate system or frame of reference in a virtual environment to a position, location, frame of reference, environment, or orientation on, or in, an actual object, structure, device, apparatus, anatomical structure, or the like. Advantageously, a reference feature can coordinate objects, models, or structures in a digital or virtual model or representation with corresponding objects or structures (e.g., anatomical structures) of actual physical objects or structures. Said another way, a reference feature can serve to map from a virtual or modeled object to an actual or physical object.

As used herein, "feature" refers to a distinctive attribute or aspect of something. (Search "feature" on google.com. Oxford Languages, 2021. Web. 20 Apr. 2021.) A feature may include one or more apparatuses, structures, objects, systems, sub-systems, devices, or the like. A feature may include a modifier that identifies a particular function or operation and/or a particular structure relating to the feature. Examples of such modifiers applied to a feature, include, but are not limited to, "attachment feature," "alignment feature," "securing feature," "placement feature," "protruding feature," "engagement feature," "disengagement feature," "resection feature", "guide feature", "alignment feature," and the like.

As used herein, a "marking" or "marker" refers to a symbol, letter, lettering, word, phrase, icon, design, color, diagram, indicator, figure, structure, device, apparatus, surface, component, system, or combination of these designed, intended, structured, organized, configured, programmed, arranged, or engineered to communication information and/or a message to a user receiving, viewing, or encountering the marking. The marking or "marker" can include one or more of a tactile signal, a visual signal or indication, an audible signal, and the like. In one embodiment, a marking may comprise a number or set letters, symbols, or words positioned on a surface, structure, color, color scheme, or device to convey a desired message or set of information.

As used herein, a "protrusion" refers to a structure or portion of a structure that protrudes or extends from at least one other structure such as a surface of the at least one other structure. Generally, the other structure is connected to, or in contact with, the protrusion.

"Set" refers to a collection of objects. A set can have zero or more objects in the collection. Generally, a set includes one or more objects in the collection.

As used herein, a "sleeve" refers to structure that is narrow and longer longitudinally than the structure is wide. In certain embodiments, a sleeve serves to surround, enclose, wrap, and/or contain something else. In certain embodiments, a sleeve may surround, enclose, wrap, and/or contain a passage or void. (Search "sleeve" on wordhippo.com. WordHippo, 2021. Web. Accessed 15 Nov. 2021. Modified.) In certain embodiments, the term sleeve may be preceded by an adjective that identifies the structure, implement, component or instrument that may be used with, inserted into or associated with the sleeve. For example, a "pin sleeve" may be configured to accept a pin or wire such as a K-wire, a "drive sleeve" may be configured to accept a drill or drill bit, a "fixation member sleeve" may be configured to accept a fastener or fixation member.

As used herein, a "fixation" or "fixation device" refers to an apparatus, instrument, structure, device, component, member, system, assembly, step, process, or module structured, organized, configured, designed, arranged, or engineered to connect two structures either permanently or temporarily. The two structures may be one or the other or both of manmade and/or biological tissues, hard tissues such as bones, teeth or the like, soft tissues such as ligament, cartilage, tendon, or the like. In certain embodiments, fixation is used as an adjective to describe a device or component or step in securing two structures such that the structures remain connected to each other in a desired position and/or orientation. Fixation devices can also serve to maintain a desired level of tension, compression, or redistribute load and stresses experienced by the two structures and can serve to reduce relative motion of one part relative to others. Examples of fixation devices are many and include both those for external fixation as well as those for internal fixation and include, but are not limited to pins, wires, Kirschner wires (K-wires), screws, anchors, bone anchors, plates, bone plates, intramedullary nails or rods or pins, implants, interbody cages, fusion cages, and the like.

"Fusion" refers to a natural process of bone growth and generation in which two separate bones and/or bone fragments grow together as new bone grows when the two separate bones and/or bone fragments contact each other. Often, fusion is facilitated by compression of the two separate bones and/or bone fragments towards each other.

As used herein, a "resection" refers to a method, procedure, or step that removes tissue from another anatomical structure or body. A resection can include an osteotomy that cuts through a bone or other tissue because the osteotomy still removes at least a minimal amount of tissue. A resection is typically performed by a surgeon on a part of a body of a patient. A resection is one type of osteotomy. (Search "surgery" on Wikipedia.com May 26, 2021. CC-BY-SA 3.0 Modified. Accessed May 26, 2021.) Resection may be used as a noun or a verb. In the verb form, the term is "resect" and refers to an act of performing, or doing, a resection. Past tense of the verb resect is "resected".

As used herein, "image registration" refers to a method, process, module, component, apparatus, and/or system that seeks to achieve precision in the alignment of two images. As used here, "image" may refer to either or both an image of a structure or object and another image or a model (e.g., a computer-based model or a physical model, in either two dimensions or three dimensions). In the simplest case of image registration, two images are aligned. One image may serve as the target image and the other as a source image; the source image is transformed, positioned, realigned, and/or modified to match the target image. An optimization procedure may be applied that updates the transformation of the source image based on a similarity value that evaluates the current quality of the alignment. An iterative procedure of optimization may be repeated until a (local) optimum is found. An example is the registration of CT and PET images to combine structural and metabolic information. Image registration can be used in a variety of medical applications: Studying temporal changes; Longitudinal studies may acquire images over several months or years to study long-term processes, such as disease progression. Time series correspond to images acquired within the same session (seconds or minutes). Time series images can be used to study cognitive processes, heart deformations and respiration; Combining complementary information from different imaging modalities. One example may be the fusion of anatomical and functional information.

Since the size and shape of structures vary across modalities, evaluating the alignment quality can be more challenging. Thus, similarity measures such as mutual information may be used; Characterizing a population of subjects. In contrast to intra-subject registration, a one-to-one mapping may not exist between subjects, depending on the structural variability of the organ of interest. Inter-subject registration may be used for atlas construction in computational anatomy. Here, the objective may be to statistically model the anatomy of organs across subjects; Computer-assisted surgery: in computer-assisted surgery pre-operative images such as CT or MRI may be registered to intra-operative images or tracking systems to facilitate image guidance or navigation. There may be several considerations made when performing image registration: The transformation model. Common choices are rigid, affine, and deformable transformation models. B-spline and thin plate spline models are commonly used for parameterized transformation fields. Non-parametric or dense deformation fields carry a displacement vector at every grid location; this may use additional regularization constraints. A specific class of deformation fields are diffeomorphisms, which are invertible transformations with a smooth inverse; The similarity metric. A distance or similarity function is used to quantify the registration quality. This similarity can be calculated either on the original images or on features extracted from the images. Common similarity measures are sum of squared distances (SSD), correlation coefficient, and mutual information. The choice of similarity measure depends on whether the images are from the same modality; the acquisition noise can also play a role in this decision. For example, SSD may be the optimal similarity measure for images of the same modality with Gaussian noise. However, the image statistics in ultrasound may be significantly different from Gaussian noise, leading to the introduction of ultrasound specific similarity measures.

Multi-modal registration may use a more sophisticated similarity measure; alternatively, a different image representation can be used, such as structural representations or registering adjacent anatomy; The optimization procedure. Either continuous or discrete optimization is performed. For continuous optimization, gradient-based optimization techniques are applied to improve the convergence speed. (Search "medical image computing" on Wikipedia.com Jun. 24, 2021. CC-BY-SA 3.0 Modified. Accessed Jun. 25, 2021.)

"Register" or "Registration" refers to an act of aligning, mating, contacting, engaging, or coupling one or more parts and/or surfaces of one object in relation to one or more parts and/or surfaces of another object. Often, the one or more parts and/or surfaces of one object include protrusions and/or depressions that are the inverse or mirror configuration of protrusions and/or depressions of one or more parts and/or surfaces of the other object.

"Registration key" refers to a structure, surface, feature, module, component, apparatus, and/or system that facilitates, enables, guides, promotes, precision in the alignment of two objects by way of registration. In one aspect a registration key can include a surface and one or more recesses and/or features of that surface that are configured to fit within corresponding recesses, projections, and/or other features of another structure such as another surface. In one aspect a registration key can include a surface and one or more projections and/or features of, extending from, or connected to that surface that are configured to fit within corresponding recesses, projections, and/or other features of another structure such as another surface. In certain aspects, the features of the registration key may be configured to fit within, or in contact, or in close contact with those of the another structure. In one embodiment, when the two structures align the registration key has served its purpose.

"Anatomical structure" or "Anatomy" refers to any part or portion of a part of a body of a person, or other patient. Examples of anatomical structures, include but are not limited to, a bone, bones, soft tissue, a joint, joints, a tissue surface, a protrusion, a recess, an opening, skin, hard tissue, teeth, mouth, eyes, hair, nails, fingers, toes, legs, arms, torso, vertebrae, ligaments, tendons, organs, or the like.

"Anatomical reference" refers to any reference(s) that is, or is on, or is in, or is otherwise associated, with an anatomical structure. Examples of anatomical structures, include but are not limited to, a bone, bones, soft tissue, a joint, joints, skin, hard tissue, teeth, mouth, eyes, hair, nails, fingers, toes, legs, arms, torso, vertebrae, ligaments, tendons, organs, a hole, a post, a plurality of holes, a plurality of posts, a fastener, a suture, a clamp, an instrument, an implant, or the like.

As used herein, "surgical field," "operative field," or "operating field" refers to an area of a patient where surgery is or will be performed and includes one or more areas of a patient's body and all personnel and equipment that is used in the surgery. (Search "surgical field" on medical-dictionary.thefreedictionary.com Copyright 2021 Farlex Inc. Modified. Accessed Sep. 8, 2021.)

As used herein, a "condition" refers to a state of something with regard to its appearance, quality, or working order. In certain aspects, a condition may refer to a patient's state of health or physical fitness or the state of health or physical fitness of an organ or anatomical part of a patient. In certain embodiments, a condition may refer to an illness, pain, discomfort, defect, disease, or deformity of a patient or of an organ or anatomical part of a patient. (Search "condition" on wordhippo.com. WordHippo, 2021. Web. Accessed 8 Dec. 2021. Modified.)

"Bone condition" refers to any of a variety of conditions of bones of a patient. Generally, a bone condition refers to an orientation, position, and/or alignment of one or more bones of the patient relative to other anatomical structures of the body of the patient. Bone conditions may be caused by or result from deformities, misalignment, malrotation, fractures, joint failure, and/or the like. A bone condition includes, but is not limited to, any angular deformities of one or more bone segments in either the lower or upper extremities (for example, tibial deformities, calcaneal deformities, femoral deformities, and radial deformities). Alternatively, or in addition, "bone condition" can refer to the structural makeup and configuration of one or more bones of a patient. Thus bone condition may refer to a state or condition of regions, a thickness of a cortex, bone density, a thickness and/or porosity of internal regions (e.g. whether it is calcaneus or solid) of the bone or parts of the bone such as a head, a base, a shaft, a protuberance, a process, a lamina, a foramen, and the like of a bone, along the metaphyseal region, epiphysis region, and/or a diaphyseal region. "Malrotation" refers to a condition in which a part, typically a part of a patient's body has rotated from a normal position to an unnormal or uncommon position.

As used herein, a "guide" refers to a part, component, member, or structure designed, adapted, configured, or engineered to guide or direct one or more other parts, components, or structures. A guide may be part of, integrated with, connected to, attachable to, or coupled to, another structure, device, or instrument. In one embodiment, a guide may include a modifier that identifies a particular function, location, orientation, operation, type, and/or a particular structure of the guide. Examples of such modifiers applied to a guide, include, but are not limited to, "pin guide" that guides or directs one or more pins, a "cutting guide" that guides or directs the making or one or more cuts, a placement, deployment, or insertion guide that guides or directs the placement, positioning, orientation, deployment, installation, or insertion of a fastener and/or implant, a "cross fixation guide" that guides deployment of a fastener or fixation member, an "alignment guide" that guides the alignment of two or more objects or structures, a "navigation guide" that guides a user in navigating a course or process or procedure such as a surgical procedure, a "resection guide" that serves to guide resection of soft or hard tissue, such as in an osteotomy, a "reduction guide" can serve to guide reduction of one or more bone segments or fragments, an "placement guide" that serves to identify how an object can be placed in relation to another object or structure, and the like. Furthermore, guides may include modifiers applied due to the procedure or location within a patient for which the guide is to be used. For example, where a guide is used at a joint, the guide may be referred to herein as an "arthrodesis guide."

Those of skill in the art will appreciate that a resection feature may take a variety of forms and may include a single feature or one or more features that together form the resection feature. In certain embodiments, the resection feature may take the form of one or more slots or cut channels. Alternatively, or in addition, a resection feature may be referenced using other names including, but not limited to, channel, cut channels, and the like.

"Lateral resection guide" refers to a resection guide designed, engineered, fabricated, or intended for use with, one, in, or about a lateral part, section, surface, portion, or aspect of an anatomical structure such as a bone, digit, limb, or other anatomical structure for one or more steps of a resection procedure.

"Medial resection guide" refers to a resection guide designed, engineered, fabricated, or intended for use with, one, in, or about a medial part, section, surface, portion, or aspect of an anatomical structure such as a bone, digit, limb, or other anatomical structure for one or more steps of a resection procedure.

"Cross section" or "cross-section" refers to the non-empty intersection of a body in three-dimensional space with a plane, or the analog in higher-dimensional spaces. (Search "cross section" on Wikipedia.com Mar. 7, 2022. Modified. Accessed Sep. 21, 2022.)

"Cut channel" refers to a channel, slot, hole, or opening, configured to facilitate making a cut. In certain embodiments, a cut channel is one example of a resection feature, resection member, and/or resection guide. "Rotation slot" refers to a channel, slot, hole, or opening, configured to facilitate rotating one structure in relation to another structure.

As used herein, "slot" refers to a narrow opening or groove. (search "slot" on Merriam-Webster.com. Merriam-Webster, 2021. Web. 4 Aug. 2021. Modified.)

"Hole" refers to a gap, an opening, an aperture, a port, a portal, a space or recess in a structure, a void in a structure, or the like. In certain embodiments, a hole can refer to a structure configured specifically for receiving something and/or for allowing access. In certain embodiments, a hole can pass through a structure. In other embodiments, an opening can exist within a structure but not pass through the structure. A hole can be two-dimensional or three-dimensional and can have a variety of geometric shapes and/or cross-sectional shapes, including, but not limited to a rectangle, a square, or other polygon, as well as a circle, an ellipse, an ovoid, or other circular or semi-circular shape. As used herein, the term "hole" can include one or more modifiers that define specific types of "holes" based on the purpose, function, operation, position, or location of the "hole." As one example, a "fastener hole" refers to an "hole" adapted, configured, designed, or engineered to accept or accommodate a "fastener."

As used herein, an "opening" refers to a gap, a hole, an aperture, a port, a portal, a slit, a space or recess in a structure, a void in a structure, or the like. In certain embodiments, an opening can refer to a structure configured specifically for receiving something and/or for allowing access. In certain embodiments, an opening can pass through a structure. In such embodiments, the opening can be referred to as a window. In other embodiments, an opening can exist within a structure but not pass through the structure. In other embodiments, an opening can initiate on a surface or at an edge or at a side of a structure and extend into the structure for a distance, but not pass through or extend to another side or edge of the structure. In other embodiments, an opening can initiate on a surface or at an edge or at a side of a structure and extend into the structure until the opening extends through or extends to another side or edge of the structure. An opening can be two-dimensional or three-dimensional and can have a variety of geometric shapes and/or cross-sectional shapes, including, but not limited to a rectangle, a square, or other polygon, as well as a circle, an ellipse, an ovoid, or other circular or semi-circular shape. As used herein, the term "opening" can include one or more modifiers that define specific types of "openings" based on the purpose, function, operation, position, or location of the "opening." As one example, a "fastener opening" refers to an "opening" adapted, configured, designed, or engineered to accept or accommodate a "fastener."

"Resection interface" refers to an interface between a resected portion of tissue and another object, structure, or thing. Often a resection interface is an interface or boundary between one resected portion of an anatomical structure and another resected portion of another anatomical structure. The two anatomical structures can be portions, parts, or fragments of one anatomical structure or two different anatomical structures. A resection interface can be embodied in a variety of shapes and/or configurations, including a point, a line, a plane, a contour, a boundary, or the like. In one embodiment, a resection interface is an interface between two or more cut planes or two or more cut surfaces or two or more cut faces.

"Cortical bone" refers to a type of bone tissue. Cortical bone is a type of bone tissue typically found between an external surface of a bone and an interior area of the bone. Cortical bone is more dense and typically stronger structurally than other types of bone tissue. "Cortical surface" refers to a surface of cortical bone.

"Cortex" refers to an area of bone that extends from an external surface of the bone towards a center part of the bone. The cortex is typically comprised of cortical bone.

"Transosseous placement feature" refers to a placement feature that extends through one or more bones and that enables, or facilitates, placement of another device, apparatus, or instrument.

"Patient-specific feature" refers to a feature, function, structure, device, guide, tool, instrument, apparatus, member, component, system, assembly, module, or subsystem that is adjusted, tailored, modified, organized, configured, designed, arranged, engineered, and/or fabricated to specifically address the anatomy, physiology, condition, abnormalities, needs, or desires of a particular patient or surgeon serving the particular patient. In one aspect, a patient specific feature is unique to a single patient and may include features unique to the patient such as a number of cut channels, a number of bone attachment features, a number of bone engagement surfaces, a number of resection features, a depth of one or more cutting channels, an angle for one or more resection channels, a surface contour, component position, component orientation, and/or other features.

"Prescription" or "Prescribed" refers to a written order, as by a physician or nurse practitioner, for the administration of a medicine, preparation of an implant, preparation of an instrument, or other intervention. Prescription can also refer to the prescribed medicine or intervention. (Search "prescription" on wordhippo.com. WordHippo, 2023. Web. Accessed 3 May 2023. Modified.)

As used herein, "end" refers to a part or structure of an area or span that lies at the boundary or edge. An end can also refer to a point that marks the extent of something and/or a point where something ceases to exist. An end can also refer to an extreme or last part lengthwise of a structure or surface. (search "end" on Merriam-Webster.com. Merriam-Webster, 2021. Web. 4 Aug. 2021. Modified.)

As used herein, "edge" refers to a structure, boundary, or line where an object, surface, or area begins or ends. An edge can also refer to a boundary or perimeter between two structures, objects, or surfaces. An edge can also refer to a narrow part adjacent to a border. (search "edge" on Merriam-Webster.com. Merriam-Webster, 2021. Web. 3 Aug. 2021. Modified.) In certain embodiments, an edge can be a one dimensional or a two-dimensional structure that joins two adjacent structures or surfaces. Furthermore, an edge may be at a perimeter of an object or within a perimeter or boundary of an object.

“Bone fragment” refers to a part of a bone that is normally part of another bone of a patient. A bone fragment may be separate from another bone of a patient due to a deformity or trauma. In one aspect, the bone the bone fragment is normally connected or joined with is referred to as a parent bone.

“Joint” or “Articulation” refers to the connection made between bones in a human body which link the skeletal system to form a functional whole. Joints may be biomechanically classified as a simple joint, a compound joint, or a complex joint. Joints may be classified anatomically into groups such as joints of hand, elbow joints, wrist joints, axillary joints, sternoclavicular joints, vertebral articulations, temporomandibular joints, sacroiliac joints, hip joints, knee joints, ankle joints, articulations of foot, and the like. (Search “joint” on Wikipedia.com Dec. 19, 2021. CC-BY-SA 3.0 Modified. Accessed Jan. 20, 2022.)

“Articular surface” refers to a surface of a structure that is coupled to, and may cooperate with, other structures of a joint of a human to enable movement of structures of the joint.

“Tarso-metatarsal joint” or “TMT joint” refers to a joint of a patient between a metatarsal bone and one or more cuneiform/tarsal/cuboid bones. The TMT joint may also be referred to as a “Lis Franc” or “Lisfranc” joint after a French surgeon Lisfranc.

“Cut surface” refers to a surface of an object that is created or formed by the removal of one or more parts of the object that includes the original surface. Cut surfaces can be created using a variety of methods, tools, or apparatuses and may be formed using a variety of removal actions, including, but not limited to, fenestrating, drilling, abrading, cutting, sawing, chiseling, digging, scrapping, and the like. Tools and/or methods used for forming a cut surface can include manual, mechanical, motorized, hydraulic, automated, robotic, and the like. In certain embodiments, the cut surface (s) are planar.

“Orientation” refers to a direction, angle, position, condition, state, or configuration of a first object, component, part, apparatus, system, or assembly relative to another object, component, part, apparatus, system, assembly, reference point, reference axis, or reference plane.

“Longitudinal axis” or “Long axis” refers to an axis of a structure, device, object, apparatus, or part thereof that extends from one end of a longest dimension to an opposite end. Typically, a longitudinal axis passes through a center of the structure, device, object, apparatus, or part thereof along the longitudinal axis. The center point used for the longitudinal axis may be a geometric center point and/or a mass center point.

“Mechanical axis” refers to an axis of a long bone such as a femur or tibia. The mechanical axis of a long bone is a straight line connecting the joint center points of the proximal and distal joint regions, whether in the frontal or sagittal plane. A mechanical axis can be useful in defining how the mechanical (weight, gait, flexion, extension, etc.) forces impact the morphology of the bone structure. A mechanical axis and anatomical axis can both help in the surgical planning in relation to deformed bones. (Search “axes of the long bones” on appropedia.com; Amit Dinanath Maurya, OpenSurgiSim (2021-2023). “Axes of the long bones—Mechanical and Anatomical”. SELF. Modified. Accessed Jun. 28, 2023.)

As used herein, a “drive”, “drive feature”, or “drive recess” refers to an apparatus, instrument, structure, member, device, component, system, or assembly structured, organized, configured, designed, arranged, or engineered to receive a torque and transfer that torque to a structure connected or coupled to the drive. At a minimum, a drive is a set of shaped cavities and/or protrusions on a structure that allows torque to be applied to the structure. Often, a drive includes a mating tool, known as a driver. For example, cavities and/or protrusions on a head of a screw are one kind of drive and an example of a corresponding mating tool is a screwdriver, that is used to turn the screw, the drive. Examples of a drive include but are not limited to screw drives such as slotted drives, cruciform drives, square drives, multiple square drives, internal polygon, internal hex drives, penta lobular sockets, hex lobular sockets, combination drives, external drives, tamper-resistant drives, and the like. (Search ‘list of screw drives’ on Wikipedia.com Mar. 12, 2021. Modified. Accessed Mar. 19, 2021.)

“Thread” or “threads” refers to a helical structure used to convert between rotational and linear movement or force. A thread is a ridge wrapped around a cylinder or cone in the form of a helix, with the ridge wrapped around the cylinder being called a straight thread and the ridge wrapped around the cone called a tapered thread. Straight threads or tapered threads are examples of external threads, also referred to as male threads. Threads that a correspond to male threads are referred to as female threads and are formed within the inside wall of a matching hole, passage, or opening of a nut or substrate or other structure. A thread used with a fastener may be referred to as a screw thread and can be a feature of a simple machine and also as a threaded fastener. The mechanical advantage of a threaded fastener depends on its lead, which is the linear distance the threaded fastener travels in one revolution. (Search ‘screw thread’ on Wikipedia.com Jul. 17, 2022. Modified. Accessed Aug. 1, 2022.)

“Cutting tool” refers to any tool that can be used to cut or resect another object. In particular, a cutting tool can refer to a manual or power tool for cutting or resecting tissue of a patient. Examples of cutting tools include, but are not limited to, a burr, an oscillating saw, a reciprocating saw, a grater saw, a drill, a mill, a side-cutting burr, or the like.

As used herein, a “shaft” refers to a long narrow structure, device, component, member, system, or assembly that is structured, organized, configured, designed, arranged, or engineered to support and/or connect a structure, device, component, member, system, connected to each end of the shaft. Typically, a shaft is configured to provide rigid support and integrity in view of a variety of forces including tensile force, compression force, torsion force, shear force, and the like. In addition, a shaft can be configured to provide rigid structural support and integrity in view of a loads including axial loads, torsional loads, transverse loads, and the like. A shaft may be oriented and function in a variety of orientations including vertical, horizontal, or any orientation between these and in two or three dimensions. A shaft may be made from a variety of materials including, but not limited to, metal, plastic, ceramic, wood, fiberglass, acrylic, carbon, biocompatible materials, biodegradable materials or the like. A shaft may be formed of any biocompatible materials, including but not limited to biocompatible metals such as Titanium, Titanium alloys, stainless steel, carbon fiber, combinations of carbon fiber and a metallic alloy, stainless steel alloys, cobalt-chromium steel alloys, nickel-titanium alloys, shape memory alloys such as Nitinol, biocompatible ceramics, and biocompatible polymers such as Polyether ether ketone (PEEK) or a polylactide polymer (e.g. PLLA) and/or others, or any combination of these materials.

"Head" refers to a device, apparatus, member, component, system, assembly, module, subsystem, circuit, or structure, organized, configured, designed, arranged, or engineered to have a prominent role in a particular feature, function, operation, process, method, and/or procedure for a device, apparatus, member, component, system, assembly, module, subsystem, circuit, or structure the includes, is coupled to, or interfaces with the head. In certain embodiments, the head may sit at the top or in another prominent position when interfacing with and/or coupled to a device, apparatus, member, component, system, assembly, module, subsystem, circuit, or structure.

As used herein, an "interface," "user interface," or "engagement interface" refers to an area, a boundary, or a place at which two separate and/or independent structures, members, apparatus, assemblies, components, and/or systems join, connect, are coupled, or meet and act on, or communicate, mechanically and/or electronically, with each other. In certain embodiments, "interface" may refer to a surface forming a common boundary of two bodies, spaces, structures, members, apparatus, assemblies, components, or phases. (search "interface" on Merriam-Webster.com. Merriam-Webster, 2021. Web. 15 Nov. 2021. Modified.) In certain embodiments, the term interface may be used with an adjective that identifies a type or function for the interface. For example, an engagement or coupling interface may refer to one or more structures that interact, connect, or couple to mechanically join or connect two separate structures, each connected to a side of the interface. In another example, a user interface may refer to one or more mechanical, electrical, or electromechanical structures that interact with or enable a user to provide user input, instructions, input signals, data, or data values and receive output, output data, or feedback.

"Cut surface" or "cut face" refers to a surface of an object that is created or formed by the removal of one or more parts of the object that includes the original surface. Cut surfaces or cut faces can be created using a variety of methods, tools, or apparatuses and may be formed using a variety of removal actions, including, but not limited to, fenestrating, drilling, abrading, cutting, sawing, chiseling, digging, scrapping, and the like. Tools and/or methods used for forming a cut surface or cut face can include manual, mechanical, motorized, hydraulic, automated, robotic, and the like.

The present disclosure discloses surgical systems and methods by which a bone condition, that can include a deformity, may be corrected or otherwise addressed. Known methods of addressing bone conditions are often limited to a finite range of discretely sized instruments. A patient with an unusual condition, or anatomy that falls between instrument sizes, may not be readily treated with such systems.

Furthermore, patient-specific instruments may be used for various other procedures on the foot, or on other bones of the musculoskeletal system. For example, patient-specific instruments and/or other instruments may be used for various procedures including resection and translation of a head of a long bone, determining where to perform an osteotomy on one or more joints or part of one or more bones, determining ligament or tendon attachment or anchoring points, determining where to form bone tunnels or position anchors, tendon or graft deployment, and the like.

FIG. 1A is a flowchart diagram depicting a method 100 for correcting a bone condition, according to one embodiment. The method 100 may be used for any of a wide variety of bone conditions, including but not limited to deformities, fractures, joint failure, and/or the like. Further, the method 100 may provide correction with a wide variety of treatments, including but not limited to arthroplasty, arthrodesis, fracture repair, and/or the like.

As shown, the method 100 may begin with a step 102 in which a CT scan (or another three-dimensional image, also referred to as medical imaging) of the patient's anatomy is obtained. The step 102 may include capturing a scan of only the particular bone(s) to be treated, or may include capture of additional anatomic information, such as the surrounding tissues. Additionally or alternatively, the step 102 may include receiving a previously captured image, for example, at a design and/or fabrication facility. Performance of the step 102 may result in possession of a three-dimensional model of the patient's anatomy, or three-dimensional surface points that can be used to construct such a three-dimensional model.

After the step 102 has been carried out, the method 100 may proceed to a step 104 in which a CAD model of the patient's anatomy (including one or more bones) is generated. The CAD model may be one example of a bone model. The CAD model may be of any known format, including but not limited to SolidWorks, Catia, AutoCAD, or DXF. In some embodiments, customized software may be used to generate the CAD model from the CT scan. The CAD model may only include the bone(s) to be treated and/or may include surrounding tissues. In alternative embodiments, the step 104 may be omitted, as the CT scan may capture data that can directly be used in future steps without the need for conversion.

In one embodiment, the CAD model generated and/or patient-specific instrumentation, implants, and/or plan for conducting an operative procedure, may be enhanced by the use of advanced computer analysis system, machine learning, and/or automated/artificial intelligence. For example, these technologies may be used to revise a set of steps for a procedure such that a more desirable outcome is achieved.

In a step 106, the CAD model and/or CT scan data may be used to model patient-specific instrumentation that can be used to correct the condition, as it exists in the patient's anatomy. In some embodiments, any known CAD program may be used to view and/or manipulate the CAD model and/or CT scan, and generate one or more instruments that are matched specifically to the size and/or shape of the patient's bone(s). In some embodiments, such instrumentation may include a targeting guide, trajectory guide, drill guide, cutting guide, tendon trajectory guide, capital fragment positioning guide, or similar guide that can be attached to one or more bones, with one or more features that facilitate work on the one or more bones pursuant to a procedure such as arthroplasty or arthrodesis. In some embodiments, performance of the step 106 may include modelling an instrument with a bone engagement surface that is shaped to match the contour of a surface of the bone, such that the bone engagement surface can lie directly on the corresponding contour.

In a step 108, the model(s) may be used to manufacture patient-specific instrumentation and/or implants. This may be done via any known manufacturing method, including casting, forging, milling, additive manufacturing, and/or the like. Additive manufacturing may provide unique benefits, as the model may be directly used to manufacture the instrumentation and/or implants (without the need to generate molds, tool paths, and/or the like beforehand). Such instrumentation may optionally include a targeting guide, trajectory guide, drill guide, cutting guide, positioner, positioning guide, tendon trajectory guide, or the like.

In addition to, or in the alternative to the step 108, the model(s) may be used to select from available sizes of implants and/or instruments or instruments having various attributes and advise the surgeon accordingly. For example, where a range of guides are available for a given procedure, analysis of the CAD data may facilitate pre-operative selection of the optimal guide and/or optimal placement of the guide on the bone. Similarly, if a range of implants and/or instruments may be used for a given procedure, analysis of the CAD data may facilitate pre-operative selection of the optimal implant(s). More particularly, properly-sized spacers, screws, bone plates, and/or other hardware may be pre-operatively selected.

Thus, the result of the step 108 may provision, to the surgeon, of one or more of the following: (1) one or more patient-specific instruments; (2) one or more patient-specific implants; (3) an instrument, selected from one or more available instrument sizes and/or configurations; (4) an implant, selected from one or more available implant sizes and/or configurations; (5) instructions for which instrument (s) to select from available instrument sizes and/or configurations; (6) instructions for which implant(s) to select from available implant sizes and/or configurations; (7) instructions for proper positioning or anchorage of one or more instruments to be used in the procedure; and (8) instructions for proper positioning or anchorage of one or more implants to be used in the procedure. These items may be provided to the surgeon directly, or to a medical device company or representative, for subsequent delivery to the surgeon.

In a step 110, the manufactured instrumentation may be used in surgery to facilitate treatment of the condition. In some embodiments, this may include placing the modelled bone engagement surface against the corresponding contour of the bone used to obtain its shape, and then using the resection feature(s) to guide resection of one or more bones. Then the bone(s) may be further treated, for example, by attaching one or more joint replacement implants (in the case of joint arthroplasty), or by attaching bone segments together (in the case of arthrodesis or fracture repair). Prior to completion of the step 110, the instrumentation may be removed from the patient, and the surgical wound may be closed.

As mentioned previously, the method 100 may be used to correct a wide variety of bone conditions. One example of the method 100 will be shown and described in connection with FIG. 1B, for correction of a bunion deformity of the foot.

In certain embodiments, one or more of a method, apparatus, and/or system of the disclosed solution can be used for training a surgeon to perform a patient-specific procedure or technique. In one embodiment, the CAD model generated and/or patient-specific instrumentation, implants, and/or plan for conducting an operative procedure can be used to train a surgeon to perform a patient-specific procedure or technique.

In one example embodiment, a surgeon may submit a CT scan of a patient's foot to an apparatus or system that implements the disclosed solution. Next, a manual or automated process may be used to generate a CAD model and for making the measurements and correction desired for the patient. In the automated process, an advanced computer analysis system, machine learning and automated/artificial intelligence may be used to generate a CAD model and/or one or more patient-specific instruments and/or operation plans. For example, a patient-specific instrument may be fabricated that is registered to the patient's anatomy using a computer-aided machine (CAM) tool. In addition, a CAM tool may be used to fabricate a 3D structure representative of the patient's anatomy, referred to herein as a patient-specific synthetic cadaver. (e.g., one or more bones of a patient's foot). Next, the patient-specific instrument and the patient-specific synthetic cadaver can be provided to a surgeon who can then rehearse an operation procedure in part or in full before going into an operating room with the patient.

In certain embodiments, the patient-specific instrument or instrument can be used to preposition and/or facilitate pre-drilling holes for a plate system for fixation purposes. Such plate systems may be optimally placed, per a CT scan, after a correction procedure for optimal fixation outcome. In another embodiment, the CAD model and/or automated process such as advanced computer analysis, machine learning and automated/artificial intelligence may be used to measure a depth of through a patient-specific resection guide for use with robotics apparatus and/or systems which would control the depth of each cut within the guide to protect vital structures below or adjacent to a bone being cut. In another embodiment, the CAD model and/or automated process such as advanced computer analysis, machine learning and automated/artificial intelligence may be used to define desired fastener (e.g. bone screw) length and/or trajectories through a patient-specific instrument and/or implant. The details for such lengths, trajectories, and components can be detailed in a report provided to the surgeon preparing to perform a procedure.

Figure 1B:
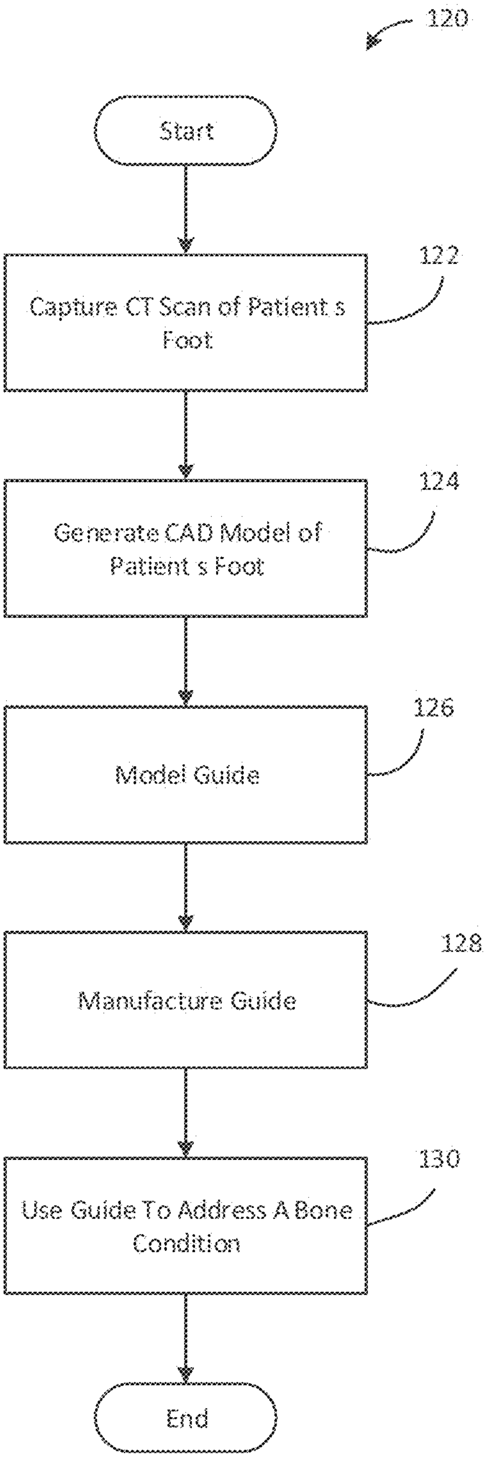
FIG. 1B is a flowchart diagram depicting a method for remediating a condition, according to one embodiment.

FIG. 1B is a flowchart diagram depicting a method 120 for correcting or remediating a bone condition, according to one embodiment. The method 120 may be used to prepare for an orthopedic procedure which corrects or remediates a bone, muscle, deformity, and/or tendon condition of a patient.

As shown, the method 120 may begin with a step 122 in which a CT scan (or another three-dimensional image) of the patient's foot is obtained. The step 122 may include capturing a scan of select bones of a patient or may include capturing additional anatomic information, such as the entire foot. Additionally, or alternatively, the step 122 may include receipt of previously captured image data. Capture of the entire foot in the step 122 may facilitate proper alignment of the first metatarsal with the rest of the foot (for example, with the second metatarsal). Performance of the step 122 may result in generation of a three-dimensional model of the patient's foot, or three-dimensional surface points that can be used to construct such a three-dimensional model.

In certain cases, a patient may have received implants in their foot due to a prior surgical procedure. When this is the case, step 122 may result in a CT scan that includes noise, distortions, or aberrations that manifest in the CT and are caused at least in part by implants already in a patient's foot. In these cases, the method 120 may further include revising the scan my adjusting the sensitivity, activating certain noise filters, or taking other tuning or refining or revision measures when obtaining the CT scan in order to get as accurate as possible of a CT scan. For example, a technician may use an existing CT scan to mark out an area that the CT scanner should avoid or using different settings within order to account to potential interference from existing implants in a patient's foot.

After the step 122 has been carried out, the method 120 may proceed to a step 124 in which a CAD model of the relevant portion of the patient's anatomy is generated. The CAD model may optionally include the bones of the entire foot, like the CT scan obtained in the step 122. In alternative embodiments, the step 124 may be omitted in favor of direct utilization of the CT scan data, as described in connection with the step 104.

In a step 126, the CAD model and/or CT scan data may be used to model patient-specific instrumentation that can be used to correct or remediate a bone condition. Such instrumentation may include a guide. In one example, the guide can seat or abut or contact a surface of a bone and including an opening that guides a trajectory for a fastener for a procedure. In some embodiments, performance of the step 126 may include modelling the guide with a bone engagement surface that is shaped to match contours of the surfaces of the bone, such that the bone engagement surface can lie directly on the corresponding contours of the bone.

In a step 128, the model(s) may be used to manufacture patient-specific instrumentation and/or instruments. This may include manufacturing an instrument with the bone engagement surface and/or other features as described above. As in the step 108, the step 128 may additionally or alternatively involve provision of one or more instruments and/or implants from among a plurality of predetermined configurations or sizes. Further, the step 128 may additionally, or alternatively, involve provision of instructions for placement and/or anchorage of one or more instruments and/or instruments to carry out the procedure.

In a step 130, the manufactured instrument may be used in surgery to facilitate treatment of the condition. In certain embodiments, a bone engagement surface of the instrument may be placed against the corresponding contours of the bone. The instrument may include an opening and/or trajectory guide to guide insertion of a trajectory guide such as a temporary fastener such as a K-wire. The instrument may then be removed, and the remaining steps of a surgical procedure performed.

Method 100 and method 120 are merely exemplary. Those of skill in the art will recognize that various steps of the method 100 and the method 120 may be reordered, omitted, and/or supplemented with additional steps not specifically shown or described herein.

As mentioned previously, the method 120 is one species of the method 100; the present disclosure encompasses many different procedures, performed with respect to many different bones and/or joints of the body. Exemplary steps and instrumentation for the method 120 will further be shown and described in connection with the present disclosure. Those of skill in the art will recognize that the method 120 may be used in connection with different instruments; likewise, the instruments of the present disclosure may be used in connection with methods different from the method 100 and the method 120.

Figure 2A:
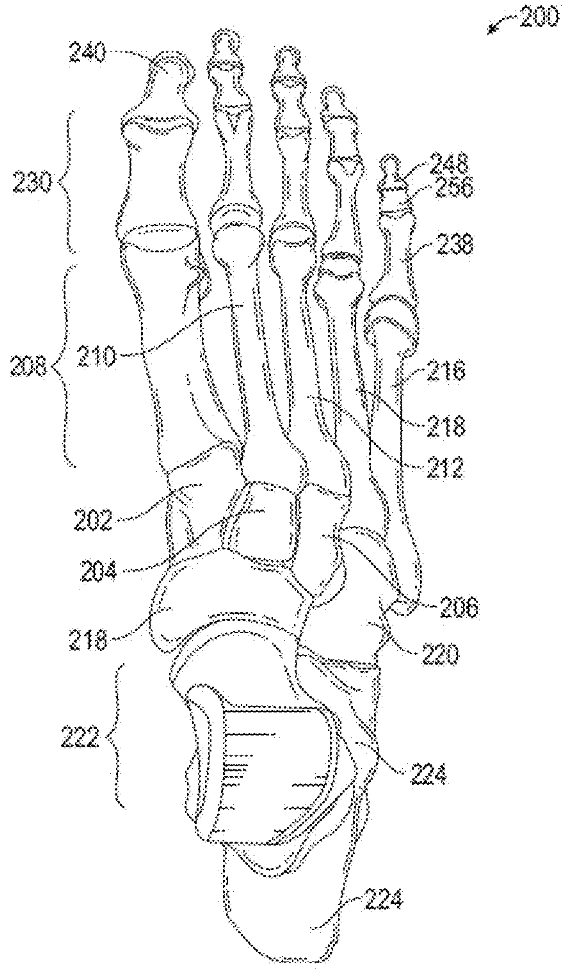
FIG. 2A is a dorsal perspective view of bones of a foot.

FIG. 2A is a perspective dorsal view of a foot 200. The foot 200 may have a medial cuneiform 202, an intermediate cuneiform 204, lateral cuneiform 206, a first metatarsal 208, a second metatarsal 210, third metatarsal 212, fourth metatarsal 214, fifth metatarsal 216, navicular 218, cuboid 220, talus 222, and calcaneus 224, among others. The medial cuneiform 202 and the intermediate cuneiform 204 may be joined together at a first metatarsocuneiform joint, and the first metatarsal 208 and the second metatarsal 210 may be joined together at a second metatarsocuneiform joint. The foot 200 includes a set of proximal phalanges numbered first through fifth (230, 232, 234, 236, 238) and a set of distal phalanges numbered first through fifth (240, 242, 244, 246, 248) and a set of middle phalanges numbered second through fifth (250, 252, 254, 256).

Figure 2B:
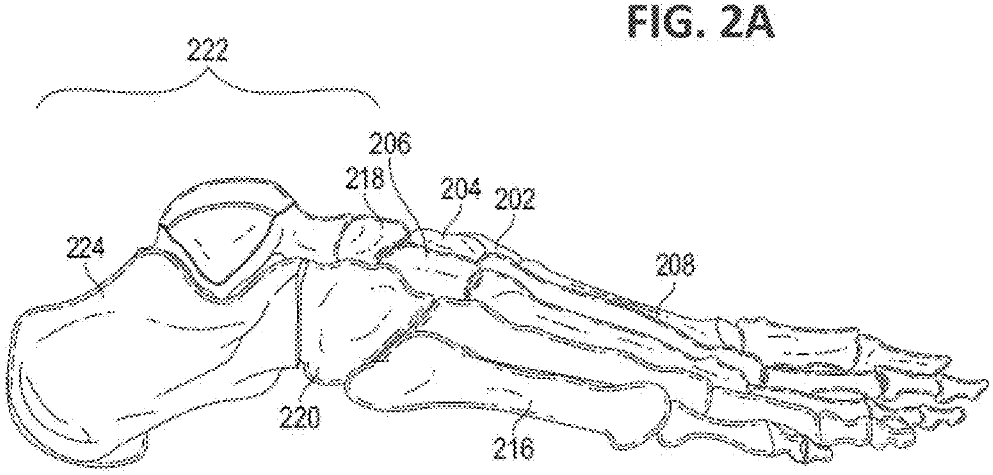
FIG. 2B is a lateral perspective view of bones of a foot.

FIG. 2B is a perspective lateral view of a foot 200, with bones of the foot labeled.

Figure 2C:
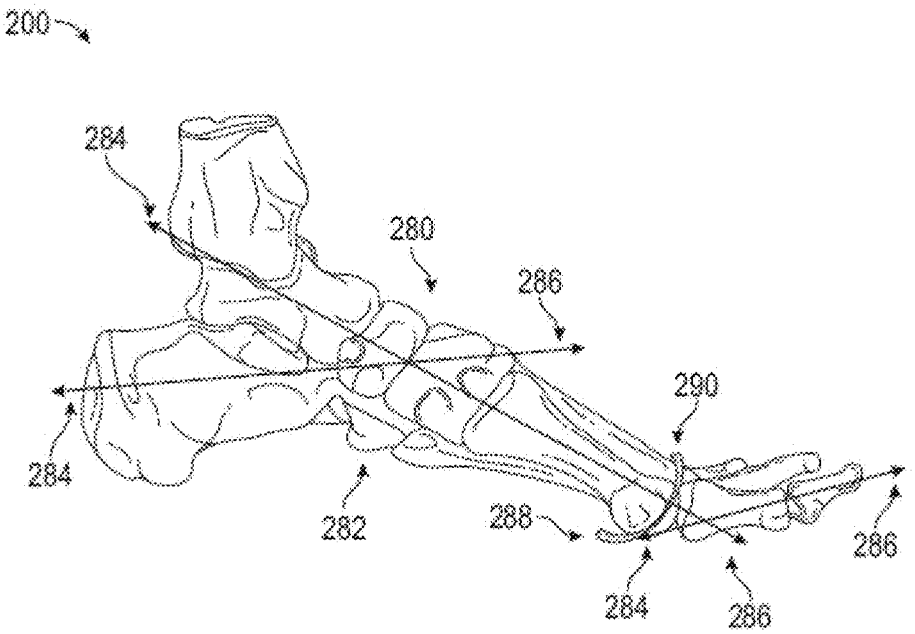
FIG. 2C is a medial perspective view of bones of a foot.
Figure 2D:
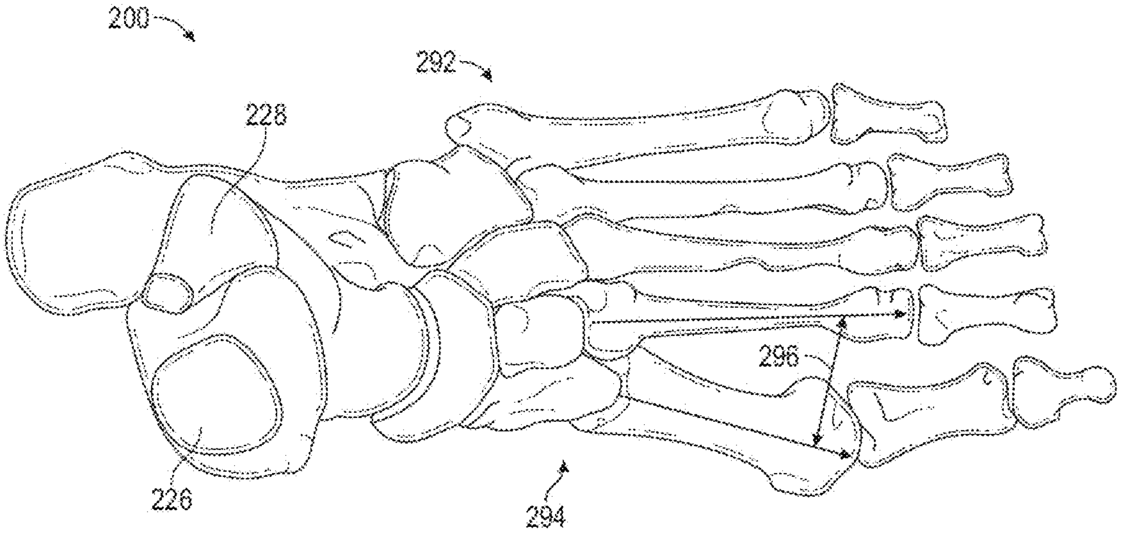
FIG. 2D is a dorsal perspective view of bones of a foot.

FIG. 2C is a perspective medial view of a foot illustrating a dorsal side 280 and a plantar side 282. The foot 200, as illustrated, may have a tibia 226 and a fibula 228, among others. Dorsal refers to the top of the foot. Plantar refers to the bottom of the foot. Proximal 284 is defined as "closer to the primary attachment point". Distal 286 is defined as "further away from the attachment point". Plantarflex or plantarflexion 288 means movement toward the plantar side 282 of a foot or hand, toward the sole or palm. Dorsiflex or dorsiflexion 290 means movement toward the dorsal side 280 of a foot or hand, toward the top. FIG. 2D is a perspective dorsal view of the foot 200. A transverse plane is the plane that shows the top of the foot. A lateral side 292 means a side furthest away from the midline of a body, or away from a plane of bilateral symmetry of the body. A medial side 294 means a side closest to the midline of a body, or toward a plane of bilateral symmetry of the body. For a Lapidus procedure, the intermetatarsal (IM) angle 296 is the angle to be corrected to remove the hallux valgus (bunion) deformity.

Figure 2E:
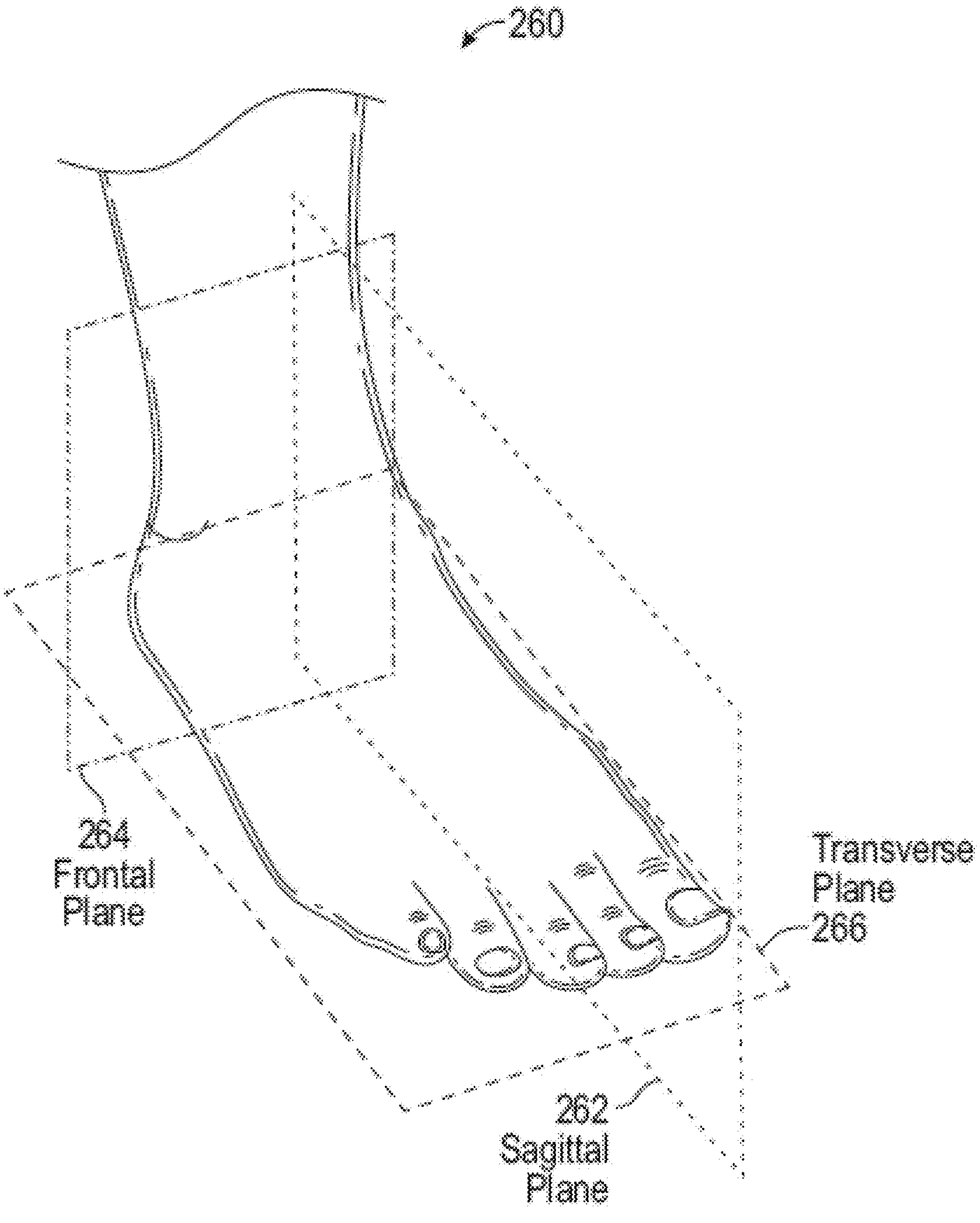
FIG. 2E is a view of a foot illustrating common planes of reference for a human foot.

FIG. 2E is a view of a foot illustrating common planes 260 of reference for a human foot. FIG. 2E illustrates a sagittal plane 262 that divides the foot into a right section and a left section half. The sagittal plane 262 is perpendicular to frontal or coronal plane 264 and the transverse plane 266. In the foot, the frontal plane 264 generally runs vertically through the ankle and the transverse plane 266 generally runs horizontally through the midfoot and toes of the foot.

Every patient and/or condition is different; accordingly, the degree of angular adjustment needed in each direction may be different for every patient. Use of a patient-specific instrument may help the surgeon obtain an optimal realignment, target, or position a bone tunnel, position one or more resections and/or fasteners and the like. Thus, providing patient-specific instruments, jigs, and/or instrumentation may provide unique benefits.

The present patient-specific instrumentation may be used to correct a wide variety of conditions. Such conditions include, but are not limited to, angular deformities of one bone in either the lower or upper extremities (for example, tibial deformities, calcaneal deformities, femoral deformities, and radial deformities). The present disclosure may also be used to treat an interface between two bones (for example, the ankle joint, metatarsal cuneiform joint, lisfranc's joint, complex Charcot deformity, wrist joint, knee joint, etc.). As one example, an angular deformity or segmental malalignment in the forefoot may be treated, such as is found at the metatarsal cuneiform level, the midfoot level such as the navicular cuneiform junction, hindfoot at the calcaneal cuboid or subtalar joint or at the ankle between the tibia and talar junction. Additionally, patient-specific instruments could be used in the proximal leg between two bone segments or in the upper extremity such as found at the wrist or metacarpal levels.

Figure 3:
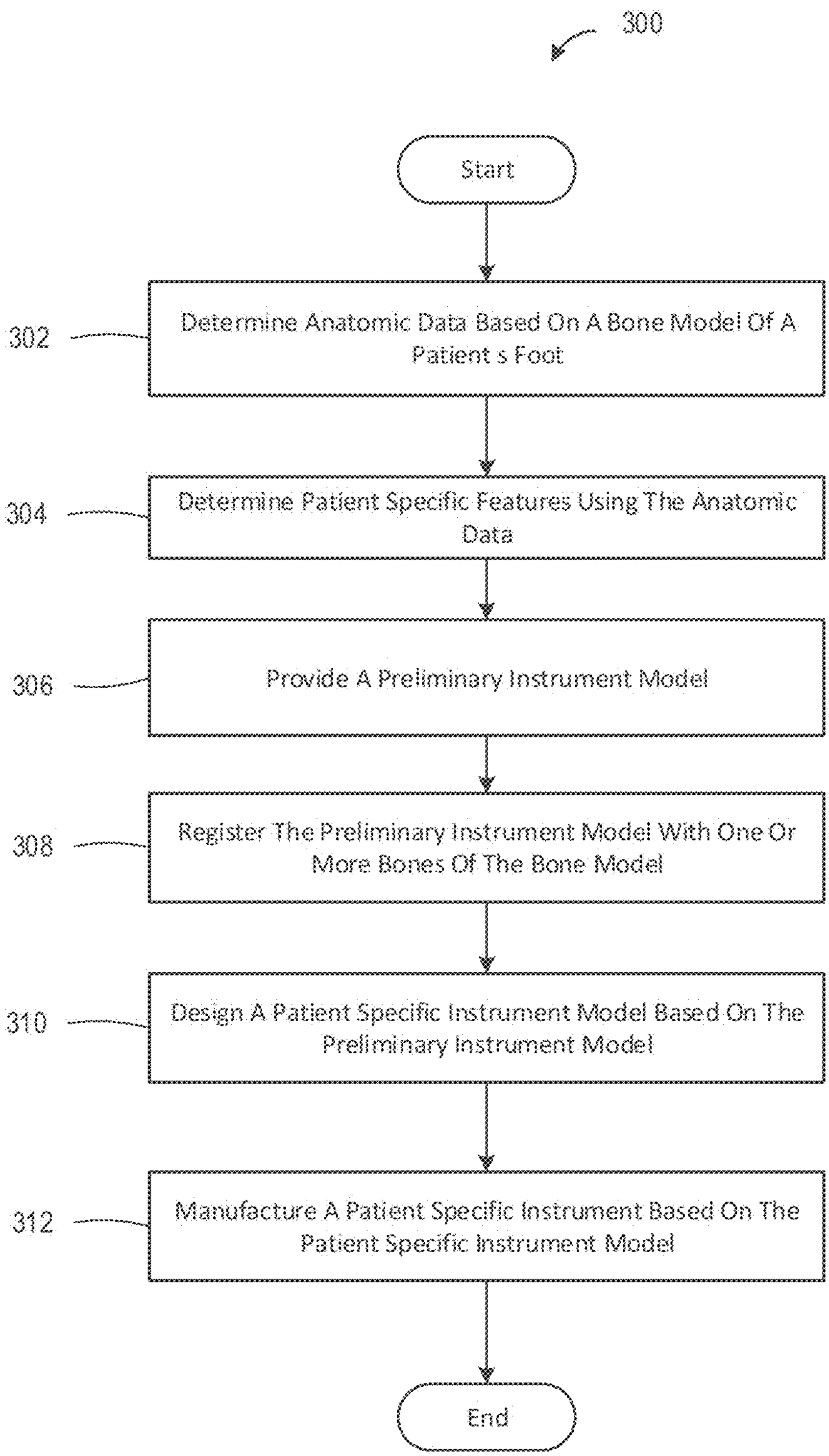
FIG. 3 is a flowchart diagram depicting a method for generating one or more patient-specific instruments, according to one embodiment.

FIG. 3 illustrates a flowchart diagram depicting a method 300 for generating one or more instruments (which may or may not be patient-specific) configured to correct or address a bone or foot condition, according to one embodiment. Prior to steps of the method 300, a bone model (also referred to as CAD model above) is generated. The bone model may be generated using medical imaging of a patient's foot and may also be referred to as an anatomic model. The medical imaging image(s) may be used by computing devices to generate patient imaging data. The patient imaging data may be used to measure and account for orientation of one or more structures of a patient's anatomy. In certain embodiments, the patient imaging data may serve, or be a part of, anatomic data for a patient.

In one embodiment, the method 300 begins after a bone model of a patient's body or body part(s) is generated. In a first step 302, the method 300 may review the bone model and data associated with the bone model to determine anatomic data of a patient's foot.

After step 302, the method 300 may determine 304 one or more angles (e.g., trajectory angle) and/or patient-specific features for a procedure using the anatomic data. "Trajectory angle" refers to a recommended angle for deployment of an instrument, graft, body part, or resection feature angle relative to a bone of a patient for a procedure. In certain embodiments, determining steps, instruments, and/or implants for a corrective procedure may employ an advanced computer analysis system, expert systems, machine learning, and/or automated/artificial intelligence.

Next, the method 300 may proceed and a preliminary instrument model is provided 306 from a repository of template models. A preliminary instrument model is a model of a preliminary instrument.

As used herein, "preliminary instrument" refers to an instrument configured, designed, and/or engineered to serve as a template, prototype, archetype, or starting point for creating, generating, or fabricating a patient-specific instrument. In one aspect, the preliminary instrument may be used, as-is, without any further changes, modifications, or adjustments and thus become a patient-specific instrument. In another aspect, the preliminary instrument may be modified, adjusted, or configured to more specifically address the goals, objectives, or needs of a patient or a surgeon and by way of the modifications become a patient-specific instrument. The patient-specific instrument can be used by a user, such as a surgeon, to guide steps in a surgical procedure, such as an osteotomy, graft harvest (e.g., autograft, allograft, or xenograft), minimally invasive surgical (MIS) procedure, and/or a tendon transfer procedure. Accordingly, a preliminary instrument model can be used to generate a patient-specific instrument. The patient-specific instrument model may be used in a surgical procedure to facilitate one or more steps of the procedure, and may be used to generate a patient-specific instrument that can be used in a surgical procedure for the patient.

In certain embodiments, the preliminary instrument model may be generated based on anatomic data and/or a bone model or a combination of these, and no model or predesigned structure, template, or prototype. Alternatively, or in addition, the preliminary instrument model may be, or may originate from, a template instrument model selected from a set of template instrument models. Each model in the set of template instrument models may be configured to fit an average patient's foot. The template instrument model may subsequently be modified or revised by an automated process or manual process to generate the preliminary instrument model used in this disclosure.

As used herein, "template instrument" refers to an instrument configured, designed, and/or engineered to serve as a template for creating, generating, or fabricating a patient-specific instrument. In one aspect, the template instrument may be used, as-is, without any further changes, modifications, or adjustments and thus become a patient-specific instrument. In another aspect, the template instrument may be modified, adjusted, or configured to more specifically address the goals, objectives, or needs of a patient or a surgeon and by way of the modifications become a patient-specific instrument. The patient-specific instrument can be used by a user, such as a surgeon, to guide making one or more resections of a structure, such as a bone for a procedure. Accordingly, a template instrument model can be used to generate a patient-specific instrument model. The patient-specific instrument model may be used in a surgical procedure to address, correct, or mitigate effects of the identified deformity and may be used to generate a patient-specific instrument that can be used in a surgical procedure for the patient.

Next, the method 300 may register 308 the preliminary instrument model with one or more bones of the bone model. This step 308 facilitates customization and modification of the preliminary instrument model to generate a patient-specific instrument model from which a patient-specific instrument can be generated. The registration step 308 may combine two models and/or patient imaging data and position both models for use in one system and/or in one model.

Next, the method 300 may design 310 a patient-specific instrument and/or procedure model based on the preliminary instrument model. The design step 310 may be completely automated or may optionally permit a user to make changes to a preliminary instrument model or partially completed patient-specific instrument model before the patient-specific instrument model is complete. A preliminary instrument model and patient-specific instrument model are two examples of an instrument model. As used herein, "instrument model" refers to a model, either physical or digital, that represents an instrument, tool, apparatus, or device. Examples, of an instrument model can include a cutting instrument model, a resection instrument model, an alignment instrument model, a reduction instrument model, a patient-specific tendon trajectory instrument model, graft harvesting instrument model, minimally invasive surgical (MIS) positioner model, or the like. In one embodiment, a patient-specific instrument and a patient-specific instrument model may be unique to a particular patient and that patient's anatomy and/or condition.

The method 300 may conclude by a step 312 in which a patient-specific instrument may be manufactured based on the patient-specific instrument model. Various manufacturing tools, devices, systems, and/or techniques can be used to manufacture the patient-specific instrument.

Figure 4:
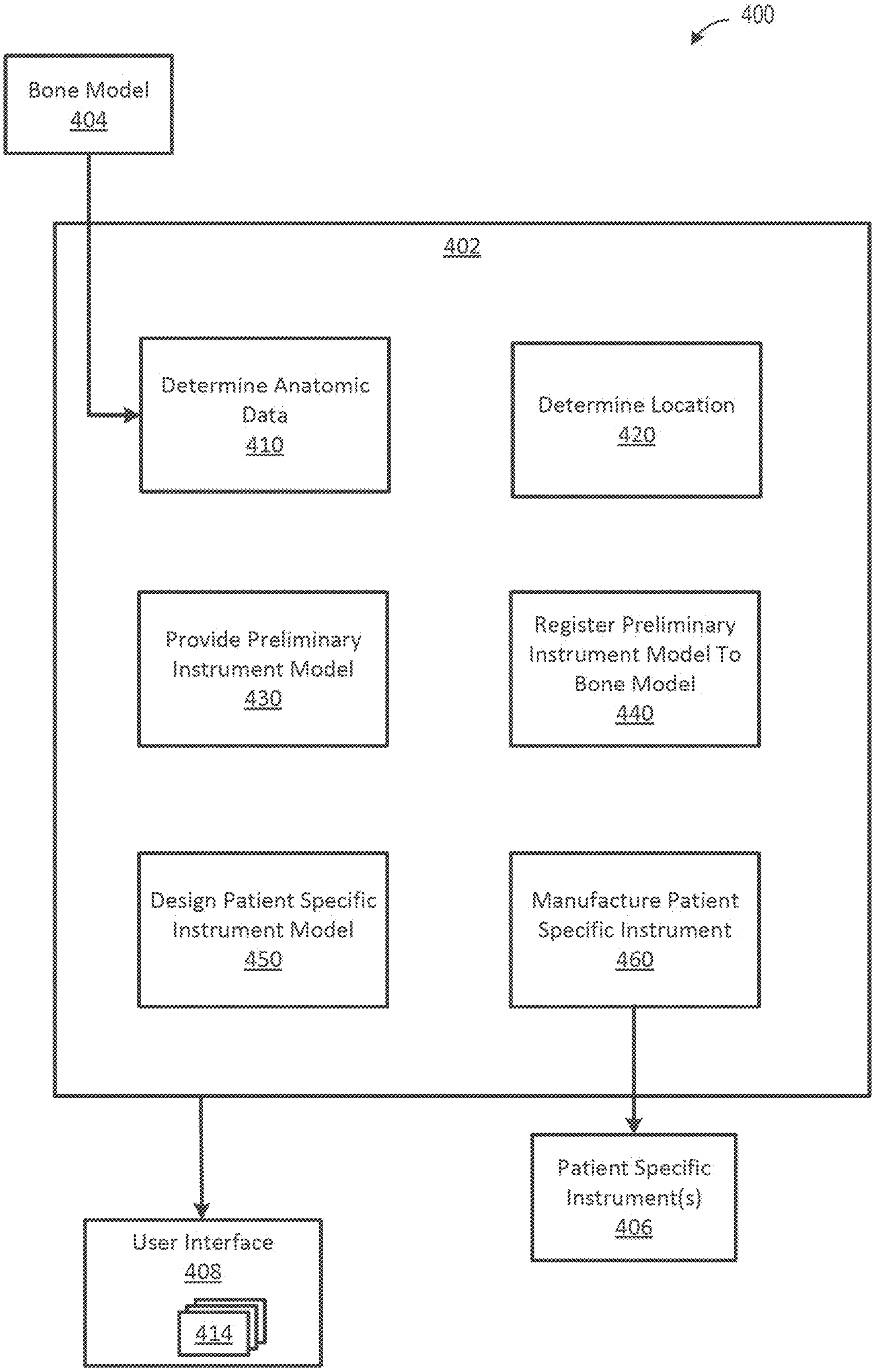
FIG. 4 illustrates an exemplary system configured to generate one or more patient-specific instruments, according to one embodiment.

FIG. 4 illustrates an exemplary system 400 configured to generate one or more patient-specific instruments configured to facilitate surgical procedures, according to one embodiment. The system 400 may include an apparatus 402 configured to accept, review, receive or reference a bone model 404 and provide a patient-specific instrument 406 or patient-specific instruments 406. In one embodiment, the apparatus 402 is a computing device. In another embodiment, the apparatus 402 may be a combination of computing devices and/or software components or a single software component such as a software application.

The apparatus 402 may include a determination module 410, a location module 420, a provision module 430, a registration module 440, a design module 450, and a manufacturing module 460. Each of which may be implemented in one or more of software, hardware, or a combination of hardware and software.

The determination module 410 determines anatomic data 412 from a bone model 404. In certain embodiments, the system 400 may not include a determination module 410 if the anatomic data is available directly from the bone model 404. In certain embodiments, the anatomic data for a bone model 404 may include data that identifies each anatomic structure within the bone model 404 and attributes about the anatomic structure. For example, the anatomic data may include measurements of the length, width, height, and density of each bone in the bone model. Furthermore, the anatomic data may include position information that identifies where each structure, such as a bone is in the bone model 404 relative to other structures, including bones. The anatomic data may be in any suitable format and may be stored separately or together with data that defines the bone model 404.

In one embodiment, the determination module 410 may use advanced computer analysis system such as image segmentation to determine the anatomic data. The determination module 410 may determine anatomic data from one or more sources of medical imaging data, images, files, or the like. Alternatively, or in addition the determination module 410 may use software and/or systems that implement one or more artificial intelligence methods (e.g., machine learning and/or neural networks) for deriving, determining, or extrapolating, anatomic data from medical imaging or the bone model. In one embodiment, the determination module 410 may perform an anatomic mapping of the bone model 404 to determine each unique aspect of the intended osteotomy procedure and/or bone resection and/or bone translation. The anatomic mapping may be used to determine coordinates to be used for an osteotomy procedure, position and manner of resections to be performed either manually or automatically or using robotic surgical assistance, a width for bone cuts, an angle for bone cuts, a predetermined depth for bone cuts, dimensions and configurations for resection instruments such as saw blades, milling bit size and/or speed, saw blade depth markers, and/or instructions for automatic or robotic resection operations.

In one embodiment, the determination module 410 may use advanced computer analysis system such as image segmentation to determine the anatomic data. The determination module 410 may determine anatomic data from one or more sources of medical imaging data, images, files, or the like. The determination module 410 may perform the image segmentation using 3D modeling systems and/or artificial intelligence (AI) segmentation tools. In certain embodiments, the determination module 410 is configured to identify and classify portions of bone based on a condition of the bone, based on the bone condition. Such classifications may include identifying bone stability, bone density, bone structure, bone deformity, bone structure, bone structure integrity, and the like. Accordingly, the determination module 410 may identify portions or sections or one or more bones based on a quality metric for the bone. Advantageously, that determination module 410 can identify high quality bone having a viable structure, integrity, and/or density versus lower quality bone having a nonviable structure, integrity, and/or density and a plurality of bone quality levels in between.

Accordingly, the determination module 410 can guide a surgeon to determine which areas of one or more bones of a patient are within a “soft tissue envelope” (bone of undesirable quality) as that bone relates to a particular deformity or pathology. Identifying the quality of one or more bones of the patient can aid a surgeon in determining what type of correction or adjustment is needed. For example, an ulceration that occurs due to a boney deformity can be mapped using the determination module 410 in a way that a correction can be performed to correct the deformity and reduce pressure to an area and address the structures that were causing the pressure ulceration/skin breakdown.

In addition, the determination module 410 and/or another component of the apparatus 402 can be used to perform anatomic mapping which may include advanced medical imaging, such as the use of CT scan, ultrasound, MRI, X-ray, and bone density scans can be combined to effectively create an anatomic map that determines the structural integrity of the underlying bone.

Identifying the structural integrity of the underlying bone can help in determining where bone resections (e.g., osteotomies) can be performed to preserve the densest bone in relation to conditions such as Charcot neuropathic, arthropathy where lesser dense bone can fail and collapse. It is well documented in the literature that failure to address and remove such lesser dense bone can ultimately lead to failure of a reconstruction and associated hardware.

The present disclosure provides, by way of at least the exemplary system 400, an anatomic map that can be part of anatomic data. The anatomic map can combine structural, deformity, and bone density information and can be utilized to determine the effective density of bone and help to determine where bone should be resected in order to remove the lesser dense bone while maintaining more viable bone to aid in the planning of the osteotomy/bone resection placement.

The location module 420 determines or identifies one or more recommended locations and/or trajectory angles for deployment of an instrument and/or soft tissue based on the anatomic data 412 and/or the bone model 404. In one embodiment, the location module 420 may compare the anatomic data 412 to a general model that is representative of most patient’s anatomies and may be free from deformities or anomalies. The location module 420 can operate autonomously and/or may facilitate input and/or revisions from a user. The location module 420 may be completely automated, partially automated, or completely manual. A user may control how automated or manual the determining of the location and/or trajectory angles is.

The provision module 430 is configured to provide a preliminary instrument model 438. The provision module 430 may use a variety of methods to provide the preliminary instrument model. In one embodiment, the provision module 430 may generate a preliminary instrument model. In the same, or an alternative embodiment, the provision module 430 may select a template instrument model for surgical procedure configured to enable locating the position and/or providing the trajectory/trajectories provided by the location module 420. In one embodiment, the provision module 430 may select a template instrument model for a minimally invasive surgical (MIS) bunion correction procedure configured to enable locating the position and/or providing the trajectory for the fixation deployment. In one embodiment, the provision module 430 may select a template instrument model from a set of template instrument models (e.g., a library, set, or repository of template instrument models).

The registration module 440 registers the preliminary instrument model 438 with one or more bones or other anatomical structures of the bone model 404. As explained above, registration is a process of combining medical imaging data, patient imaging data, and/or one or more models such that the preliminary instrument model can be used with the bone model 404.

In certain embodiments, the location module 420, provision module 430, and/or registration module 440 may be used together or one or more of these may be used individually to plan and design instrumentation for a surgical procedure. In one embodiment, the instrumentation designed may be used by a user for the procedure. In another embodiment, the apparatus 402 may include one or more instruments and/or tools that are used together within the apparatus 402 to design, validate, and/or fabricate one or more instruments for a surgical procedure. In one embodiment, the apparatus 402 may design, validate, and/or fabricate one or more patient-specific instruments for a surgical procedure.

For example, in one embodiment, the bone model 404 may include a plurality of models for a plurality of bones of a patient. The plurality of bones of the patient may be organized and associated with each other in a manner that substantially corresponds to how those same plurality of bones of the patient are organized and associated with each other. Advantageously, this means that any deformity or any patient-specific characteristic or attribute of the patient's bones is included in the bone model 404. Alternatively, or in addition, the bone model 404 may include one or more soft tissue models or other representations for soft tissue of a patient and include those soft tissue models in substantially the same location and configuration in relation to the plurality of bone models.

In one embodiment, the apparatus 402 includes a user interface 408. The user interface 408 can include software, hardware, and/or a combination of hardware and software that enable a user such as a surgeon and/or a technician to interact with the apparatus 402 and/or one or more modules of the apparatus 402. Accordingly, the user interface 408 may include a display, a keyboard, a mouse, a touch screen, a stylus, a microphone, a speaker, and/or one or more other peripherals that accept input from a user and/or provide output to the user as the user interacts with the apparatus 402.

The user interface 408 may be used to control, operate, and/or interact with any one of the determination module 410, location module 420, provision module 430, registration module 440, design module 450, and manufacturing module 460 either alone and independently and/or in combination of any of them together. Those of skill in the art will appreciate that the user interface 408 may be part of or coupled directly to the apparatus 402. Alternatively, or in addition, the user interface 408 may interface with the apparatus 402 from a remote location over a computer network.

The user interface 408 can include an operating system, a graphical user interface, and/or one or more other software applications that enable the user to interact with and guide the development of one or more patient-specific instruments 406. In the illustrated embodiment, the user interface 408 may include a plurality of design tools 414. The design tools 414 can be any tool that a user may use to prepare, refine, adjust, plan, design, and/or organize the bone model 404 and/or instruments that are going to be used in a surgical procedure. Examples of design tools 414 include but are not limited to rulers, protractors, alignment guides, model translation and/or rotation tools, spaces, sizers, trial guide models, clamps, forceps, spreaders, distractors, compressors, and the like. In certain embodiments, the design tools 414 may be specific to the apparatus 402. In another embodiment, the design tools 414 may be modeled to represent and/or behave just like actual tools that a user might use.

In one embodiment, the design tools 414 can include a set of digital instruments or digital tools that are configured for use within the apparatus 402 but are not going to be fabricated. For example, in one embodiment, one of the design tools may be a digital fulcrum. The digital fulcrum may operate like a spacer or positioner and may be designed to be positioned between two model bones. Once positioned between two model bones, the digital fulcrum may serve as a fulcrum as a user translates and/or rotates one model bone in relation to another.

A digital fulcrum design tool 414 can be useful in planning for a particular surgical procedure, such as a Lapidus procedure. In a Lapidus procedure, a user may seek to move a first metatarsal 208 until the longitudinal axis of the first metatarsal 208 is parallel or near parallel to a longitudinal axis of a second metatarsal 210. A digital fulcrum design tool 414 may include a body connected to a handle. The body may be sized, shaped, and/or configured to fit between a base of a bone model of the first metatarsal 208 and the base of a bone model of the second metatarsal 210. The handle facilitates positioning and manipulating the digital fulcrum design tool 414.

Once a digital fulcrum design tool 414 is positioned, the body maintains a desired spacing between the bone model of the first metatarsal 208 and the bone model of the second metatarsal 210 as a user manipulates the bone model of the first metatarsal 208. A user may manipulate the bone model of the first metatarsal 208 to put the bone model of the first metatarsal 208 in a corrected position for planning the Lapidus surgical procedure.

With the digital fulcrum design tool 414 in position and the bone model of the first metatarsal 208 and the bone model of the second metatarsal 210 in a desired position and/or orientation relative to each other. A user can now proceed with the planning and design of one or more instruments for use in the surgical procedure. In particular, a user can plan and design positions and orientations for one or more fasteners, for a resection guide (which can be patient-specific), for one or more resection features, and for one or more other instruments the user plans to use in the surgical procedure.

Advantageously, the digital fulcrum design tool 414 enables a user to do in a virtual environment the same steps that the user might do in an actual environment during a surgical procedure. For example, in certain surgical procedures, a user may manipulate the position of the first metatarsal 208 in relation to the second metatarsal 210 and use a physical fulcrum instrument or positioner to guide this positioning and/or manipulation. In such a technique, the physical fulcrum instrument or positioner may remain in place as a surgeon determines position and/or trajectories for one or more fasteners and/or guides such as a resection guide. Using the system 400, a user can determine the positions and/or trajectories for fasteners (e.g., K-wires or pins), a resection guide, patient-specific aspects of the resection guide or other instrumentation, in the virtual environment. Those determinations can be preserved by the features created in a patient-specific instrument 406 fabricated using the apparatus 402. For example, holes formed in a resection guide may be positioned and oriented based on a configuration done using the apparatus 402. Fasteners or pins deployed into one or more bones of a patient through the holes may be used to secure a resection guide and then subsequently used to translate and/or rotate the one or more bones during a reduction and/or subsequent fusion of the one or more bones (e.g., a compressor may slide over the fasteners to assist in a reduction).

In one embodiment, the digital fulcrum design tool 414 has a standard size and/or one of a plurality of standard sizes. Alternatively, or in addition, the digital fulcrum design tool 414 is patient-specific and may be generated virtually using the methods and/or apparatuses described herein.

In certain embodiments, the digital fulcrum design tool 414 enables a user to work with models of bones of a patient using the apparatus 402 in a similar manner to how the user would work with the actual bones of the patient during a surgical procedure. In this manner, the digital fulcrum design tool 414 can assist a user in planning a surgical procedure such that adjustments can be made as needed to ensure a successful outcome.

In certain embodiments, the design tool 414 may be tools or models used by a user with the apparatus 402 to perform a step in a design and/or planning process for a surgical procedure and/or for fabrication of one or more patient-specific instruments 406. These design tools 414 may be configured to operate like a physical counterpart and may thus have similar, look, feel, behavior features, characteristics, and the like. Alternatively, or in addition, the design tools 414 may have features and/or functionality that differs from a physical counterpart and may be useful in a virtual environment.

Alternatively, or in addition, the design tools 414 may not resemble a physical device and/or tool. Instead, the design tools 414 may include a set of computer executable code that implements a process and/or an algorithm to accomplish a particular feature and/or task for a user. For example, one or more of the bone models of a bone model 404 may include certain attributes, reference features, anatomical feature, anatomical landmark, and/or attributes that can be used to facilitate the design and/or planning process. Examples of these reference features may include an axis, a plane, a surface, a pivot point, a manipulation point, or the like.

In one embodiment, rather than use a design tool 414, a user may access a feature or function of the apparatus 402 to perform a particular operation during the planning and design stages. For example, one feature may refer to one or more reference features to maintain a certain offset, orientation, position, or other characteristic of one bone model versus another bone model. This feature may be configured to maintain a particular relationship between two bone models, particularly where one bone model is manipulated using the user interface 408.

For example, in one embodiment, a user of the user interface 408 may activate a relationship feature that maintains a particular offset, orientation, and/or position of a bone model of a second metatarsal 210 with respect to a bone model of a first metatarsal 208. This relationship can be a relationship derived based on anatomic data, defined by a technician, defined by a process, or defined by a user. Such a relationship feature may be used in place of a design tool 414 such as a digital fulcrum design tool 414.

The relationship feature may be activated by a user once the bone model of a second metatarsal 210 and the bone model of a first metatarsal 208 have a desired relationship to each other. The relationship feature may be configured to maintain the desired relationship (e.g., offset, orientation, etc.) even if a user manipulates one or the other of the bone model of a second metatarsal 210 and the bone model of a first metatarsal 208. In this manner, a relationship feature can be used by a user in a similar manner to how a design tool 414 such as a digital fulcrum design tool 414 could be used. Once a user makes final adjustments to positions and/or orientations of the bone model of a second metatarsal 210 and the bone model of a first metatarsal 208, the user may proceed with a design and/or planning process to complete the design and/or configuration of one or more instruments, one or more patient-specific instruments 406, one or more surgical technique, and the like.

The design module 450 designs a patient-specific instrument (or patient-specific instrument model) based on the preliminary instrument model. The design operation of the design module 450 may be completely automated, partially automated, or completely manual. A user may control how automated or manual the designing of the patient-specific instrument (or patient-specific instrument model) is.

The manufacturing module 460 may manufacture a patient-specific instrument 406 using the preliminary instrument model. The manufacturing module 460 may use a patient-specific instrument model generated from the preliminary instrument model. The manufacturing module 460 may provide the patient-specific instrument model to one or more manufacturing tools and/or fabrication tool (e.g., additive and/or subtractive). The patient-specific instrument model may be sent to the tools in any format such as an STL file or any other CAD modeling or CAM file or method for data exchange. In one embodiment, a user can adjust default parameters for the patient-specific instrument such as types and/or thicknesses of materials, dimensions, and the like before the manufacturing module 460 provides the patient-specific instrument model to a manufacturing tool.

Effective connection of the guide to one or more bones can ensure that surgical steps are performed in desired locations and/or with desired orientations and mitigate undesired surgical outcomes.

Figure 5:
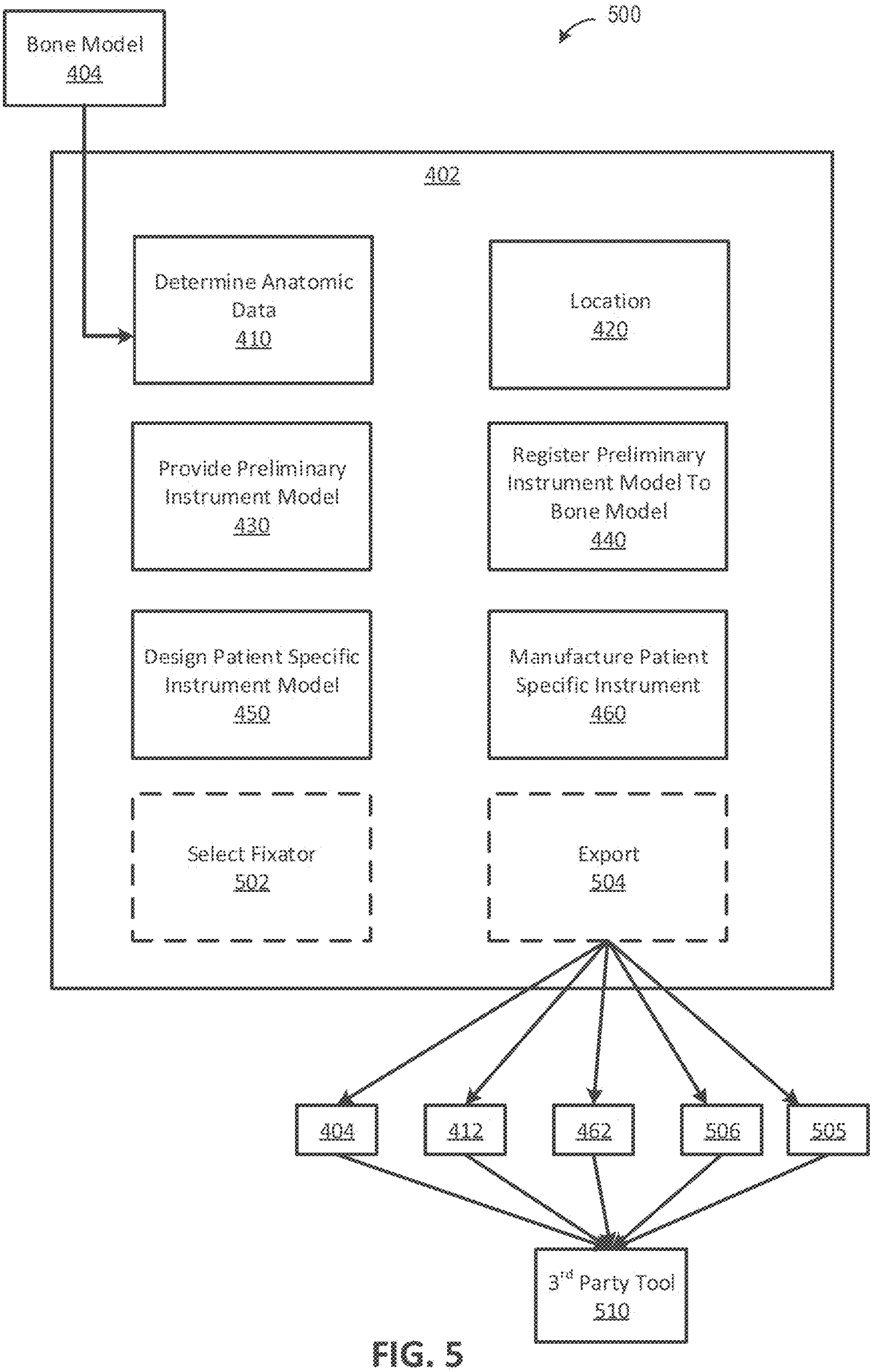
FIG. 5 illustrates an exemplary system configured to generate one or more patient-specific instruments, according to one embodiment.

FIG. 5 illustrates an exemplary system 500 configured to generate one or more patient-specific instruments configured to correct a bone condition, according to one embodiment. The system 500 may include similar components or modules to those described in relation to FIG. 4. In addition, the system 500 may include a fixator selector 502 and/or an export module 504.

The fixator selector 502 enables a user to determine which fixator(s) to use for a MIS bunion correction procedure planned for a patient. In one embodiment, the fixator selector 502 may recommend one or more fixators based on the bone model 404, the location, the trajectory, or input from a user or a history of prior MIS bunion correction procedures performed. The fixator selector 502 may select a fixator model from a set of predefined fixator models or select a physical fixator from a set of fixators. The fixators may include a plate and associated accessories such as screws, anchors, and the like.

In one embodiment, the fixator selector 502 includes an artificial intelligence or machine learning module. The artificial intelligence or machine learning module is configured to implement one or more of a variety of artificial intelligence modules that may be trained for selecting fixator(s) based on anatomic data 412 and/or other input parameters. In one embodiment, the artificial intelligence or machine learning module may be trained using a large data set of anatomic data 412 for suitable fixator(s) identified and labeled in the dataset by professionals for use to treat a particular condition. The artificial intelligence or machine learning module may implement, or use, a neural network configured according to the training such that the artificial intelligence or machine learning module is able to select or recommend suitable fixator(s).

The export module 504 is configured to enable exporting of a patient-specific instrument model 462 for a variety of purposes including, but not limited to, fabrication/manufacture of a patient-specific instrument 406 and/or fixator(s), generation of a preoperative plan, generation of a physical bone model matching the bone model 404, and the like. In one embodiment, the export module 504 is configured to export the bone model 404, anatomic data 412, a patient-specific instrument model 462, a preoperative plan 506, a fixator model 508, or the like. In this manner the custom instrumentation and/or procedural steps for a procedure (e.g., a graft harvesting procedure, minimally invasive surgical (MIS) procedure, or the like) can be used in other tools.

The preoperative plan 506 may include a set of step-by-step instructions or recommendations for a surgeon or other staff in performing a procedure (e.g., a graft harvesting procedure, minimally invasive surgical (MIS) procedure, or the like). The preoperative plan 506 may include images and text instructions and may include identification of instrumentation to be used for different steps of the procedure (e.g., a graft harvesting procedure, minimally invasive surgical (MIS) procedure, or the like). The instrumentation may include the patient-specific instrument 406 and/or one or more fixators/fasteners. In one embodiment, the export module 504 may provide a fixator model which can be used to fabricate a fixator for the procedure.

The exports (404, 412, 462, 506, and 508) may be inputs for a variety of 3rd party tools 510 including a manufacturing tool, a simulation tool, a virtual reality tool, an augmented reality tool, an operative procedure simulation tool, a robotic assistance tool, and the like. A surgeon can then use these tools when performing a procedure or for rehearsals and preparation for the procedure. For example, a physical model of the bones, patient-specific instrument 406, and/or fixators can be fabricated, and these can be used for a rehearsal operative procedure. Alternatively, a surgeon can use the bone model 404, preliminary instrument model 438, and/or a fixator model to perform a simulated procedure using an operative procedure simulation tool.

Referring now to FIGS. 3-5, certain methods, systems, and/or apparatuses are disclosed herein for preparing for, planning, outlining, and/or instrumenting, one or more surgical procedures. Alternatively, or in addition, the methods, systems, and/or apparatuses a disclosed herein can be used for preoperative development and design of systems, instrumentation, and/or implants and/or for preoperative rehearsal and/or instruction of a surgeon before the surgical procedure. For example, a surgeon can use the method 300, bone model(s) 404, patient instrument(s) 406, system 400, and/or apparatus 402 to perform a mock surgical procedure virtually before an actual surgical procedure.

These techniques and/or technologies can greatly advance the medical field and provide valuable instruction and experience to a surgeon prior to an actual surgical procedure. Furthermore, these techniques and/or technologies are made effective owing to the accuracy and precision of the models because of the fidelity of the medical imaging of the patient anatomy. This virtual modeling of patient anatomy has become accurate and helpful, particularly for hard tissue such as bones and the surfaces of these bones.

The fidelity and accuracy of soft tissue models is not as advanced as hard tissue models. Models soft tissue of a patient such as sinews, skin, tendons, ligaments, muscles, fat, and the like may be of limited help preoperatively. Thus, rehearsal of a surgical procedure, particularly one that includes translating and/or reorienting one or more bone fragments may have limited benefits. In such cases, because the surgeon cannot predict or know beforehand how much movement and reorientation the soft tissue of a patient will permit, the surgeon may need to revise or adapt a surgical procedure intraoperatively to achieve optimal outcomes. The system, apparatus, and methods of the present disclosure enable a surgeon to make intraoperative adjustments to surgical plan based on what the surgeon learns during the surgery.

However, the present disclosure can provide a very accurate representation because bone models of the bone model 404 can originate from medical imaging taken with soft tissue in place, the bone model 404 initially reflects bone orientation and/or relationships based on the current soft tissue arrangement. A surgeon, recognizing the role soft tissue may play during the surgical procedure, the surgeon may arrange for two or more preoperative plans and/or one or more patient-specific instruments to accommodate what is found during the surgical procedure.

The present disclosure leverages the use of models, such as computer models, and particularly models of a specific patient to provide and/or generate instrumentation, implants, and/or surgical plans that advanced patient care. Advantageously, these models are unique and customized for a particular patient. Thus, the models reflect the actual anatomical features and aspects of the patient.

However, the utility and helpfulness of the models, methods, systems, and/or apparatuses of FIGS. 3-5, may be dependent on how effectively a surgeon can navigate within, on, or in relation to one or more anatomical references or anatomical features of a patient such that the steps of the surgical procedure can be performed on a patient in the same manner as those modeled using models of the anatomy of the patient. This process of navigation is referred to as a mapping or translation between the virtual or model environment to a physical or real-world environment that includes the patient anatomy and the operating field.

Advantageously, the models, methods, systems, and/or apparatuses of the present disclosure facilitate mapping or translating between a virtual or model environment and/or instrumentation to a physical or real-world environment for a surgical procedure. The present disclosure provides this feature or benefit by providing an apparatus, system, and method, that enables a surgeon to identify, create, form, and/or use reference features for a surgical procedure. The reference feature provides a reference and/or starting point on, in, or associated with anatomy of a patient such that steps, stages, features, or aspects planned and configured within the model can be accurately performed on, with, or to the anatomy of the patient. In certain embodiments, one or more steps of a surgical procedure can be done in connection with or in relation to the reference feature.

The reference feature facilitates moving from one coordinate system or frame of reference in a virtual environment to a position, location, frame of reference, environment, or orientation on, or in, an actual object, structure, device, apparatus, anatomical structure, or the like. Advantageously, the reference feature can coordinate objects, models, or structures in a digital or virtual model or representation with corresponding objects or structures (e.g., anatomical structures) of actual physical objects or structures. Said another way, the reference feature can serve to map from a virtual or modeled object to an actual or physical object.

Advantageously, the embodiment of the present disclosure includes features and aspects that assist a surgeon in locating at least one reference feature, which can then be used in one or more stages of a surgical procedure. In certain embodiments, the actual instruments fabricated using the present disclosure may include one or more references (e.g., a model references). The one or more model instruments may use the one or more references to position and/or orient the one or more model instruments such that other steps of a surgical procedure can be performed in relation to those one or more model instruments and/or model references. Certain model references may key off or related to anatomical references of modeled anatomical body parts. The reference feature(s) correspond to the model references and together enable a surgeon to identify reference features on actual anatomy of a patient for a surgical procedure.

In certain embodiments, one or more fasteners deployed in an instrument such as a resection guide can serve as reference features, for an initial stage of the surgical procedure and/or for subsequent stages of the surgical procedure. In certain embodiments, a bone engagement feature can serve as a reference feature for an osteotomy system and/or surgical procedure.

Advantageously, the embodiments of the present disclosure leverage patient-specific models of patient anatomy and the use of these models to generate patient-specific instruments as well as input from users of the osteotomy (e.g., surgeons). In one embodiment, this input is provided in the form of user directions. Combining patient-specific medical imaging, patient-specific anatomical models, and user directions enable the present disclosure to provide a customized or patient-specific osteotomy that serves the patient's needs as well as aides the surgeon in performing the surgical procedure. In this manner, a surgeon can perform the surgical procedure with higher confidence and assurance that the procedure performed on the patient will coincide with the plan set forth using models in a virtual environment. Consequently, the present disclosure improves the level of patient care and positive outcomes.

Figure 6:
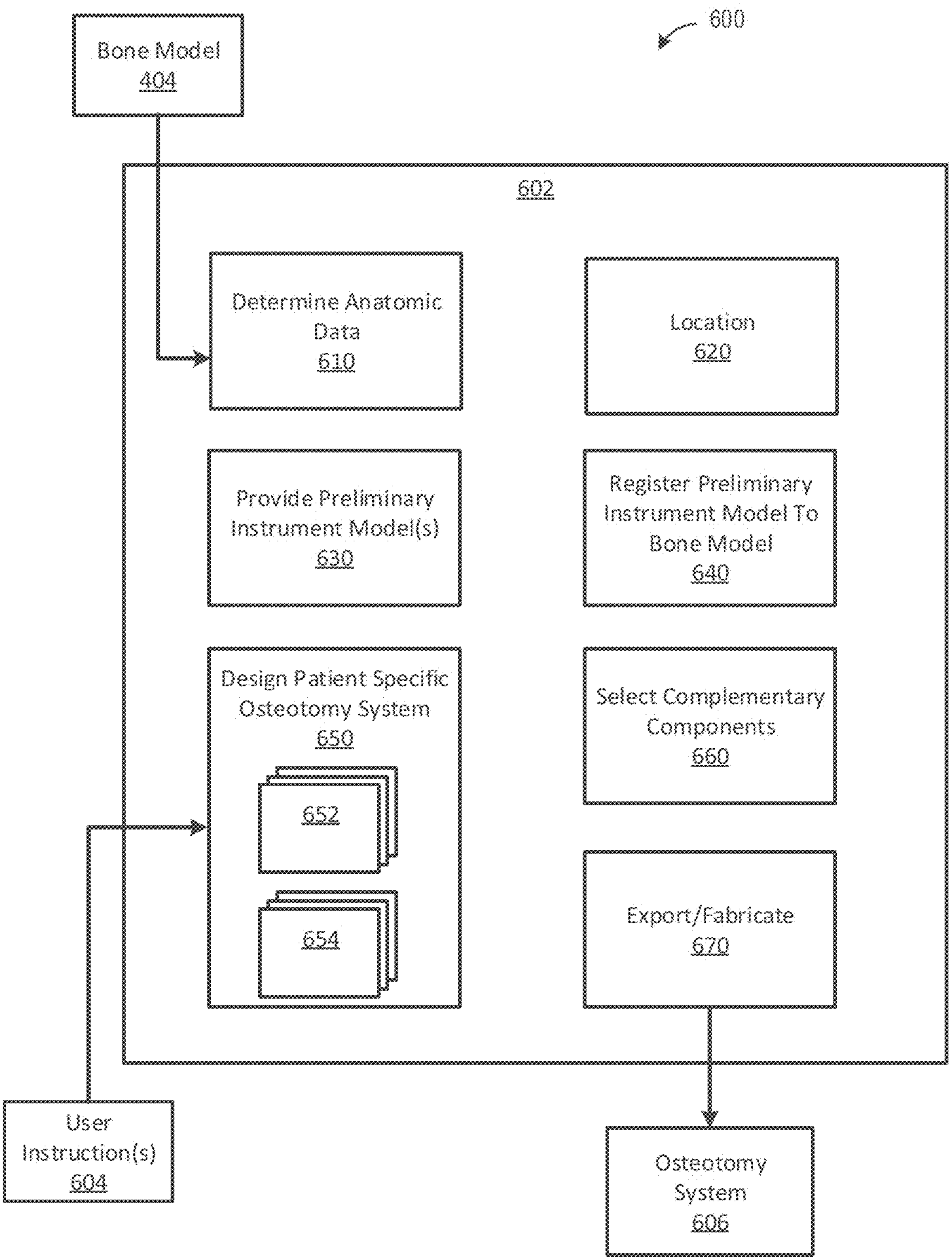
FIG. 6 illustrates an exemplary system configured to generate a patient-specific osteotomy system, according to one embodiment.

FIG. 6 illustrates an exemplary system 600 configured to design, generate, develop, and/or produce an osteotomy system, according to one embodiment. In certain embodiments, the osteotomy system can be patient-specific. One advantage of the present disclosed embodiments is that an end user of an osteotomy system (e.g., instruments, preoperative plan, implants, etc.) can have as much, or as little control or input, over one or more or all of the aspects of the osteotomy system. Furthermore, this osteotomy system can be customized both to the needs and specific aspects of the patient as well as to the needs and/or preferences and/or desires of the user (e.g., surgeon).

The system 600 may include similar components or modules to those described in relation to FIG. 4. The structures, features, and functions, operations, and configurations of the system 600 may be similar or identical to components or modules of system 400, like parts identified with similar reference numerals. Accordingly, the system 600 may include an apparatus 602 configured to accept, review, receive or reference a bone model 404 and user instructions 604 and provide a patient-specific osteotomy system 606. In one embodiment, the apparatus 602 is a computing device. In another embodiment, the apparatus 602 may be a combination of computing devices, systems, apparatuses, software components, single software component such as a software application, one or more third party manufacturers, or the like.

The apparatus 602 may include a determination module 610, a location module 620, a provision module 630, an optional registration module 640, a design module 650, a selection module 660, and an export/fabrication module 670. Each of which may be implemented in one or more of, software, hardware, or a combination of hardware and software. In certain embodiments, one or more parts of the system 600 may be operated by a user (e.g., a technician), a plurality of users, and may include input, involvement, and/or feedback from an end user of the osteotomy system developed. Generally, the end user of the osteotomy system will be a surgeon. Those of skill in the art will appreciate that depending on the surgical procedure being performed, one or more of the modules of the apparatus 602 may or may not be used.

The determination module 610 may operate in a similar manner to the determination module 410. The location module 620 may operate in a similar manner to the location module 420. The provision module 630 may operate in a similar manner to the provision module 430. The registration module 640 may operate in a similar manner to the registration module 440.

The design module 650 enables one or more users to design an osteotomy system 606 and in particular a patient-specific osteotomy system 606. A patient-specific osteotomy system 606 can include a number of different instruments, components, and/or systems, including but not limited to one or more cutting tools, one or more resection guides, one or more provisional fasteners, one or more fixation systems and/or instruments, a preoperative plan, one or more kits of implants and/or trial components, one or more alignment guides, one or more positioning guides, one or more reduction guides, one or more, one or more navigation guides, one or more fixation guides, one or more, one or more compression guides, one or more rotation guides, and the like. In addition, one or more of these components can be patient-specific. For example, the patient-specific osteotomy system 606 can include a patient-specific instrument, patient-specific trajectory guide, a patient-specific resection guide, a patient-specific cutting guide, a patient-specific positioning guide or positioner, another patient-specific instrument, or the like.

Alternatively, or in addition, the patient-specific osteotomy system 606 can include one or more subparts or components of each of the instruments, components and/or systems of the patient-specific osteotomy system 606. For example, in one embodiment, the design module 650 may enable a user and/or end user to determine and/or define a number, size, shape, position, orientation, trajectory and/or configuration for one or more bone attachment features, a number, size, shape, position, orientation, trajectory and/or configuration for one or more resection features, a number, size, shape, position, orientation, trajectory and/or configuration for one or more bone engagement features, a number, size, shape, position, orientation, trajectory and/or configuration for one or more bone engagement surfaces, a number, size, shape, position, orientation, trajectory and/or configuration for one or more fixators (either or both provisional or permanent), and the like.

Those of skill in the art will appreciate that the design module 650 offers a large variety of different options and combinations for the constituents of the patient-specific osteotomy system 606 as well as a plurality of options for the components of the patient-specific osteotomy system 606 and that such options may be overwhelming. Advantageously, the surgical procedure to be performed, the bone model 404, and user instructions 604 each alone and/or in combination define an initial set of members for the patient-specific osteotomy system 606. For example, certain well known surgical techniques have specific names and surgeons understand and/or have experience doing these procedures and therefore know what instruments will be needed for the surgical procedure.

In addition, each surgeon is different just as each patient is different. Therefore, surgeon experience and/or preferences may factor into the members of the patient-specific osteotomy system 606 a particular surgeon wants and/or the configuration of the members of the patient-specific osteotomy system 606. For example, where one surgeon may prefer to use two resection guides another surgeon may want to use one resection guide and perform other osteotomies for the surgical procedure manually or free-hand.

Based on the surgical procedure to be performed, many decisions about the design and/or make up of the patient-specific osteotomy system 606 can be made as recommendations and/or proposals by a technician to a surgeon. These decisions can be based in whole or in part on the surgical procedure to be performed, the bone model 404 and/or the user instructions 604.

For example, suppose a surgeon would like a patient-specific osteotomy system 606 for an ankle fusion procedure. One goal of the ankle fusion procedure may be to relieve pain of the patient and to remove a minimal amount of bone in the process of completing the procedure. In such an example, the bone model 404 may be of one or more bones of a foot and/or ankle of the patient. The surgeon may provide a request and/or a set of user instructions 604 for a patient-specific osteotomy system 606 for this ankle fusion procedure.

Those of skill in the art will appreciate that the user instructions 604 may be of a variety of different types, lengths, number of details and may be provided in a variety of different formats including oral, written, or the like. In one embodiment, the user instructions 604 may be a request for a patient-specific osteotomy system 606 that includes a set of default instruments, preoperative plan, implants, or the like. For example, the user instructions 604 may as short and simple as "Please provide an osteotomy system for an ankle fusion of the left ankle for patient <<identifying information (e.g., name, dob, etc.)>> with an anterior approach." The user instructions 604 may be provided in the form of a product order, a purchase order, a prescription, or the like. The user instructions 604 may be provided in written manual/analog form, include a manual signature, digital form, include an e-signature, or the like. In addition, the user instructions 604 may include security and/or authorization features that enable the receiver to confirm that the user instructions 604 are valid and are authorized by a particular surgeon or doctor. The user instructions 604 may indicate the approach to the surgical site (e.g., an ankle or foot joint or bone) the surgeon wants to take, anterior, posterior, medial, lateral, or the like.

In another embodiment, the user instructions 604 may include specific instructions for the number and/or kind or type of components in the patient-specific osteotomy system 606 and/or the configuration of one or more of these components. For example, the user instructions 604 may identify a specific fixation product or fixation system the surgeon will be using for permanent fixation of the osteotom(ies). Alternatively, or in addition, the user instructions 604 may include designation of one or more complementary components and/or configurations for these components to be included in the patient-specific osteotomy system 606.

In one embodiment, the user instructions 604 may designate a particular material and/or mass for fabricating one or more guides to be included in the patient-specific osteotomy system 606. Some surgeons may find that patient-specific instruments, such as a patient-specific resection guide may more readily register to one or more bone surfaces if the instrument has a greater mass and/or weight. With the greater mass and a sufficient fidelity bone engagement surface, a patient-specific instrument may seem to find its own way or seek out a desired position on a bone that matches or substantially matches a position planned when the patient-specific osteotomy system 606 was developed. Consequently, a surgeon may request in the user instructions 604 that the instrument be made from a metal such as titanium.

With the bone model 404 and user instructions 604 a user such as a technician may operate the design module 650 alone or together with other modules of the apparatus 602 to develop a patient-specific osteotomy system 606. In certain embodiments, a single user operates the apparatus 602. Alternatively, or in addition, a plurality of users, which may include an end user, such as surgeon can operate or interact with one or more modules of the apparatus 602 as the patient-specific osteotomy system 606 is designed or developed.

In one embodiment, a technician may provide a patient-specific osteotomy system 606 that includes one or more complementary components and one or more resection guides, which may be patient-specific. The technician may also provide a preoperative plan. These may be provided to an end user (e.g., surgeon) either directly or by accessing the apparatus 602 remotely. The end user may review the preoperative plan and/or the components of the patient-specific osteotomy system 606 (e.g., resection guides) and may approve of the patient-specific osteotomy system 606 or may request changes. In certain embodiments, these changes may include the addition of one or more added bone engagement features, one or more resection guides, a change in a trajectory for a bone attachment feature, a change in trajectory for an osteotomy, an addition of openings in a guide to coincide with openings needed for a fixation system, as well as a plurality of other possible changes to the patient-specific osteotomy system 606. The technician may then make the requested changes and present a revised patient-specific osteotomy system 606 for the surgeon to review again. Next, the surgeon may approve of the revised patient-specific osteotomy system 606 and/or request additional changes.

In the illustrated embodiment, the design module 650 may include a plurality of resection features 652 and/or a plurality of bone engagement features 654. A technician may select one or more resection features 652 and/or one or more bone engagement features 654 and include them in the patient-specific osteotomy system 606. Alternatively, or in addition, a surgeon may designate which resection features 652 and/or bone engagement features 654 to include in the patient-specific osteotomy system 606.

In certain embodiments, the surgeon and technician may collaborate and/or consult with each other regarding the design and/or configuration of the patient-specific osteotomy system 606 and its components. The technician may share with the surgeon information about the technological features and/or limitations of the components of the patient-specific osteotomy system 606 and use the technician's experience and know-how to make recommendations to the surgeon. The surgeon can present ideas and/or requests regarding what the surgeon would like for components of the patient-specific osteotomy system 606 and the technician can determine whether those ideas/requests can be satisfied using a patient-specific osteotomy system 606.

The apparatus 602 uses both the bone model 404 and user instructions 604 to provide a patient-specific osteotomy system 606. Advantageously, the apparatus 602 enables a surgeon to be involved in the design and development of a patient-specific osteotomy system 606 that is suited not just for the patient, but also for the needs, skills and/or preferences of the surgeon. In this manner, a patient-specific osteotomy system 606 can be provided that improves patient care and accomplishing of desired outcomes.

In one embodiment, the operation of the design module 650 may be completely automated, partially automated, or completely manual. A user may control how automated or manual the designing of the patient-specific osteotomy system 606 is, including patient-specific instrument models, patient-specific instruments, and/or other components of the patient-specific osteotomy system 606.

The apparatus 602 may include a selection module 660 and an export/fabrication module 670. The selection module 660 facilitates the selection and/or customization of one or more complementary components for a patient-specific osteotomy system 606. Complementary components are described herein, but can include certain guides or other aids to facilitate completing a surgical procedure as planned. In one embodiment, the operation of the selection module 660 may be completely automated, partially automated, or completely manual. A user may control how automated or manual the selection module 660 is.

The export/fabrication module 670 is configured to enable exporting of a patient-specific osteotomy system 606 for a variety of purposes including, but not limited to, fabrication/manufacture of one or more patient-specific instruments and/or fixator(s), ordering or fabricating one or more members of the patient-specific osteotomy system 606, generation of a preoperative plan, generation of a physical bone model matching the bone model 404, and the like.

In one embodiment, the export/fabrication module 670 is configured to export the bone model 404, anatomic data 412, one or more patient-specific instrument models 462, a preoperative plan 506, a fixator model 508, or the like. In this manner the custom instrumentation and/or procedural steps for a procedure can be used in other tools. The preoperative plan 506 may include a set of step-by-step instructions or recommendations for a surgeon or other staff in performing a procedure (e.g., a graft harvesting procedure, minimally invasive surgical (MIS) procedure, or the like). The preoperative plan 506 may include images and text instructions and may include identification of instrumentation to be used for different steps of the procedure (e.g., a graft harvesting procedure, minimally invasive surgical (MIS) procedure, or the like). The instrumentation may include a patient-specific instrument, bone engagement features, and/or one or more fixators/fasteners.

Figure 7:
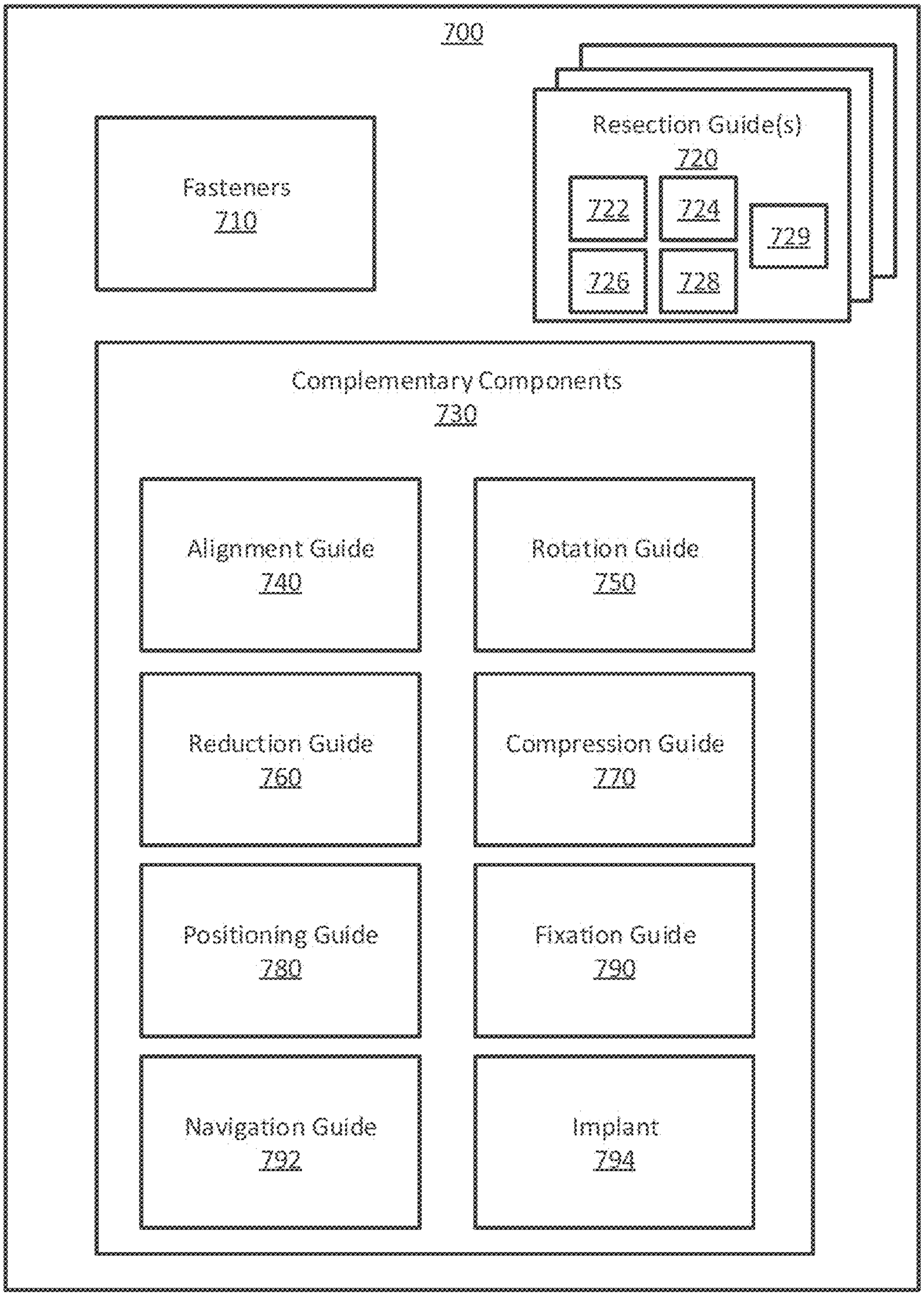
FIG. 7 illustrates an exemplary system for remediating a condition present in a patient's foot, according to one embodiment.

FIG. 7 illustrates an exemplary system 700 for remediating a condition present in a patient's foot, according to one embodiment. The system 700 can include one or more fasteners 710, one or more resection guides 720, and one or more complementary components 730. While a system 700 can be used for a variety of procedures on one or more body parts, one or more features, components, and/or aspects of the system 700 may be particularly suited for one or more osteotomies on one or more bones of a structure such as a patient's foot, ankle, wrist, hand, shoulder, or the like.

In certain embodiments, the one or more fasteners 710 can include one or more permanent fasteners and/or one or more temporary fasteners. Typically, the fasteners 710 may be used during a variety of different steps of a procedure. Temporary fasteners are often used because they can securely hold bone or parts/fragments of bones while steps of the procedure are conducted. A common temporary fastener that can be used with system 700 is a K-wire, also referred to as a pin, guide pin, and/or anchor pin. Permanent fasteners 710 (also referred to as implants) such as bone screws, bone staples, sutures, tethers or the like are other examples of fasteners 710 that can be used in a surgical procedure.

The one or more resection guides 720 assist a surgeon in performing different resection or dissection steps for an osteotomy or other procedure. In certain embodiments, a resection guide 720 includes one or more resection features 722 and one or more bone attachment features 724. The resection features 722 can take a variety of forms and/or embodiments. In one embodiment, the resection features 722 take the form of a cut channel or slot or other opening. Alternatively, or in addition, resection features 722 can be of a variety of geometric shapes including: ovals, squares, circles, rectangles, triangles, prisms, and the like.

The resection features 722 provide a guide for a surgeon using a cutting tool to resect a bone, one or more bones, or other tissues of a patient. The resection feature 722 exposes a bone, one or more bones, one or more joints, and/or other hard or soft tissue to the cutting tool while keeping the cutting tool in a predefined area and/or angle and/or trajectory during the resection of the tissue. In certain embodiments, the resection features 722 may guide a surgeon in performing a resection, an osteotomy, and/or a dissection.

The bone attachment features 724 can take a variety of forms and/or embodiments. The bone attachment features 724 may serve to secure the resection guide 720 and/or other instrumentation to one or more bones and/or one or more other structures. For example, the bone attachment features 724 may secure the resection guide 720 during formation of one or more osteotomies. Often, a bone attachment feature 724 can take the form of a hole in and/or through the resection guide 720 that includes a temporary fastener such as a K-wire, pin, or guide pin to secure at least part of the resection guide 720.

The bone attachment features 724 facilitate attachment (at least temporarily) of a resection guide 720 to one or more bones, or bone fragments, of a patient. The bone attachment features 724 may include any of a wide variety of fasteners or structures including, but not limited to, holes, spikes, prongs, screws, fastening devices, and/or the like. Effective connection of the resection guide 720 to one or more bones across one or more joints and/or to one or more bones can ensure that cut surfaces are formed in desired locations and orientations and mitigate removal of hard tissue and/or soft tissue in undesired locations and/or orientations.

In certain embodiments, a resection guide 720 may include one or more bone engagement surfaces 726 and/or one or more landmark registration features 728. In certain embodiments, a landmark registration feature 728 may extend from one or more sides or ends of a resection guide 720 and engage with one or more landmarks of a bone or joint or anatomical structure of a patient. Registration of the landmark registration feature 728 to a landmark of a bone, joint, or other anatomical part can serve to confirm and/or ensure that a surgeon has located a desired placement and/or orientation for a resection guide 720. This confirmation can assist a surgeon in positioning a resection guide 720 in a predetermined position.

In certain embodiments, the bone engagement surfaces 726 are patient-specific: contoured to match a surface of: one or more bones and/or bone surfaces the resection guide 720 contacts (or is adjacent to) during the procedure or one or more joints proximal to the resection guide 720 during the procedure. Alternatively, or in addition, the bone engagement surface 726 may not be patient-specific, and may, or may not, contact a bone surface during use of the resection guide 720. In certain embodiments, a bone engagement surface 726 may include sections that are patient-specific and other sections that are not patient-specific. in one embodiment, the nonpatient-specific sections may be configured to avoid interfering with placement and securement of the resection guide 720.

In one embodiment, a skin contact surface may be used in addition to, or in place of, a bone engagement surface. Those of skill in the art appreciate that one or more sides of any of the members of the system 700 may include one or more bone engagement surfaces 726. Consequently, one or more sides of the fasteners 710, the resection guide(s) 720, the complementary components 730, navigation guides 792, and/or the implants 794 may include one or more bone engagement surfaces 726.

In certain embodiments, the resection guides 720 and/or aspects of the resection guides 720 may be integrated into other components and/or instruments, such as a pin guide, a trajectory guide, an alignment guide, or the like.

The complementary components 730 serve to assist a surgeon during one or more steps of a procedure. Those of skill in the art appreciate that a number of components can serve as complementary components 730. One or more of the features, functions, or aspects of the complementary components 730 can include patient-specific features.

Examples of complementary components 730 include, but are not limited to, an alignment guide 740, a rotation guide 750, a reduction guide 760, a compression guide 770, a positioning guide 780, a fixation guide 790, navigation guides 792, and/or one or more implants 794. In general, the complementary components 730 serve to assist a surgeon in performing the function included in the name of the complementary component 730. Thus, an alignment guide 740 can help a surgeon align bones, parts of bones, or other parts of a patient as part of a procedure. A rotation guide 750 can help a surgeon rotate one or more bones, parts of bones, or other parts of a patient as part of a procedure. In one embodiment, a rotation guide 750 may hold one bone fragment stable while another bone fragment is rotated into a desired position.

A reduction guide 760 can help a surgeon position and/or orient one or more bones, parts of bones, or other parts of a patient as part of a procedure in order to reduce the bone, bones, bone parts, or other parts and/or in order to position and/or orient the bone, bones, bone parts, or other parts to a desired position and/or orientation. In certain embodiments, aspects and/or features of a reduction guide 760 can be integrated into one or more other components of an osteotomy system 700, such as components of the complementary components 730. A compression guide 770 can help a surgeon compress one or more bones, parts of bones, or other parts of a patient together or against an implant as part of a procedure. In certain embodiments, compression guide 770 can be a separate instrument such as a compressor and/or a combined compressor/distractor. The compressor/distractor can be used to compress two or more cut faces formed by an osteotomy until fixation is deployed or distract bones or parts of bones involved in a procedure. In certain embodiments, a compression guide 770 may serve a dual purpose as both a compression guide 770 and as a positioning guide 780. The same instrument may be used to both translate and/or rotate bones or bone fragments and compress two or more cut faces formed by an osteotomy until fixation can be deployed.

A positioning guide 780 (also referred to as a positioner) can help a surgeon position one or more bones, parts of bones, or other parts of a patient as part of a procedure. For example, a positioning guide 780 may hold one bone or bone fragment stable and hold one or more other bone fragments in a desired position while permanent or temporary fixation is deployed. In certain embodiments, the positioning guide 780 may hold bone fragments in a reduced position, and thus may function as both a positioning guide 780 and/or a reduction guide 760.

In certain embodiments, the positioning guide 780 may be designed and fabricated to be patient-specific. The patient-specific aspects can include a patient-specific bone engagement surface, a predefined angle for reorienting one or more bone or bone parts within one or more planes, a predefined position for bone attachment features 724 or fasteners 710, a predefined or patient-specific offset or amount of translation that is provided, or the like. Alternatively, or in addition, the positioning guide 780 may be selected from a kit, collection, or repository of a number of positioning guides 780: each having a different configuration for one or more aspects/attributes of the positioning guide 780. For example, each member of the repository/kit may include a different positioning angle (repositioning or correction angle), the angles may differ by 2 degrees for example. In such an embodiment, each positioning guide 780 may not be patient-specific to a particular patient but may provide the desired amount of positioning to meet the goals of the surgeon. In certain embodiments, a preoperative plan generated based on the present disclosure may include a recommendation for the positioning guide 780 to be used, even if the recommended positioning guide 780 is not patient-specific to the particular patient.

A fixation guide 790 can help a surgeon in completing one or more temporary or permanent fixation steps for one or more bones, parts of bones, or other parts of a patient as part of a procedure. The fixation guide 790 may include and/or may use one or more components of a fastener or fixation system including implant hardware of the fastener or fixation system.

Those of skill in the art will appreciate that the other complementary components 730 may each have functions, purposes, and/or advantages with respect to one or more anatomical parts of the patient. Alternatively, or in addition, the other complementary components 730 may each have functions, purposes, and/or advantages with respect to one or more instruments and/or one or more anatomical parts of the patient. For example, a trajectory guide may be a type of alignment guide 740 in that the trajectory guide facilitates alignment of fixation with the desired location and/or trajectory/orientation with respect to one or more anatomical parts of the patient. Alternatively, or in addition, a trajectory guide may also be considered a type of fixation guide 790 because the trajectory guide facilitates deployment of one or more fasteners 710.

Advantageously, the system 700 can help a surgeon overcome one or more of the challenges in performing an osteotomy procedure, particularly on small bones of a hand or of a foot of a patient, such as on the forefoot, midfoot, or hindfoot. One challenge during an osteotomy procedure can be maintaining control of, and/or position, and/or orientation of a bone, one or more bones, and/or bone pieces/fragments, particularly once a resection or dissection is performed. Advantageously, the fasteners 710, resection guide(s) 720, and/or complementary components 730 can be configured to assist in overcoming this challenge.

Advantageously, system 700 can help a surgeon in positioning, placing, and/or orienting a resection guide accurately. Modern techniques may include preoperative planning, simulation, or even practice using computer models, 3D printed models, virtual reality systems, augmented reality systems or the like. However, simulations and models are still different from actually positioning a resection guide on a patient's bone, joint, or body part during the procedure. System 700 can include a number of features, including patient-specific features, to assist the surgeon with the positioning. In one embodiment, the resection guide 720 can include one or more landmark registration features 728.

Advantageously, the system 700 can help a surgeon in securing guides of the osteotomy system 700, such as a resection guide, as well as how to readily remove the guide (e.g., resection guide) without disturbing a reduction, shifting, reorienting, or repositioning one or more bones or parts of bones while removing the guide. In certain embodiments, the system 700 is configured to permit removal of a guide while keeping temporary fasteners in place for use in subsequent steps of an osteotomy procedure. Alternatively, or in addition, system 700 may facilitate positioning of temporary fasteners during one step of a wedge osteotomy procedure for use in a subsequent step of the wedge osteotomy procedure. Removal of a guide during an osteotomy procedure can be particularly challenging where translation and/or rotation of the bones involved in the osteotomy procedure is required for the success of the osteotomy procedure. Advantageously, system 700 accommodates translation and/or rotation of the bones during the osteotomy procedure while facilitating a successful outcome for the osteotomy procedure.

Advantageously, the components of the system 700 can be specifically designed for a particular patient. Alternatively, or in addition, the components of the system 700 can be specifically designed for a class of patients. Each of the components of system 700 can be designed, adapted, engineered and/or manufactured such that each feature, attribute, or aspect of the component is specifically designed to address one or more specific indications present in a patient. Advantageously, the cuts made for the osteotomy procedure can be of a size, position, orientation, and/or angle that provides for an optimal osteotomy with minimal risk of undesirable resection. In one embodiment, the components of system 700 can be configured such that an osteotomy is performed that enables a correction in more than one plane in relation to the parts of the body of the patient. For example, cut channels or resection features 722 in a resection guide 720 can be oriented and configured such that when the bones are fused/fixated the correction results from translation, rotation, and/or movement of bones or bone parts in two or more planes (e.g., sagittal and transverse) once the fragments or bones are reduced.

In certain embodiments, the exemplary system 700 may include a plurality of fasteners 710, resection guides 720, and/or complementary components 730. For example, a surgeon may plan to resect a plurality of osteotomies from the bone(s) in order to accomplish a desired correction. In one example, one or more wedge segments may be resected from a medial side of a patient's foot and another one or more wedge segments may be resected from a lateral side of the patient's foot. These wedge segments may extend part way into the foot, or through from one side of the foot to the other. Of course, multiple wedge segments may be formed on one side of the foot as well.

Additionally, a surgeon may use one or more components in an exemplary system 700 to make multiple cuts in the bone(s). The multiple cuts may be centered over or around an apex of a deformity or positioned at other locations within the foot such that when the multiple cuts are made, any resected segments removed, or added bone void fillers introduced, and/or bones and/or bone fragments translated and/or rotated the combined angles, surfaces, removed segments, and/or added portions cooperate to provide a desired correction. Each of the components of the exemplary system 700 can be identified, defined, and reviewed using the apparatuses, systems, and/or methods of the present disclosure.

In certain embodiments, the components of system 700 may be made as small as possible to minimize the amount of soft tissue that is opened in the patient for the osteotomy procedure. Alternatively, or in addition, walls and/or sides of the components may be beveled and/or angled to avoid contact with other hard tissue or soft tissues in the operating field for the osteotomy procedure.

Those of skill in the art will appreciate that for certain osteotomy procedures a complementary component 730 may not be needed or a given complementary component 730 may be optional for use in the osteotomy procedure. Similarly, those of skill in the art will appreciate that certain features of the fasteners 710, resection guides 720, and/or complementary components 730 can be combined into one or more of apparatus or devices or may be provided using a plurality of separate devices.

Figure 8:
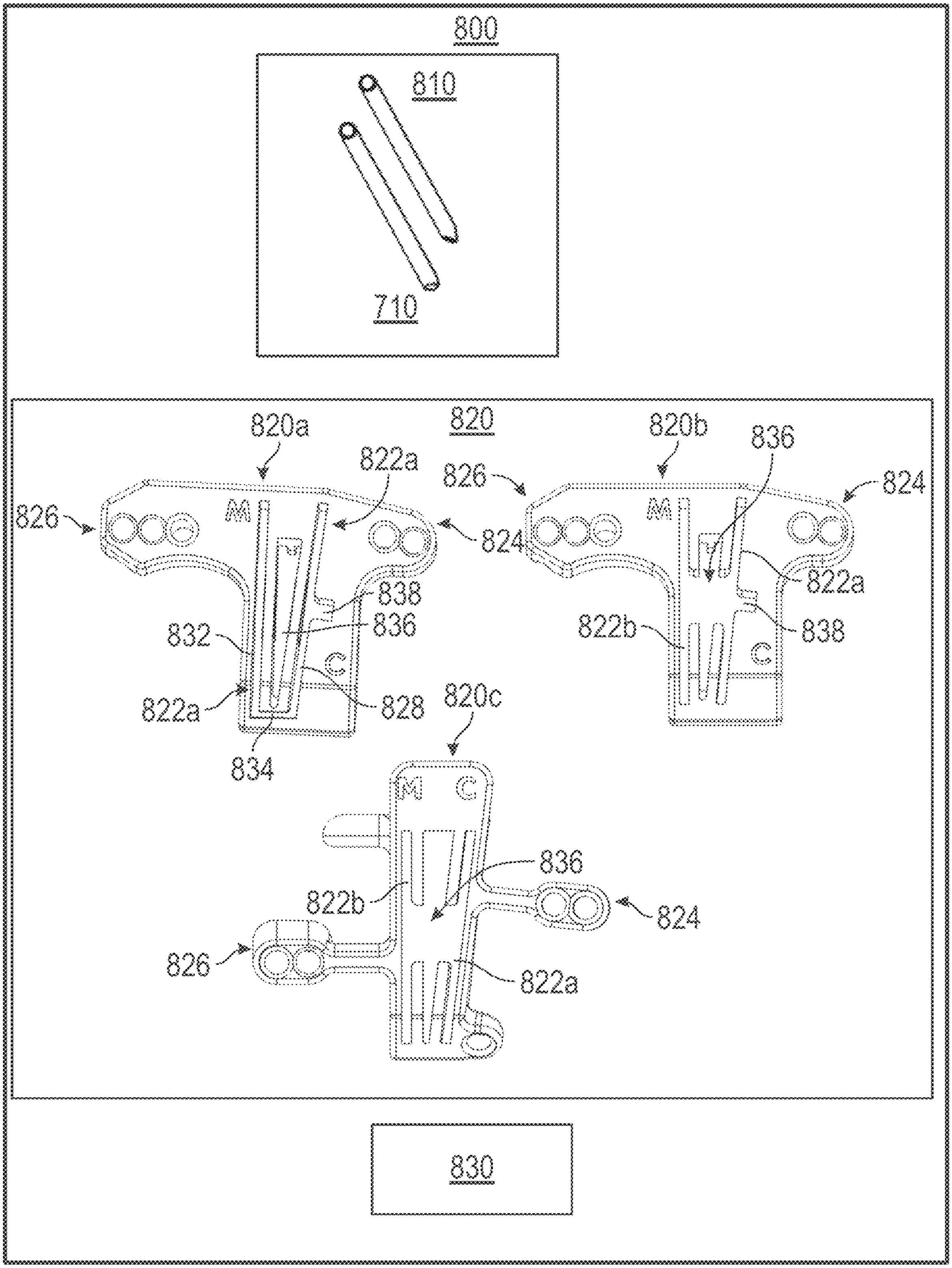
FIG. 8 illustrates an exemplary guide system for a surgical procedure, according to one embodiment.

FIG. 8 illustrates an exemplary system 800, according to one embodiment. The system 800 may include one or more fasteners 810, such as fasteners 710, a resection guide 820, such as resection guide **820*a* or resection guide 820*b* or resection guide 820*c* and may include one or more other complementary components 830. The resection guides 820*a*, 820*b*, 820*c*** facilitate resection of one or more bones of a patient for a surgical procedure.

In one embodiment, the resection guides **820*a*, 820*b*, 820*c* include a proximal side, a distal side, a medial side, a lateral side, a superior side, and an inferior side. The resection guides 820*a*, 820*b*, 820*c* may include a bone engagement feature, a resection feature, and a bone attachment feature. In such embodiments, the bone engagement feature may be configured to engage at least a portion of at least one foot bone to position the resection guide 820**. in one embodiment, the bone engagement feature is at least partially determined based on a model of a patient's foot. The model can be defined based on medical imaging of the patient's foot.

In certain embodiments, the resection guides **820*a*, 820*b*, 820*c* may also include a window and/or one or more landmark registration features. In another embodiment, a resection guide 820*a*, 820*b*, 820*c* may include one member of a coupler configured to engage a corresponding member of the coupler configured to couple the resection guide 820*a*, 820*b*, 820*c*** to an alignment guide.

In another embodiment, a resection guide **820*a-c* may include a body that includes the sides, bone engagement feature, one or more resection features, a window, a landmark registration feature, and/or one or more bone attachment features. Alternatively, or in addition, the resection guide 820*a-c*** may include the sides, bone engagement feature, one or more resection features, a window, a landmark registration feature, and/or one or more bone attachment features connected to each other using structures other than a body.

The resection features 822 guide a surgeon in performing a resection by facilitating keeping a cutting tool in line with and/or within an opening of the resection features 822 (at a desired trajectory relative to one or more bones of the patient). In the illustrated embodiments, the resection features 822 are shaped like slots or channels and include two closed ends. In another embodiment, a resection feature 822 may include an open end and a closed end. In certain embodiments, a resection feature 822 can include a plurality of slots, openings, and/or channels. In other embodiments, a resection guide 820 may include a plurality of resection features 822.

One difference between embodiments of the resection guides **820*a*, 820*b*, 820*c* may be the number of resection features 822 each includes. In the illustrated embodiments, resection guide 820*a* includes a single resection feature 822*a*. Resection guides 820*b*, 820*c* illustrate alternative embodiments that include two resection features 822*a*, 822*b*. In other embodiments, the resection guides 820 may include one resection feature 822, two resection features 822, three resection features 822, four resection features 822, more than four resection features 822**, or the like.

In the illustrated embodiments, resection guides 820 include a proximal end 824 and a distal end 826. The resection guide 820*a* includes a single resection feature 822*a*. The single resection feature 822*a* may extend through the body from a superior side of the body to an inferior side. The resection feature 822*a* may be configured to guide a cutting tool to form a first osteotomy in a first bone along a first trajectory. In certain embodiments, a single resection feature 822*a* is configured to guide a cutting tool to form a second osteotomy in a second bone along a second trajectory.

The first trajectory and/or second trajectory may be determined based on an angle of at least of portion of the single resection feature 822*a* through the body. In certain embodiments, one or more of the first trajectory and the second trajectory may be at least partially determined based on a model (e.g., a bone model) of a patient's foot. The model may be defined at least in part based on medical imaging of the patient's foot. The first trajectory and the second trajectory determined at least in part based on the model may determine a final trajectory or a proposed trajectory that a surgeon can then alter or revise as needed to accomplish a desired outcome.

Advantageously, the angle of each resection feature (e.g., slot or part of a slot), and thus the first trajectory and/or the second trajectory relative to: another resection feature, to one or more bones, to one or more bone surfaces, to one or more reference points, to one or more reference lines, and/or to one or more reference planes can be patient-specific and/or can be determined, selected, or indicated by a surgeon before the resection guide 820 is fabricated. In addition, a surgeon can designate which sides of the resection features 822 are open end or closed end.

The single resection feature 822*a* may be implemented in the form of a single slot and/or a plurality of connected slots. For example, the single resection feature 822*a* may include a proximal slot 828 closer to a proximal end 824 and a distal slot 832 closer to the distal end 826 and a connector slot 834 that connects the proximal slot 828 to the distal slot 832. In this manner, the resection feature 822*a* may form a "V" shape. In such an embodiment, a single resection feature 822*a* may guide a cutting tool in forming both a first osteotomy along a first trajectory and a second osteotomy along a second trajectory.

In the illustrated embodiments, resection guides 820*b*, 820*c* include two resection features 822 (e.g., resection feature 822*a* and resection feature 822*b*). Resection feature 822*a* may be similar to, or may be, a proximal slot 828 and may be near the proximal end 824. Resection feature 822*b* may be similar to, or may be, a distal slot 832 and may be near the distal end 826. Thus, as with a proximal slot 828 and/or a distal slot 832, the resection feature 822*a* and resection feature 822*b* can guide a cutting tool to form a first osteotomy in a first bone and a second osteotomy in a second bone, respectively.

The first osteotomy in the first bone along the first trajectory and the second osteotomy in the second bone along the second trajectory may have a first trajectory and a second trajectory determined based on an angle of at least of portion of the respective resection feature 822*a*, 822*b* through the body. In certain embodiments, one or more of the first trajectory and the second trajectory may be at least partially determined based on a bone model of a patient's foot. The bone model may be defined at least in part based on medical imaging of the patient's foot.

The first trajectory and the second trajectory determined at least in part based on the bone model may determine final trajectory for cuts of the bone(s). Alternatively, the first trajectory and the second trajectory may define a proposed trajectory that a surgeon can then alter or revise as needed to accomplish a desired outcome. The bone model may be a model of both the first bone and the second bone or of one of the first bone and the second bone. In one embodiment, the first bone is a cuneiform, and the second bone is a metatarsal. In certain embodiments, the cuneiform and the metatarsal may be of a patient and may be a cuneiform and a metatarsal that are both part of a particular joint such as a TMT joint. In one embodiment, the cuneiform and the metatarsal form the $1^{st}$ TMT joint.

Those of skill in the art will appreciate that the resection guide 820 may have a variety of shapes, sizes and configurations. In one embodiment, these attributes can each be customized and adapted to meet needs or preferences of patients, a patient's anatomy, the nature of the deformity, and/or surgeon preferences. Advantageously, the features of the resection guides 820 can facilitate one or more osteotomies as well as other steps in a surgical procedure.

In the illustrated embodiment, each of the resection guides 820*a*, 820*b*, 820*c* may be configured for use on a medial side of a midfoot of a patient, with the side visible in FIG. 8 facing away from the bone(s). The parts of the resection feature 822*a* or resection features 822*a*, 822*b* may be positioned and oriented relative to each other to facilitate an arthrodesis surgical procedure that remediates a deformity with a goal of correcting a deformity.

In certain embodiments, the resection guides 820*a*, 820*b*, 820*c* include a bone engagement feature configured to engage at least a portion of at least one foot bone to position or assist in positioning the resection guide. In one embodiment, the bone engagement feature is patient-specific. In another embodiment, the bone engagement feature is patient-matched.

In certain embodiments, the bone engagement feature is determined at least in part based on a model of the patient's foot. The model may be defined based on medical imaging of the patient's foot. In one example, this means that the size, structures, surfaces, and/or configuration of the bone engagement feature may be defined based on corresponding structures, surfaces, and/or configuration parts of the model (e.g., surfaces, protuberances, openings, clearances, etc. on one or more bone models alone and/or in relation to each other in a model of a patient's foot). Thus, a bone engagement feature is a structure the couples to, connects to, contacts, engages, intersects, or fits between one or more bones of a patient. For example, a bone engagement feature can be seeker, a lateral metatarsal tab, a landmark registration feature, or the like.

In certain embodiments, the resection guides 820 can include one or more bone attachment features. In the illustrated embodiments, the resection guides 820*a*, 820*b*, 820*c* include a first bone attachment feature configured to accept a first fastener that engages a first bone, and a second bone attachment feature configured to accept a second fastener that engages a second bone. The bone attachment features secure the resection guide 820 to one or more bones of the patient during a surgical procedure.

In certain embodiments, the resection guide 820 is configured to provide visibility of one or more anatomical structures inferior to the resection guide 820 when the resection guide 820 is used in a surgical procedure. Those of skill in the art will appreciate that various structures and/or techniques can be used with the resection guide 820 to provide this visibility. For example, the resection guide 820 may include one or more resection features 822 sized and/or configured to enable a surgeon to view one or more bones underneath the resection guide 820 when the resection guide 820 is positioned to one or more osteotomies. In other words, the resection feature 822 may be sized or oversized to permit a surgeon to see at least part of one or more bones inferior to the resection guide 820 during a surgical procedure. In another example, the resection guide 820 may include a solid section that is radiolucent such that bones beneath the resection guide 820 are visible to a surgeon using medical imaging such a fluoroscopy.

In another example, the resection guide 820 may include one or more openings that extend from a superior side of the resection guide 820 to an inferior side. These one or more openings may be referred to as windows. In the illustrated embodiment, the resection guides 820*a*, 820*b*, 820*c* include a window 836. In one embodiment, the window 836 is positioned in the resection guide 820 between a proximal slot 828 and a distal slot 832. In one embodiment, the window 836 extends from a superior side of the resection guide 820 to an inferior side of the resection guide 820.

In another embodiment, the window 836 is radiolucent such that the window 836 provides visibility of at least one anatomical structure inferior to the resection guide, when the resection guide is in use. In one embodiment, the window 836 is an opening or hole. In another embodiment, the window 836 may be a structure that includes a plurality of openings or holes. In yet another embodiment, the window 836 may be a structure that is opaque to light but is radiolucent when used with an imaging device such as an X-ray machine fluoroscopy machine, or other imaging device. These aspects, as well as others, will be described in further detail in subsequent paragraphs.

Alternatively, or in addition, the resection guide 820*a* and resection guide 820*b* in the illustrated embodiments include a member of a coupler configured to engage a corresponding member of the coupler coupled to an alignment guide. Those of skill in the art appreciate that various designs of a coupler may be used. In the illustrated embodiment, the coupler may include an opening 838 that may extend from the superior side into the body through to the inferior side. The opening 838 may be configured to accept a post or extension from part of the alignment guide, when the post or extension is inserted into the opening 838.

FIGS. 9A-9F illustrate views of an example resection guide 820*b* of the system 800 of FIG. 8, according to one embodiment. The resection guide 820*b* includes a proximal end 824 and a distal end 826. The resection guide 820*b* may include a body 900, resection features embodied as a proximal resection feature 902 and a distal resection feature 904, a window 906, and a bone attachment feature. In the illustrated embodiment, the bone attachment feature is embodied as a first bone attachment feature 908, a second bone attachment feature 910. In addition, the resection guide 820*b* may include a bone engagement feature 912. In certain embodiments, the bone engagement feature 912 is patient-specific. In certain embodiments, the resection guide 820*b* may include one or more landmark registration features 960. Other embodiments may not include landmark registration features 960.

In embodiments with a body 900, the body 900 connects and/or supports the structures and/or features and/or aspects of the resection guide 820*b*. The resection guide 820*b* includes a superior side 914, an inferior side 916, a proximal side 918, a distal side 920, a medial side 922, and a lateral side 924. In one embodiment, the resection guide 820*b* is configured for use on a dorsal side of a midfoot of a patient. The surgical procedure may include a medial approach and/or a dorsal approach or an approach between the medial and the dorsal sides of the midfoot. The names of the sides of the resection guide 820*b* refer to the position of the sides when the resection guide 820*b* is in use on one or more bones of a midfoot of a patient.

In the illustrated embodiment, the proximal resection feature 902 and distal resection feature 904 may extend through the body 900 from the superior side 914 to the inferior side 916. In one embodiment, the proximal resection feature 902 may guide a cutting tool to form a first osteotomy in one or more bones that extends along a first trajectory 928 (See FIG. 9F, 9G). Similarly, the distal resection feature 904 may guide a cutting tool to form a second osteotomy in one or more bones that extends along a second trajectory 930 (See FIG. 9F, 9G). In one embodiment, the first trajectory may be determined at least partially based on a bone model of a patient's foot, the bone model defined based on medical imaging of the patient's foot. Alternatively, or in addition, the second trajectory may be at least partially determined based on the bone model and/or the first trajectory.

In embodiments with a body 900, the body 900 may include resection features 902, 904 that guide a cutting tool to resect one or more bones, such as a medial cuneiform and/or a first metatarsal in the manner needed to make the desired resection. For example, the resection features 902, 904 may be used to guide a planar cutting blade, an arcuate cutting blade, a drill or mill, a burr, and/or the like. The resection features 902, 904 may guide a reciprocating planar blade, such as that of a surgical bone saw, that forms planar cuts in a first cuneiform and a first metatarsal. Various manual or powered tools may be used to form the cuts. In one embodiment, a sagittal bone saw can be used.

In one embodiment, the proximal resection feature 902 guides a cutting tool to form a first osteotomy in one or more bones of a patient. Similarly, the distal resection feature 904 is used to form a second osteotomy in one or more bones of the patient. Advantageously, the first osteotomy and the second osteotomy can be configured to resect a desired amount, size, and/or shape of bone or bones and/or soft tissue from a midfoot of the patient.

In one example, the resection features 902, 904 may take the form of a proximal resection feature 902 and a distal resection feature 904. In one embodiment, the proximal resection feature 902 and the distal resection feature 904 extend from the superior side 914 to the inferior side 916. For example, the proximal resection feature 902 may extend through the body 900 of the resection guide 820*b* from the superior side 914 to the inferior side 916 along a first trajectory 928. Similarly, the proximal resection feature 902 may extend through the body 900 of the resection guide 820*b* from the superior side 914 to the inferior side 916 along a second trajectory 930.

The position of the proximal resection feature 902 and/or distal resection feature 904 within the body 900, with relation to each other, the orientation of the proximal resection feature 902 and/or distal resection feature 904 between the proximal side 918 and the distal side 920, and/or the angle of the proximal resection feature 902 and/or distal resection feature 904 through the body 900 may be at least partially determined based on a model (e.g., a bone model) of a patient's foot. The model may be of one bone or of a plurality of bones. The model may be defined based on medical imaging of the patient's foot.

In one embodiment, the first trajectory 928 may be at least partially determined based on the model. Similarly, the second trajectory 930 may be at least partially determined based on at least one of the model and the first trajectory 928. In this manner, at least in certain embodiments, the number, position, orientation, size, length, angle of incidence to the inferior side 916, and the like are or can be patient-specific. Of course, a surgeon can alter or adjust any of these aspects of the resection guide 820*b* to enable fabrication of a guide that meets the surgeon's needs, preferences, and/or the needs of the patient and/or the surgical procedure. In one embodiment, the first trajectory 928 and/or the second trajectory 930 are patient-specific.

In the illustrated embodiment, both the proximal resection feature 902 and the distal resection feature 904 are implemented as slots having two closed ends. Of course, the proximal resection feature 902 and/or distal resection feature 904 can be implemented using a variety of openings, holes, and/or structures. For example, in one embodiment, a proximal resection feature 902 and/or distal resection feature 904 can be implemented as a series of adjacent holes that can be used with a burr cutting tool to form holes in bone for a resection.

Those of skill in the art will appreciate that the proximal resection feature 902 and/or distal resection feature 904 can have an open end. Alternatively, or in addition, the proximal resection feature 902 and/or distal resection feature 904 can be connected to the body 900 between the ends and both ends can be open ends.

Advantageously, the proximal resection feature 902 and/or distal resection feature 904 can be defined based on, in connection with, and/or may be defined at least partially based on a bone model 404 of one or more bones of a midfoot of a patient. The bone model 404 provides a detailed and accurate representation of the midfoot bones of the patient. Using the apparatuses, systems, and/or methods of the present disclosure the resection guide 820*b* and/or its components such as the proximal resection feature 902 and distal resection feature 904 can be configured for a specific patient, for a specific surgical procedure, and/or according to specific user instructions and/or preferences of a user (e.g., surgeon).

In one embodiment, the first trajectory 902 is wholly or at least partially determined based on a bone model 404 of the patient's foot. In particular, the bone model 404 may be of one or more bones, joints, and/or tissues of a midfoot of the patient. The bone model 404 is defined based on medical imaging of the patient's foot such that the bone model 404 and surfaces and structures of the bone model 404 are highly accurate representations of the actual midfoot bones of a particular patient. The accuracy of the bone model 404 is such that any protuberance, eminence, bony topography, anatomical features, calcifications, void, divot, concave section, sesamoid, bone spur or other feature on, or extending from, a bone of a patient are represented in the bone model 404 (including on surfaces of model bones of the bone model 404).

Alternatively, or in addition, the second trajectory 904 can be wholly or at least partially determined based on one or both of the bone model 404 and the first trajectory 902. For example, in one embodiment, the bone model 404 is used to determine, at least in part, the second trajectory 904. Alternatively, the second trajectory 904 can be defined to be a certain offset, orientation, and/or angle in relation to the first trajectory 902.

Thus, upon desired positioning of the resection guide 820*b* for use, the proximal resection feature 902 may be positioned over at least a portion of a bone such as a first medial cuneiform or other midfoot bone while the distal resection feature 904 may be positioned over, for example, a portion of another bone such as a first metatarsal 208. In one embodiment, the proximal resection feature 902 is positioned close to the distal end of a first cuneiform and the distal resection feature 904 is positioned near a proximal end of the first metatarsal. The proximal resection feature 902 and distal resection feature 904 are positioned to guide resection of one or more midfoot bones during a surgical osteotomy for correcting a condition.

In alternative embodiments, a resection feature may be designed to guide a different type of cutter, such as a drill, mill, or side-cutting burr. In such embodiments, the resection feature may not be a slot, but may instead be a translatable or rotatable cutter retainer that guides translation and/or rotation of the cutter relative to the bone. In certain embodiments, two or more resection features may be replaced by a single resection feature sized to permit a surgeon to resect multiple midfoot bones using a resection guide 820*b*.

In one embodiment, a proximal resection feature 902 is configured to define a first cut surface that can be formed by resecting a first bone. A distal resection feature 904 is configured to define a second cut surface that can be formed by resecting a second bone. In such an embodiment, one or the other or both of the first cut surface and the second cut surface can be oriented according to one or more angles relative to landmarks on the bones or other anatomical structures.

Alternatively, or in addition, in certain embodiments, one or both of, the proximal resection feature 902 and distal resection feature 904 may be positioned on, or in, the body 900 and/or have an orientation based on patient imaging data. The patient imaging data can be used to position and orient one, or both, of the proximal resection feature 902 and distal resection feature 904 such that formation of one, or both, of the first cut surface and the second cut surface and fixation of the two cut surfaces against each other mitigates a condition of the patient. For example, as described in the present disclosure, patient imaging data can be used to generate bone models of bones of the patient. The bone models can be used to determine and/or define contours for a bone engagement surface, a position for a proximal resection feature 902, an orientation for a proximal resection feature 902, a position for a distal resection feature 904, an orientation for a distal resection feature 904, as well as other features, aspects, and/or attributes of one or more patient specific instruments that can be used in a procedure.

Figures 9A, 9B, 9C, 9D, 9E, 9F, 9G:
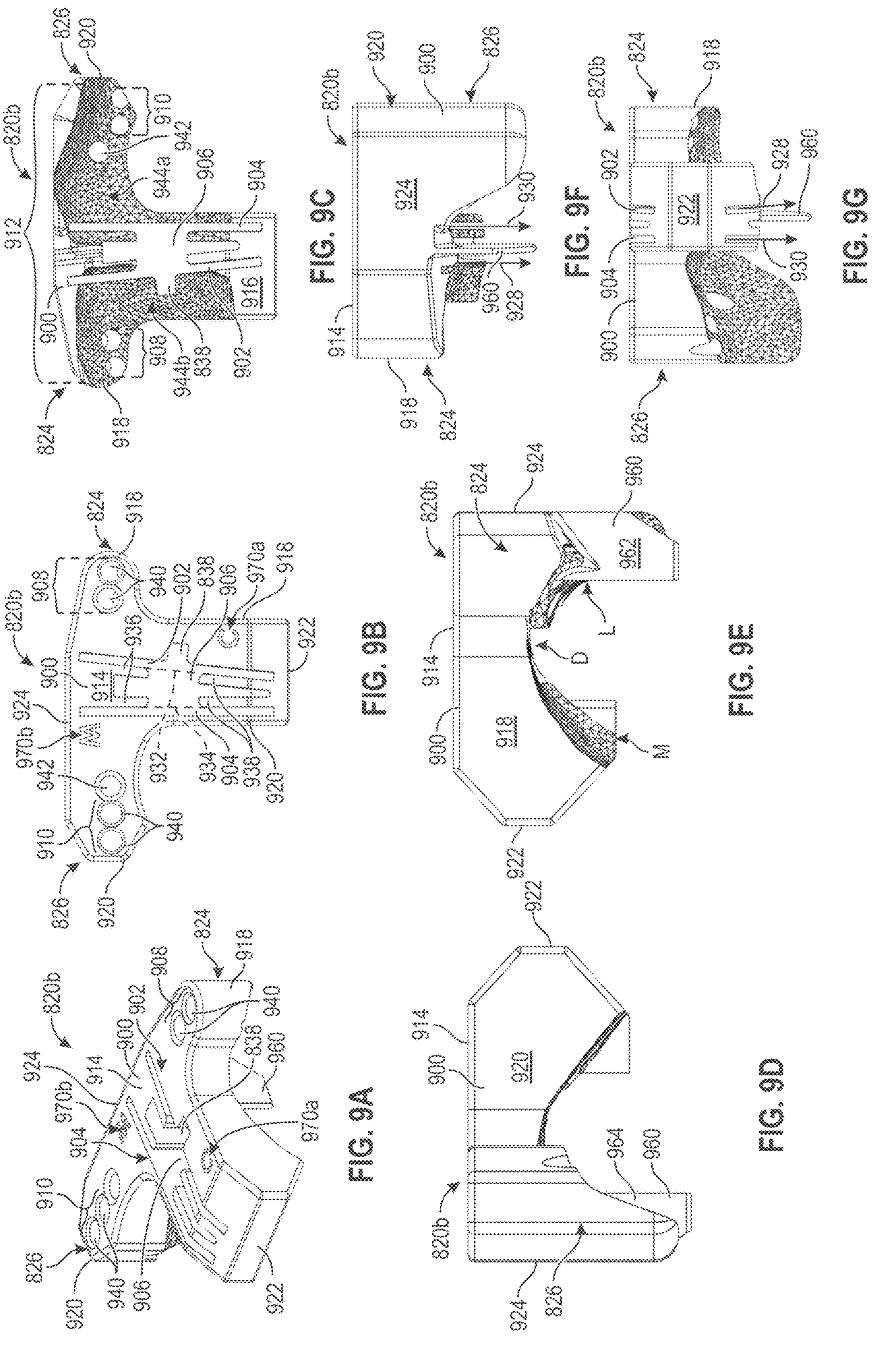
FIGS. 9A-9G illustrate views of a patient-specific guide of the guide system of FIG. 8, according to one embodiment.

FIG. 9A is a medial-proximal perspective view of one example resection guide 820*b*. This figure illustrates the proximal side 918, one example of a landmark registration feature 960, and a number of the aspects of the resection guide 820*b*. In addition, FIG. 9A illustrates one or more markings 970*a*, 970*b* or indicators. In the illustrated embodiment, marking 970*a* is a letter "C" formed by a recessed structure in the shape of the letter "C" and marking 970*b* is a letter "M" formed by a recessed structure in the shape of the letter "C". The marking 970*a* and/or marking 970*b* can be debossed or embossed. In one embodiment, the one or more markings 970*a*, 970*b* or indicators may extend through the resection guide. For example, the one or more markings 970*a*, 970*b* or indicators may extend from the superior side 914 to the inferior side 916.

Marking 970*a* is in the shape of "C" which stands for "Cuneiform" and marking 970*b* is in the shape of "M" which stands for "Metatarsal". The marking 970*a* is positioned towards the proximal end 824 to indicate that this side of the resection guide 820*b* is to be positioned over the cuneiform of a patient. The marking 970*b* is positioned towards the distal end 826 to indicate that this side of the resection guide 820*b* is to be positioned over the metatarsal of a patient. Advantageously, the marking 970*a* and marking 970*b* indicate for a surgeon and/or a technician the proper distal to proximal orientation of the resection guide 820*b* for the surgical procedure. Furthermore, the use of the first character for names of bones derived from Latin and/or the use of markings for letters in a "Latin script" or "Roman script" in which letters and words are written and read from left to right and from top to bottom, enables a user to quickly orient the resection guide 820*b* such that the medial side 922 is on the medial side of the foot bones and/or a joint (e.g., TMT joint) and the lateral side 924 is on the lateral side of the foot bones and/or the joint. Thus, the marking 970*a* and marking 970*b* assist in accurate and correct placement and/or orientation of the resection guide 820*b* relative to the anatomy of a patient.

In certain embodiments, the one or more markings 970*a*, 970*b* or indicators may be positioned on one side of the resection guide. (See FIGS. 10A, 10B) In such an embodiment, the one or more markings 970*a*, 970*b* or indicators may extend from the superior side 914 to the inferior side 916 which may facilitate identification of a correct and/or desired positioning of the resection guide when viewed with fluoroscopy. In particular, markings 970*a*, 970*b* that extend through the material of the resection guide will show up more readily on the scope and can permit visibility to structures underneath the markings 970*a*, 970*b*.

FIG. 9B is a superior side view of one example resection guide 820*b*. FIG. 9B illustrates the window 906 and its relationship to the proximal resection feature 902 and/or distal resection feature 904, in one embodiment. In the illustrated embodiment, the window 906 is positioned between the proximal resection feature 902 and the distal resection feature 904. In addition, the window 906, in this embodiment, is an opening that extends from the superior side 914 to the inferior side 916.

The window 906 serves to enable a surgeon to visualize anatomy (e.g., anatomical structure(s)) below the resection guide 820*b* when the resection guide 820*b* is positioned on one or more bones of a patient (e.g., on a dorsal side). In the illustrated embodiment, the window 906 is an opening. Alternatively, or in addition, the window 906 can be a solid structure that is opaque to light but radiolucent to electromagnetic waves (e.g., X-rays, both still x-rays and fluoroscopy). Where the window 906 is an opening, a surgeon may be able to sufficiently see the bones and articular surfaces, however, a surgeon may also choose to use medical imaging such as fluoroscopy to view the resection guide 820 together with inferior bones for an enhanced and/or more clear and precise view of the bones, ends of the bones, and the resection feature(s) 822 of the resection guide 820.

The window 906 can have a variety of sizes and/or shapes and can be patient-specific or patient-matched. Alternatively, or in addition, the size and/or shape of the window 906 can be determined at least in part by the surgeon which plans to use the resection guide 820*b*. In certain embodiments, the window 906 is sized and/or shaped to enable visualization of as much of the anatomy of the patient as possible, while maintaining the structural integrity of the body 900, proximal resection feature 902, and/or distal resection feature 904. Advantageously, the window 906 is sized to enable visualization of one or more articular surfaces of one or more bones facing the inferior side 916 of the resection guide 820*b*. In one embodiment, the window 906 is configured to enable observation of an articular surface and/or an end of both a cuneiform and a metatarsal of a TMT joint. In certain embodiments, the window 906 provides visibility of a distal end of a first bone (e.g., a cuneiform) and visibility of a proximal end of a second bone (e.g., a first metatarsal). In certain embodiments, the visibility provided is medical imaging visibility.

Due to the small size of the cuneiform and a metatarsal of a TMT joint and potential for significant improvement in quality of life for patients undergoing an arthrodesis of the TMT joint, a surgeon may appreciate the opportunity to view the anatomy of the bones in relation to the resection guide 820*b* and/or the trajectories of resections to be made using the proximal resection feature 902 and/or distal resection feature 904. Thus, having a resection guide 820*b* with a window 906 can provide a significant level of confidence and relief of stress prior to making any resections of the bones. For example, a surgeon can position and secure the resection guide 820*b* to one or more bones of the foot of the patient and then use fluoroscopy to visualize where the ends of the bones in relation to the proximal resection feature 902 and/or distal resection feature 904 that will be used to resect the bones. Having the ability to see where the bones end can provide certainty and/or clarity to a surgeon prior to performing any of the osteotomies. In certain embodiments, because the window 906 facilitates resection or performance of osteotomies, the window 906 may be referred to as a resection window.

In the illustrated embodiment, the window 906 has a lateral end that begins towards the lateral side 924 of the body 900 and a medial end that is near the medial side 922. Furthermore, the window 906 has a proximal side 932 that extends into and/or connects with the proximal resection feature 902. In one embodiment, the window 906 may also include a distal side 934 that extends into and/or connects with the distal resection feature 904. The extension of the proximal side 932 and distal side 934 may also be referred to as "cut-outs" since part of the body 900 is omitted or missing or has been removed to increase the effectiveness (i.e., size) of the window 906.

The extension of the proximal side 932 and the distal side 934 may form a pair of lateral fingers 936 that extend towards the medial side 922 and a pair of medial fingers 938 that extend towards the lateral side 924. In certain embodiments, the lateral fingers 936 and/or medial fingers 938 are configured to have sufficient structural integrity to retain a cutting tool within the proximal resection feature 902 and/or distal resection feature 904 and may be as short as possible to maximize the size of the window 906 while still enabling the proximal resection feature 902 and/or distal resection feature 904 to guide a cutting tool for the resection(s). Advantageously, the space between the proximal side 932 and distal side 934 enables visualization of the ends of one or more bones that the surgeon will resect using the resection guide 820*b*.

The window 906 may be configured to show one or more bones on an inferior side of the resection guide 820*b* when the resection guide 820*b* is in use. In the illustrated embodiment, the window 906 is positioned between the resection features 902, 904. The window 906 can be made up of a single opening, a pair of openings, or a plurality of openings. In one embodiment, the window 906 includes a plurality of openings that extend from the superior side 914 to the inferior side 916. The single opening and/or plurality of openings may have a variety of forms, shapes, sizes, and/or configurations. In one embodiment, the window 906 may be a rectangular or other polygonal opening. The window 906 enables a surgeon to view past the resection guide 820*b* to visualize progress before, during or after one or more dissection or resection steps.

FIG. 9B also illustrates the first bone attachment feature 908 and second bone attachment feature 910. The bone attachment features 908, 910 are configured to engage one or more bones of the patient to couple the body 900 to one or more bones of the patient. As embodied in FIGS. 9A through 9G, the bone attachment features 908, 910 may take the form of one or more holes 940 that extend from the superior side 914 to the inferior side 916 and/or one or more fixation devices (e.g., fasteners 710, a first fastener and a second fastener). The holes 940 may be shaped to accommodate pins, K-wires, and/or other elongated bone fixation elements that can be anchored in a cuneiform and/or a metatarsal to keep the resection guide 820*b* in place. In one embodiment, a first bone attachment feature 908 can include a single hole 940 and a second bone attachment feature 910 can include a single hole 940.

In one embodiment, the first bone attachment feature 908 and the second bone attachment feature 910 may each include a set of two holes 940 each hole configured to accept a fastener 710. Two holes 940 may be used to prevent rotation or pivoting of the resection guide 820*b* about a single fastener 710 in one hole. The holes 940 may be referred to as a set of openings, such that the resection guide 820*b* may include a set of proximal openings configured to accept a first pair of fasteners and a set of distal openings configured to accept a second pair of fasteners.

Alternatively, or in addition, in certain embodiments, the holes may have a non-circular geometric shaped cross section (e.g., triangle, square, oval, etc.) and the fastener 710 may have a similar and corresponding non-circular geometric shaped cross section such that a single hole and a single fastener 710 can be used for one or more of the first bone attachment feature 908 and the second bone attachment feature 910.

In the illustrated embodiment, the first bone attachment feature 908 is near the proximal end 824 and the second bone attachment feature 910 is near the distal end 826. In such an embodiment, the first bone attachment feature 908 may be referred to as a proximal bone attachment feature and the second bone attachment feature 910 may be referred to as a distal bone attachment feature. In one embodiment, the holes 940 of the first bone attachment feature 908 may be aligned, or may be substantially aligned, with the holes 940 of the second bone attachment feature 910. Alternatively, or in addition, the first bone attachment feature 908 and second bone attachment feature 910 are not aligned, longitudinally along the body 900, with each other.

When a surgeon prepares to do an osteotomy, they take care to prepare for the surgical procedure by gathering as much information as possible about the patient's anatomy, the surgical procedure, the instrumentation that will be used, and/or any implants to be used such that the goals of the surgical procedure can be realized. This preparation helps because once an osteotomy is performed changing or remediating the impact of the osteotomy can be challenging and can require time for bones to heal and recover. Thus, a surgeon seeks to perform osteotomies that are specific to the desired locations, with the desired trajectories, and to a desired depth. The goal of the osteotomies is to provide a correction and/or relief for a patient.

To facilitate a successful surgical procedure, surgeons appreciate guidance and advanced indications of signs as to where an osteotomy will be made and/or how the osteotomy will extend into the bone and/or tissue of the patient and how a reduction after the osteotomy will do in providing for the desired outcome. One sign or indicator that surgeons appreciate is a trajectory marker that is in one or more bones of the patient and indicates the trajectory the osteotomy will take. Advantageously, the present disclosure can provide such indicators (e.g., trajectory markers) by way of the bone attachment features 908, 910.

In one example embodiment, the bone attachment features 908, 910 are configured to enable fasteners 710 used with the bone attachment features 908, 910 to extend into one or more bones of the patient. Specifically, the holes 940 are configured such that fasteners deployed into the bone attachment features 908, 910 will show a surgeon the trajectory an osteotomy formed using the resection features 902, 904. In certain embodiments, this can be accomplished because one or more holes 940 of a bone attachment feature (e.g., first bone attachment feature 908 and/or second bone attachment feature 910) may extend through the body 900 to guide the fasteners 710 along a trajectory that is parallel to a trajectory of the resection feature (e.g., proximal resection feature 902 and/or distal resection feature 904) for the osteotomy that the cutting tool will cut. Of course, this parallel relationship can be implemented in one or more of the bone attachment features 908, 910 of the resection guide 820.

Advantageously, a surgeon can leverage this feature prior to making any cuts, forming any osteotomies. For example, a surgeon can secure the resection guide 820*b* to one or more bones of the patient on a dorsal or dorsomedial or medial side of the midfoot. The fasteners 710 cooperating with the bone attachment features 908, 910 can extend into the middle, and/or through to an opposite side of the midfoot. Since the fasteners 710 are often made of metal, the surgeon can then use fluoroscopy to visually see, validate, and/or check the trajectory for each fastener 710 into the midfoot. The surgeon knows that an adjacent and parallel osteotomy formed using the resection features 902, 904 will track (i.e., run parallel to) with the trajectories of the fasteners 710 in the bone attachment features 908, 910. In this manner, a surgeon can confirm trajectories for the planned osteotomies before the actually making the osteotomies. If the surgeon is not satisfied with the trajectories indicated by the bone attachment features 908, 910 by way of the deployed fasteners 710 within one or more bones a surgeon can make an adjustment. Removing the fasteners 710 if they are in an undesired location and/or trajectory can have a minimal impact on the patient and/or the success of the procedure.

In the illustrated embodiment, the resection guide 820*b* may include one or more anchor features 942 (an anchor feature 942 can also be referred to as an auxiliary bone attachment feature). The anchor feature 942 can be an optional feature for a resection guide 820*b* or may be a required feature. The anchor feature 942 can serve a variety of purposes. For example, an anchor feature 942 can serve to engage with one or more bones or bone fragments that are to be resected from the patient. For example, a surgeon may position the resection guide 820*b*, secure the resection guide 820*b* to one or more bones using the bone attachment features 908, 910. Next, a surgeon may deploy a pin or K-wire in an opening of the anchor feature 942 to engage with one or more bone fragments (e.g., a wedge) that will be resected when the surgeon resects using the resection features 902, 904. After the resection, the resection guide 820*b* can be removed while a pin of the anchor feature 942 remains in place. That pin can then be used to manipulate, reposition, and/or remove a resected bone fragment.

Alternatively, or in addition, an anchor feature 942 can be included to provide additional engagement with one or more bones of the patient during the osteotomies. The anchor feature 942 can be connected to the body 900. The anchor feature 942 can include one or more openings configured to receive one or more fasteners 710. The one or more fasteners 710 engage one or more bones of the patient.

The anchor feature(s) 942 can be strategically positioned using the bone model 404 (and/or a model of a resection guide 820*b*) such that a fastener 710 in an opening of an anchor feature 942 engages higher quality and/or stronger bone than the bone beneath one or more other openings in other bone attachment features 908, 910. Advantageously, a position for an anchor feature 942 can be determined by a surgeon (e.g., a user) of the resection guide 820*b*. In this manner, the resection guide 820*b* can be further customized to the needs or preferences of a particular patient and/or surgeon.

In one embodiment, the anchor feature 942 may be referred to as an oblique hole or an oblique feature. For example, where the first bone attachment feature 908 and/or second bone attachment feature 910 are angled to deploy a fastener 710 into a bone with a trajectory that is parallel to a trajectory for a resection directed by a proximal resection feature 902 and/or distal resection feature 904, the fasteners 710 in the first bone attachment feature 908 and/or second bone attachment feature 910 may not provide a desired level of engagement to retain the resection guide 820*b* in place during the forming of the osteotomies. Accordingly, a strategically placed anchor feature 942 can be angled (e.g., an oblique angle) relative to one or more bones of the patient such that a fastener 710 in the anchor feature 942 prevents or mitigates movement of the resection guide 820*b* during a surgical procedure. In one embodiment, the anchor feature 942 is configured to guide a third fastener 710 into a bone at an angle that is not parallel to one or more of the angles of a first fastener 710 deployed in a first bone attachment feature 908 and/or a second fastener 710 deployed in a second bone attachment feature 910.

FIG. 9C illustrates an inferior view of an example resection guide 820*b*. Referring now to FIGS. 9C, 9D (distal side view), 9E (proximal side view), 9F (lateral side view), and 9G (medial side view), the resection guide 820*b* includes at least one bone engagement feature. A bone engagement feature serves to engage with one or more bones and/or other tissue of a patient to position or identify a position of a resection guide relative to the one or more bones. In one embodiment, the position of a resection guide relative to the one or more bones satisfies and/or matches a predetermined position defined using the models (e.g., bone model 404 and/or preliminary model of the resection guide). In certain embodiments, a bone engagement feature is one example of a reference feature that can assist a user (e.g., surgeon).

FIG. 9C illustrates one example of a bone engagement feature 912. In certain embodiments, the bone engagement feature 912 is a patient-specific bone engagement feature. The bone engagement feature 912 is configured to engage at least a portion of one or more bones of a patient during a surgical procedure. The bone engagement feature 912 engages the one or more bones and/or joints in a manner that positions the resection guide 820*b* in a predetermined position.

Advantageously, the bone engagement feature 912 includes features, structures, and/or aspects that can provide feedback to a user moving the resection guide 820*b* in relation to surfaces of one or more bones of the patient. These features, structures, and/or aspects of the bone engagement feature 912 may cause the resection guide 820*b* to shift and tilt as a user moves the resection guide 820*b* to an approximate position on the bones. However, since the features, structures, and/or aspects are mirror images of the recesses, bumps, projections, and/or surface features of the one or more bones, the resection guide 820*b* will not sit stable and secure until the resection guide 820*b* locks/seats into place once the resection guide 820*b* is moved to the same (or substantially the same) position on, or relative to, the one or more bones as in a predetermined position. The bone engagement feature 912 causes the resection guide 820*b* to lock and/or snap into place once the user locates the correct position that matches the predetermined position.

Those of skill in the art will appreciate that a bone engagement feature 912 can take a variety of forms and/or configurations and can include a single structure or a plurality of structures that together form the bone engagement feature 912. The bone engagement feature 912 can be a single surface (e.g., a bone engagement surface) that is contoured, a plurality of surfaces or portions or sections that are contoured to match a contour of a bone or tissue surface, a surface in cooperation with a body structure that accounts for rises or falls in a contour of the one or more bones. Alternatively, or in addition, a bone engagement feature 912 can include a structure and/or arm or other structure that extends from the body 900 and supports a contoured bone engagement surface.

In the example of FIG. 9C, the bone engagement feature 912 can take the form of a bone engagement surface 944. The bone engagement surface 944 may include a portion, some, or all of a surface of one side of a resection guide 820*b*. In certain embodiments, a bone engagement surface 944 can include two or more sections 944*a*, 944*b*. Each section may be a bone engagement surface 944. Alternatively, or in addition, one section may be a bone engagement surface 944 and another section may be planar, or not contoured, to match or mirror a surface of one or more bones and/or other tissue of a patient.

In certain embodiments, the bone engagement surface 944 includes a patient-specific feature that is defined to interface with at least a portion of a surface that includes one or more bones of a patient. The patient-specific feature can be a single feature or a plurality of features. These features may be structures that are configured and sized to fit into and/or engage with corresponding features of a surface. For example, one feature may be a protrusion, projection, extension, or the like sized and shaped to fit within a recess or opening or cavity in a surface of, or between, bones of a patient. Alternatively, a patient-specific feature can be an opening, recess, cavity, detent, or the like sized and shaped to accept a projection, extension or the like from a surface or other structure (e.g., a part of an implant) of, or between bones, of a patient.

In one embodiment, an example bone engagement feature 912 includes a bone engagement surface 944 that is on at least a portion of one side of the resection guide 820*b*. The bone engagement surface 944 includes one or more patient-specific features. In one embodiment, the feature is a contoured surface. In another embodiment, the feature may be a plurality of extensions and/or recesses that match, mate, and/or fit within corresponding extensions and/or recesses of a surface. The patient-specific feature is defined to interface with at least a portion of a surface that includes one or more bones of a patient. In the illustrated embodiment, the bone engagement surface 944 covers some of the inferior side 916 of the resection guide 820*b*. In another embodiment, the bone engagement surface 944 can cover all of the inferior side 916.

In one embodiment, the bone engagement surface 944 is on a bone facing and/or bone contacting side of a resection guide 820*b*. In certain embodiments, the bone engagement surface 944 can extend across at least sixty-percent of a surface area of a side of the resection guide 820*b*. In another embodiment, can extend across at least ninety-percent of a surface area of a side of the resection guide 820*b*. In another embodiment, can extend across one hundred percent of a surface area of a side of the resection guide 820*b*. In another embodiment, can extend across at least twenty-percent of a surface area of a side of the resection guide 820*b*.

Referring to FIG. 9E, in certain embodiments, the bone engagement feature (e.g., a bone engagement surface 944) is coupled to, or formed as part of, an inferior side 916 of the resection guide 820 (i.e., body 900). Alternatively, or in addition, a body 900 of the resection guide 820*b* can extend from a medial surface M of a foot bone over a dorsal surface D of the foot bone to a lateral surface L of the foot bone. In this manner, the bone engagement feature can contact at least three parts (i.e., surfaces) on the foot bone. These three contacts can provide a stable and secure placement of the resection guide 820*b*. In one embodiment, the bone engagement feature is on the inferior side 916 and is configured to extend from a medial surface ("M") of at least one the bones (e.g., 1$^{st}$ metatarsal) of a joint (e.g., 1$^{st}$ TMT joint) over a dorsal surface ("D") of the at least one bone (e.g., 1$^{st}$ metatarsal) to a lateral surface ("L") of the at least one bone (e.g., 1$^{st}$ metatarsal).

In certain embodiments, the bone engagement feature (e.g., a bone engagement surface 944) is configured to engage at least a portion of a cuneiform and at least a portion of a metatarsal of a patient when the resection guide 820*b* is used. The bone engagement feature, such as a bone engagement surface 944 and/or a landmark registration feature 960 (discussed below), can include a contour that is at least partially determined based on a bone model of a patient's foot. The bone model may be defined based on medical imaging of the patient's foot.

FIGS. 9A, 9D, 9E, 9F, and 9G illustrate a landmark registration feature 960. The landmark registration feature 960 serves to facilitate registration of a guide 820*b*. In one embodiment, the landmark registration feature 960 is configured to contact and/or engage with a surface of one or more bones. In another embodiment, the landmark registration feature 960 is configured to contact and/or engage with one or more landmarks of one or more bones or other tissues of a patient. In another embodiment, the landmark registration feature 960 is configured to contact and/or engage with a joint and/or parts of a joint, such as a TMT joint, of a patient. For example, in one embodiment, the landmark registration feature 960 is configured to fit between articular surfaces of a cuneiform and a metatarsal of a TMT joint.

The resection guide 820*b* can include one or a plurality of landmark registration features 960. In the illustrated embodiment, the resection guide 820*b* includes a landmark registration feature 960 that may also be referred to as a "joint seeker" or "seeker". Given the shape of the example landmark registration feature 960, the landmark registration feature 960 may also be referred to as a blade.

The landmark registration features 960 can extend from one or more sides of the resection guide 820*b*. In the illustrated embodiment, the landmark registration feature 960 extends from inferior side 916. Specifically, in the illustrated example, the landmark registration feature 960 extends from a lateral side of the inferior side 916. Those of skill in the art will appreciate that the landmark registration features 960 can have various lengths, widths, and thicknesses.

Advantageously, the landmark registration features 960 can also include a bone engagement surface section that may function like a bone engagement surface 944. For example, the landmark registration feature 960 may include a proximal surface 962 and a distal surface 964. In certain embodiments, one or the other, or both of the proximal surface 962 and the distal surface 964 may be contoured to correspond to an articular or other surface of one or more bones of a patient. Thus, the proximal surface 962 and/or the distal surface 964 may include a bone engagement surface 944.

In the illustrated embodiment, one landmark registration feature 960 extends from the inferior side 916. Advantageously, the landmark registration feature 960 can provide a surgeon with confidence and assurance in the placement and positioning of the resection guide 820*b* in a joint (e.g., TMT joint) because the landmark registration feature 960 can be configured to engage with a particular landmark of the joint, on one of the bones, or other patient anatomy (e.g., a projection or a depression or cavity). In this manner, a surgeon can be assured intraoperatively that the resection guide 820*b* is being positioned in a desired position in accordance with a preoperative plan.

In certain embodiments, the landmark registration feature 960 can be shaped like a hook, arm, or extension that extends to engage a surface of bone (See FIGS. 10A-10G). Alternatively, or in addition, the resection guide 820*b* may include a landmark registration feature 960 on different sides or on opposite sides. Together the landmark registration features 960 can engage one or more landmarks of a surface of the bone and/or a joint such that the surgeon can accurately position and register the resection guide 820*b*.

The landmark registration features 960 are connected to the body 900 and configured to contact or engage with one or more bones of the patient. Advantageously, the landmark registration feature 960 can be defined from the bone model 404. Consequently, the landmark registration feature 960 can be sized, shaped, and/or configured to engage particular landmarks of one or more bones, one or more surfaces, and/or one or more joints of the bones of the patient.

Referring to FIGS. 9B and 9C, the example resection guide 820*b* has a length that extends from the proximal end 824 or proximal side 918 to the distal end 826 or distal side 920 such that the body 900 spans a tarsometatarsal ("TMT") joint of a patient. Specifically, the body 900 can be sized to extend from a cuneiform to a metatarsal of a patient. In one embodiment, the body 900 extends from a medial cuneiform 202 across a first TMT and to a first metatarsal 208. Advantageously, a resection guide 820*b* that spans the TMT is configured to prepare both a cuneiform and a metatarsal for an arthrodesis procedure using a single resection guide 820*b*.

As described in the present disclosure, a resection guide 820*b* can be specifically designed for a particular patient. The resection guide 820*b* is patient-specific. The resection guide 820*b* facilitates making one or more osteotomies through one or more bones of a midfoot of a patient. In addition, the resection guide 820*b* assists a surgeon in knowing that a position of a resection guide 820*b* during surgery is the same or substantially the same as a predetermined position defined earlier. In one embodiment, the predetermined position is a position that has been defined and/or confirmed and/or agreed to by the surgeon using the bone model 404 and/or a model of the resection guide 820*b*. In the system 400, for example, a surgeon can use a registration module 440 to register a preliminary model of the resection guide 820*b* to one or more bones of the bone model 404. Using the apparatus 402, a surgeon can leverage a patient-specific model of one or more bones of a patient and a model of the resection guide 820*b* to define one or more bone engagement features for the resection guide 820*b*. In this manner, the predetermined position includes a position on one or more bones of a patient. The predetermined position may be defined preoperatively using a model of a resection guide and a bone model.

Referring still to FIGS. 9A through 9G, the body 900 may further have features that facilitate visualization of a user an orientation and/or axes of one or more bones of the midfoot. For example, in the illustrated embodiment, the resection guide 820*b* may include at least one alignment feature. An alignment feature may be integrated into the resection guide 820*b* or the alignment feature may be a separate feature from the resection guide 820*b*. The alignment feature can be a strategically placed opening sized to hold a guide pin or K-wire such that the K-wire indicates a direction and/or trajectory of a bone or an axis of a bone.

Figure 9H:
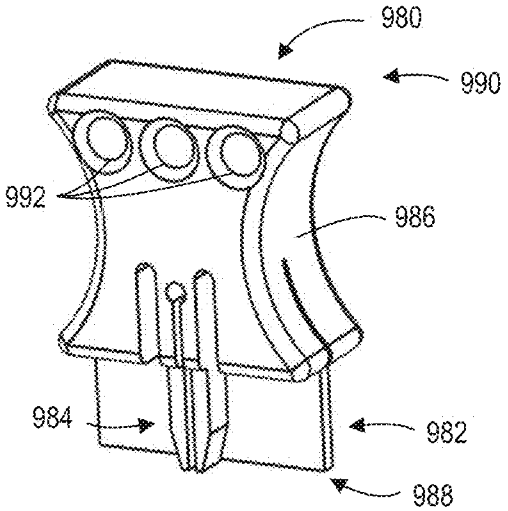
FIG. 9H illustrates a perspective view of an alignment guide that can be used with certain embodiments.

FIG. 9H illustrate a perspective view of an alignment guide 980*a* that can be used with certain embodiments. Prior to resection or making any osteotomies, a surgeon may desire to check or confirm that the desired resection guide 820*b* is being used and that a selected resection guide 820*b* will provide a desired alignment between the bones of the foot after the resection and fixation steps.

Accordingly, in the illustrated embodiment, the resection guide 820*b* may include one member of a coupler configured to engage a corresponding member of the coupler coupled to an alignment guide 980*a*. Those of skill in the art appreciate that various designs of a coupler may be used. In the illustrated embodiment, the coupler includes an opening 838 (See FIGS. 9A-9C) that may extend from the superior side 914 into the body 900 through to the inferior side 916 and a post 982. In one embodiment, the opening 838 may include one of the slots or resection features, such as proximal resection feature 902. The post 982 may include an engagement member 984.

In one embodiment, the opening 838 and the post 982 engage each other in a friction fit. For example, the post 982 may slide into the proximal resection feature 902 and the engagement member 984 may slide into the opening 838. In one embodiment, the engagement member 984 may include tabs that are biased outward and greater than a diameter of the opening 838 such that the tabs engage the opening 838 when inserted and release the opening when the tabs are pressed together.

The alignment guide 980*a* includes a body 986, an inferior end 988, and superior end 990 and one or more openings 992 near the superior end 990. The openings 992 may be aligned. A surgeon may use the alignment guide 980*a* by engaging the coupler to couple the alignment guide 980*a* to the resection guide 820*b*. Next, a surgeon may insert one or more K-wires through the openings 992. The openings 992 and alignment guide 980*a* may be configured such that K-wires within the openings extend along an anterior-posterior axis and indicate the orientation and alignment of a first cuneiform and first metatarsal once an osteotomy procedure is completed. A surgeon may compare this alignment with the orientation and alignment of other bones of the patient (e.g., a 2$^{nd}$ metatarsal or a 3$^{rd}$ metatarsal). In this manner, a surgeon can confirm that an osteotomy procedure will accomplish the desired outcome once completed.

Figure 9I:
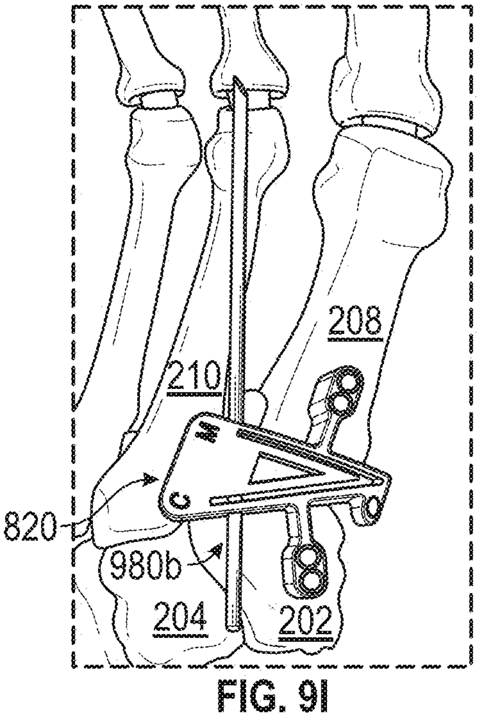
FIG. 9I illustrates a perspective view of an alignment guide incorporated into a patient-specific guide according to one embodiment.
Figure 9J:
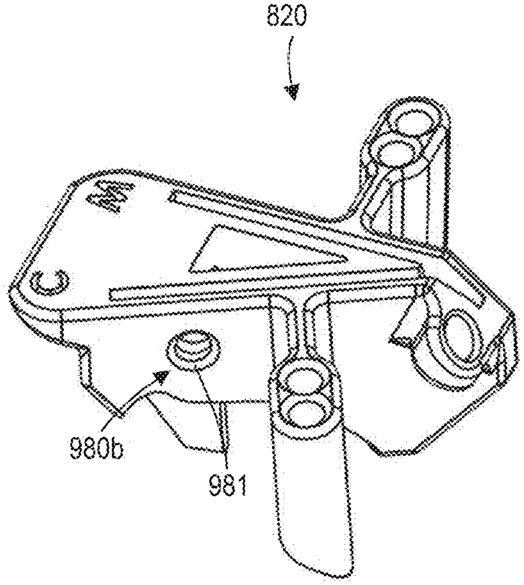
FIG. 9J illustrates a perspective view of the alignment guide of FIG. 9I according to one embodiment.

Those of skill in the art will appreciate that instead of an opening 838, a resection guide 820*a*, 820*b*, 820*c* may include one or more holes in the body 900 sized to accept one or more pins or K-wires. These holes alone or together with one or more pins or K-wires may serve as an alternative embodiment of an alignment guide. FIGS. 9I and 9J illustrate views of a resection guide 820 configured to include an alignment guide 908*b* implemented in the form of holes that accept one or more pins or K-wires and can serve the same or similar purpose as alignment guide 980*a* described in relation to FIG. 9H.

In the embodiments of FIGS. 9I and 9J, the holes 981 in the body 900 can be strategically positioned such that with the resection guide 820 in a desired position, K-wires or pins that are deployed through the holes indicate trajectories for one or more bones involved in the surgical procedure. In one example, these K-wires/pins may extend through the body 900 parallel to a longitudinal axis of a cuneiform bone and/or a metatarsal. These K-wires/pins may be used to check a position of a resection guide in relation to a longitudinal axis of one or more of the bones.

A surgeon may deploy and use K-wires/pins passing through the body 900 to check positions and/or alignments before completing the surgical procedure. Alternatively, or in addition, the K-wires or pins that deployed through the holes 981 may indicate trajectories for where longitudinal axes of the one or more bones will be after the surgical procedure. In this manner, the alignment guide (implemented as holes through the body 900 and pins deployed in the holes) indicate a corrected position of a second bone (e.g., a metatarsal) relative to another bone (e.g., a cuneiform) of the patient. Thus, in certain embodiments, holes 981 in the body 900 and K-wires/pins passing through the holes (i.e., alignment guide 980*b*) may be used to check position and/or trajectories before an osteotomy and/or holes 981 in the body 900 and K-wires/pins passing through the holes may be used to check position and/or trajectories for where bones will be postoperatively.

Figure 9K:
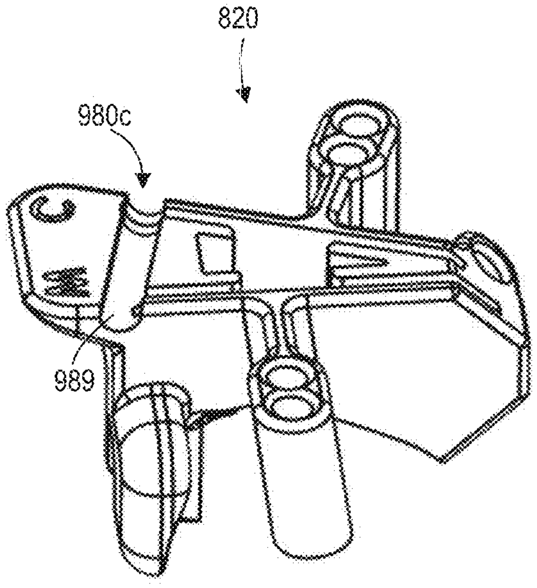
FIG. 9K illustrates a perspective view of an alignment guide incorporated into a patient-specific guide according to one embodiment.

Those of skill in the art will appreciate that an alignment guide 980 may be implemented in a variety of ways and have a variety of different structure and/or configurations. FIG. 9K illustrates a perspective view of an alignment guide 980*c* incorporated into a patient-specific guide according to an embodiment. The alignment guide 980*c* includes K-wires or pins and a trough 989 formed in the body 900 that holds an orients the K-wires or pins rather than holes 981. The trough 989 is positioned and/or oriented to accept a K-wire or pin and position and orient the K-wire or pin to indicate the same information as the K-wire or pin in the other alignment guide 820*a*, 820*b*, embodiments.

Figure 9L:
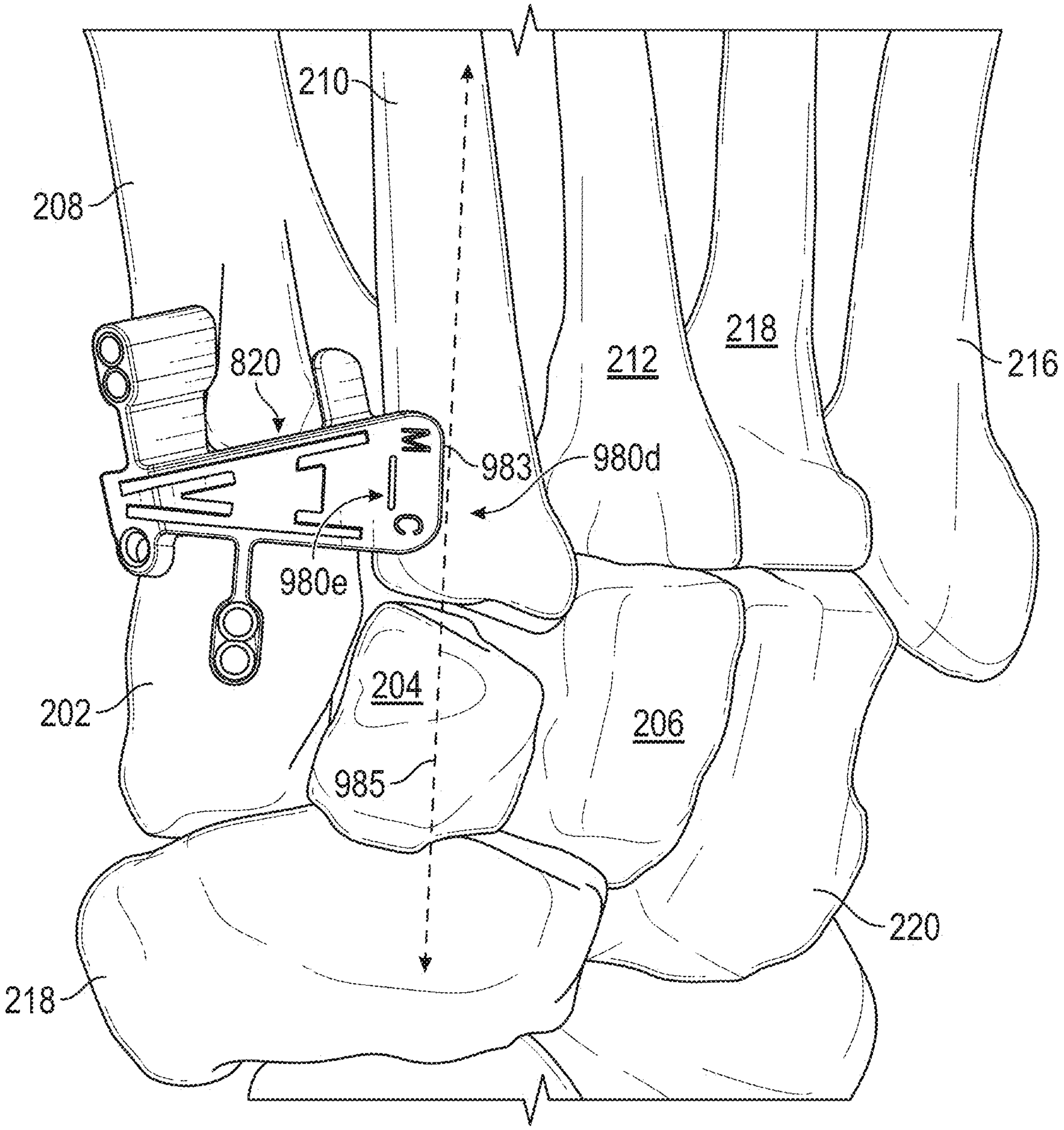
FIG. 9L illustrates a perspective view of a patient-specific guide according to one embodiment.

FIG. 9L illustrates a perspective view of two alternative embodiments of an alignment guide incorporated into a patient-specific guide 820 according to one embodiment. In the illustrated embodiment, the resection guide 820 includes one alignment guide 980*d* implemented as an edge 983 of the resection guide 820. The edge 983 is a straight edge of a side (e.g., lateral side 924) of the resection guide 820. The edge 983 indicates a trajectory 985 that shows the orientation for a second bone (e.g., 1$^{st}$ metatarsal) when the second bone is in the corrected position.

In the illustrated embodiment, the resection guide 820 includes another alignment guide 980*e* implemented as a slot 987 formed in the superior side 914 of the resection guide 820. Like the edge 983 the slot 987 is a straight slot that indicates a trajectory similar to trajectory 985 that shows the orientation for a second bone (e.g., 1$^{st}$ metatarsal) when the second bone is in the corrected position. Those of skill in the art will appreciate that other variations of an alignment guide 980 may be used. For example, instead of a slot 987 the resection guide 820 may include a marking such as an arrow made with a medical grade luminescent coating.

FIGS. 10A-10G illustrate views of resection guide 820*c*. The resection guide 820*c* may have many structures, features, and functions, operations, and/or configuration similar or identical to those of the resection guide 820*b* described in relation to FIGS. 7-9F, like parts are identified with the same reference numerals. Accordingly, the resection guide 820*c* may include one or more resection features 902, 904, a window 906, a first bone attachment feature 908 or set of proximal openings, a second bone attachment feature 910 or set of distal openings, a bone engagement feature 912 that can include one or more bone engagement surfaces 944, one or more landmark registration features, and the like. The resection guide 820*c* may include a body 900, a superior side 914, an inferior side 916, a proximal side 918, a distal side 920, a medial side 922, and/or a lateral side 924. And embodiments of the resection guide 820*c* may include an anchor feature 942 and one or more markings 970. As with the resection features 722 of other embodiments of resection guide 720, the resection features 722*a,b* can include an open end 729 and a closed end 731.

In addition, the resection guide 820*c* may have a different design and/or configuration than the resection guide 820*b*. For example, the size, shape, and/or design of the body 900 may be different. Furthermore, certain features of the resection guide 820*c* may be different from the resection guide 820*b*.

In the illustrated embodiment, the body 900 connects the proximal resection feature 902 to the distal resection feature 904. Alternatively, or in addition, the body 900 also connects to the first bone attachment feature 908 and the second bone attachment feature 910.

In the illustrated embodiment, the body 900 connects to the first bone attachment feature 908 by way of a connector 1002*a* or coupler 1002. Alternatively, or in addition, the body 900 may include a body 900 that connects to the second bone attachment feature 910 by way of a connector 1002*b* or coupler 1002. The connectors 1002 may be a part of the body 900 or separate components. The connector 1002*a* is between the first bone attachment feature 908 and the proximal resection feature 902. The connector 1002*b* is between the second bone attachment feature 910 and the distal resection feature 904.

In the illustrated embodiment, the bone attachment features, connectors, and/or size and shape of the body can be optimized to use enough material such as biocompatible materials (e.g., titanium) to provide the required strength and structural integrity, while minimizing the amount of material used to fabricate the resection guide 820*c*. Such optimizations can result in the use of connectors in place of using a larger main body portion of the body. Furthermore, the length, width, and height of the body 900 may be optimized to use the least amount of material and still provide the desired level of structural strength and integrity.

In certain embodiments, a user may provide user instructions that affect the size, shape, and/or configuration of the body 900, the connectors, bone attachment features, anchors, and/or landmark registration features. For example, the user may wish to make the body 900 as small and narrow as possible. A larger resection guide 820*c* may require larger incisions which could lead to longer recovery times for a patient. However, the smaller the body 900, the less surface area of certain bone engagement features, such as a bone engagement surface on a bone facing side of the resection guide 820*c*. The smaller bone engagement feature may make positioning the resection guide 820*b* in a predetermined position more challenging. Thus, the user (e.g., surgeon) may weigh the benefits and challenges in the trade-off between the size and shape of the body 900 and corresponding size of a bone engagement feature versus the ease of positioning the resection guide 820*b* during the surgical procedure. Those of skill in the art will appreciate that the resection guide 820*c* can have a variety of features, configurations, sizes and/or attributes that can be based at least in part on needs or preferences of patients, the nature of the deformity, and/or surgeon preferences.

Figure 10A:
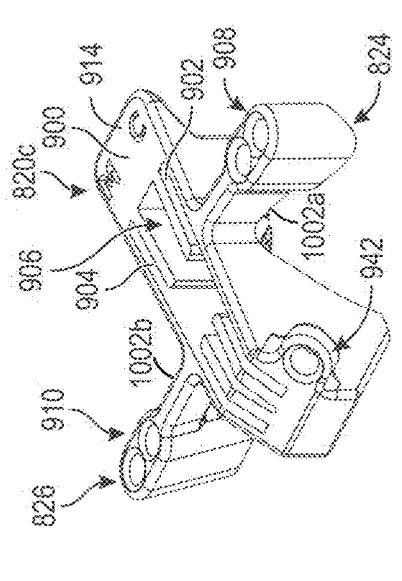
FIGS. 10A-10F illustrate views of a patient-specific guide of the guide system of FIG. 8, according to one embodiment.

FIG. 10A is a proximal perspective view of the resection guide 820*c*. FIG. 10A illustrates that the first bone attachment feature 908 is offset relative to the second bone attachment feature 910, these bone attachment features are not aligned along a longitudinal axis of the resection guide 820*c*, in certain embodiments. In certain embodiments, the alignment or nonalignment of the bone attachment features may be due patient-specific needs, a preoperative plan, surgeon preferences, or the like.

Figure 10B:
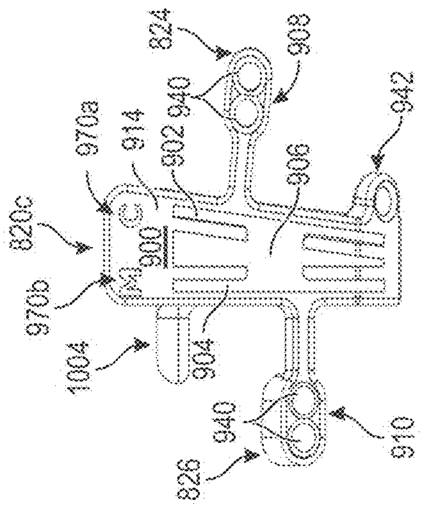

FIG. 10B is a superior view of the resection guide 820*c*. FIG. 10B illustrates a first bone attachment feature 908 that extends from the proximal side 918 and a second bone attachment feature 910 that extends from the distal side 920. FIG. 10B also illustrates a landmark registration feature 1004 that extends from the distal side 920. In one embodiment, the landmark registration feature 1004 extending from the distal side 920 is distinct from other landmark registration features of other embodiments. In another embodiment, the landmark registration feature 1004 may be similar to the landmark registration feature of other embodiments.

FIG. 10B also illustrates bone attachment features 908, 910. Certain bone attachment features may be positioned to engage with a resected segment, wedge, or bone fragment and other bone attachment features may engage with remaining bones or bone segments after resection. Furthermore, the resection guide 820*c* may include bone attachment features that are strategically positioned in the resection guide 820*c* to serve as trajectory guides, attachment points, compression anchors, distraction anchors, reduction guides or the like. For example, bone attachment features 908, 910 and the pins or fasteners deployed in holes of the bone attachment features 908, 910 can be strategically placed in a way that following the osteotomies, the fasteners/pins can then be manipulated to aid in the reduction/correction of the osteotomies either manually and/or using specialized instrumentation and/or customized instrumentation or compression blocks.

In addition, the bone attachment features and associated fasteners (e.g., pins) can be designed, positioned, oriented, and utilized to target provisional and/or permanent fixation devices such as pins, staples (using holes formed by the fasteners), screws, bolts, beams, nail or strategically placed reduction wires that can be utilized for external devices such as external fixators. Furthermore, customized guides can be placed over strategically placed fasteners used with bone attachment features and these fasteners can be used for the purposes of pre-drilling fixation components or features of implants such as for screws or strategic placement of fixation, plates, staples, etc.

Figure 10C:
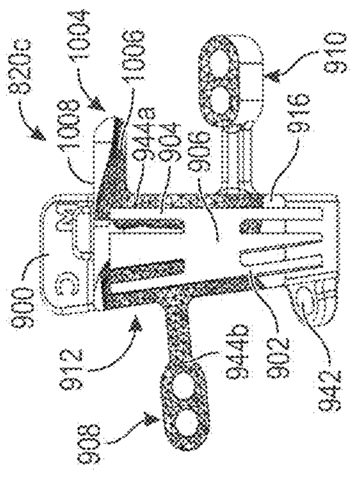

FIG. 10C is an inferior view of the resection guide 820*c*. FIG. 10C illustrates a bone engagement feature 912. The bone engagement feature 912, in this embodiment, includes a bone engagement surface 944*b* near the proximal end 824 and a bone engagement surface 944*a* near the distal end 826.

FIG. 10C also illustrates that the size and shape of the body 900 have been configured to provide a sufficient size for the bone engagement surface 944*a* and/or bone engagement surface 944*b* for registration with one or more bones of a patient. However, the size and shape of the body 900 may be no larger than needed for accurate registration and strength of the guide while having a minimal size and shape.

In certain embodiments, the bone engagement feature 912 can include a plurality of sections such as bone engagement surface 944*a* and/or bone engagement surface 944*b*. In certain embodiments, each of these bone engagement surfaces together or separately can be specifically configured based on the patient anatomy, surface topography, and/or surgeon preferences to facilitate positioning and/or placement of the resection guide 820*c*. In one embodiment, one bone engagement surface can have a different level of detail and/or fidelity than others. In certain embodiments, parts of the inferior side 916 may include a depression, opening, and/or void that is sized to not contact the bone of a patient and instead provides clearance for desired positioning of the resection guide 820*c*. This can be helpful in reducing the complexity and/or fabrication costs for the resection guide 820*c*.

FIG. 10C also illustrates details in the illustrated embodiment of the landmark registration feature 1004. In the illustrated embodiment, the landmark registration feature 1004 includes a medial surface 1006 and a lateral surface 1008. (See also FIGS. 10F and 10G). In one embodiment, the landmark registration feature 1004 may be configured to engage with a metatarsal of a patient. Specifically, the landmark registration feature 1004 may be configured to engage with a base of the metatarsal of a patient that is part of a TMT joint of a patient. The base of the metatarsal may be a landmark the landmark registration features 1004 is configured to engage.

In one embodiment, the landmark registration feature 1004 may include a medial surface 1006 that is contoured to match a surface of at least a portion of a base of a metatarsal of the patient. In certain embodiments, the medial surface 1006 is a bone engagement surface configured to engage a lateral surface of the base of the metatarsal. In certain embodiments, the bone engagement surface of the medial surface 1006 may be defined based at least in part on a model of a metatarsal of a specific patient. The lateral surface 1008 may be planar or include a one or more edges and/or planes configured to avoid, or prevent, contact of the lateral surface 1008 with a bone (e.g., $2^{nd}$ metatarsal) adjacent to the base of the metatarsal.

When the resection guide 820*c* is in use and positioned in a desired position, the medial surface 1006 with its bone engagement surface may contact and/or engage with at least a portion of a lateral surface of the base of a metatarsal of the TMT joint. In this manner, the landmark registration feature 1004 facilitates engagement and placement of the resection guide 820*c* in a predetermined position.

In certain embodiments, the landmark registration feature 1004 may be referred to as a lateral metatarsal tab, at least in part because the landmark registration feature 1004 is configured to engage with a lateral surface of a base of a metatarsal. In another embodiment, the landmark registration feature 1004 may include a plurality of planes for additional surfaces of the landmark registration feature 1004. These planes can be oriented in a variety of directions and can be configured to be patient-specific surfaces, patient-matched surfaces, or the like. Advantageously, a landmark registration feature 1004 having a plurality of surfaces can enable fabrication of instrumentation (e.g., resection guides) that are further tailored, configured, and/or designed to meet the needs of a particular patient and/or user.

In the illustrated embodiment, the landmark registration feature 1004 extends from the distal side 920 of the body 900. The position along the distal side 920 and the length and/or configuration of the landmark registration feature 1004 can be patient-specific and can be determined at least in part based on a bone model of one or more bones of a patient. In certain embodiments, the landmark registration feature 1004 may be referred to as a "met base arm" because it extends from the body 900 like an appendage towards a metatarsal of a patient. Those of skill in the art will appreciate that the landmark registration feature 1004 may not include a bone engagement surface on the medial surface 1006. Similarly, the resection guide 820*c* can include a plurality of landmark registration features. In such an embodiment, one or more landmark registration features 1004 may extend toward and/or engage with a cuneiform or other bone of a patient and/or one or more landmark registration features 1004 may extend toward and/or engage with a metatarsal or other bone of a patient. Alternatively, or in addition, a user such as a surgeon may request that a landmark registration feature 1004 be included in the resection guide 820*c* or may request that a landmark registration feature 1004 be omitted. Or a user may request one or more landmark registration features 1004 configured to engage other parts of one or more bones of a patient.

Figure 10D:
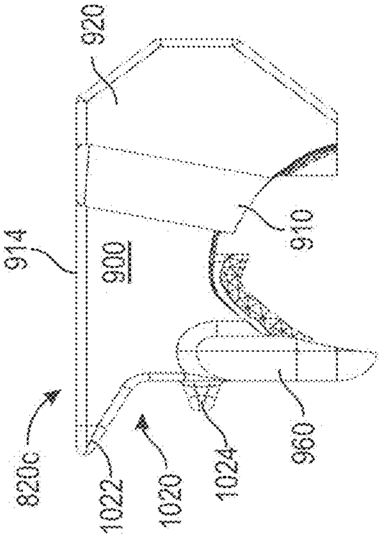

FIG. 10D is a distal side view of the resection guide 820*c*. FIG. 10D illustrates a profile view of a soft tissue engagement feature 1020. The soft tissue engagement feature 1020 moves and/or holds soft tissue in a displaced condition/state while the resection guide 820*c* is in use. In one embodiment, the soft tissue engagement feature 1020 engages soft tissue that is adjacent to one or more bones when the resection guide 820*c* is in use. Those of skill in the art will appreciate that the soft tissue engagement feature 1020 can be simple or complex. Furthermore, the configuration, size, and/or location, of the soft tissue engagement feature 1020 can be based on specific soft tissue the soft tissue engagement feature 1020 is intended to engage, hold/retain, and/or displace. In one embodiment, the soft tissue displacement feature 1020 is patient-specific. In another embodiment, the soft tissue displacement feature 1020 is not patient-specific. In certain embodiments, the soft tissue displacement feature 1020 is configured and/or determined based at least partially on a model of a patient's foot. The model is defined based on medical imaging of the patient's foot.

In certain embodiments, the soft tissue engagement feature 1020 can simply be a surface of a side of the body 900 (e.g., lateral side 924). In other embodiments, the soft tissue engagement feature 1020 can include a recess, slot, or channel configured to engage with the soft tissue when the resection guide 820*c* is in use. In one embodiment, the soft tissue engagement feature 1020 is configured to engage with the soft tissue and/or displace the soft tissue while not damaging the soft tissue, or at least mitigating damage to the soft tissue. In one example, the soft tissue displacement feature 1020 may hold back, hold down, and/or retain skin, tendons, and/or ligaments on the side of the body 900 during a surgical procedure. Advantageously, the soft tissue displacement feature 1020 keeps the soft tissue from riding up over the resection guide 820 and/or interfering with the work of the surgeon during the surgical procedure.

In the illustrated embodiment, the soft tissue engagement feature 1020 includes a superior protrusion 1022 and an inferior protrusion 1024. Those of skill in the art will appreciate that the different embodiments of the soft tissue engagement feature 1020 may include the superior protrusion 1022, the inferior protrusion 1024, or both. The superior protrusion 1022 and/or inferior protrusion 1024 may also be referred to as lips and/or tabs. In certain embodiments, the soft tissue displacement feature 1020 includes just the superior protrusion 1022.

The superior protrusion 1022 and/or inferior protrusion 1024 guide and/or retain a specific soft tissue in a particular location during use of the resection guide 820*c*. In the illustrated embodiment, the particular location may be a part of the lateral side 924 between the superior protrusion 1022 and the inferior protrusion 1024. In the illustrated embodiment, the specific tissue may be an Extensor Hallucis Longus (EHL) tendon which typically extends from the extensor hallucis longus muscle towards the big toe, hallux. In certain embodiments, a surgeon may position the EHL between the superior protrusion 1022 and the inferior protrusion 1024 once the resection guide 820 is in a desired position. Tension in the EHL may press against the resection guide 820 from the lateral direction and assist in holding the resection guide 820 in place.

In one embodiment, the superior protrusion 1022 may have a planar superior surface and a sloped inferior surface. The planar superior surface may also serve as a handle and/or finger position for a user as a user positions the resection guide 820*c* during use. The sloped inferior surface can facilitate displacement of the soft tissue towards the lateral side 924 between the superior protrusion 1022 and inferior protrusion 1024. The superior protrusion 1022 may extend two to three times further laterally from the body 900 than the inferior protrusion 1024.

The inferior protrusion 1024 can include a sloped superior surface and a sloped inferior surface. The sloped superior surface can facilitate displacement of the soft tissue towards the lateral side 924 between the superior protrusion 1022 and inferior protrusion 1024. The sloped inferior surface can mitigate damage to other soft tissue while the resection guide 820*c* is in use.

FIG. 10D illustrates that in the example resection guide 820*c* the second bone attachment feature 910 extends from the superior side 914 to the inferior side 916 at an angle that is not perpendicular to the superior side 914.

Figure 10E:
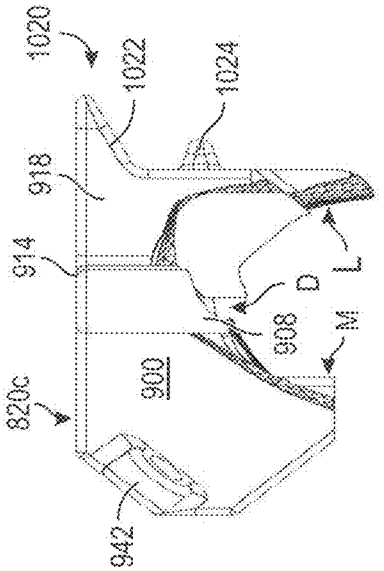

FIG. 10E is a proximal side view of the resection guide 820*c*. FIG. 10E illustrates a proximal view of the soft tissue engagement feature 1020. FIG. 10E illustrates that in the example resection guide 820*c* the first bone attachment feature 908 extends from the superior side 914 to the inferior side 916 at an angle that is perpendicular to the superior side 914. FIG. 10E also illustrates the anchor feature 942. In the illustrated embodiment, the anchor feature 942 is configured to direct a fastener (e.g., K-wire or pin) towards a bone at an angle different from the angle fasteners are deployed using either the first bone attachment feature 908 or the second bone attachment feature 910. In certain embodiments, the anchor feature 942 deploy a fastener at an oblique angle. In the illustrated embodiment, the anchor feature 942 is implemented as a hole configured to receive a fasteners (e.g., K-wire or pin). The anchor feature 942 extends from a surface at or between the superior side 914 and the medial side 922 towards the inferior side 916. Note that in the illustrated embodiment, the anchor feature 942 extends towards the inferior side 916 a relatively short distance (e.g., a few millimeters).

FIG. 10E illustrates an embodiment in which the body 900 extends from a medial surface M (M Arrow) of a foot bone over a dorsal surface D (D Arrow) of the foot bone to a lateral surface L (L Arrow) of the foot bone. In this manner, a bone engagement feature on an inferior side 916 of the resection guide 820*c* can contact at least three parts on the foot bone. These three contacts can provide a stable and secure placement of the resection guide 820*b*. This facilitates more precise and accurate and efficient registration of the resection guide 820 to the bone(s) during the surgical procedure. In one embodiment, the bone engagement feature is on the inferior side 916 and is configured to extend from a medial surface ("M") of at least one the bones (e.g., $1^{st}$ metatarsal) of a joint (e.g., $1^{st}$ TMT joint) over a dorsal surface ("D") of the at least one bone (e.g., $1^{st}$ metatarsal) to a lateral surface ("L") of the at least one bone (e.g., $1^{st}$ metatarsal).

In certain embodiments, the bone engagement feature (e.g., a bone engagement surface 944) is configured to engage at least a portion of a cuneiform and at least a portion of a metatarsal of a patient when the resection guide 820*b* is used. The bone engagement feature, such as a bone engagement surface 944 and/or a landmark registration feature 1004 (discussed below), can include a contour that is at least partially determined based on a bone model of a patient's foot. The bone model may be defined based on medical imaging of the patient's foot.

Figure 10F:
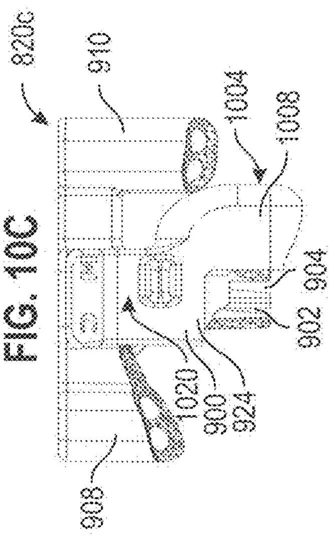

FIG. 10F is a lateral side view of the resection guide 820*c*. FIG. 10F illustrates the soft tissue engagement feature 1020. In one embodiment, the soft tissue engagement feature 1020 includes a superior protrusion 1022 and an inferior protrusion 1024 as illustrated in FIG. 10F. However, in another embodiment, the soft tissue engagement feature 1020 may not include an inferior protrusion 1024.

In yet another embodiment, the lateral side 924 of the body 900 may be configured to facilitate placement and/or registration of the resection guides 820*c* to anatomy of the patient. In one example, the lateral side 924 of the body 900 below the superior protrusion 1022 and between the proximal side 918 and the distal side 920 of the lateral side 924 may be divided into two or more planes (e.g., a proximal plane starting from to the proximal side 918 and a distal plane starting from to the distal side 920). In certain embodiments, the lateral side 924 includes a proximal plane that meets a distal plane at a ridge. Advantageously, in certain embodiments, the proximal plane can be oriented to be parallel or substantially parallel to a longitudinal axis of the medial cuneiform 202 when deployed onto a patient and before the surgical procedure is completed. Similarly, the distal plane can be oriented to be parallel or substantially parallel to a longitudinal axis of the first metatarsal 208 when deployed onto a patient and before the surgical procedure is completed. A ridge between the proximal plane and the distal plane may run vertically between the superior protrusion 1022 and the inferior side 916. In this manner, the proximal plane and/or distal plane can be patient-specific. Of course, a surgeon can give instructions regarding an angle for one or more of the proximal plane and/or distal plane. Alternatively, or in addition, the orientation of the proximal plane and/or distal plane can be a standard orientation.

Or the orientation of the proximal plane and/or distal plane can be predefined such that the orientation selected is based on criteria for a certain set of characteristics for a patient (e.g., similar to or the same as patient-matched). Where the orientation of the proximal plane and/or distal plane is set based on a patient-matched embodiment, a plurality of resection guides 820*c* may be pre-fabricated and the one selected for a particular surgical procedure may be selected based on a set of patient-matched criteria.

Figure 10G:
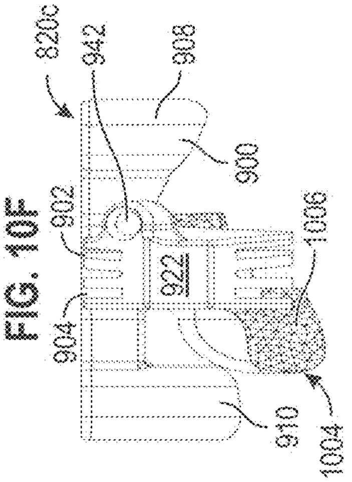

FIG. 10G is a medial side view of the resection guide 820*c*. FIG. 10G illustrates the anchor feature 942 and a sloped surface between the medial side 922 and the superior side 914 and a sloped surface between the medial side 922 and the inferior side 916. These sloped surfaces may facilitate deployment of the resection guide 820*c* and/or may enable deployment with smaller incisions and/or may mitigate damage to surrounding soft tissue during a surgical procedure.

Figure 11:
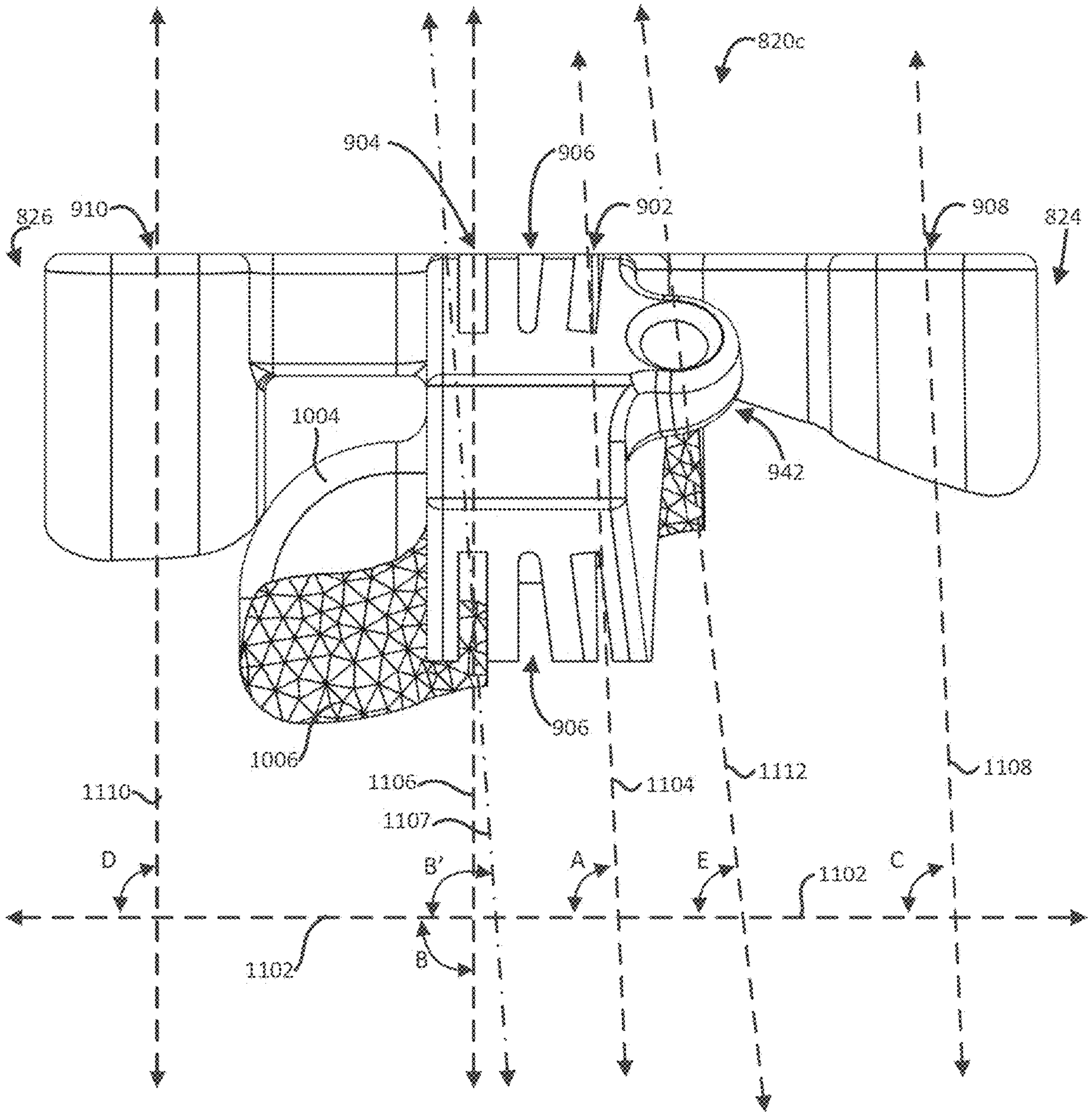
FIG. 11 illustrates a medial side view of a patient-specific guide according to one embodiment.

FIG. 11 illustrates a medial side view of resection guide 820*c* according to one embodiment. This figure illustrates trajectories for different aspects of the resection guide 820*c*. FIG. 11 also illustrates positions and/or angles (e.g., orientation) of one, or both of the resection features (e.g., proximal resection feature 902 and/or distal resection feature 904) and first bone attachment feature 908 and second bone attachment feature 910 relative to each other. FIG. 11 also illustrates the positions and orientations of resection features and/or bone attachment features in relation to a reference axis 1102, identified as the longitudinal axis. This axis extends through the cuneiform and metatarsal of the TMT joint when the guide is in use.

Those of skill in the art will appreciate that either the proximal resection feature 902 or the distal resection feature 904 or both the proximal resection feature 902 and the distal resection feature 904 may be angled and/or oriented in relation to the longitudinal axis 1102 and/or a ML (Medial-Lateral) axis (not shown, that extends into and out of FIG. 11) and/or an AP (Anterior-Posterior) axis (vertical in FIG. 11). For example, in certain embodiments, the distal resection feature 904 may be oriented such that an osteotomy formed using the distal resection feature 904 is at an angle perpendicular to the longitudinal axis 1102 and the proximal resection feature 902 may be oriented such that an osteotomy formed using the proximal resection feature 902 is at an angle non perpendicular to the longitudinal axis 1102 and determined to provide correction of orientation of the bones fused in the surgical procedure. Similarly, the angles for the proximal resection feature 902 and/or distal resection feature 904 can be defined relative to the ML axis and/or the AP axis. Alternatively, or in addition, both the proximal resection feature 902 and the distal resection feature 904 can be defined to direct formation of an osteotomy that extends along a trajectory that is angled relative to the longitudinal axis 1102, ML axis, and/or AP axis in order to provide a deformity correction.

In the illustrated embodiment, the proximal resection feature 902 is positioned between the proximal side 918 and the window 906. As explained, the proximal resection feature 902 extends through the body 900 from the superior side 914 to the inferior side 916 along a first trajectory 1104 in a plantar direction at an angle A in relation to longitudinal axis 1102. This orientation of the proximal resection feature 902 enables a cutting tool forming a first osteotomy into a bone to form a cut surface that is also at angle A relative to longitudinal axis 1102. In certain embodiments, angle A can range between about 0 degrees to about 170 degrees. In certain embodiments, angle A may start at 0 degrees and then increase to a positive number of degrees as illustrated or decrease to a negative number of degrees depending on how a surgeon may prescribe adjustments for a correction.

Similarly, the distal resection feature 904 is angled relative to the longitudinal axis 1102. In the illustrated embodiment, the distal resection feature 904 extends through the body 900 from the superior side 914 to the inferior side 916 along a second trajectory 1106 in a plantar direction at an angle B in relation to longitudinal axis 1102. This orientation of the distal resection feature 904 enables a cutting tool forming a second osteotomy into a bone to form a cut surface that is also at angle B relative to longitudinal axis 1102. In certain embodiments, angle B can range between about 0 degrees to about 170 degrees. In certain embodiments, angle B may start at 0 degrees and then increase to a positive number of degrees as illustrated or decrease to a negative number of degrees depending on how a surgeon may prescribe adjustments for a correction. In the illustrated embodiment, the angle B is a 90-degree angle. Making one of the angles A or B for the first trajectory 1104 or second trajectory 1106 perpendicular to the longitudinal axis 1102 can be desirable since a perpendicular cut or resection may be easier to complete, and in particular may be easier to complete on certain bones.

The proximal resection feature 902 and the distal resection feature 904 can be oriented relative to the longitudinal axis 1102, ML axis, and/or AP axis and/or relative to each other at a variety of angles. Thus, the proximal resection feature 902 and/or distal resection feature 904 can be angled in one or more planes to provide a biplanar or multiplanar correction.

Similarly, those of skill in the art will appreciate that just as the angle of orientation for the resection features 902, 904 can be predefined and determined, the orientation of one or more holes 940 of one or more bone attachment features 908, 910 can be predefined and/or determined. A first bone attachment feature 908 and/or second bone attachment feature 910 can direct a fastener into a bone along a predetermined trajectory.

In certain embodiments, rather than define one of the second trajectory 1106 and/or the first trajectory 1104 relative to the longitudinal axis 1102, a different reference feature may be used. In the illustrated embodiment, a TMT joint axis 1107 may be defined that extends between a metatarsal (e.g., a $1^{st}$ metatarsal) and a cuneiform (e.g., a medial cuneiform). The TMT joint axis 1107 may have a similar trajectory to the second trajectory 1106, however, the TMT joint axis 1107 may be extend towards the distal end 826 of the resection guide 820 between about 5-7 degrees more distally than the second trajectory 1106. In the illustrated embodiment, the second trajectory 1106 is about perpendicular to the superior side 914 of the resection guide 820. The TMT joint axis 1107 may extend about 5-7 degrees less than 90 degrees in relation the superior side 914 and towards the distal end 826.

The TMT joint axis 1107 is a reference feature that may be represented by a single axis, a plane, or the like. The TMT joint axis 1107 indicates an anterior/dorsal to posterior/plantar path through a TMT joint that has the most clearance between a cuneiform and metatarsal that make up the TMT joint. The TMT joint axis 1107 can be determined by a method, system, device, or apparatus. In one embodiment, the TMT joint axis 1107 is determined based on a model of the patient's foot.

In certain embodiments, a surgeon/user can identify the TMT joint axis 1107 by viewing the foot under fluoroscopy in an AP view and adjusting/rotating the normal AP view within the sagittal plane 262 until the most open space is visible between the cuneiform and metatarsal of the TMT joint. This position defines the TMT joint axis 1107.

Referring now to FIG. 11, the TMT joint axis 1107 may be measured relative to the longitudinal axis 1102. In certain embodiments, angle B is perpendicular to the longitudinal axis 1102. Angle B' is less than perpendicular, less than 90 degrees, relative to the longitudinal axis 1102.

In one embodiment, the second trajectory 1106 may not be perpendicular to the longitudinal axis 1102 and instead may be coincident with the TMT joint axis 1107. Similarly, the angle of the first trajectory 1104 may not be determined relative to the longitudinal axis 1102. Instead, the first trajectory 1104 may be determined relative to the TMT joint axis 1107. In one embodiment, the first trajectory 1104 is coincident with the TMT joint axis 1107.

In this manner, at least one of the first trajectory 1104 and the second trajectory 1106 may at least partially be determined based on a TMT joint axis 1107. The TMT joint axis 1107 may be determined based on a model of the patient's foot.

In one embodiment, the first bone attachment feature 908 (e.g., holes 940 of the first bone attachment feature 908) may direct a first fastener, or set of fasteners, into a bone at an angle C relative to the longitudinal axis 1102. The angle C may be the same, or a similar, to angle A. Accordingly, the first bone attachment feature 908 directs the first fastener, or set of fasteners, into the bone along a third trajectory 1108 that is parallel or substantially parallel to the first trajectory 1104.

In addition, the second bone attachment feature 910 (e.g., holes 940 of the second bone attachment feature 910) may direct a second fastener, or set of fasteners, into a bone at an angle D relative to the longitudinal axis 1102. The angle D may be the same, or a similar, to angle B. Accordingly, the second bone attachment feature 910 directs the second fastener, or set of fasteners, into the bone along a fourth trajectory 1110 that is parallel or substantially parallel to the second trajectory 1106. In certain embodiments, where angle B is a 90-degree angle, angle D may also be a 90-degree angle.

Advantageously, the first bone attachment feature 908 can direct the fasteners by way of holes 940 that extend into the body 900 at an angle C that provides the third trajectory 1108. The second bone attachment feature 910 can direct the fasteners by way of holes 940 that extend into the body 900 at an angle D that provides the fourth trajectory 1110. The angled holes 764 cause the fasteners to enter the bone at substantially the same angle as the hole extends into the body 900.

Advantageously, fasteners deployed in holes 940 of the first bone attachment feature 908 and/or second bone attachment feature 910 can serve more than one purpose. First, the fasteners may retain the resection guide 820*c* in place during formation of the osteotomies. Second, the fasteners may guide a surgeon regarding the planned trajectories for an osteotomy through the proximal resection feature 902 and/or distal resection feature 904. The surgeon can use the deployed fasteners as a proxy for the angles and/or orientations of the osteotomies in the resection features.

In certain embodiments, a surgeon may use medical imaging to confirm that the trajectories of deployed fasteners into the bone(s) using the holes 940 are where the surgeon had planned them and/or wants them, and that the surgeon still wants to proceed with the resections. If the surgeon is not comfortable proceeding with the procedure with a given resection guide 820*c* after reviewing the trajectories indicated by the fasteners under fluoroscopy, in certain embodiments, the surgeon may deploy an alternative resection guide 820*c* that is configured to provide a different trajectory for one or more resection cuts into one or more bones. Alternatively, the surgeon may make a different change to the surgical plan to accommodate the needs of the patient and/or preferences of the surgeon.

In one example, when a surgeon uses the resection guide 820*c*, the surgeon may deploy a first fastener in an opening of first bone attachment feature 908 and a second fastener in an opening of second bone attachment feature 910 into one or more bones of a patient's midfoot. In one embodiment, the fasteners are made from a radiopaque material, such as metal. Next, a surgeon may use an X-ray or fluoroscopy to see where the first fastener and/or second fastener extend into one or more bones of the midfoot of the patient. Advantageously, the surgeon knows that the trajectories (e.g., third trajectory 1108 and fourth trajectory 1110) of the first fastener and second fastener are parallel to the first trajectory 1104 and/or second trajectory 1106. Thus, the surgeon can visualize where the first trajectory 1104 and second trajectory 1106 will extend into the one or more bones. In this example, the third trajectory 1108 indicates the first trajectory 1104 and the fourth trajectory 1110 indicates the second trajectory 1106.

In certain embodiments, each bone attachment feature may include one or more holes 940. More than one or two holes 940 for each bone attachment feature can be advantageous because additional holes 940 can provide a more stable placement of the resection guide 820*c*. For example, a fastener in a second or third hole can help keep the resection guide 820*c* from pivoting or rotating about a single fastener in a single hole.

Referring now to FIG. 11, in the illustrated embodiment, the proximal resection feature 902 comprises an opening that starts on the superior side 914 and extends to the inferior side 916. The opening of the proximal resection feature 902 extends through the body 900 along a first trajectory 1104. In the illustrated embodiment, the distal resection feature 904 comprises an opening that starts on the superior side 914 and extends to the inferior side 916. The opening of the distal resection feature 904 extends through the body 900 along a second trajectory 1106.

The opening of the proximal resection feature 902 and/or the opening of the distal resection feature 904 has a width and/or length large enough to accommodate, or accept, a cutting element of a cutting tool. In one embodiment, the opening of the proximal resection feature 902 is configured to guide and/or enable a cutting tool to form a first osteotomy into, and/or through, the bone. It may be desirable for the osteotomy to pass though the bone both along the AP axis and along the ML axis. Advantageously, the first osteotomy tracks, follows, and/or is aligned with the first trajectory 1104. In one embodiment, the opening of the distal resection feature 904 is configured to guide and/or enable a cutting tool to form a second osteotomy into, and/or through, the bone. Advantageously, the second osteotomy tracks, follows, and/or is aligned with the second trajectory 1106. Thus, a surgeon operating the cutting tool within the opening of the proximal resection feature 902 and the distal resection feature 904 can readily form a first osteotomy and a second osteotomy that matches a design that may have been set out in a model of the resection guide 820*c* and/or a model of the patient's bone(s).

In one embodiment, the first trajectory 1104 may be determined and/or defined to be a patient-specific feature. Similarly, the second trajectory 1106 may be determined and/or defined to be a patient-specific feature. Advantageously, using the apparatus, methods, and/or systems of the present disclosure a user may determine and/or at least partially determine the first trajectory 1104 and/or the second trajectory 1106 based on a model of at least a portion a bone of the patient that is to receive one or more osteotomies. The model of at least a portion of the bone can be derived from, and/or based on, medical imaging of a patient's foot. In certain embodiments, the model used to determine, or at least partially determine, the first trajectory 1104 and/or the second trajectory 1106 is configured to resemble, substantially resemble, or match the anatomy of the patient's foot.

As used herein, in certain embodiments, partial determination of the first trajectory 1104 and/or the second trajectory 1106 based on a bone model may mean that the bone model for a bone of a patient that will receive the osteotomies is used together with other imaging data, anatomic data, patient imaging data, patient data, information from a prescription from a doctor, information about surgeon preferences, measurement data taken from the bone model or medical imaging, or the like to determine the first trajectory 1104 and/or the second trajectory 1106.

The first trajectory 1104 may be at least partially determined based on a bone model of at least a portion of a bone of a patient's foot. The bone model may be based on medical imaging of the patient's foot and is configured to resemble, significantly resemble, and/or match the anatomy of the patient's foot. The second trajectory 1106 may be at least partially determined based on a bone model of at least a portion of a bone of a patient's foot. The bone model may be based on medical imaging of the patient's foot and is configured to resemble, significantly resemble, and/or match the anatomy of the patient's foot.

In certain embodiments, determination of the first trajectory 1104 and second trajectory 1106 may be done based on a revised model of a patient's foot. Suppose a surgeon plans to do a plurality of surgical procedures on a patient's foot. For example, a surgeon may plan to do a metatarsus adductus procedure and a Lapiplasty procedure. In addition, the surgeon may plan to perform the metatarsus adductus procedure followed by a Lapiplasty procedure. In one embodiment, the apparatus, methods, and/or systems of the present disclosure can be used to prepare and/or provide a resection guide for either the metatarsus adductus procedure, the Lapiplasty procedure, or both.

Where the surgeon plans to do a metatarsus adductus procedure followed by a Lapiplasty procedure, the apparatus, methods, and/or systems of the present disclosure can be used provide the resection guide 820 for the Lapiplasty procedure. In particular, a surgeon and/or user can provide details about how the metatarsus adductus procedure is intended to change the position and/or orientation of one or more other model bones in a bone model of the patient's foot. The changed position and/or orientation can be applied to the model bones to create a revised model, a revised bone model of the bones of the patient's foot.

The revised model can be used to at least partially determine the first trajectory 1104 and/or the second trajectory 1106. The revised model represents the changes to the bones of the patient's foot made by a surgical procedure (and not just a metatarsus adductus procedure) prior to using a resection guide 820 for a second surgical procedure on a patient's foot. The revised model can be advantageous for example, because a metatarsus adductus procedure may reposition the second through the fourth metatarsals and a surgeon may plan to adjust the position and/or orientation of first metatarsal to be natural and consistent with the other metatarsals.

FIG. 11 illustrates one example of an anchor feature 942. The anchor feature 942 may include an anchor and in one embodiment, the anchor may be implemented by way of a hole or opening in a structure configured to guide a fastener into a bone at a predetermined angle in one or more of a dorsal plane, a frontal plane, and a transverse plane.

In the illustrated embodiment, the anchor feature 942 includes an anchor that is positioned near the medial side 922 and extends towards the proximal end 824. The anchor includes a hole sized to receive a fastener such as a K-wire or pin that can be deployed into a bone after passing through the hole. The anchor is configured to guide the fastener along a fifth trajectory 1112. In certain embodiments, the fifth trajectory 1112 is different from one or the other, or both, of the first trajectory 1104 and the second trajectory 1106. Of course, the fifth trajectory 1112 can be the same or substantially the same as the first trajectory 1104 or the second trajectory 1106.

In the illustrated embodiment, the anchor feature 942, such as an anchor may extend from the superior side 914 mediolaterally towards the inferior side 916 for a distance sufficient to guide a fastener in a hole of the anchor feature 942 along a particular trajectory. Those of skill in the art will appreciate that this means that the length of a body of the anchor defining the hole can be minimized to reduce the size, weight and use of material of a resection guide 820*c*. Alternatively, or in addition, body of the anchor defining the hole to a variety of lengths between the superior side 914 and the inferior side 916.

Advantageously, a surgeon can determine what values are desired for angles A, B, C, D, and E. In this manner, a surgeon can customize the surgical procedure for a particular patient. Advantageously, the various aspects of the design of the resection guide 820 and/or an accompanying surgical technique and/or complementary components 730 can be done prior to fabrication of one or more components of the osteotomy system. Thus, a surgeon can define or adjust the position of the resection features, the position and/or orientation of the bone attachment features, a height of the body 900 (measured between the superior side 914 and the inferior side 916), and the like. Of course, certain of these aspects may be predefined for a surgeon and/or recommendations made to a surgeon. Alternatively, or in addition, certain of these aspects may be patient-specific while others may be standard based on experience and/or established practice for a particular procedure.

Those of skill in the art will appreciate that the position and orientation of the proximal resection feature 902 and distal resection feature 904 and the corresponding cut surfaces a surgeon can form using these resection features can vary depending on the anatomical structures of the patient, the osteotomy procedure being performed, preferences of the surgeon, the nature of the condition, and the like.

Figure 12:
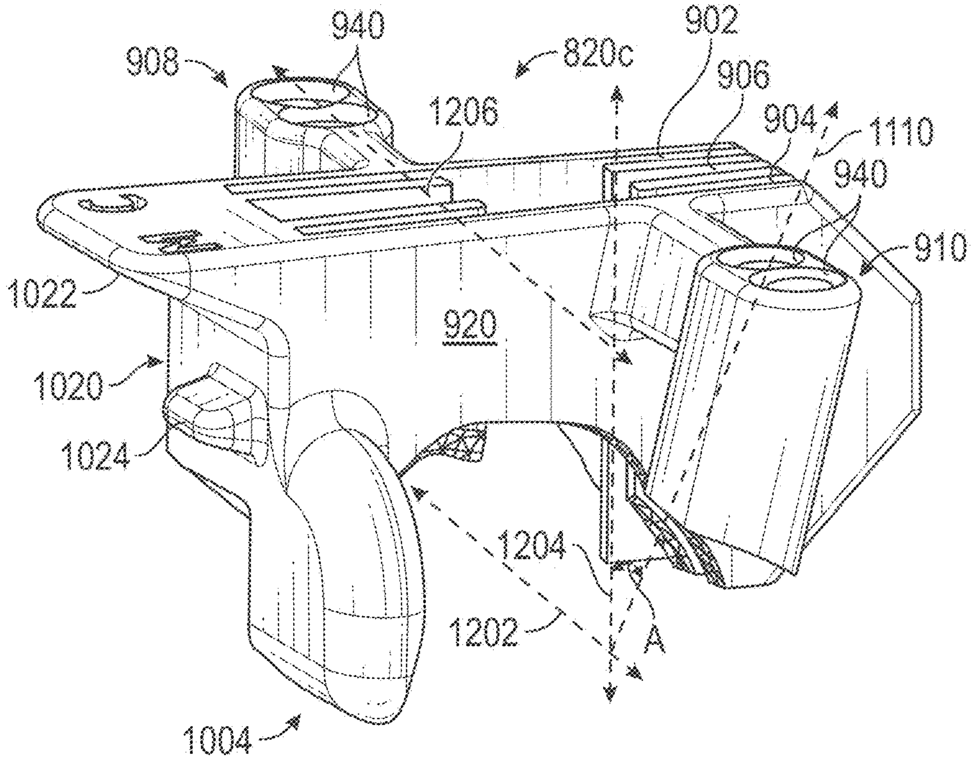
FIG. 12 illustrates a lateral perspective view of a patient-specific guide according to one embodiment.

FIG. 12 illustrates a lateral perspective view of a resection guide 820*c* according to one embodiment. FIG. 12 illustrates a longitudinal axis 1202 that runs in a longitudinal direction from the calcaneus towards the phalanges when the resection guide 820*c* is positioned on a patient. In certain embodiments, the longitudinal axis 1202 may be coincident with the longitudinal axis 1102. In the illustrated embodiment, the longitudinal axis 1202 is coincident with a longitudinal axis of a cuneiform when the resection guide 820*c* is positioned for use. Alternatively, or in addition, the longitudinal axis 1202 may be coincident with a longitudinal axis of a metatarsal when the resection guide 820*c* is positioned for use.

Whether the longitudinal axis 1202 is coincident with a longitudinal axis of the foot, one goal of a surgical procedure to correct a deformity of the metatarsal (i.e., the metatarsal is in a deformed position) may include translating the metatarsal in the transverse plane such that a longitudinal axis of the metatarsal is coincident with, or parallel to, the longitudinal axis 1202 of the foot as a result of the surgical procedure.

FIG. 12 also illustrates an anterior-posterior (AP) axis 1204 that is perpendicular to the longitudinal axis 1202. FIG. 12 illustrates that the first bone attachment feature 908 is configured to align longitudinally with a dorsal axis 1206 that runs parallel to the longitudinal axis 1202. In the illustrated embodiment, the holes 940 of the first bone attachment feature 908 are configured such that fasteners in the holes are parallel to each other and the pair of fasteners are aligned with the dorsal axis 1206. As described above, a first pair of fasteners deployed in the holes 940 of the first bone attachment feature 908 are directed by the holes 940 along a third trajectory 1108 (See FIG. 11) that is parallel to the first trajectory 1104. In certain embodiments, the position of the first bone attachment feature 908 can be configured to be patient-specific and can be configured to direct the fasteners into approximately a center of the dorsal cortex of a bone, such as a cuneiform.

In one embodiment, one or more of the bone attachment features may be positioned along a side of the resection guide in order to aid a surgeon in accurate positioning of the resection guide for the surgical procedure. In one example, the first bone attachment feature 908 may be specifically positioned along the proximal side 918 so that an arm that connects the first bone attachment feature 908 to the body is aligned with the dorsal axis 1206 that runs parallel to the longitudinal axis 1202.

In one embodiment, the longitudinal axis 1202 may be coaxial with a long axis of a cuneiform involved in the surgical procedure. In another embodiment, the longitudinal axis 1202 may be coaxial with a long axis of a metatarsal involved in the surgical procedure in a deformed position (preoperatively). In yet another embodiment, the longitudinal axis 1202 may be coaxial with a long axis of a metatarsal involved in the surgical procedure in a corrected condition (postoperatively).

Advantageously, the surgeon can use the arm that connects the first bone attachment feature 908 to the body as a guide using fluoroscopy to gauge where the parallel long axis 1202 runs and thereby determine and/or confirm whether the resection guide is in a desired position relative to bone(s) of the patient. Furthermore, this can be done before forming any osteotomies, this can help assure the surgeon that the surgical procedure is proceeding as planned.

FIG. 12 also illustrates that the second bone attachment feature 910 is not aligned longitudinally with the first bone attachment feature 908. Instead, the second bone attachment feature 910 is positioned towards the medial side 922 of the resection guide 820*c*. In the illustrated embodiment, the second bone attachment feature 910 is configured to direct a second pair of fasteners along a fourth trajectory 1110 (See FIG. 11) that is parallel to the second trajectory 1106. FIG. 12 illustrates that the fourth trajectory 1110 is offset from the AP axis 1204 by an angle A. The angle A can be configured to position and direct the pair of fasteners deployed in the second bone attachment feature 910 into approximately a center of a surface of a bone (e.g., a metatarsal) that faces the second bone attachment feature 910.

In certain embodiments, such as the illustrated embodiment, the position of the second bone attachment feature 910 along the distal side 920 and/or size of the angle A are determined to enable an additional correction to a deformity of anatomy of a patient. Often, when a patient has a deformity that calls for a Lapidus surgical procedure to correct the deformity, the patient also has a condition in which the metatarsal has rotated medially or laterally about the longitudinal axis 1202 such that sesamoids near the distal end of the metatarsal extend laterally or medially rather than plantarly. Advantageously, embodiments of the present disclosure enable correction of both the orientation of the metatarsal as well as rotation of the metatarsal within the frontal plane to correct the position of the sesamoids.

In the illustrated embodiment, angle A can be set to enable a rotation (which can be referred to as a derotation) of the metatarsal in a frontal plane from a deformed position to a corrected position. Advantageously, as with the various other aspects of the resection guide 820*c* and/or a surgical procedure based on the teachings of the present disclosure, the size of angle A and/or the position of second bone attachment feature 910 can be patient-specific and/or can be determined at least in part based on a model of one or more bones of a patient and/or a model for a resection guide 820*c*. In certain embodiments, angle A can range from about 2 degrees to about 60 degrees. The size of angle A can be also defined, determined, revised, or adjusted based on user preferences, and/or surgeon preferences.

The rotational correction of a bone such as a metatarsal is based on an initial position of fasteners deployed in the second bone attachment feature 910 and/or first bone attachment feature 908. In the illustrated embodiment, a first fastener or first pair fasteners of the first bone attachment feature 908 and a second fastener or second pair fasteners are initially deployed such that the fasteners are not aligned with each other along the longitudinal axis 1202 and/or dorsal axis 1206.

Certain embodiments of the present disclosure leverage the position of fasteners (e.g., pins) deployed in the first bone attachment feature 908 and in the second bone attachment feature 910 for multiple purposes. First, the fasteners can be used to indicate for a surgeon the trajectories of osteotomies formed using the proximal resection feature 902 and/or the distal resection feature 904 that are directed along trajectories that are parallel to trajectories that the fasteners are deployed in one or more bones. Second, the fasteners serve to retain the resection guide 820*c* and keep the resection guide 820*c* in place while osteotomies are formed.

And third, the fasteners are positioned and/or oriented for use to facilitate and aid in reduction of the osteotomies and/or correction of bones as part of the reduction. In the illustrated embodiment, the fasteners in the second bone attachment feature 910 enable rotational correction of the metatarsal as the fasteners of the second bone attachment feature 910 are brought towards and into alignment with the fasteners of the first bone attachment feature 908. This alignment is along longitudinal axis 1202.

In the illustrated embodiment, in one example surgical technique, a surgeon deploys a first pair of fasteners in first bone attachment feature 908 or second bone attachment feature 910 and a second pair of fasteners in the other one of the first bone attachment feature 908 or second bone attachment feature 910. Next, the surgeon forms a first osteotomy in a cuneiform or a metatarsal. Next, the surgeon forms a second osteotomy in the other one of the cuneiform or the metatarsal.

Next, the surgeon may slide the resection guide 820*c* off the fasteners of the first bone attachment feature 908. Next, the surgeon may slide the resection guide 820*c* off the second bone attachment feature 910. In certain embodiments, the size of angle A and/or the length of the fasteners may impede removal of the resection guide 820*c* by sliding off the fasteners while the fasteners remain in the bone(s). In such embodiments, a surgeon may temporarily remove fasteners such as those in first bone attachment feature 908 to facilitate removal of the resection guide 820*c* and then replace the fasteners used in the first bone attachment feature 908 into the same holes in the bone they were in previously.

Advantageously, with the resection guide 820*c* removed, a surgeon may prepare the cut faces for a fusion and then proceed with a reduction of the bones and/or bone fragments. In one embodiment, the surgeon may slide a compression block (e.g., or a positioning guide or a reduction guide or a compressor or distractor) over the fasteners used with the first bone attachment feature 908 and those used with the second bone attachment feature 910. Alternatively, or in addition, the surgeon may reduce the bones manually.

In one embodiment, a compression block may include four holes one for each fastener of the first bone attachment feature 908 and the second bone attachment feature 910. These four holes may be parallel to each other as they extend through the compression block and may be aligned with each other longitudinally (e.g., along dorsal axis 1206). Consequently, as the compression block is slid down the fasteners, the fasteners of the second bone attachment feature 910 are aligned with the fasteners of the first bone attachment feature 908 along the longitudinal axis 1202 and/or the dorsal axis 1206. This alignment causes the metatarsal to rotate about its long axis, about longitudinal axis 1202, within the frontal plane. This rotation can correct a position of sesamoids of the metatarsal. The metatarsal rotates from a deformed position to a corrected position.

Referring still to FIG. 12, reduction of a first osteotomy of a cuneiform with a second osteotomy of a metatarsal closes the angle A from its initial number of degrees to zero degrees or substantially zero degrees and brings fourth trajectory 1110 into alignment and to be parallel to AP axis 1204. The metatarsal rotates within the frontal plane to provide a correction. Those of skill in the art will appreciate that alternative embodiments of the resection guide 820*c* may include a first bone attachment feature 908 and a second bone attachment feature 910 that deploys fasteners that are aligned along dorsal axis 1206 and longitudinal axis 1202. In such embodiments, a surgeon may manually rotate the metatarsal. Alternatively, or in addition, a compression block and/or reduction guide may include holes that are not aligned (e.g., proximal holes may not align with distal holes, which extend into the device at an angle similar to angle A) that receive the fasteners such that sliding of the compression block and/or reduction guide over the fasteners rotates the metatarsal.

Advantageously, the patient-specific apparatus, methods, and systems of the present disclosure can be implemented based on patient imaging data to address these various conditions. In addition, the medical techniques that incorporate the patient-specific apparatus, methods, and systems of the present disclosure can include certain conventional steps and stages and new stages or steps that are enabled by the present disclosure. If the imaging confirms the fasteners are in a desired position with a desired orientation, a surgeon may resect one or more bones by moving a cutting tool between and/or along the deployed fasteners. In this manner the fasteners may serve as a stop or guide to prevent resection beyond the position of the fasteners.

Figure 13:
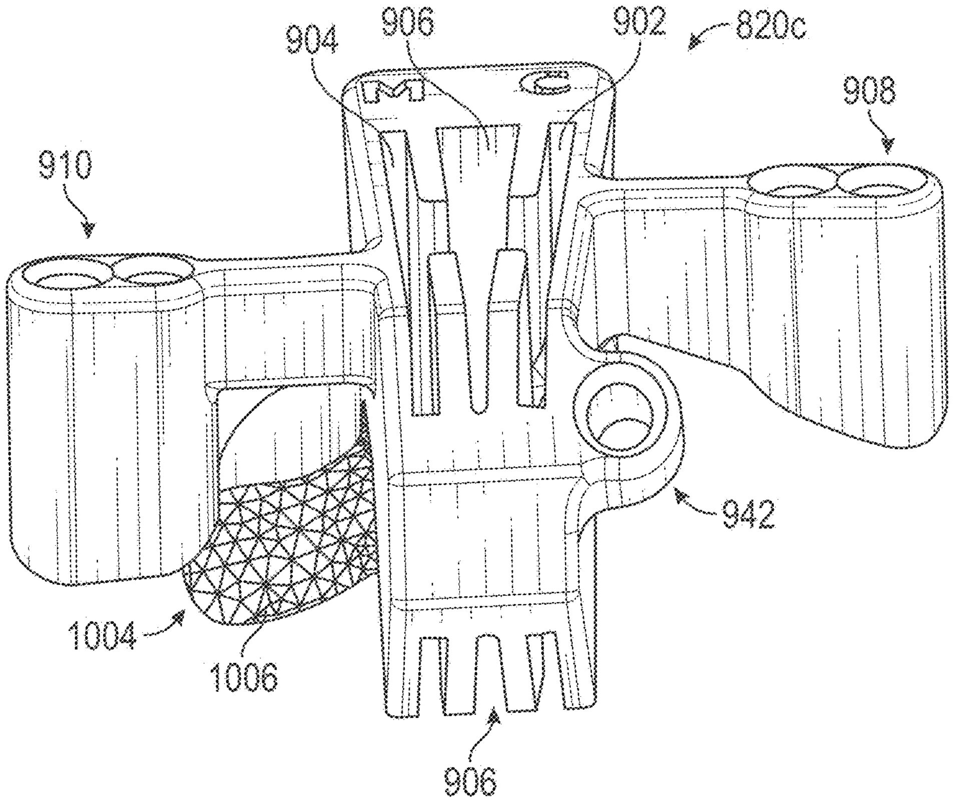
FIG. 13 illustrates a medial perspective view of a patient-specific guide according to one embodiment.

FIG. 13 illustrates a medial perspective view of a resection guide according to one embodiment. FIG. 13 illustrates the proximal resection feature 902, distal resection feature 904, window 906, first bone attachment feature 908, second bone attachment feature 910, and landmark registration feature 1004. In the illustrated embodiment, the landmark registration feature 1004 includes a medial surface 1006 that is contoured to match a lateral surface of a portion of a base of a metatarsal of the patient. Advantageously, the window 906 extends into the proximal resection feature 902 and the distal resection feature 904 such that a surgeon using the resection guide 820*c* can see (both visually and/or with the aid of fluoroscopy) the distal end of a cuneiform and a proximal end of a metatarsal of a TMT prior to making any cuts.

The present disclosure includes a method of using the resection guide 820*c* and/or other components of the system 800. Initially, a surgeon may form an incision transverse to a tarsometatarsal ("TMT") joint and/or a cuneonavicular joint with a dorsal approach. The resection guide 820*c*, in one example, may be configured (e.g., using one or more bone engagement features) to seat on and between a dorsal surface of both the medial cuneiform 202 and the first metatarsal 208. The surgeon forms the incision down to the cortical bone surface. The surgeon also cuts, or moves to the side, soft tissue covering the cortical bone surface of the bones sufficient to seat the bone engagement features to the cortical bone surface. In certain embodiments, this can include capturing and displacing the Extensor Hallucis Longus (EHL) tendon that may run along a lateral side of the TMT joint.

Next, the surgeon positions the resection guide 820*c* on one or more bones so as to span the TMT joint and may extend into and/or cross a cuneonavicular joint. As described herein, the resection guide 820*c* is patient-specific and has been designed and/or fabricated specifically for this patient and/or for this surgical procedure.

In addition, the body 900 of the resection guide 820*c* includes a bone engagement surface (not visible in FIG. 13). The bone engagement surface may span the inferior side 916 of the body 1110. Advantageously, the bone engagement surface includes a patient-specific surface that includes a contour that mirrors a contour of a plurality of bones. The patient-specific surface is defined at least in part using a bone model 404 of at least one bone of the patient's foot. The bone engagement surface is on a bone-facing surface of the body 900 when the resection guide 820*c* is in use. The bone engagement surface assists a surgeon in positioning the resection guide 820*c* in the same or substantially the same position as predetermined using a model of the resection guide 820*c* and/or one or more models of one or more bones of the patient.

The bone engagement surface 944 can extend across the entire inferior side 916 including features such as inferior sides of the first bone attachment feature 908 and/or second bone attachment feature 910, anchor feature 942 and the like. Alternatively, or in addition, the bone engagement surface 944 may extend over a smaller portion of the inferior side 916.

One goal of the bone engagement feature 912 is to accurately engage with and/or position a structure in relation to one or more bones, bone fragments, or parts of a bone such as one or more cortical surfaces of one or more bones. Advantageously, embodiments of the present disclosure can accurately position a patient-specific such as a resection guide 820*c* in relation to one or more bones, such as those of a TMT joint. In certain embodiments, a bone engagement feature 912 may be configured to accurately engage with the one or more bones or bone parts or bone surfaces using a minimal number of contact points and/or contact surfaces.

For example, referring to FIGS. 13, 10D and 10E, a bone engagement feature 912 can be configured to wrap around multiple surfaces of a bone. With such a configuration, the bone engagement feature 912 may not need to contact more than three or four parts of the bone in order to accurately register and orient a resection guide 820*c* with the bone. In FIGS. 10D and 10E, a proximal and distal view of the distal side 920 and medial side 922 is illustrated. This view shows a concave area where a bone such as a metatarsal will be positioned, when the resection guide 820*c* is positioned before being secured to the bone(s). Advantageously, the body 900 and bone engagement feature 912 are configured to contact the bone (which has a medial, dorsal, and lateral cortex with an irregular semicircle and/or wedge-shaped cross section) in about three areas (e.g., a medial cortex area M, a dorsal cortex area D, and a lateral cortex area L). In certain embodiments, contact with the bone in these three areas can be sufficient to register the resection guide 820*c* in the desired location relative to the bone. Of course, more contact areas can be employed to further facilitate placement and registration of the resection guide 820*c* relative to the bone.

In certain embodiments, four contact points may be used. Those of skill in the art will appreciate that with respect to the contact points for the bone engagement feature 912 structures other than a contoured surface can be used. For example, projections from the inferior side 916 can extend towards and contact the bone. Alternatively, or in addition, sections of the inferior side 916 can be recessed such that sections, portions, or areas of contoured sections can be formed that are contoured to mirror and match and/or mate with corresponding areas on a surface of a bone. The size, shape, surface contour, and configuration of these contoured sections can be patient-specific and can be defined using a bone model of a bone of a patient. These areas of contoured sections may resemble pads or feet that contact a surface or other structure of a bone.

Returning to an example medical procedure that uses the resection guide (e.g., any of the embodiments of resection guides of the present disclosure), after a surgeon positions the resection guide 820*c* on a surface of one or more bones, a surgeon may next translate and/or rotate the resection guide 820*c* until the bone engagement feature 912 engages with one or more bones and/or bone structures (e.g., surfaces) and registers with the bone(s). For example, the bone engagement surface 944 may interlock with a cortical surface of one or more bones. Similarly, a landmark registration feature 1004 may engage with a bone structure, such as joint and/or a base of a metatarsal.

This registration can, in certain embodiments, be detected by a tactile change in how the resection guide 820*c* moves in relation to the bone. At one point, the resection guide 820*c* may move freely, but once registered, the resection guide 820*c* may "lock into place" and no longer readily move or translate in relation to the bone.

After the resection guide 820*c* "locks into place" a surgeon may deploy one or more fasteners into the first bone attachment feature 908 and/or the second bone attachment feature 910 to secure the resection guide 820*c* to one or more bones. A fastener deployed in the first bone attachment feature 908 can enter the medial cuneiform 202. A fastener deployed in the second bone attachment feature 910 can enter the first metatarsal 208. Additional fasteners may be deployed into the bones using the first bone attachment feature 908 and second bone attachment feature 910.

At this stage, a surgeon may use fluoroscopy to confirm that the trajectories of fasteners in the first bone attachment feature 908 and/or second bone attachment feature 910 have trajectories that correlate to desired trajectories that osteotomies formed using the proximal resection feature 902 and distal resection feature 904 will have. This is because the trajectory of the proximal resection feature 902 is parallel to the trajectory of the first bone attachment feature 908 and the trajectory of the distal resection feature 904 is parallel to the trajectory of the second bone attachment feature 910.

In certain embodiments, a surgeon may also deploy a fastener in an anchor feature 942 to provide further stability and engagement of the resection guide 820*c* with the one or more bones.

Next, a surgeon can resect the first metatarsal 208 using the distal resection feature 904 and the medial cuneiform 202 using the proximal resection feature 902. After resection, the two cut surfaces may be prepared for fusion of the two bones by pressing the two cut surfaces against each other. Alternatively, or in addition, a surgeon may prepare the cut surfaces using a rasp or other instrument to facilitate a union of the bones.

With the resection(s) completed, the resection guide can be removed and one or more fasteners 710 retained in one or more bones. The retained fasteners may be used to translate and/or rotate the proximal and distal bone or bone fragments. In one embodiment, a compressor or distractor can be deployed over the fasteners 710 to facilitate joining, translating, holding, and/or positioning the cut surfaces and/or fusing the bones. Those of skill in the art will appreciate that for certain patients with certain pathologies, the form and/or shape of the resection guide can be different. As explained above, the resection guide can be positioned, sized, configured, and oriented and/or trajectories set for the resection guide preoperatively using bone models. Additionally, a surgeon can provide a prescription for the location of guide features (e.g., resection features) to account for other conditions of a particular patient. Those of skill in the art will appreciate that the resection guide can be used for a variety of procedures in a hindfoot, midfoot, forefoot, hand, wrist, elbow, shoulder, and/or the like. One skilled in the art can appreciate that the presented embodiments may be modified, revised, or repositioned to address a surgeon's particular angles, approach, entry locations and/or preferences.

Next, a surgeon may remove a fastener of the anchor feature 942 and/or one or more fasteners in the first bone attachment feature 908 and/or second bone attachment feature 910 and remove the resection guide 820*c*. All the fasteners may be removed, or select fasteners may be removed, such that the resection guide 820*c* can be removed and certain fasteners may remain in the bone(s). In certain embodiments, certain fasteners may be reinserted into the same holes used previously.

Next, a surgeon may reduce the osteotomies and combine the two bones at the cut surfaces. This can be done manually, or a compressor and/or a compression block may engage one or more of the fasteners. As described herein, this reduction and/or compression translates one or more of the bones and/or can rotate one or more of the bones to provide a rotational correction for a deformity. After compression, a surgeon may secure the two bones together with either provisional or permanent fixation and may deploy one or more implants to hold the bones in place.

Advantageously, the apparatuses, systems, and methods of the present disclosure can be used to plan these osteotomies, determine the desired angles (in one, two, or three planes) for cuts for each wedge segment, a desired depth for the cuts, define suitable resection guides for the surgical procedure, manufacture suitable resection guides for the surgical procedure, and demonstrate how the anatomy will look or reduce once the osteotomies are completed, the bones are positioned, and the surgical procedure is completed.

Those of skill in the art will appreciate that, in one embodiment, anatomical data about the patient can be used to define other structures of the system (e.g., system 700 or system 800) or other patient specific instruments. For example, anatomical data about the patient that can be captured in the patient imaging data (e.g., due to the fidelity of the technology providing the patient imaging data) can be used to define how deep one or more resection features are. Controlling the depth of the resection features can be used to manage how deep a surgeon's cutting instruments can reach within the resection features. Managing a depth for one or more resection features may be referred to as defining a patient specific height for a resection guide.

For example, in one embodiment, patient imaging data can be used to define a distance between at a top edge (e.g., superior side 914) of a resection guide (e.g., resection guide 820*a*, resection guide 820*b*, resection guide 820*c*) and a first surface (e.g., a surface of a first bone such as a medial cuneiform) or a bottom edge (e.g., an inferior side 916). Managing the distance between a top edge and a bone surface or bottom edge is one way to provide a stop within the resection guide. The stop can serve to limit how deep a surgeon will resect hard tissue/soft tissue when using the resection guide for a procedure. If a surgeon resects until the resection instruments engages the stop, the surgeon can be assured that the resection extends to a desired depth (not too far and not too short). Such control can enable a surgeon to accurately make clean and complete resections of bone without damaging other tissue.

In another example, the anatomical data about a patient available from the medical imaging and/or a model of patient anatomy (e.g., bone model) can be used to define other instruments for a surgical procedure. For example, when a Lapidus procedure is performed it can be helpful to have a positioner that can be placed between the first metatarsal 208 and the second metatarsal 210 to position the first metatarsal 208 for the surgical procedure. The positioner can be patient-specific and/or can be patient-matched (patient-matched refers to an instrument or device that is selected from a set of pre-fabricated instruments or devices to satisfactorily service a user based on a set of characteristics, such as size of the foot, size of the deformity, angles for certain landmarks, angles for a deformity, type of deformity, size of the bone, and the like). Alternatively, or in addition, a positioner can be used with the bone model 404 to assist in positioning one or more models of bones of a patient in order to define, determine, and/or design one or more other instruments of a system (e.g., resection guide 820*a*, resection guide 820*b*, resection guide 820*c*, or the like).

Figure 14:
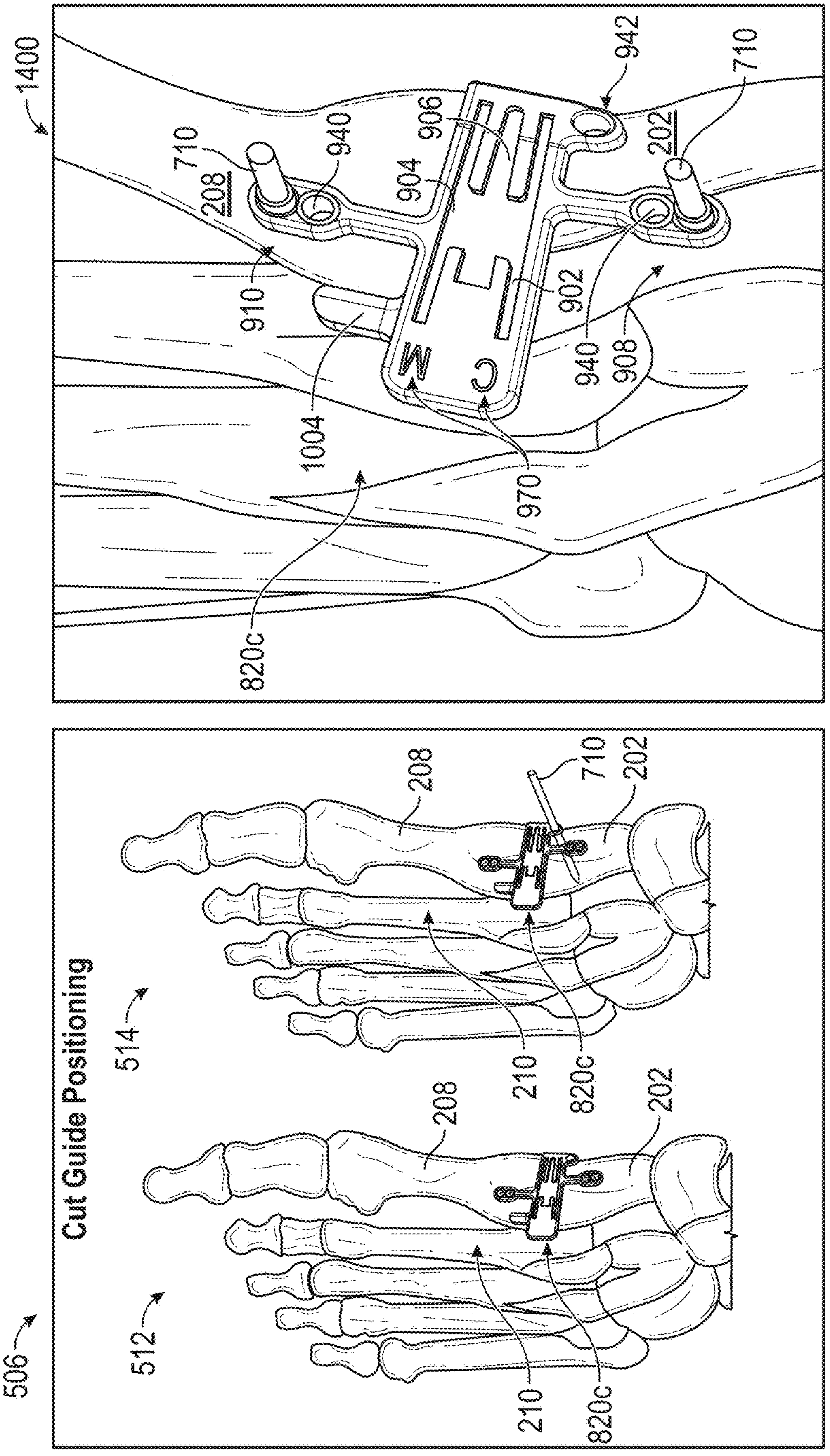
FIG. 14 illustrates a page from a preoperative plan and a medical image of a patient-specific guide positioned on a patient according to one embodiment.

FIG. 14 illustrates a page from a preoperative plan 506 and a medical image 1400 of a patient-specific guide positioned on a patient according to one embodiment. FIG. 14 illustrates two steps in an example preoperative plan 506. The example preoperative plan 506 shown may be similar to the preoperative plans 506 described in relation to FIG. 5. The preoperative plan 506 can include a plurality of steps. The preoperative plan 506 can exist in a variety of formats including data on a computer storage device or memory, a printed format, a set of physical models, or the like. FIG. 14 illustrates one page of a preoperative plan 506 showing two steps 512, 514.

One step 512, includes a drawing or illustration of bones of a foot. The illustration can include accurate drawings, prints, and/or representations of the bones of a foot of a particular patient. For example, the illustration can be generated based on the medical imaging referred to in the present disclosure. In one embodiment, the illustration shows the bones of the foot of a patient prior to completing a surgical procedure. In the example illustration, the bones of the foot are configured to represent bones of a patient foot that includes a deformity. The illustration shows the first metatarsal 208 extends medially rather than parallel to the second metatarsal 210. The illustration also shows a representation of a resection guide 820 (e.g., resection guide 820*c*) positioned on a dorsal surface of a medial cuneiform 202, extending over a first TMT joint, and on a dorsal surface of a first metatarsal 208.

In the illustrated embodiment, step 514 includes the same drawing or illustration of bones of the same foot as in step 512. Similarly, step 514 illustrates the same example resection guide 820 (e.g., resection guide 820*c*) in the same position as in step 512. Step 514 also illustrates a fastener 710 deployed in an anchor feature 942 of the resection guide 820*c*. Step 514 illustrates the medial cuneiform 202 in a transparent state so a user can visualize a trajectory for the fastener 710 deployed in the anchor feature 942.

The preoperative plan 506 assists the user, a surgeon, in performing the surgical procedure according to a recommended operative technique. Of course, the surgeon can revise, change, adjust, or not follow each step of the preoperative plan 506 as the surgeon decides in their own discretion.

In the illustrated embodiment, the medical image is a anteroposterior/dorsoplantar projection/view using an X-ray or a fluoroscopy device. In one embodiment, the medical image 1400 shows bones of a patient and a resection guide 820*c* positioned on a dorsal side of the bones at a stage of a surgical procedure. At this stage, a surgeon has created an incision and taken steps to permit an inferior side 916 of the resection guide 820*c* to rest on a dorsal surface of the medial cuneiform 202 and the first metatarsal 208. The surgeon appears to have deployed a fastener 710 in a distal hole 940 of the bone attachment feature 910 and deployed a fastener 710 in a proximal hole 940 of the bone attachment feature 908.

Medical image 1400 shows a number of advantages of the present disclosure available to a surgeon. First, different parts of the resection guide 820*c* described herein can be seen in the medical image 1400. For example, the resection guide 820*c* includes and the medical image 1400 shows a proximal resection feature 902, a distal resection feature 904, a window 906, a bone attachment feature 908, a bone attachment feature 910, an anchor feature 942, and one or more markings 970.

Medical image 1400 shows clearly where the proximal resection feature 902 and distal resection feature 904 are in relation to each other and in relation to the bones of the patient. Advantageously, a surgeon can see the distal end of the medial cuneiform 202 and the proximal end of the first metatarsal 208 by way of the window 906. This visual indicator for the surgeon can provide clarity that osteotomies formed using the resection features are in the desired positions and/or desired angles relative to the bones in a preoperative condition. If a surgeon determines that something is not as planned or as needed, the surgeon can alter the surgical procedure to account for this.

Medical image 1400 shows a landmark registration features 1004 that extends distally and engages a lateral side of a base of the first metatarsal 208. In addition, in the example embodiment, the markings 970 extend from a superior side 914 to an inferior side 916. This enables the markings 970 to show clearly when using X-rays for the medical image 1400.

Medical image 1400 shows the advantages of using the embodiments of the present disclosure. A surgeon may use fluoroscopy or take a number of X-ray images during different stages of a surgical procedure. For example, before deploying fasteners 710 in one or both of the bone attachment feature 908 and the bone attachment feature 910, a surgeon may take an X-ray to confirm that the resection guide 820*c* is a desired position relative to the bones and/or a joint. In addition, further use of fluoroscopy and/or capturing additional X-ray images can produce the medical image 1400 of FIG. 14.

At any stage of a surgical procedure, a surgeon can use fluoroscopy or take a number of X-ray images to confirm and/or validate a preoperative plan 506 and/or to confirm that steps have been taken and proceed according to the surgeon's plan. In one example preoperative plan 506, a surgeon may have virtually repositioned a bone model of the first metatarsal 208 from a deformed orientation to a desired orientation (e.g., such that a longitudinal axis of the first metatarsal 208 will be parallel or substantially parallel to a longitudinal axis of the second metatarsal 210, IM angle of about 0). Based on a preoperative plan 506 that includes such a correction for the first metatarsal 208, the surgeon next may use an image like medical image 1400 to check a number of other characteristics of the resection guide 820*c*.

In one example, before deploying fasteners 710, as in the illustrated example before capturing medical image 1400, a surgeon may initially position the resection guide 820*c* in the position shown in medical image 1400. Once in this position, a surgeon may review multiple landmarks of the bones and/or structures of the patient in relation to one or more structures of the resection guide 820*c*.

For example, a surgeon may visually check, using medical image 1400, that the proximal resection feature 902 extends from medial to lateral on a trajectory that is perpendicular to a longitudinal axis of the second metatarsal 210. Alternatively, or in addition, a surgeon may check (e.g., visually) that the distal resection feature 904 extends from medial to lateral on a trajectory that is perpendicular to a longitudinal axis of the first metatarsal 208 (e.g., when the first metatarsal 208 is in a deformed position). Alternatively, or in addition, a surgeon may check (e.g., visually) that an arm and holes 940 of a proximal bone attachment feature 908 extend from the body 900 proximal to distal on a trajectory that is parallel to a longitudinal axis of the second metatarsal 210. Further, the surgical procedure may check (e.g., visually) that the arm and holes 940 of the proximal bone attachment feature 908 will align from proximal to distal with an arm and holes 940 of the distal bone attachment feature 910 postoperatively once the osteotomies are completed and the first metatarsal 208 is brought in contact with the medial cuneiform 202 during reduction. Such visual checks at one or more stages of a surgical procedure may assist a surgeon in validating that the preoperative plan 506 is the plan to continue and may provide assurance that osteotomies formed using the resection guide 820*c* will be in and where the surgeon desires to form them.

Alternatively, or in addition, these check can assist a surgeon in positioning and/or registering the resection guide 820*c* to one or more bones and/or to a position that matches the position planned in a preoperative plan 506. Such position and registration checks can help a surgeon to complete the surgical procedure in the manner desired and prior to finalizing a position of the resection guide 820*c* and initiating one or more osteotomies.

Figure 15A:
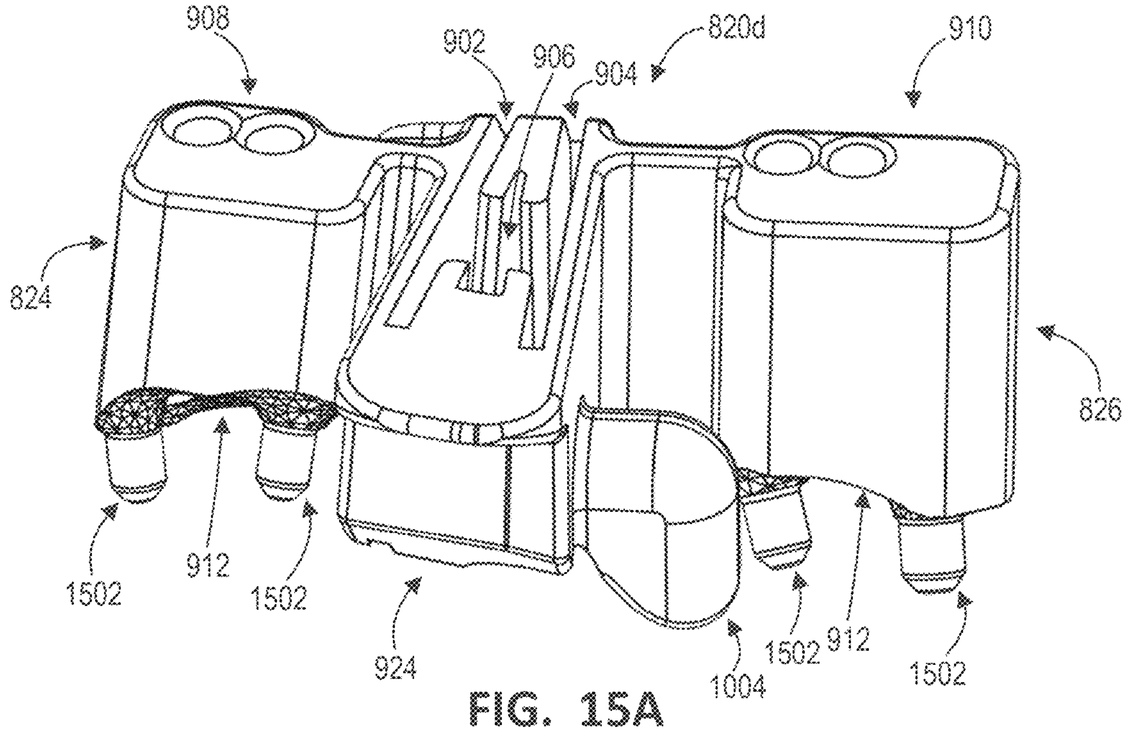
FIG. 15A illustrates a perspective view of a patient-specific resection guide according to one embodiment.
Figure 15B:
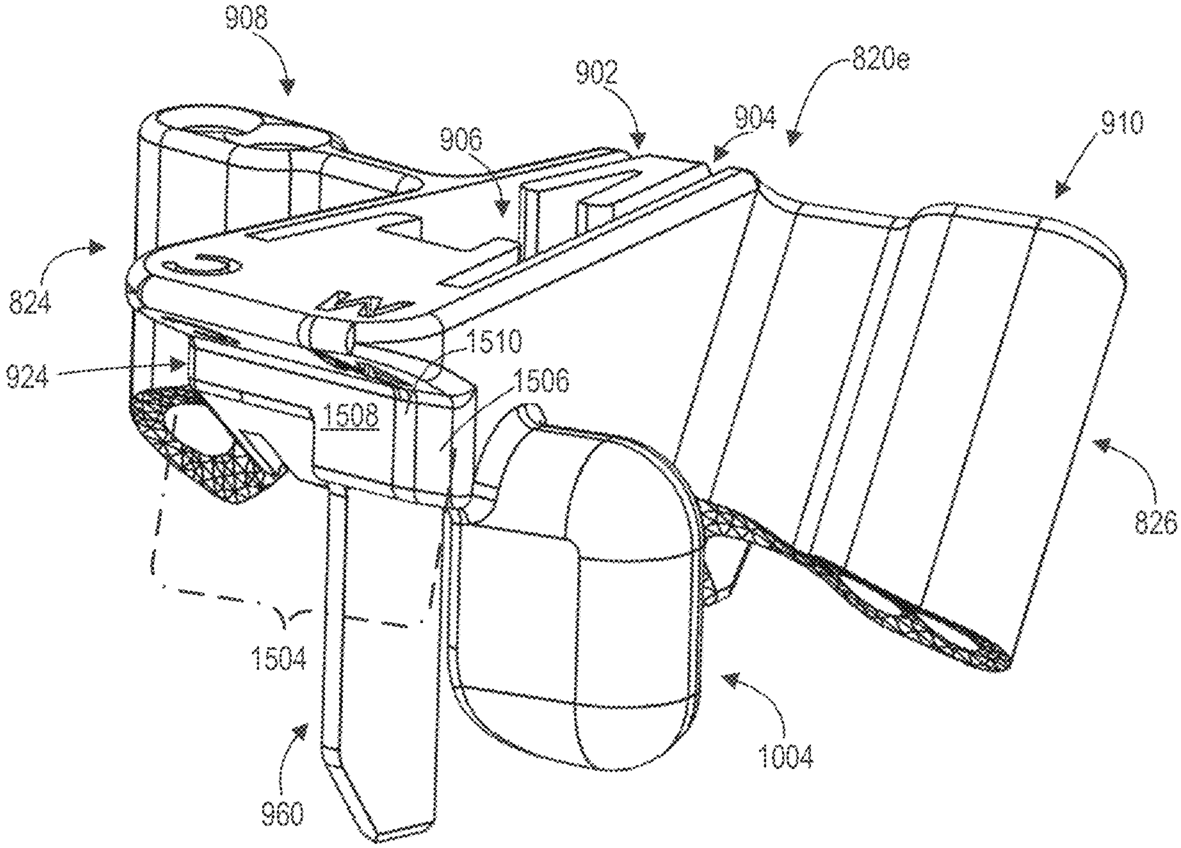
FIG. 15B illustrates a perspective view of a patient-specific resection guide according to one embodiment.

FIGS. 15A and 15B illustrate alternative embodiments for a resection guide, namely resection guide 820*d* and resection guide 820*e*, respectively. The resection guides 820*d*, 820*e* can have structures, features, aspects, characteristics, and functions, operations, and configurations that are similar or identical to those of the resection guide 820*a*, resection guide 820*b*, resection guide 820*c*, described in relation to FIGS. 8-13, like parts are identified with the same reference numerals.

FIG. 15A illustrate a perspective view of a patient-specific resection guide 820*d* according to one embodiment. The resection guide 820*d* may include a proximal resection feature 902, a distal resection feature 904, a window 906, a bone attachment feature 908, and a bone attachment feature 910 (See FIGS. 10A-10G).

In the illustrated embodiment, the resection guide 820*d* includes one or more landmark registration features 1502 distinct from the landmark registration feature 960 and/or the landmark registration features 1004 described with respect to other embodiments. In certain embodiments, the resection guide 820*d* may be used for a revision surgical procedure. Advantageously, the landmark registration features 1502 is configured to accommodate and/or account for one or more aspects of the surgical site due to a prior surgical procedure. Furthermore, the landmark registration features 1502 can be configured to leverage the one or more aspects of the surgical site present as a result of a prior surgical procedure.

For example, a revision surgical procedure may include implants such as bone plates, bone screws, bone staples, or the like that are on, in, coupled to, connected to, or integrated with the bones of a patient. Advantageously, the model of the patient's foot created according to the present disclosure can include model representations of these implants and/or other aspects of a prior surgical procedure. This model can be used to determine, defined, and/or configure one or more landmark registration features 1502 for use with a resection guide 820*d*.

Alternatively, or in addition, one or more models can include aspects and/or represent a condition of one or more bones after one or more implants are removed from the patient. These aspects and/or condition may include aspects such as holes in bone left after removing bone screws, bone staples, and/or bone plates. Or, the aspects and/or condition may include cavities, openings, depressions, protuberances, or the like formed by removing one or more bone plates from the patient. In certain embodiments, these aspects of a prior surgical procedure (both those removed for a present surgical procedure and those that are retained) are features that are landmarks for use by landmark registration features 1502. In one embodiment, the landmark (also known as a reference feature) used by one or more landmark registration features 1502 is a feature of an implant deployed in a patient in a prior surgical procedure.

In certain embodiments, the apparatuses, methods, and/or systems of the present disclosure can be used to provide a resection guide 820*d* that includes one or more landmark registration features 1502. The landmark registration features 1502 may be customized, configured, and/or determined to match, engage, connect, couple to, and/or contact one or more aspects of the surgical site created by a prior surgical procedure. In certain embodiments, the aspects may include at least part of existing implants that are to remain in the patient, at least part of aspects created or formed by removing one or more parts of implants, or any other aspects present when the medical imaging is completed for the creation of the model and/or creation of the landmark registration features 1502.

Advantageously, the shape, size, configuration, and/or number of landmark registration features 1502 can be customized to the specific needs, preferences, and/or desires of a patient, a surgeon, or other user. Thus, a landmark registration feature 1502 may take a variety of forms, including, but not limited to a protuberance, an extension, a peg, a spike, a cavity, a boss, a hole, an opening, or the like. In certain embodiments, a landmark registration feature 1502 may take a form of a conformal cavity or impression sized, shaped, and/or contoured to match part or all of an implant such as a bone plate. Alternatively, a landmark registration feature 1502 may take a form of a protuberance or extension sized, shaped, and/or contoured to match part or all of a cavity or void formed by removing a bone plate.

In certain embodiments, the apparatuses, methods, and/or systems of the present disclosure can be used to provide a surgeon with a plurality of resection guides 820*d* that each include different configurations and/or numbers of landmark registration features 1502. For example, one resection guide 820*d* may include no landmark registration features 1502. Another resection guide 820*d* may include a single landmark registration features 1502. Yet another resection guide 820*d* may include one or more landmark registration features 1502 of different sizes, shapes, and/or configurations. In this manner, a surgeon can have a plurality of resection guides 820*d* prepared such that an optimal resection guide 820*d* can be used and/or determined intraoperatively.

Those of skill in the art will appreciate that the landmark registration features 1502 can be coupled with, connected to, integrated with, and/or extend from a variety of structures of the resection guide 820*d*. FIG. 15A illustrates an embodiment of the resection guide 820*d* having four landmark registration features 1502 that are part of, connected to, or integrated with a bone engagement feature 912.

In the illustrated embodiment, the landmark registration features 1502 are implemented in the form of pegs that extend from a bone engagement surface 944 on an inferior side 916 of the resection guide 820*d*. The pegs (landmark registration features 1502) may be configured to fit within bone screw holes left in one or more bones when prior bone screws have been removed. Advantageously, the landmark registration features 1502 can facilitate and/or enhance registration of the resection guide 820*d*. When the landmark registration features 1502 engage the landmark (e.g., bone screw holes) a surgeon is assured that the resection guide 820*d* is positioned and/or oriented as planned for the surgical procedure.

FIG. 15B illustrate a perspective view of a patient-specific resection guide according to one embodiment. FIG. 15B provide a view of a resection guide 820*e* that includes an accommodation feature 1504. An accommodation feature 1504 is a feature of the resection guide 820*e* that is specifically designed and/or configured to account for and/or accommodate one or more other aspects of the surgical site and/or environment and/or anatomy of the patient. For example, in a Lapiplasty surgical procedure a cuneiform is resected, a metatarsal is resected, and cuneiform and metatarsal are fused to change the metatarsal from a deformed position to a corrected position. However, placement and registration of a resection guide 820*e* may result in interference between at least a part of the resection guide 820*e* (e.g., a part of the body) and another bone (e.g., a base of the $2^{nd}$ metatarsal). Advantageously, an accommodation feature 1504 can be included in the resection guide 820*e* to accommodate the other bone (e.g., the base of the $2^{nd}$ metatarsal). Those of skill in the art will appreciate that the accommodation feature 1504 can be positioned on a lateral side 924, another side of the resection guide 820*e*, or at any location where an accommodation feature 1504 can be utilized. In certain embodiments, the accommodation feature 1504 may be patient-specific in another embodiment the accommodation feature 1504 is not patient-specific.

In the illustrated example embodiment, the accommodation feature 1504 is on the lateral side 924 and includes a first surface 1506, a second surface 1508, and an edge 1510 that connects the first surface 1506 and second surface 1508. In this embodiment, the second surface 1508 is angled relative to the first surface 1506 such that the second surface 1508 avoids contact with a base of a $2^{nd}$ metatarsal of the patient when the resection guide 820*e* is positioned for use (and/or properly registered to anatomy of the patient). The angle that the second surface 1508 meets the first surface 1506 at the edge may be patient-specific and/or may be adjusted or changed by a surgeon as needed. In this manner, a surgeon can have a resection guide 820*e* that provides a desired level of clearance in relation to adjacent anatomical structures.

Figure 16A:
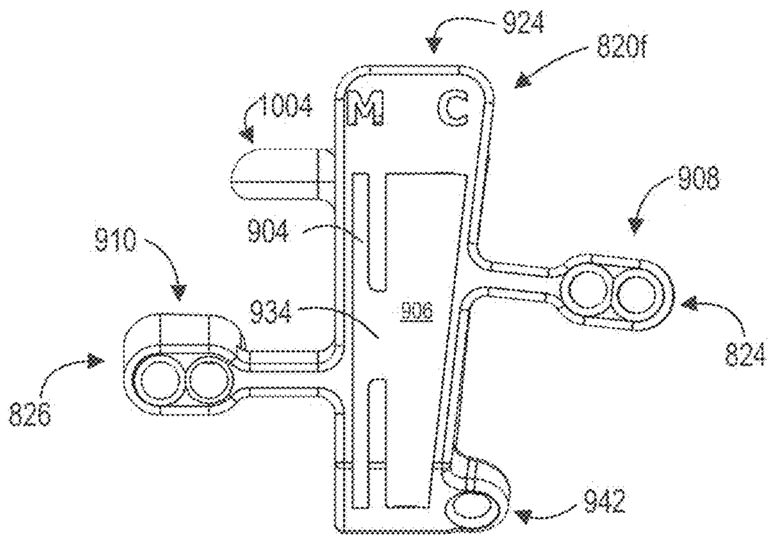
FIG. 16A-16C illustrate a superior view of a patient-specific resection guide according to certain embodiments.
Figure 16B:
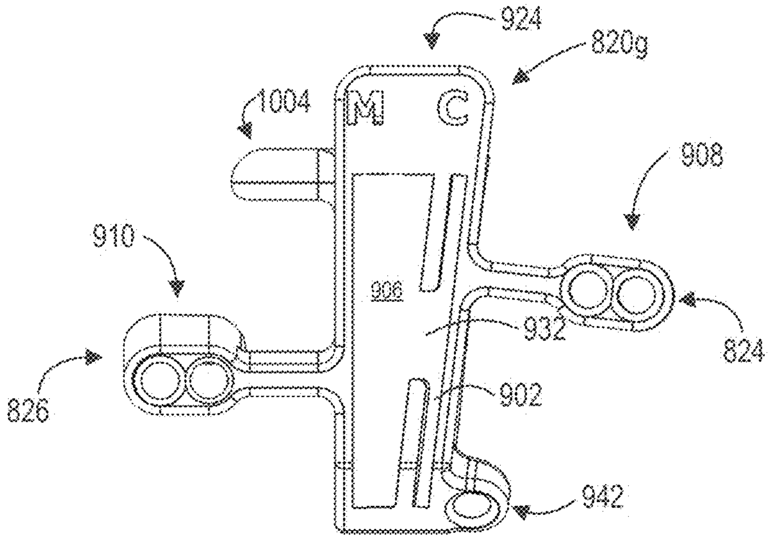
Figure 16C:
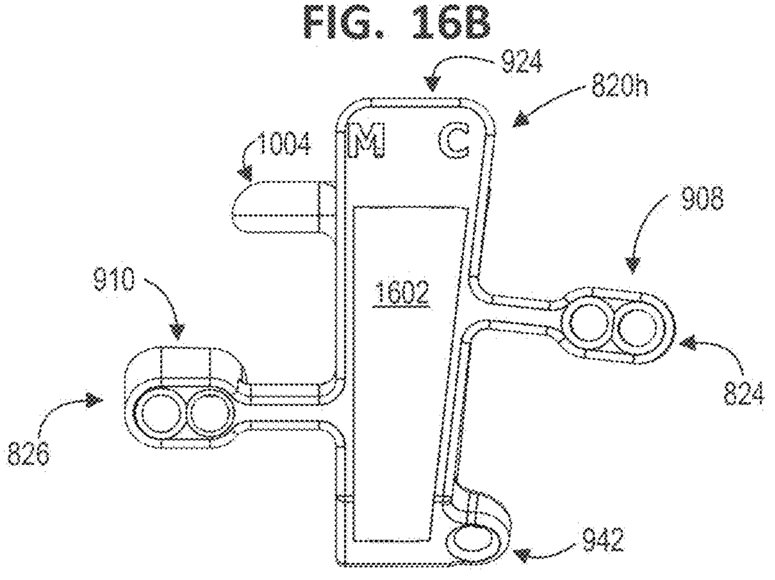

FIGS. 16A-16C illustrate alternative embodiments for a patient-specific resection guide, namely resection guide 820*f*, resection guide 820*g*, and resection guide 820*h*, respectively. The resection guides 820*f*, 820*g*, 820*h* can have structures, features, aspects, characteristics, and functions, operations, and configurations that are similar or identical to those of the resection guides 820*a-e*, described in relation to FIGS. 8-15, like parts are identified with the same reference numerals. Accordingly, the resection guide 820*f*, resection guide 820*g*, and resection guide 820*h* each include a proximal end 824, a distal end 826, a bone attachment feature 908, a bone attachment feature 910, a lateral side 924, an anchor feature 942, and a landmark registration feature 1004.

The resection guide 820*f*, resection guide 820*g*, and resection guide 820*h* differ in the configuration of the resection feature(s) and how a window 906 may or may not be included. In particular, resection guide 820*h* includes a single resection feature 1602. This single resection feature 1602 is configured to provide visibility of an anatomical structure (e.g., one or more of a cuneiform and/or a metatarsal) inferior to the resection guide 820*h* when the resection guide 820*h* is in use. In one embodiment, the single resection feature 1602 is an alternative configuration for the proximal resection feature 902. In another embodiment, the single resection feature 1602 is an alternative configuration for the distal resection feature 904. In yet another embodiment, the single resection feature 1602 is an alternative configuration for the window 906.

Referring to FIG. 16C, in the resection guide 820*h*, the single resection feature 1602 may guide a cutting tool to form a first osteotomy by enabling a surgeon to move the cutting tool along a proximal edge of the single resection feature 1602. The single resection feature 1602 may guide a cutting tool to form a second osteotomy by enabling a surgeon to move the cutting tool along a distal edge of the single resection feature 1602. The single resection feature 1602 is larger than other embodiments described and thus provides a large resection window for a surgeon to view the bones beneath the resection guide 820*h*. The surgeon may view the bones with or without the aide of medical imaging technologies.

FIG. 16B illustrates an embodiment of the resection guide 820*g* that includes a proximal resection feature 902 and a window 906. Alternatively, or in addition, the resection guide 820*g* includes a proximal side 932 that is removed to enhance visibility of bones beneath the resection guide 820*g*. In such an embodiment, the window 906 is implemented as an opening coupled to the proximal resection feature 902.

Similarly, FIG. 16A illustrates an embodiment of the resection guide 820*f* that includes a distal resection feature 904 and a window 906. Alternatively, or in addition, the resection guide 820*f* includes a distal side 934 that is removed to enhance visibility of bones beneath the resection guide 820*f*. In such an embodiment, the window 906 is implemented as an opening coupled to the distal resection feature 904.

Those of skill in the art will appreciate that embodiments of the system disclosed herein can be used on humans and on bones that are relatively small in comparison to other bones of the body (e.g., bones of the foot and hand). Advantageously, the embodiments of the system seek to minimize the number of fasteners or pins placed within the bones of a patient by planning a surgical procedure such that pins or fasteners placed in one stage are and/or can be reused in subsequent stages. Consequently, pins initially deployed can remain in the bone or bone fragment as instruments are deployed and/or subsequent stages of the surgical procedure are performed.

Advantageously, because the present disclosure uses a bone model of the patient's bones the sizes, dimensions, lengths and configurations of the components of the example systems can each be changed, adapted, revised, and/or customized to meet the needs and/or preferences of the patient and/or surgeon. Advantageously, using the apparatus, systems, and/or methods of the present disclosure the surgeon may have a preoperative plan that identifies which specific bone screw (length, width, diameter, thread, pitch, etc.) to use for the fasteners.

Advantageously, the present disclosure provides an apparatus, system, and/or method that can remediate a condition in a patient's foot. Those of skill in the art will appreciate that the methods, processes, apparatuses, systems, devices, and/or instruments of the present disclosure can be used to address a variety of conditions in a variety of procedures and/or parts of the body of the patient.

Conventionally, correction methods, systems, and/or instrumentation for a condition such as, for example, a bunion and/or a hallux valgus, face several challenges. One example is how to cut the bone such that the cut faces have a desired angle in relation to each other. Advantageously, the present disclosure can address many, if not all, of these challenges to assist a surgeon in performing the surgical procedure and improve the quality of patient care and outcomes.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles set forth herein.

While specific embodiments and applications of the present disclosure have been illustrated and described, it is to be understood that the scope of this disclosure is not limited to the precise configuration and components disclosed herein. Various modifications, changes, and variations which will be apparent to those skilled in the art may be made in the arrangement, operation, and details of the methods and systems of the present disclosure set forth herein without departing from it spirit and scope.

The invention claimed is:

1. A resection guide for remediating a condition present in a patient, the resection guide comprising:

a bone engagement feature configured to engage at least a portion of at least one foot bone to position the resection guide;

wherein the bone engagement feature is at least partially determined based on a model of a patient's foot, the model defined based on medical imaging of the patient's foot;

a first resection feature extending through the resection guide from a superior side of the resection guide to an inferior side, the first resection feature comprising an elongate opening that extends from near a first side of the resection guide to near a second side of the resection guide, the first resection feature configured to guide a cutting tool to form a first osteotomy in a first bone along a first trajectory;

a second resection feature extending through the resection guide from a superior side of the resection guide to an inferior side, the second resection feature comprising an elongate opening that extends from near the first side of the resection guide to near the second side of the resection guide, the second resection feature configured to guide a cutting tool to form a second osteotomy in a second bone along a second trajectory;

a window formed in the resection guide between the first resection feature and the second resection feature;

wherein, when viewed from the superior side of the resection guide, the first resection feature is non-parallel to the second resection feature;

a first bone attachment feature configured to engage the first bone; and a second bone attachment feature configured to engage the second bone.

2. The resection guide of claim 1, wherein the window is configured to provide visibility of an anatomical structure inferior to the resection guide when in use.

3. The resection guide of claim 1, wherein the window extends from the superior side of the resection guide to the inferior side, the window providing visibility of an anatomical structure inferior to the resection guide when in use.

4. The resection guide of claim 3, wherein the window comprises an opening coupled to at least one of the first resection feature and the second resection feature.

5. The resection guide of claim 3, wherein the window is configured to provide visibility of a distal end of the first bone and a proximal end of the second bone.

6. The resection guide of claim 1, wherein the bone engagement feature is on an inferior side of the resection guide and is configured to extend from a medial surface of the at least one foot bone, over a dorsal surface of the at least one foot bone, and to a lateral surface of the at least one foot bone.

7. The resection guide of claim 1, wherein the second bone attachment feature is positioned relative to the first bone attachment feature such that reduction of the first osteotomy and the second osteotomy aligns the second bone attachment feature and the first bone attachment feature and rotates the second bone within a frontal plane.

8. The resection guide of claim 1, further comprising an alignment guide configured to identify a position of the second bone relative to a third bone of the patient.

9. The resection guide of claim 1, further comprising a landmark registration feature configured to engage a landmark of the patient.

10. The resection guide of claim 9, wherein the landmark registration feature extends from a distal side of the resection guide, wherein the landmark comprises a lateral side of a base of the second bone, the landmark registration feature configured to engage the base of the second bone.

11. The resection guide of claim 9, wherein the landmark comprises a feature of an implant deployed in the patient in a prior surgical procedure.

12. A resection guide for remediating a condition present in a patient, the resection guide comprising:

a bone engagement feature configured to engage at least a portion of at least one foot bone to position the resection guide;

a proximal slot configured to guide a cutting tool to form a first osteotomy in a cuneiform, the proximal slot extending through the resection guide from a superior side to an inferior side along a first trajectory, the proximal slot further extending from near a first side of the resection guide to near a second side of the resection guide;

a distal slot configured to guide a cutting tool to form a second osteotomy in a metatarsal, the distal slot extending through the resection guide from the superior side to the inferior side along a second trajectory, the distal slot further extending from near the first side of the resection guide to near the second side of the resection guide;

a resection window between the proximal slot and the distal slot, the resection window extending from the superior side to the inferior side, the resection window configured to enable observation of an articular surface of both the cuneiform and the metatarsal;

a first bone attachment feature configured to accept a first fastener that engages the cuneiform;

a second bone attachment feature configured to accept a second fastener that engages the metatarsal; and wherein, when viewed from the superior side of the resection guide, the proximal slot is non-parallel to the distal slot.

13. The resection guide of claim 12, wherein one of the first trajectory and the second trajectory is at least partially determined based on a revised model of a patient's foot, the revised model defined based on changes made by a surgical procedure performed prior to using the resection guide for a second surgical procedure on a patient's foot.

14. The resection guide of claim 12, wherein at least one of the first trajectory and the second trajectory is at least partially determined based on a tarsometatarsal (TMT) joint axis, the TMT joint axis determined based on a model of a patient's foot.

15. The resection guide of claim 12, further comprising a soft tissue engagement feature comprising a superior protrusion and an inferior protrusion spaced from the superior protrusion so as to engage at least a portion of soft tissue between the superior protrusion and the inferior protrusion within an operating field.

* * * * *